United States Patent
Groarke et al.

(10) Patent No.: US 11,289,661 B2
(45) Date of Patent: Mar. 29, 2022

(54) NITROGEN-CONTAINING HETEROCYCLIC COMPOUNDS FOR ORGANIC LIGHT EMITTING DEVICES

(71) Applicant: IDEMITSU KOSAN CO., LTD., Chiyoda-ku (JP)

(72) Inventors: Michelle Groarke, Binningen (CH); Takushi Shiomi, Chiba (JP); Masahiro Kawamura, Basel (CH); Hideaki Nagashima, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 390 days.

(21) Appl. No.: 16/346,753

(22) PCT Filed: Dec. 28, 2017

(86) PCT No.: PCT/JP2017/047425
§ 371 (c)(1),
(2) Date: May 1, 2019

(87) PCT Pub. No.: WO2018/124313
PCT Pub. Date: Jul. 5, 2018

(65) Prior Publication Data
US 2020/0058881 A1    Feb. 20, 2020

(30) Foreign Application Priority Data

Dec. 29, 2016    (EP) .................................. 16207289

(51) Int. Cl.
*C07D 487/04* (2006.01)
*C07D 223/14* (2006.01)
(Continued)

(52) U.S. Cl.
CPC ........ *H01L 51/0072* (2013.01); *C07D 487/04* (2013.01); *C07D 487/22* (2013.01);
(Continued)

(58) Field of Classification Search
CPC ........................... C07D 487/04; C07D 223/14
See application file for complete search history.

(56) References Cited

U.S. PATENT DOCUMENTS

| 2013/0092922 A1 | 4/2013 | Stoessel et al. |
| 2015/0207083 A1 | 7/2015 | Schaefer et al. |

(Continued)

FOREIGN PATENT DOCUMENTS

| EP | 3 054 498 A1 | 8/2016 |
| WO | WO 2014/009317 A1 | 1/2014 |

OTHER PUBLICATIONS

International Search Report dated Mar. 6, 2018 in PCT/JP2017/04725 filed Dec. 28, 2017.

(Continued)

*Primary Examiner* — Vu A Nguyen

(74) *Attorney, Agent, or Firm* — Oblon, McClelland, Maier & Neustadt, L.L.P.

(57) ABSTRACT

A compound of formula (I), a material for an organic electroluminescence device comprising at least one compound of formula (I); an organic electroluminescence device which comprises an organic thin film layer between a cathode and an anode, wherein the organic thin film layer comprises one or more layers and comprises a light emitting layer, and at least one layer of the organic thin film layer comprises at least one compound of formula (I); an electronic equipment comprising the organic electroluminescence device; and a process for preparing the compound of formula (I).

(Continued)

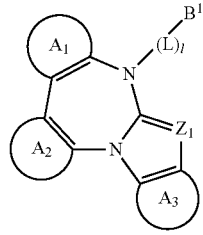

15 Claims, 1 Drawing Sheet

(51) Int. Cl.
    *C07D 487/22* (2006.01)
    *C07D 519/00* (2006.01)
    *C09K 11/06* (2006.01)
    *H01L 51/00* (2006.01)
    *C07F 9/6561* (2006.01)
    *H01L 51/50* (2006.01)

(52) U.S. Cl.
    CPC .......... *C07D 519/00* (2013.01); *C07F 9/6561* (2013.01); *C09K 11/06* (2013.01); *H01L 51/0052* (2013.01); *H01L 51/0067* (2013.01); *H01L 51/0073* (2013.01); *H01L 51/0074* (2013.01); *C09K 2211/1018* (2013.01); *H01L 51/5016* (2013.01); *H01L 51/5072* (2013.01); *H01L 51/5096* (2013.01)

(56) References Cited

U.S. PATENT DOCUMENTS

2017/0244051 A1    8/2017  Schaefer et al.
2018/0315935 A1\*  11/2018  Dyatkin .............. C07F 15/0033

OTHER PUBLICATIONS

Bindra, A. P. et al., "10,10'-Bi[4.5,6.7]Dibenz[1.3]Diazepino[2.1-a]-Isoindolinylidenes," Tetrahedron, vol. 25, No. 22, Jan. 1, 1969, pp. 5465-5473, XP055345514.

Zhang, T. et al., "N-Heterocyclic Carbene-Acetylamide Palladium Complexes and Their Catalytic Activities in Heck-Mizoroki Reactions," Synthesis, vol. 2008, No. 17, Sep. 1, 2008, pp. 2819-2824, XP055213811.

\* cited by examiner

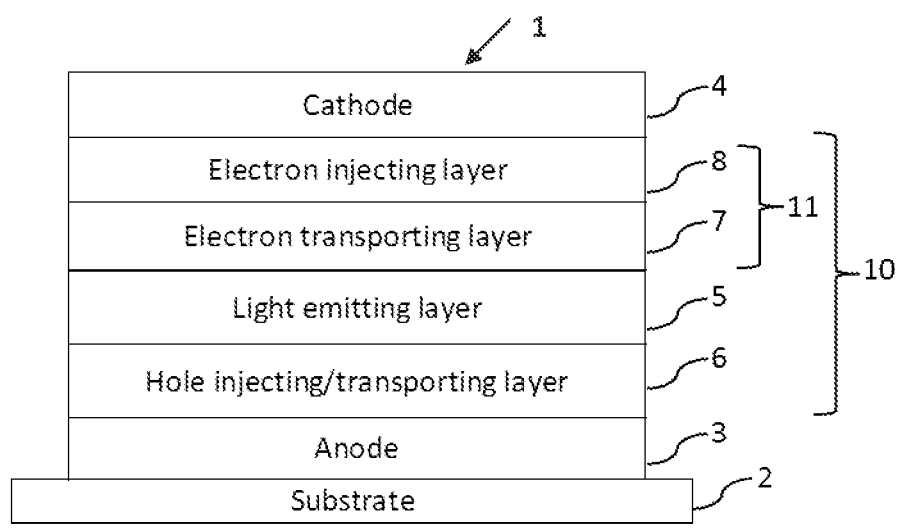

NITROGEN-CONTAINING HETEROCYCLIC COMPOUNDS FOR ORGANIC LIGHT EMITTING DEVICES

TECHNICAL FIELD

The present invention relates to specific nitrogen-containing heterocyclic compounds and organic electroluminescence devices comprising the same.

BACKGROUND ART

Tetrahedron 25, 22, 1969, 5465-5473 discloses the preparation of 10,10'-bi[4.5,6.7]dibenz[1.3]-diazepino[2.1-a]-isoindolinylidenes as annelated analogues of diimino-β-isoindigo.

Synthesis 2008 (7):2819-2824 discloses the synthesis of an N-heterocyclic carbene-acetylamide ligand derived from binaphthyl-2,2'-diamine (BINAM) and its dinuclear NHC-Pd(II) complex as well as its corresponding complex bearing weakly coordinating acetate counterions. These complexes are quite effective in Heck-Mizoroki reactions and give the corresponding products in good to excellent yields. In said document, the following compound is shown:

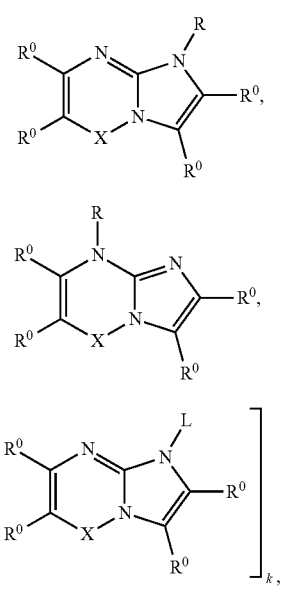

US 2013/0092922 A1 relates to an electronic device comprising at least one compound of the formula (I) to (IV), to the use of compounds of the formula (I) to (IV) in an electronic device and to a compound of the formula (Ic) to (IVc).

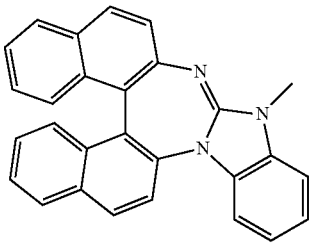 [SMILES: CN1C2=Nc3ccc4ccccc4c3-c3c(ccc4ccccc34)N2c2ccccc21]

(I)

(II)

(III)

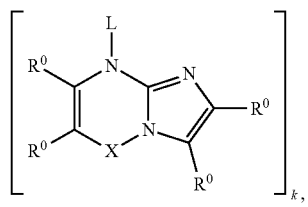

(IV)

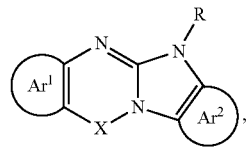

(Ic)

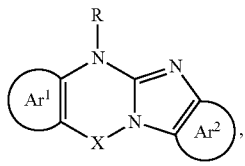

(IIc)

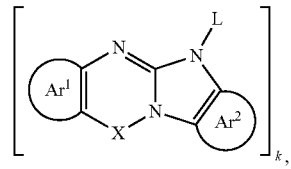

(IIIc)

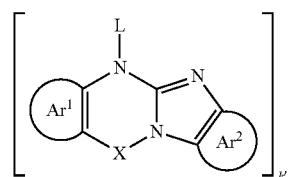

(IVc)

Dibenzo-1,3-diazepinobenzimidazoles are not explicitly mentioned in US 2013/0092922 A1.

CITATION LIST

Patent Literature

Patent Literature 1: US 2013/0092922 A1

Non Patent Literature

Non Patent Literature 1: Tetrahedron 25 1969, 5465-5473
Non Patent Literature 2: Synthesis 2008 (17), 2819-2824

SUMMARY OF INVENTION

Technical Problem

Notwithstanding these developments, there remains a need for organic light emitting devices comprising new materials, especially host (=matrix) materials, charge blocker materials, e.g. hole blocker materials and/or charge transport materials, e.g. electron transport materials, to provide improved performance of electroluminescent devices.

Accordingly, it is an object of the present invention, with respect to the aforementioned related art, to provide further materials suitable for use in organic electronic devices and further applications in organic electronics. More particularly, it should be possible to provide charge transport materials, e.g. electron transport materials, and/or charge blocker materials, e.g. hole blocker materials, and/or host (=matrix) materials for use in organic electronic devices. The materials should be suitable especially for organic electronic devices which comprise at least one emitter, which is a phosphorescence emitter and/or a fluorescence emitter, preferably a phosphorescence emitter, for example at least one green emitter—or—in a further embodiment—preferably a fluorescent emitter, for example at least one blue emitter.

Furthermore, the materials should be suitable for providing organic electronic devices which ensure good performance of the organic electronic devices, especially good external quantum efficiencies.

Solution to Problem

Said object is solved by a compound of formula (I)

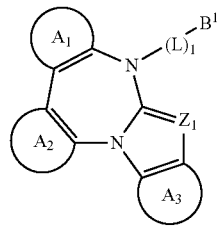

(I)

wherein $A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms, preferably represent a substituted or unsubstituted naphthalene ring or benzene ring, more preferably represent a substituted or unsubstituted benzene ring, $Z_1$ is N or $CR^1$, preferably N, $R^1$ is hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms;

$B^1$ is H, CN, a substituted or unsubstituted aromatic hydrocarbon group having 6 to 30 ring carbon atoms; a substituted or unsubstituted heterocyclic group having 5 to 30 ring atoms; or a substituted or unsubstituted cycloalkyl group having 3 to 30 ring carbon atoms; L is a single bond, a substituted or unsubstituted alkylene group having 1 to 30 carbon atoms, a substituted or unsubstituted cycloalkylene group having 3 to 30 carbon atoms, a substituted silyl group having 2 to 30 carbon atoms, a substituted or unsubstituted aromatic hydrocarbon group having 6 to 30 ring carbon atoms, or a substituted or unsubstituted heterocyclic group having 5 to 30 ring atoms, preferably a single bond, a substituted or unsubstituted phenylene group, a substituted or unsubstituted biphenylene group, a substituted or unsubstituted naphthylene group, or combinations thereof; and l is 1, 2 or 3, in the case that l is 2 or 3, L is the same or different in each occurrence.

The compound of the present invention according to formula (I) which comprises an imidazole ring structure or indole ring structure and a nitrogen-containing seven-membered ring may be used as a material, especially host, charge transport or charge blocking materials, that are highly suitable in organic electronic devices. Moreover, a balanced charge transport and/or charge blocking in devices is achieved, especially resulting in good external quantum efficiencies.

The compounds of the present invention may be used in organic electronic devices such as electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and organic electroluminescence devices, for example, organic light-emitting diodes (OLEDs).

Accordingly, a further subject of the present invention is directed to an organic electronic device, comprising a compound according to the present invention. The organic electronic device is preferably an organic electroluminescence device (EL device), such as an organic light-emitting diode (OLED).

The compounds of formula (I) can in principal be used in any layer of an EL device, but are preferably used as host, charge transport, especially electron transport, and/or charge blocking, especially hole blocking, material. Particularly, the compounds of formula (I) are used as host material, hole blocking material and/or electron transport material for phosphorescence or fluorescence emitters.

Hence, a further subject of the present invention is directed to an emitting layer, comprising a compound of formula (I) according to the present invention. In said embodiment a compound of formula (I) is preferably used as host material or as co-host material together with one or more, preferably one, further host materials. More preferably, a combination of a compound of formula (I) as host material or as co-host material together with a phosphorescent emitter is used.

A further subject of the present invention is directed to an electron transporting layer comprising a compound of formula (I) according to the present invention. Preferably, the electron transporting layer is provided between the cathode and the light emitting layer of an EL device such as an OLED.

A further subject of the present invention is directed to a hole blocking layer comprising a compound of formula (I) according to the present invention. Preferably, the hole blocking layer is provided between the electron transporting layer and the light emitting layer of an EL device such as an OLED.

In another aspect, the invention provides a material for an organic electroluminescence device comprising at least the compound of formula (I).

In still another aspect, the invention provides an organic electroluminescence device which comprises an organic thin film layer between a cathode and an anode, wherein the organic thin film layer comprises one or more layers and comprises a light emitting layer, and at least one layer of the organic thin film layer comprises at least the compound of formula (I).

In still another aspect, the invention provides an electronic equipment comprising the organic electroluminescence device.

In still another aspect, the invention provides a process for preparing the compound of formula (I), wherein $Z_1$ is N, comprising the following steps Ai) Reaction of a diamine (II) with an isothiocyanate (111) followed by cyclization with a carbodiimide (IV), whereby a seven membered heterocycle (V) is formed,

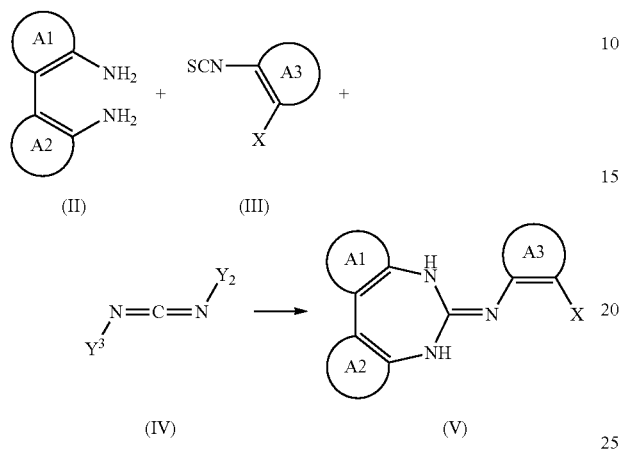

(II)  (III)

(IV)  (V)

wherein $Y_2$ and $Y_3$ are each independently a substituted or unsubstituted alkyl group having 1 to 30 carbon atoms; a substituted or unsubstituted cycloalkyl group having 3 to 30 ring carbon atoms; a substituted or unsubstituted aromatic hydrocarbon group having 6 to 30 ring carbon atoms; or a substituted or unsubstituted heterocyclic group having 5 to 30 ring atoms; and X is a halogen, preferably Br or I; and Aii) Cyclization of the seven membered heterocycle (V) in the presence of a copper salt, whereby a heterocyclic system (VI) is formed

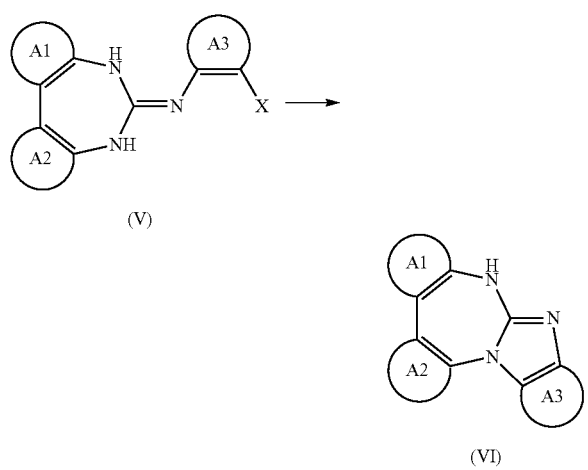

(V)

(VI)

wherein $A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms.

In still another aspect, the invention provides a process for preparing the compound of formula (I), wherein $Z_1$ is $CR^1$, comprising the following step Bi) Acid mediated ring closure of a compound of formula (VII) whereby a heterocyclic system of formula (VIII) is formed

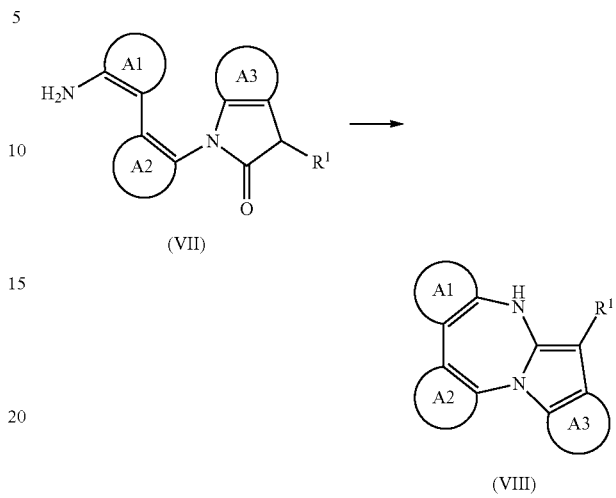

(VII)

(VIII)

wherein $A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms, and $R^1$ is hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms.

Advantageous Effects of Invention

Organic EL devices produced by using the compound of formula (I) are improved in their performance.

BRIEF DESCRIPTION OF DRAWINGS

The FIGURE shows a schematic configuration of one example of the organic EL device of the invention.

DESCRIPTION OF EMBODIMENTS

The terms aromatic hydrocarbon group having 6 to 30 ring carbon atoms, heterocyclic group having 5 to 30 ring atoms, alkyl group having 1 to 30 carbon atoms, cycloalkyl group having 3 to carbon atoms, aralkyl group having 7 to 24 carbon atoms, alkylene group having 1 to 30 carbon atoms, cycloalkylene group having a ring structure formed of 3 to 20 carbon atoms, substituted silyl group having 2 to 30 carbon atoms, divalent aromatic hydrocarbon group having a ring structure formed of 6 to 30 carbon atoms, divalent heterocyclic group having a ring structure formed of 5 to 30 atoms, silyl group, halogen atom, alkoxy group having 1 to 20 carbon atoms, haloalkyl group having 1 to 20 carbon atoms, haloalkoxy group having 1 to 20 carbon atoms, aryloxy group having 6 to 30 ring carbon atoms, alkylthio group having 1 to 20 carbon atoms, arylthio group having 6 to 30 ring carbon atoms, an alkylamino group having 1 to 20 carbon atoms, an arylamino group having 6 to 30 carbon atoms, a carboxyalkyl group having 1 to 20 carbon atoms, a carboxamidalkyl group having 1 to 20 carbon atoms, a carboxyaryl group having 6 to 30 carbon atoms, a carboxamidaryl group having 6 to 30 carbon atoms are known in the art and generally have the following meaning, if said groups are not further specified in specific embodiments mentioned below:

The aromatic hydrocarbon group having 6 to 30 ring carbon atoms, preferably 6 to 18 ring carbon atoms, may be a non-condensed aromatic hydrocarbon group or a condensed aromatic hydrocarbon group. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, anthracenyl group, chrysenyl group, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group, with phenyl group, naphthyl group, biphenyl group, terphenyl group, phenanthryl group, triphenylenyl group, fluorenyl group, spirobifluorenyl group, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group being more preferred.

The heterocyclic group having 5 to 30 ring atoms, preferably 5 to 18 ring atoms, may be a non-condensed heterocyclic group or a condensed heterocyclic group. The heterocyclic group having 5 to 30 ring atoms, preferably 5 to 18 ring atoms, may be an aromatic or a non-aromatic group. Specific examples thereof include the residues of pyrrole ring, isoindole ring, benzofuran ring, isobenzofuran ring, benzothiophene ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyran ring, dibenzofuran ring and benzo[c]dibenzofuran ring, and the residues of derivatives of these rings, with the residues of dibenzofuran ring, carbazole ring, dibenzothiophene ring, and derivatives of these rings being preferred, and the residues of dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group being more preferred.

Examples of the alkyl group having 1 to 30 carbon atoms include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, with methyl group, ethyl group, n-propyl group, isopropyl group, n-butyl group, s-butyl group, isobutyl group, and t-butyl group being preferred.

Examples of the cycloalkyl group having 3 to 20 carbon atoms include cyclopropyl group, cyclobutyl group, cyclopentyl group, cyclohexyl group, cyclooctyl group, and adamantyl group, with cyclopentyl group, and cyclohexyl group being preferred.

Examples of an aralkyl group having 7 to 24 carbon atoms, preferably 7 to 20 carbon atoms, include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

Examples of the alkylene group (i.e. alkane-diyl group) having 1 to 30 carbon atoms represented include methylene group, ethylene group, n-propylene group, isopropylene group, n-butylene group, s-butylene group, isobutylene group, t-butylene group, n-pentylene group, n-hexylene group, n-heptylene group, n-octylene group, n-nonylene group, n-decylene group, n-undecylene group, n-dodecylene group, n-tridecylene group, n-tetradecylene group, n-pentadecylene group, n-hexadecylene group, n-heptadecylene group, n-octadecylene group, neopentylene group, and 1-methylpentylene group, with methylene group, ethylene group, n-propylene group, isopropylene group, n-butylene group, s-butylene group, isobutylene group, and t-butylene group being preferred.

Examples of the cycloalkylene group (i.e. cycloalkane-diyl group) having 3 to 20 carbon atoms include cyclopropylene group, cyclobutylene group, cyclopentylene group, cyclohexylene group, cyclooctylene group, and adamantylene group, with cyclopentylene group, and cyclohexylene group being preferred.

Examples of the substituted divalent silyl group having 2 to 30 carbon atoms include divalent dimethylsilyl group, divalent diethylsilyl group, divalent dibutylsilyl group, divalent methylethylsilyl group, divalent t-butylmethylsilyl group, divalent vinylmethylsilyl group, divalent propylmethylsilyl group, divalent methylisopropylsilyl group, divalent methylpropylsilyl group, divalent methylbutylsilyl group, divalent methyltertiarybutylsilyl group, divalent ethylisopropylsilyl group, divalent phenylmethylsilyl group, divalent phenylmethylsilyl group, divalent phenyltertiarybutylsilyl group, and divalent diphenylsilyl group, with divalent dimethylsilyl group, divalent diethylsilyl group, divalent t-butylmethylsilyl group, divalent vinylmethylsilyl group, and divalent propylmethylsilyl group being preferred.

The divalent aromatic hydrocarbon group having 6 to 30 ring carbon atoms may be a non-condensed divalent aromatic hydrocarbon group or a condensed divalent aromatic hydrocarbon group. Specific examples thereof include phenylene group, naphthylene group, phenanthrylene group, biphenyl-diyl group, terphenyl-diyl group, quaterphenyl-diyl group, fluoranthen-diyl group, triphenylenylene-diyl group, phenanthrene-diyl group, fluorene-diyl group, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylenylene-diyl group, dibenzo[a,c]triphenylenylene-diyl group, and benzo[b]fluoranthene-diyl group, with phenylene group, naphthylene group, biphenyl-diyl group, terphenyl-diyl group, phenanthryl-diyl group, triphenylenylen-diyl group, fluorene-diyl group, spirobifluorene-diyl group, and fluoranthene-diyl group being preferred, and 1,2-phenylene group, 1,3-phenylene group, 1,4-phenylene group, 1,4-naphthylene group, 1,8-naphthylene group, 2,6-naphthylene group, 2,7-naphthylene group, biphenyl-2,2'-diyl group, biphenyl-2,3'-diyl group, biphenyl-2,4'-diyl group, biphenyl-2,5'-diyl group, biphenyl-2,6'-diyl group, biphenyl-3,3'-diyl group, biphenyl-3,4'-diyl group, biphenyl-3,5'-diyl group, biphenyl-3,6'-diyl group, biphenyl-4,4'-diyl group, biphenyl-4,5'-diyl group, biphenyl-4,6'-diyl group, biphenyl-5,5'-diyl group, biphenyl-5,6'-diyl group, biphenyl-6,6'-diyl group, phenanthrene-9,10-diyl group, phenanthrene-2,3-diyl group, phenanthrene-2,7-diyl group, phenanthrene-2,8-diyl group, phenanthrene-2,6-diyl group, phenanthrene-2,9-diyl group, phenanthrene-2,10-diyl group, phenanthrene-3,9-diyl group, phenanthrene-3,10-diyl group, triphenylene-2,3-diyl group, triphenylene-2,5-diyl group, triphenylene-2,6-diyl group, triphenylene-2,7-diyl group, triphenylene-2,8-diyl group, 9,9-dimethylfluorene-2,7-diyl group, 9,9-dimethylfluorene-3,7-diyl group, 9,9-dimethylfluorene-1,4-diyl group, fluoranthene-3,9-diyl group, fluoranthene-3,8-diyl group, fluoranthene-3,4-diyl group, fluoranthene-3,5-diyl group, fluoranthene-3,6-diyl group, fluoranthene-2,9-diyl group, fluoranthene-2,8-diyl group, fluoranthene-2,4-diyl group, fluoranthene-2,5-diyl group, fluoranthene-2,6-diyl group, fluoranthene-1,9-diyl group, fluoranthene-1,8-diyl group, fluoranthene-1,4-diyl group, fluoranthene-1,5-diyl group, and fluoranthene-1,6-diyl group being more preferred.

The divalent heterocyclic group having 5 to 30 ring atoms may be a non-condensed heterocyclic group or a condensed heterocyclic group. The divalent heterocyclic group having 5 to 30 ring atoms may be an aromatic or a non-aromatic group. Specific examples thereof include the divalent residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyran ring, dibenzofuran ring, and benzo[c]dibenzofuran ring, and the divalent residues of derivatives of these rings, with the divalent residues of dibenzofuran ring, carbazole ring, dibenzothiophene ring, and derivatives of these divalent rings being preferred, and the dibenzofuran-diyl group, 9-phenylcarbazole-diyl group and dibenzothiophene-diyl group being more preferred.

Examples of silyl groups include alkylsilyl groups having 1 to 10 carbon atoms, preferably 1 to 5 carbon atoms, including trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, and arylsilyl groups having 6 to 30 carbon atoms, preferably 6 to 18 carbon atoms, including phenyldimethylsilyl group, diphenylmethylsilyl group, diphenyltertiarybutylsilyl group, and triphenylsilyl group, with trimethylsilyl group, triethylsilyl group, t-butyldimethylsilyl group, vinyldimethylsilyl group, and propyldimethylsilyl group being preferred.

Examples of halogen atoms include fluorine, chlorine, bromine, and iodine, with fluorine being preferred.

Examples of an alkoxy group having 1 to 20 carbon atoms include those having an alkyl portion selected from the alkyl groups mentioned above.

Examples of a haloalkyl group having 1 to 20 carbon atoms include the alkyl groups mentioned above wherein the hydrogen atoms thereof are partly or entirely substituted by halogen atoms.

Examples of a haloalkoxy group having 1 to 20 carbon atoms include the alkoxyl group mentioned above wherein the hydrogen atoms thereof are partly or entirely substituted by halogen atoms.

Examples of an aryloxy group having 6 to 30 ring carbon atoms include those having an aryl portion selected from the aromatic hydrocarbon groups mentioned above.

Examples of an alkylthio group having 1 to 20 carbon atoms include those having an alkyl portion selected from the alkyl groups mentioned above.

Examples of an arylthio group having 6 to 30 ring carbon atoms include those having an aryl portion selected from the aromatic hydrocarbon groups mentioned above.

Examples of an alkylamino group having 1 to 20 ring carbon atoms include those having an alkyl portion selected from the alkyl groups mentioned above.

Examples of an arylamino group having 6 to 30 ring carbon atoms include those having an aryl portion selected from the aromatic hydrocarbon groups mentioned above.

Examples of a carboxyalkyl group having 1 to 20 carbon atoms, preferably 1 to 5 carbon atoms, include those having an alkyl portion selected from the alkyl groups mentioned above.

Examples of a carboxamidalkyl group having 1 to 20 carbon atoms, preferably 1 to 5 carbon atoms include those having an alkyl portion selected from the alkyl groups mentioned above.

Examples of a carboxyaryl group having 6 to 30 carbon atoms, preferably 6 to 18 carbon atoms, include those having an aryl portion selected from the aromatic hydrocarbon groups mentioned above.

Examples of a carboxamidaryl group having 6 to 30 carbon atoms, preferably 6 to 18 carbon atoms, include those having an aryl portion selected from the aromatic hydrocarbon groups mentioned above.

Examples of the optional substituent(s) indicated by "substituted or unsubstituted" and "may be substituted" referred to above or hereinafter include a halogen atom (fluorine, chlorine, bromine, iodine), a cyano group, an alkyl group having 1 to 30, preferably 1 to 6 carbon atoms, a cycloalkyl group having 3 to 20, preferably 5 to 12 carbon atoms, an alkoxyl group having 1 to 20, preferably 1 to 5 carbon atoms, a haloalkyl group having 1 to 20, preferably 1 to 5 carbon atoms, a haloalkoxyl group having 1 to 20, preferably 1 to 5 carbon atoms, an alkylamino group having 1 to 20 carbon atoms, preferably 1 to 5 carbon atoms, a carboxyalkyl group having 1 to 20 carbon atoms, preferably 1 to 5 carbon atoms, a carboxamidalkyl group having 1 to 20 carbon atoms, preferably 1 to 5 carbon atoms, a silyl group, an aromatic hydrocarbon group having 6 to 30 ring carbon atoms, preferably 6 to 18 ring carbon atoms, an aryloxy group having 6 to 30, preferably 6 to 18 ring carbon atoms, an aralkyl group having 7 to 24, preferably 7 to 20 carbon atoms, an alkylthio group having 1 to 20, preferably 1 to 5 carbon atoms, an arylthio group having 6 to 30, preferably 6 to 18 ring carbon atoms, an arylamino group having 6 to 30 carbon atoms, preferably 6 to 18 carbon atoms, a carboxyaryl group having 6 to 30 carbon atoms, preferably 6 to 18 carbon atoms, a carboxamidaryl group having 6 to 30 carbon atoms, preferably 6 to 18 carbon atoms, and a heterocyclic group having 5 to 30 ring atoms, preferably 5 to 18 ring atoms.

The optional substituent is preferably a fluorine atom, a cyano group, an alkyl group having 1 to 30 carbon atoms, an aromatic hydrocarbon group having 6 to 30 ring carbon atoms, preferably 6 to 18 ring carbon atoms, and an heterocyclic group having 5 to 30 ring atoms, preferably 5 to 18 ring atoms; more preferably a fluorine atom, a phenyl group, a naphthyl group, a biphenyl group, a terphenyl group, a phenanthryl group, a triphenylenyl group, a fluorenyl group, a spirobifluorenyl group, a fluoranthenyl group, a residue based on a dibenzofuran ring, a residue based on a carbazole ring, a residue based on a dibenzothiophene ring, and their derivatives, with a methyl group, an ethyl group, an n-propyl group, an isopropyl group, an n-butyl group, an s-butyl group, an isobutyl group, a t-butyl group, a cyclopentyl group, a cyclohexyl group, a phosphoryl group, a phenylphosphoryl group, and a diphenylphosphoryl group.

The optional substituent mentioned above may be further substituted by one or more of the optional substituents mentioned above.

The number of the optional substituents depends on the group which is substituted by said substituent(s). Preferred are 1, 2, 3 or 4 optional substituents, more preferred are 1, 2 or 3 optional substituents, most preferred are 1 or 2 optional substituents. In a further preferred embodiment, the groups mentioned above are unsubstituted.

The "carbon number of a to b" in the expression of "substituted or unsubstituted X group having a to b carbon atoms" is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium.

The compound in an aspect of the invention is represented by formula (I):

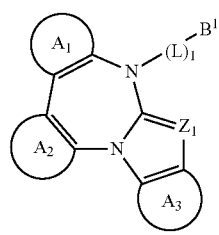

(I)

wherein
$A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms, $Z_1$ is N or $CR^1$, preferably N,
$R^1$ is hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms;

$B^1$ is H, CN, a substituted or unsubstituted aromatic hydrocarbon group having 6 to 30 ring carbon atoms; a substituted or unsubstituted heterocyclic group having 5 to 30 ring atoms; or a substituted or unsubstituted cycloalkyl group having 3 to 30 ring carbon atoms; L is a single bond, a substituted or unsubstituted alkylene group having 1 to 30 carbon atoms, a substituted or unsubstituted cycloalkylene group having 3 to 30 carbon atoms, a substituted silyl group having 2 to 30 carbon atoms, a substituted or unsubstituted aromatic hydrocarbon group having 6 to 30 ring carbon atoms, or a substituted or unsubstituted heterocyclic group having 5 to 30 ring atoms; and l is 1, 2 or 3, in the case that l is 2 or 3, L is the same or different in each occurrence.

The Groups $A_1$, $A_2$ and $A_3$

In the compounds of formula (I), the groups $A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms.

Preferably, $A_1$, $A_2$ and $A_3$ each independently represent a substituted or unsubstituted aromatic hydrocarbon group having a ring structure formed of 6 to 10 carbon atoms or a substituted or unsubstituted aromatic heterocyclic group having a ring structure formed of 6 to 13 atoms; more preferably, $A_1$, $A_2$ and $A_3$ each independently represent a substituted or unsubstituted aromatic hydrocarbon group having a ring structure formed of 6 to 10 carbon atoms; still more preferably represent a substituted or unsubstituted naphthalene ring or benzene ring; most preferably represent a substituted or unsubstituted benzene ring.

Preferred suitable optional substituents of $A_1$, $A_2$ and $A_3$ are in each occurrence independently CN, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms, provided that, in the case of two adjacent substituents, said adjacent substituents may be bonded each other to form a ring structure;

more preferred suitable optional substituents of $A_1$, $A_2$ and $A_3$ are in each occurrence independently CN, a substituted or unsubstituted aromatic hydrocarbon group having ring structure formed of 6 to 30 carbon atoms or a substituted or unsubstituted heterocyclic group having a ring structure formed of 5 to 30 atoms, provided that, in the case of two adjacent substituents, said adjacent substituents may be bonded each other to form a ring structure;

most preferred suitable optional substituents of $A_1$, $A_2$ and $A_3$ are in each occurrence independently CN or a substituted or unsubstituted aromatic hydrocarbon group having ring structure formed of 6 to 18 carbon atoms, provided that, in the case of two adjacent substituents, said adjacent substituents may be bonded each other to form a ring structure.

The total number of the optional substituents of $A_1$, $A_2$ and $A_3$, is preferably 1, 2, 3, 4 or 5, more preferably 1, 2 or 3, most preferably 1 or 2.

Most preferably, $A_1$, $A_2$ and $A_3$ are unsubstituted or substituted by two adjacent substituents which are bonded each other to form a ring structure.

Preferably one, two or all of $A_1$, $A_2$ and $A_3$ are unsubstituted and the others of $A_1$, $A_2$ and $A_3$—in the case that one or two of $A_1$, $A_2$ and $A_3$ are unsubstituted—are substituted by two adjacent substituents which are bonded each other to form a ring structure. Most preferably, two of $A_1$, $A_2$ and $A_3$ are unsubstituted and one of $A_1$, $A_2$ and $A_3$ is substituted by two adjacent substituents which are bonded each other to form a ring structure, or all of $A_1$, $A_2$ and $A_3$ are unsubstituted. Further most preferably, all of $A_1$, $A_2$ and $A_3$ are unsubstituted.

Examples for suitable ring structures formed by two adjacent substituents are selected from the group consisting of:

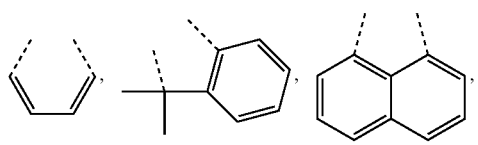

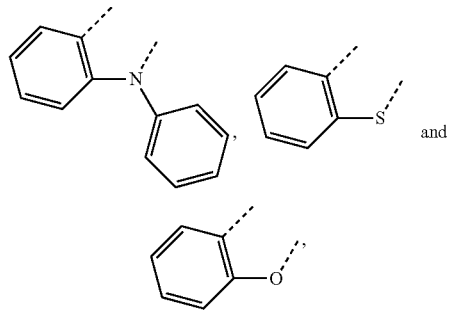

wherein the dotted lines are bonding sites. One preferred ring structure is

Preferred groups $A_1$, $A_2$ and $A_3$ are therefore:

$A_1$:

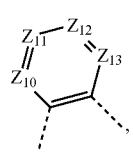

preferably

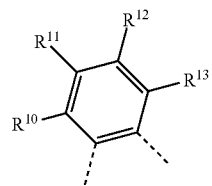

$A_2$:

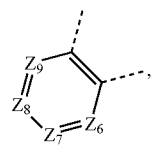

preferably

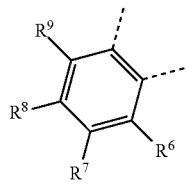

$A_3$:

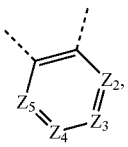

preferably

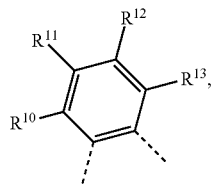

wherein
$Z_2$ is N or $CR^2$; $Z_3$ is N or $CR^3$; $Z_4$ is N or $CR^4$; $Z_5$ is N or $CR^5$, $Z_6$ is N or $CR^6$; $Z_7$ is N or $CR^7$; $Z_8$ is N or $CR^8$; $Z_9$ is N or $CR^9$; $Z_{10}$ is N or $CR^{10}$; $Z_{11}$ is N or $CR^{11}$; $Z_{12}$ is N or $CR^{12}$; $Z_{13}$ is N or $CR^{13}$; preferably, 0, 1 or 2, more preferably 0 or 1 of $Z_2$, $Z_3$, $Z_4$ or $Z_5$ are N and the others of $Z_2$, $Z_3$, $Z_4$ or $Z_5$ are $CR^2$, $CR^3$, $CR^4$ or $CR^5$ respectively, 0, 1 or 2, more preferably 0 or 1 of $Z_6$, $Z_7$, $Z_8$ or $Z_9$ are N and the others of $Z_6$, $Z_7$, $Z_8$ or $Z_9$ are $CR^6$, $CR^7$, $CR^8$ or $CR^9$ respectively, and 0, 1 or 2, more preferably 0 or 1 of $Z_{10}$, $Z_{11}$, $Z_{12}$ or $Z_{13}$ are N and the others of $Z_{10}$, $Z_{11}$, $Z_{12}$ or $Z_{13}$ are $CR^{10}$, $CR^{11}$, $CR^{12}$ or $CR^{13}$ respectively;

$R^2$, $R^3$, $R^4$, $R^5$ $R^6$, $R^7$, $R^8$, $R^9$, $R^{10}$, $R^{11}$, $R^{12}$ and $R^{13}$ each independently represent hydrogen, CN, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring; provided that, two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ may be bonded to each other to form a ring structure;

preferably, $R^2$, $R^3$, $R^4$, $R^5$ $R^6$, $R^7$, $R^8$, $R^9$, $R^{10}$, $R^{11}$, $R^{12}$ and $R^{13}$ each independently represent hydrogen, CN, a substituted or unsubstituted aromatic hydrocarbon group having ring structure formed of 6 to 30 carbon atoms or a substituted or unsubstituted heterocyclic group having a ring structure formed of 5 to 30 atoms, provided that, two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ may be bonded to each other to form a ring structure;

most preferably, $R^2$, $R^3$, $R^4$, $R^5$ $R^6$, $R^7$, $R^8$, $R^9$, $R^{10}$, $R^{11}$, $R^{12}$ and $R^{13}$ each independently represent hydrogen, CN or a substituted or unsubstituted aromatic hydrocarbon group having ring structure formed of 6 to 18 carbon atoms, provided that, two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ may be bonded to each other to form a ring structure;

further most preferably, $R^2$, $R^3$, $R^4$, $R^5$ $R^6$, $R^7$, $R^8$, $R^9$, $R^{10}$, $R^{11}$, $R^{12}$ and $R^{13}$ each independently represent hydrogen, provided that, two or more substituents, preferably two substituents, selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ may be bonded to each other to form a ring structure.

Examples for suitable ring structures formed by two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ are mentioned above.

Preferred compounds of formula (I) are therefore compounds of formula (Ia)

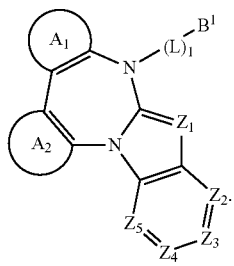

(Ia)

More preferred compounds of formula (I) are compounds of formula (Ia1) and (Ia2)

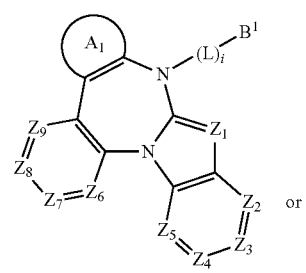

(Ia1)

or

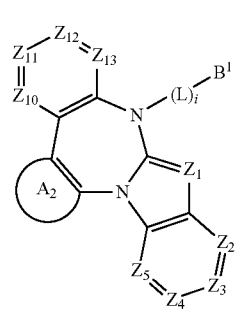

(Ia2)

Most preferred compounds of formula (I) are compounds of formula (Iaa)

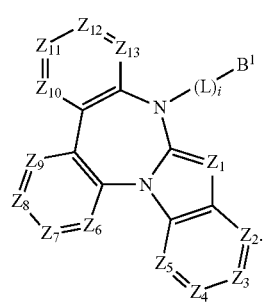

(Iaa)

Further most preferred compounds of formula (I) are compounds of formula (Iaaa)

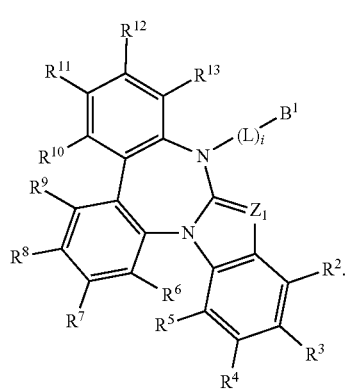

(Iaaa)

The residues and groups and indices $R^2$, $R^3$, $R^4$, $R^5$ $R^6$, $R^7$, $R^8$, $R^9$, $R^{10}$, $R^{11}$, $R^{12}$ and $R^{13}$, L, l, $B^1$ and $Z_1$ in formulae (Ia), (Ia1), (Ia2), (Iaa) and (Iaaa) are defined above and below.
Even further most preferred compounds of formula (I) are the following compounds:
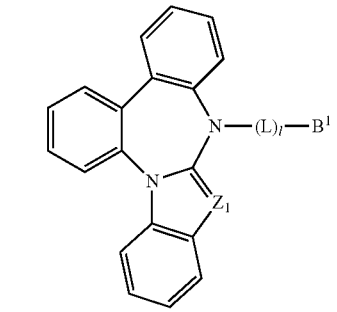
(Iaaa-1)
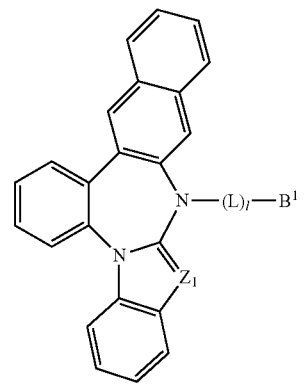
(Iaaa-2)
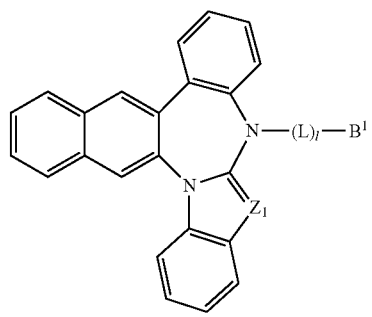
(Iaaa-3)
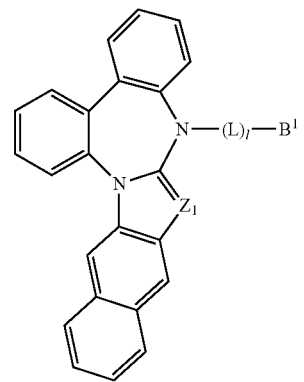
(Iaaa-4)
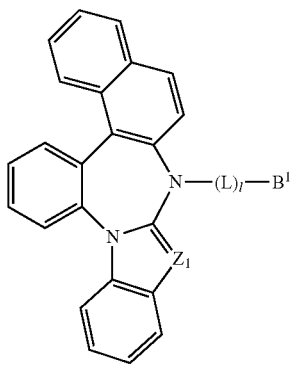
(Iaaa-5)
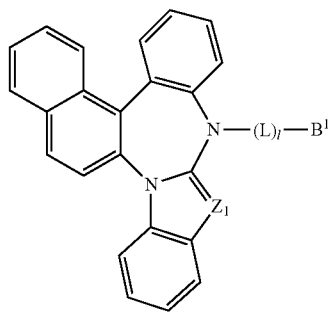
(Iaaa-6)
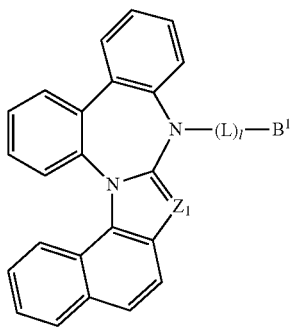
(Iaaa-7)
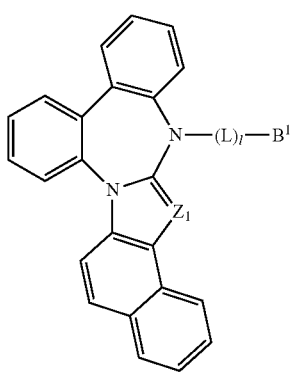
(Iaaa-8)

-continued
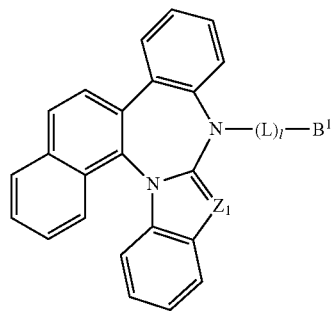
(Iaaa-9)
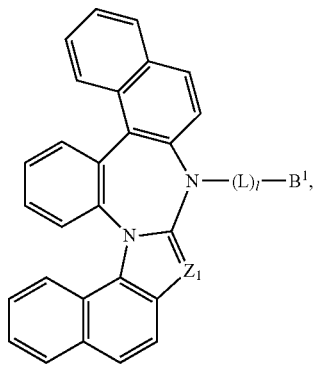
(Iaaa-13)
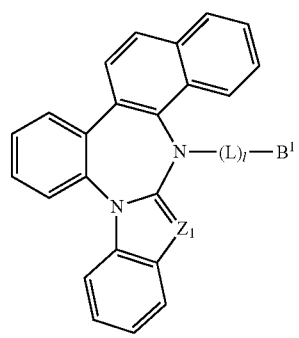
(Iaaa-10)
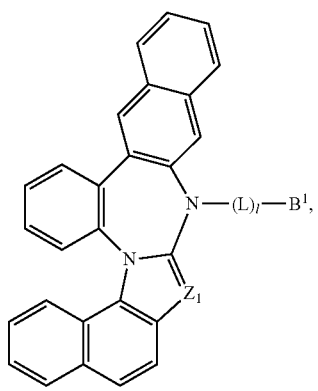
(Iaaa-14)
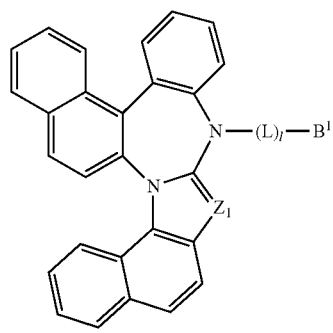
(Iaaa-11)
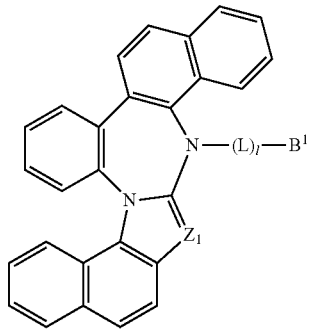
(Iaaa-15)
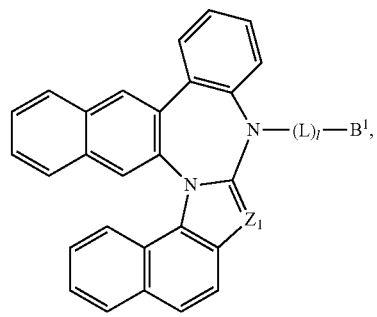
(Iaaa-12)
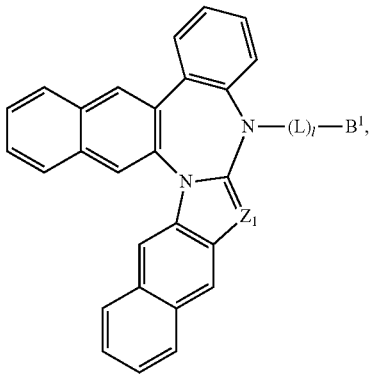
(Iaaa-16)

-continued
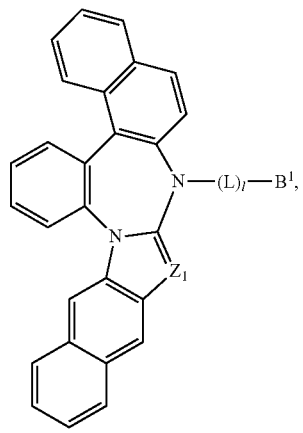
(Iaaa-17)
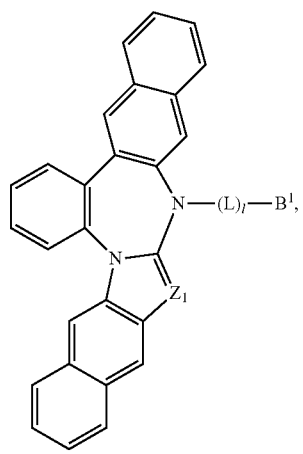
(Iaaa-18)
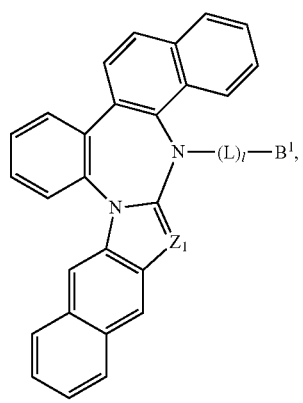
(Iaaa-19)
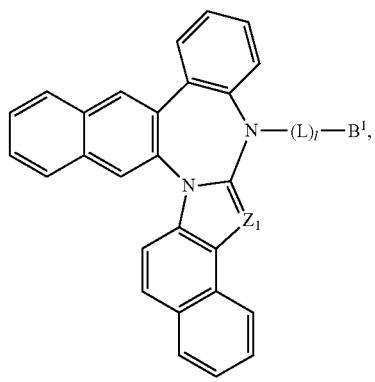
(Iaaa-20)
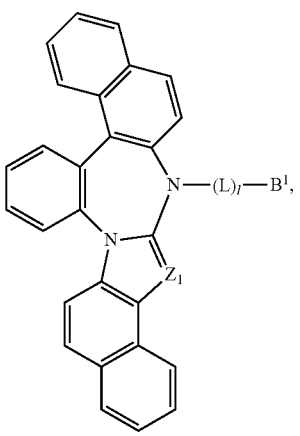
(Iaaa-21)
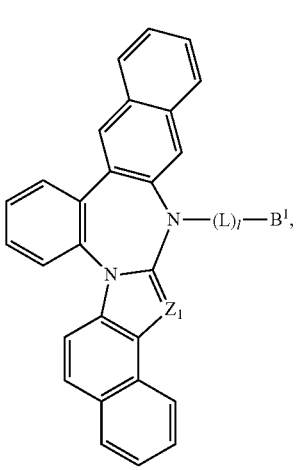
(Iaaa-22)
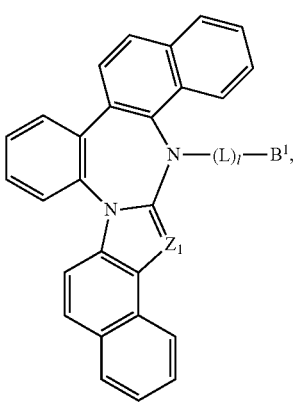
(Iaaa-23)

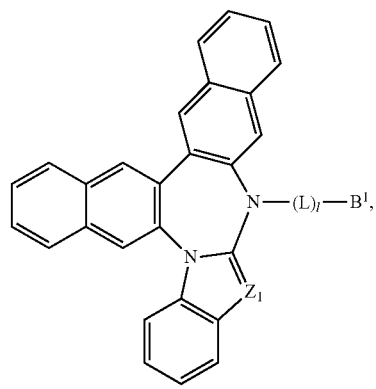
(Iaaa-24)
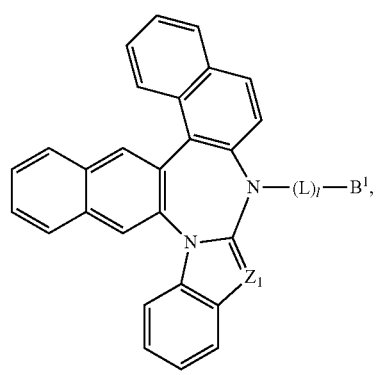
(Iaaa-25)
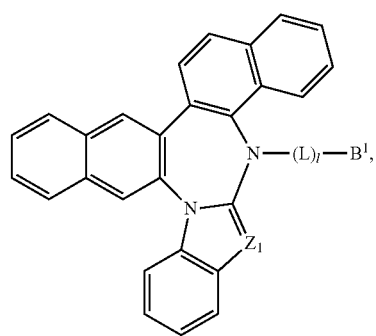
(Iaaa-26)
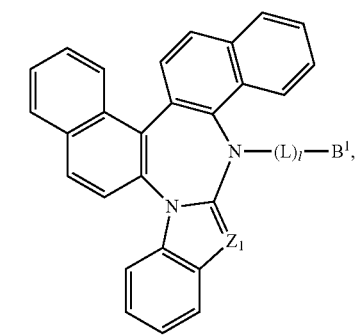
(Iaaa-27)
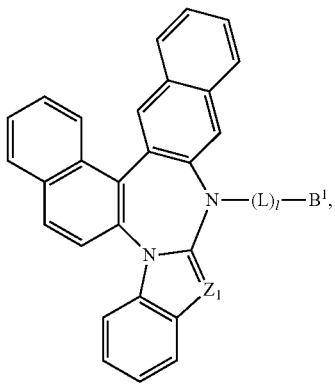
(Iaaa-28)
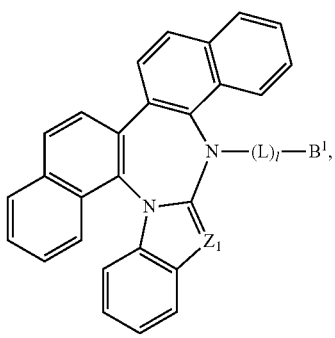
(Iaaa-29)
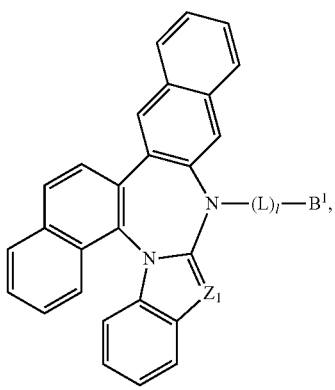
(Iaaa-30)

(Iaaa-31)
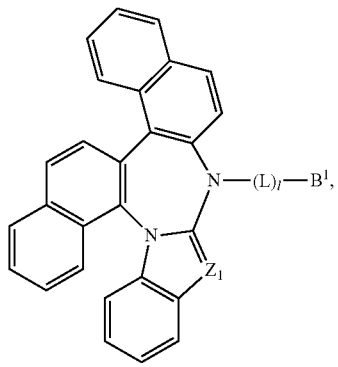
(Iaaa-32)
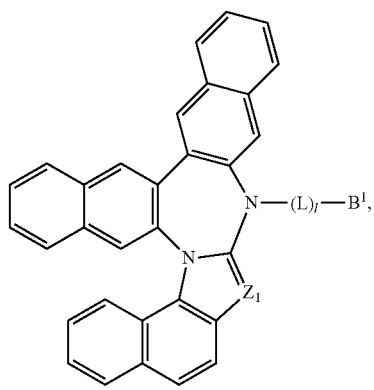
(Iaaa-33)
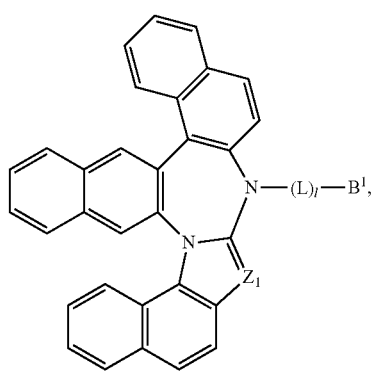
(Iaaa-34)
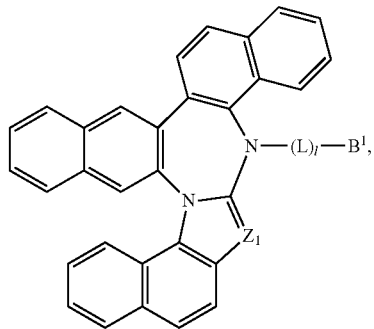
(Iaaa-35)
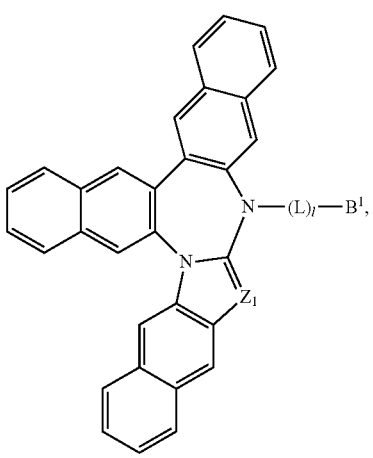
(Iaaa-36)
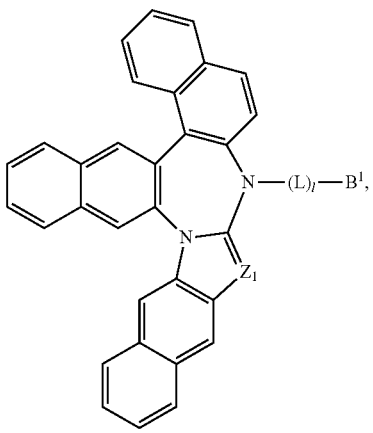
(Iaaa-37)
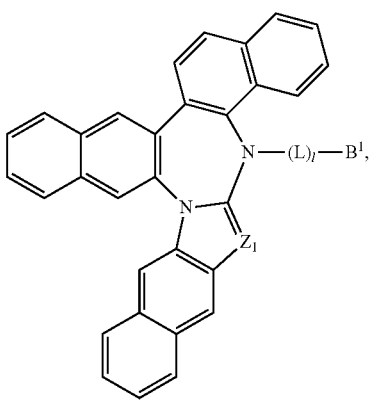

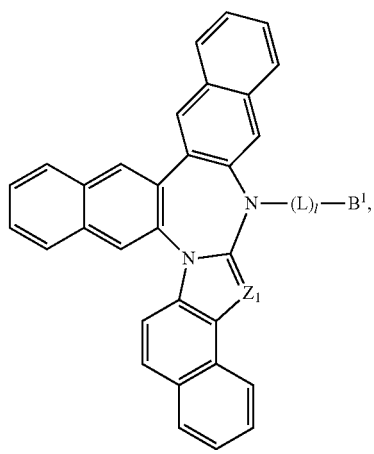
(Iaaa-38)
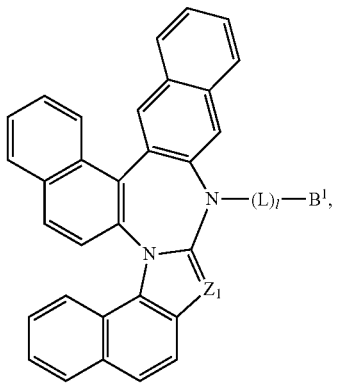
(Iaaa-41)
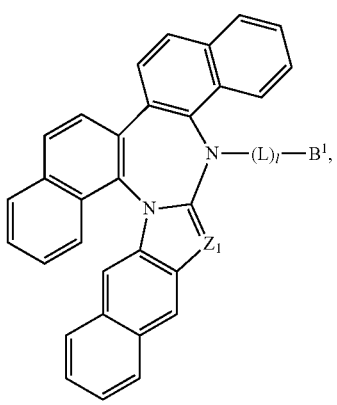
(Iaaa-42)
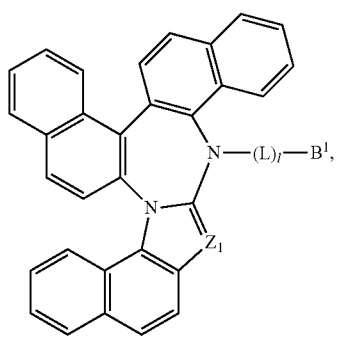
(Iaaa-39)
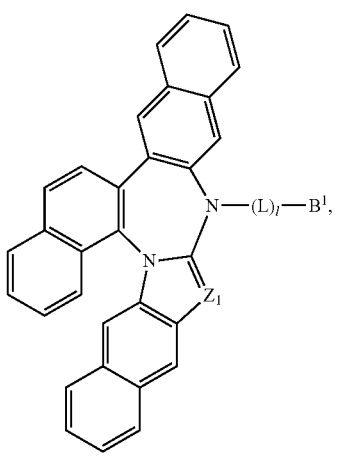
(Iaaa-43)
(Iaaa-40)

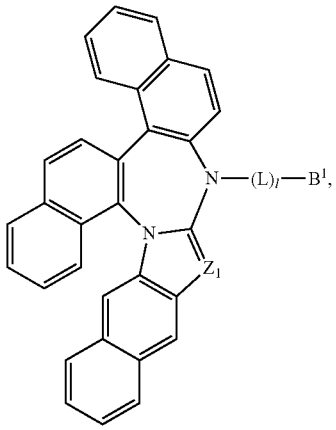

(Iaaa-44)

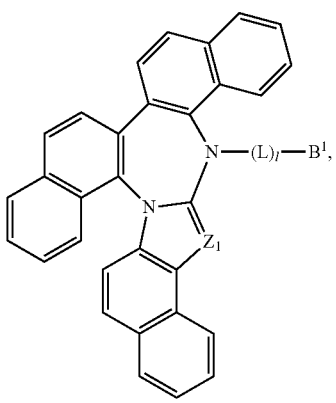

(Iaaa-45)

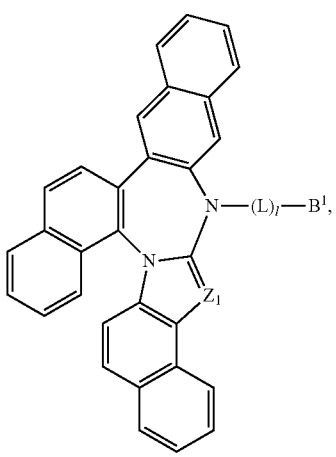

(Iaaa-46)

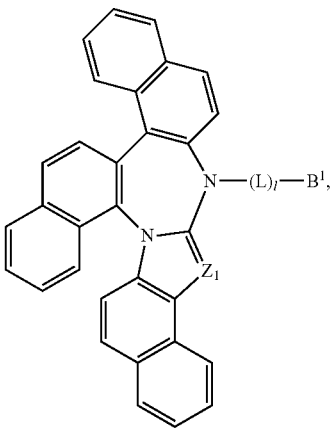

(Iaaa-47)

wherein the groups and indices L, l, $B^1$ and $Z_1$ are defined above and below.

The Group $Z_1$ $Z_1$ is N or $CR^1$, preferably N, $R^1$ is hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms;

preferably, $R^1$ is hydrogen, a substituted or unsubstituted alkyl group having 1 to 30 carbon atoms; a substituted or unsubstituted aromatic hydrocarbon group having 6 to 30 ring carbon atoms; or a substituted or unsubstituted heterocyclic group having 5 to 30 ring atoms; more preferably, $R^1$ is hydrogen, a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; or a substituted or unsubstituted heterocyclic group having 5 to 18 ring atoms, preferably triazine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; a cyano group;

more preferably, $R^1$ is hydrogen, a substituted or unsubstituted alkyl group having 1 to 30 carbon atoms; a substituted or unsubstituted aromatic hydrocarbon group having 6 to 30 ring carbon atoms; or a substituted or unsubstituted heterocyclic group having 5 to 30 ring atoms; most preferably, $R^1$ is hydrogen.

$Z_1$ is therefore most preferably N or CH, further most preferably N.

The Group $-(L)_l-B^1$

L is a single bond, a substituted or unsubstituted alkylene group having 1 to 30 carbon atoms, a substituted or unsubstituted cycloalkylene group having 3 to 30 carbon atoms, a substituted silylene group having 2 to 30 carbon atoms, a substituted or unsubstituted aromatic hydrocarbon group having 6 to 30 ring carbon atoms, or a substituted or unsubstituted heterocyclic group having 5 to 30 ring atoms;

preferably, L is a single bond, a substituted or unsubstituted aromatic hydrocarbon group having 6 to 30 ring carbon atoms, preferably selected from above mentioned divalent aryl groups, more preferably phenylene group, biphenylene group, terphenylene group, naphthylene group, anthrylene group, phenenthrylene group, triphenylenylene group, pyrenylene group, benzophenanthrylene group, fluorenylene group, spirobifluorenylene group, most preferably phenylene group, biphenylene group or terphenylene group; or a substituted or unsubstituted heterocyclic group having 5 to 30 ring atoms, preferably selected from above mentioned divalent heterocyclic groups, more preferably pyridylene group, pyrimidylene group, triazinylene group, dibenzofuranylene group, dibenzothiphenylene group, or carbazolylene group. More preferably, L is a single bond, a substituted or unsubstituted phenylene group, a substituted or unsubstituted biphenylene-group, a substituted or unsubstituted naphthylene group, or combinations thereof.

l is 0, 1, 2 or 3; in the case that l is 2 or 3, L is the same or different in each occurrence, preferably l is 1 or 2, in the case that l is 2, L is the same or different in each occurrence.

$B^1$ is H, CN, a substituted or unsubstituted aromatic hydrocarbon group having 6 to 30 ring carbon atoms; a substituted or unsubstituted heterocyclic group having 5 to 30 ring atoms; or a substituted or unsubstituted cycloalkyl group having 3 to 30 ring carbon atoms; preferably, $B^1$ is H, CN or a substituted or unsubstituted aromatic hydrocarbon group having 6 to 30 ring carbon atoms; or a substituted or unsubstituted heterocyclic group having 5 to 30 ring atoms.

In one embodiment, L represents substituted or unsubstituted aryl group having 6 to 30 carbon atoms and $B^1$ represents CN.

In one preferred embodiment, $B^1$ is represented by formula (IX)

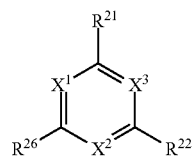

(IX)

wherein $X^1$, $X^2$ and $X^3$ each independently represent $CR^{23}$ or N, preferably at least one of $X^1$, $X^2$ and $X^3$ is N;

$R^{21}$, $R^{22}$, $R^{23}$ and $R^{26}$ each independently represent hydrogen, a halogen atom, a substituted or unsubstituted alkyl group having 1 to 30 carbon atoms, a substituted or unsubstituted alkenyl group having 2 to 31 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{21}$, $R^{22}$, $R^{23}$ and $R^{26}$ each independently represent hydrogen, a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{21}$, $R^{22}$, $R^{23}$ and $R^{26}$ each independently represent hydrogen, a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, pyrimidine ring, pyridine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group;

provided that, among $R^{21}$, $R^{22}$, $R^{26}$ and $R^{23}$, if $X^1$, $X^2$ and/or $X^3$ are $CR^{23}$, any two of $R^{21}$, $R^{22}$, $R^{23}$ and $R^{26}$ may be bonded each other to form a ring structure;

wherein one of $R^{21}$, $R^{22}$, $R^{26}$ and, if $X^1$, $X^2$ and/or $X^3$ are $CR^{23}$, $R^{23}$, represents a bonding site to -(L)$_l$-.

Preferred groups of formula (IX) are selected from formulae (IXa), (IXb), (IXc), (IXd), (IXe), and (IXf).

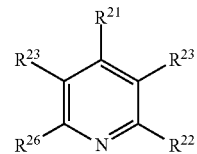

(IXa)

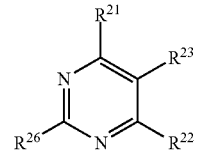

(IXb)

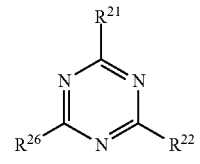

(IXc)

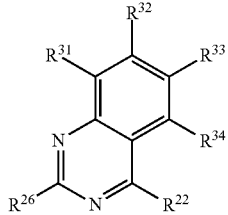

(IXd)

-continued

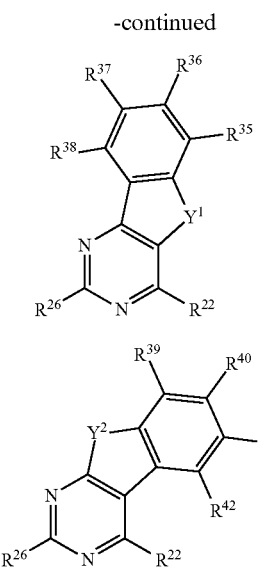

(IXe)

(IXf)

wherein $Y^1$ and $Y^2$ each independently represent O, S, $NR^{43}$ or $CR^{44}R^{45}$, $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ each independently represent hydrogen, a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, pyrimidine ring, pyridine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group;

provided that, among from $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$, any two of from $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ may be bonded each other to form a ring structure;

wherein one of $R^{21}$, $R^{22}$, $R^{23}$, $R^{26}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ represents a bonding site to -(L)$_l$-.

In another preferred embodiment, $B^1$ is represented by formula (Xa)

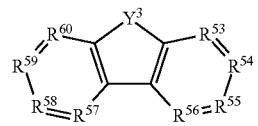

(Xa)

wherein
$Y^3$ represents O, S, $NR^{48}$ or $C(R^{49})_2$
$R^{53}$, $R^{54}$, $R^{55}$, $R^{56}$, $R^{57}$, $R^{58}$, $R^{59}$, $R^{60}$ are each independently $CR^{46}$ or N, wherein 0, 1, 2 or 3 of $R^{53}$, $R^{54}$, $R^{55}$, $R^{56}$, $R^{57}$, $R^{58}$, $R^{59}$, $R^{60}$ are N, preferably 0, 1 or 2 of $R^{53}$, $R^{54}$, $R^{55}$, $R^{56}$, $R^{57}$, $R^{58}$, $R^{59}$,
$R^{60}$ are N, and the others of $R^{53}$, $R^{54}$, $R^{55}$, $R^{56}$, $R^{57}$, $R^{58}$, $R^{59}$, $R^{60}$ are $CR^{46}$; $R^{46}$ is in each occurrence independently hydrogen, a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{46}$ independently in each occurrence represents hydrogen, a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{46}$ independently in each occurrence represents hydrogen, a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, pyrimidine ring, pyridine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group; most preferably, $R^{46}$ represents in each occurrence hydrogen;

$R^{48}$ and $R^{49}$ each independently represent a halogen atom, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkoxy group having 1 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted aryloxy group having 6 to 30 ring carbon atoms, a substituted or unsubstituted alkylthio group having 1 to 30 carbon atoms, a substituted or unsubstituted arylthio group having 6 to 30 ring carbon atoms, a substituted silyl group having 3 to 60 carbon atoms, or a cyano group, preferably, $R^{48}$ and $R^{49}$ each independently represent a substituted or unsubstituted alkyl group having 1 to 30 carbon atoms, a substituted or unsubstituted aromatic hydrocarbon group having 6 to 30 ring carbon atoms, a substituted or unsubstituted heterocyclic group having 5 to 30 ring atoms, or a cyano group, more preferably, $R^{48}$ and $R^{49}$ each independently represent a substituted or unsubstituted alkyl group having 1 to 8 carbon atoms, preferably methyl group, ethyl group, n-propyl group, isopropyl group, n-butyl group, s-butyl group, isobutyl group, t-butyl group; a substituted or unsubstituted aromatic hydrocarbon group having 6 to 18 ring carbon atoms, preferably phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group; a substituted or unsubstituted heterocyclic group having 5 to 18 ring atoms, preferably triazine ring, pyrimidine ring, pyridine ring, dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group; or a cyano group; when more than one residues $R^{46}$ are present, the $R^{46}$s may be the same or different and are allowed to be bonded to each other to form a ring structure, wherein one of $R^{46}$, $R^{48}$ or $R^{49}$ represents a bonding site to -(L)$_l$-, preferably one of $R^{46}$ or $R^{48}$ represents a bonding site to -(L)$_l$-.

In a further embodiment, $B^1$ represents H, CN or a substituted or unsubstituted aromatic hydrocarbon group having 6 to 30 ring carbon atoms, preferably, $B^1$ represents H, CN or a substituted or unsubstituted aromatic hydrocarbon group having 6 to 18 ring carbon atoms, preferably phenyl group, biphenyl group, terphenylenyl group, naphthyl group, phenanthryl group, triphenylenyl group, fluorenyl group, fluoranthenyl group or benzochrysenyl group, more preferably phenanthryl group, triphenylenyl group, fluoranthenyl group.

In a further embodiment, $B^1$ represents CN, and L represents a substituted or unsubstituted aromatic hydrocarbon group having 6 to 18 ring carbon atoms, preferably phenylene group, biphenylene group, terphenylenylene group, naphthylene group, phenanthrylene group, triphenylenylene group, fluorenylene group, fluoranthenylene group or benzochrysenylene group, more preferably phenanthrylene group, triphenylenylene group, fluoranthenylene group.

Compounds of Formula (I)

The compounds of formula (I) as well as preferred residues, groups and indices of the compounds of formula (I) have been described above.

Below, examples for compounds of formula (I) are given:

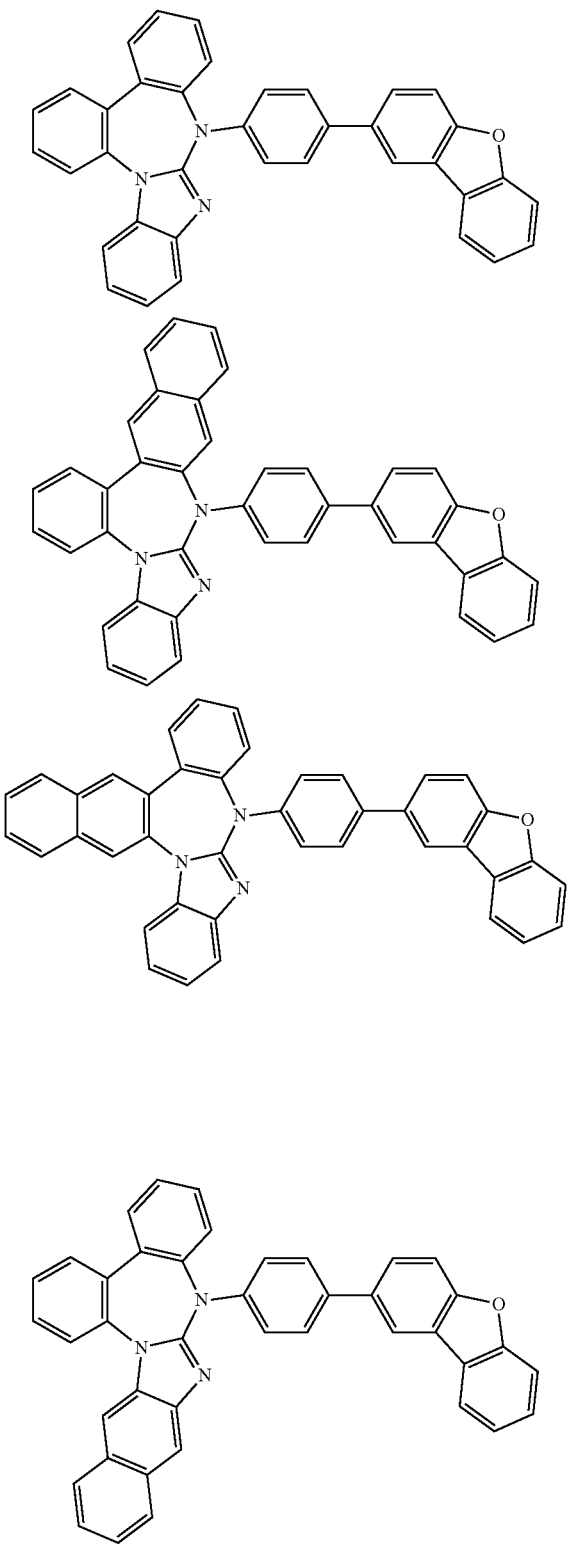

-continued
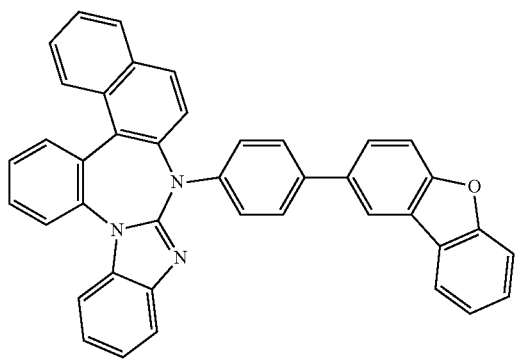
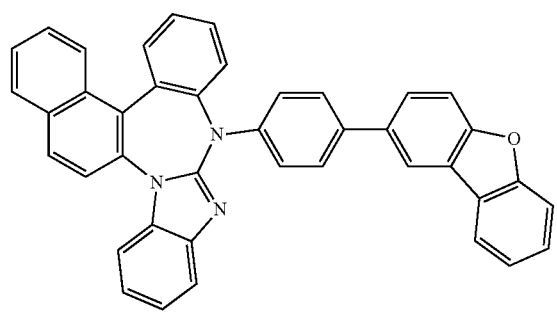
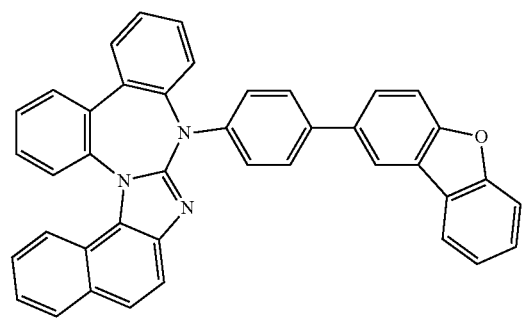
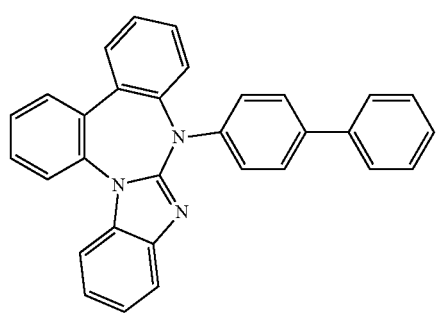
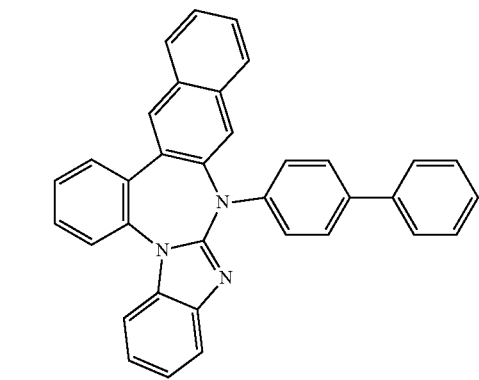
-continued
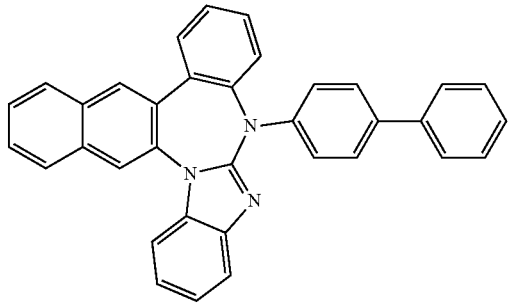
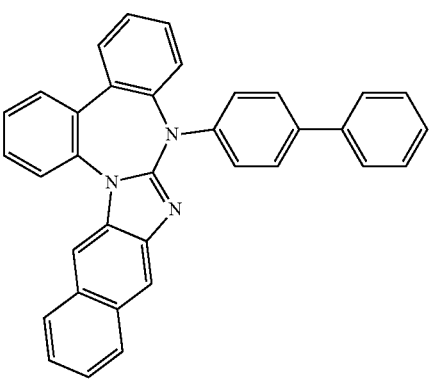
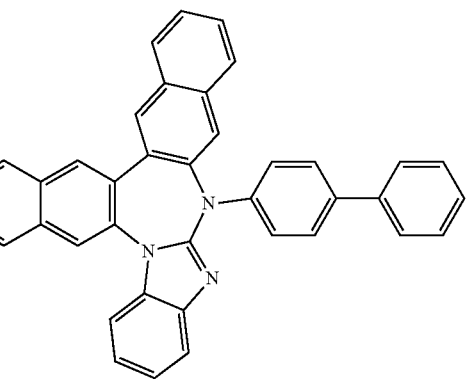
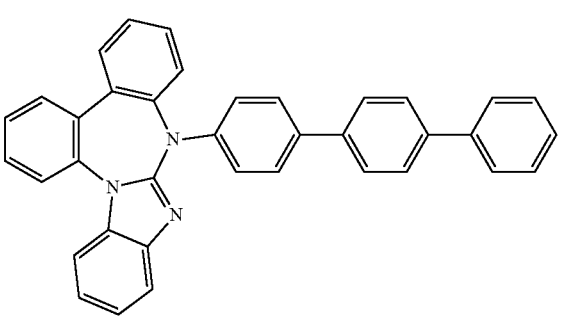

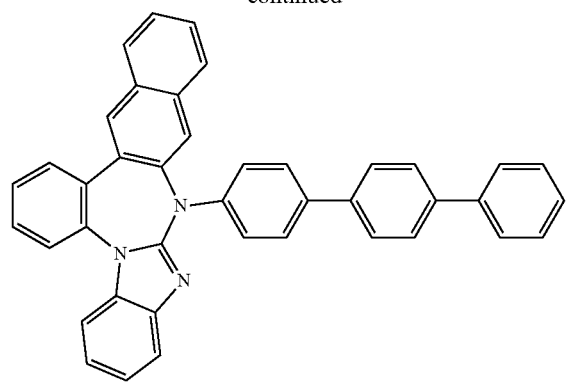
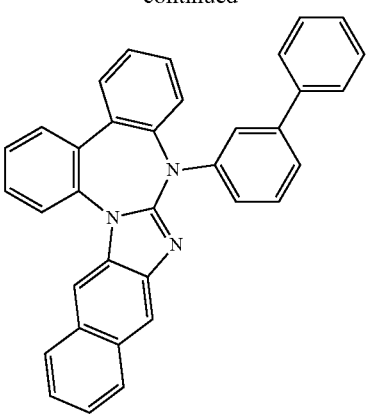
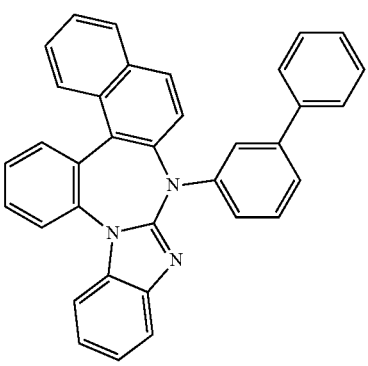
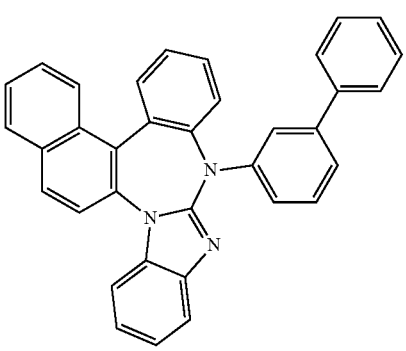
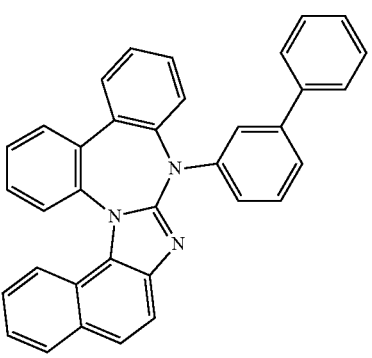

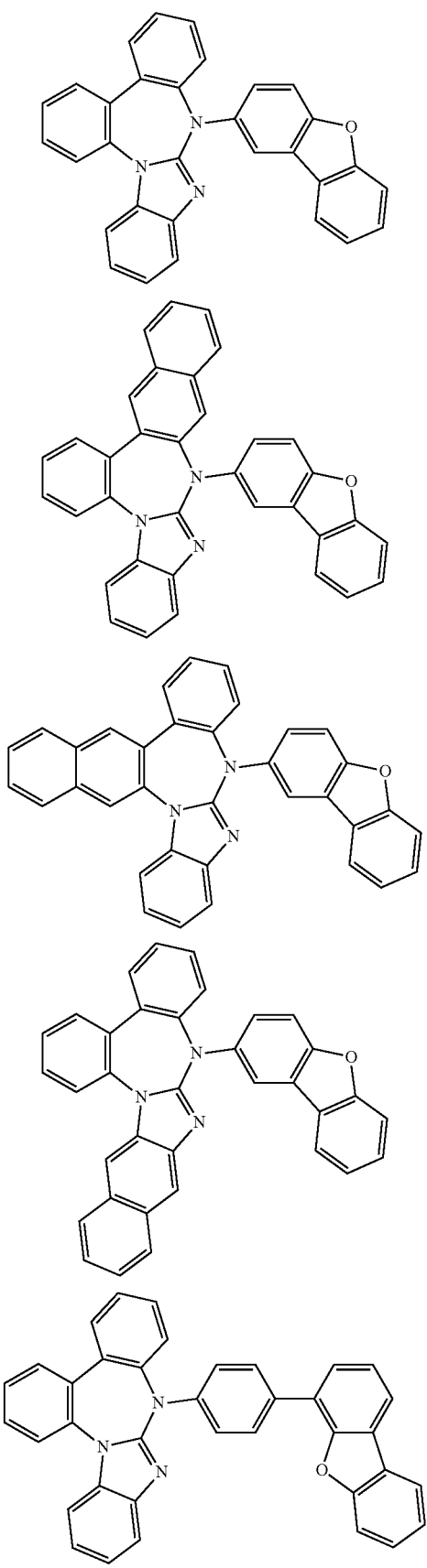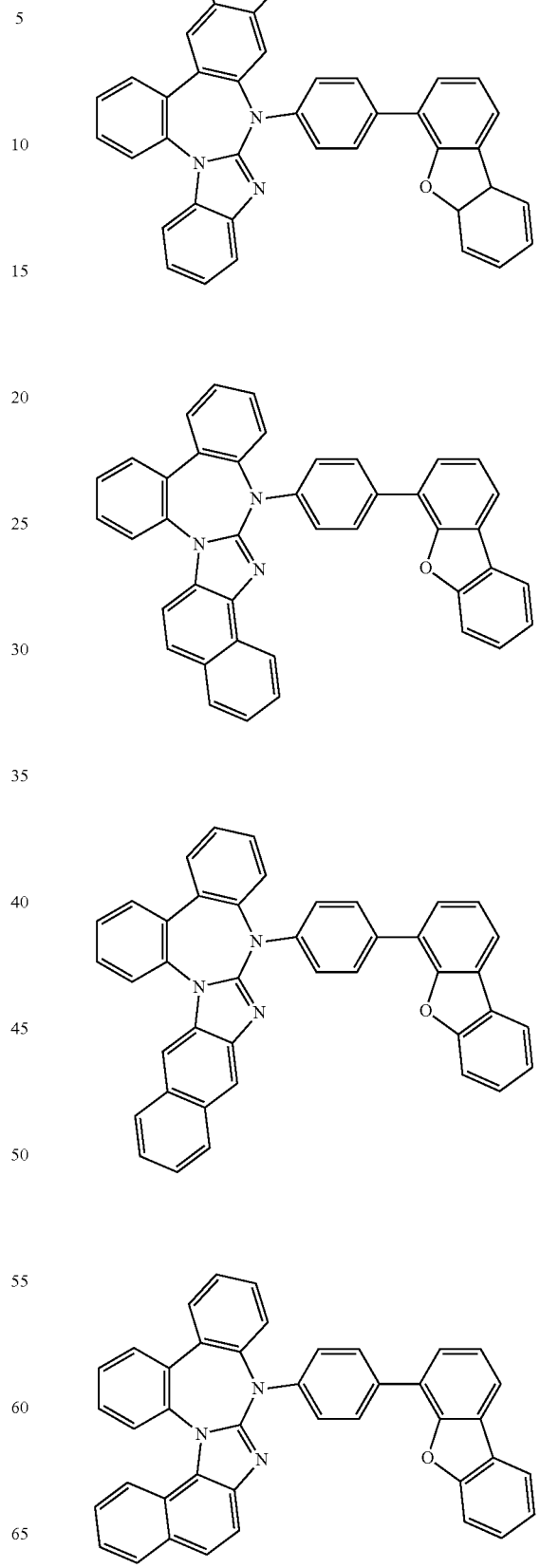

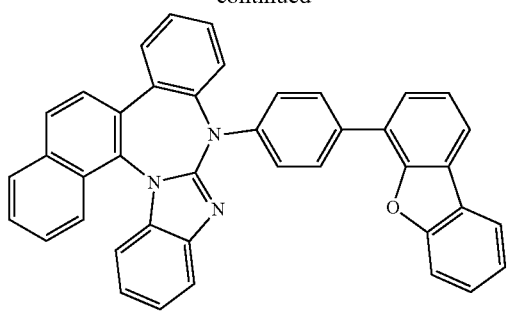
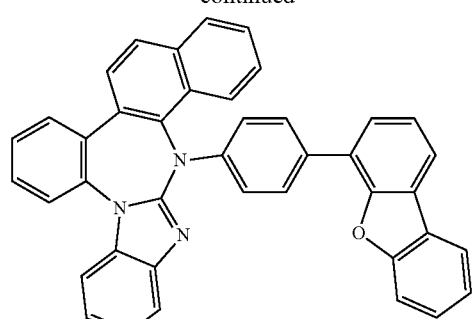
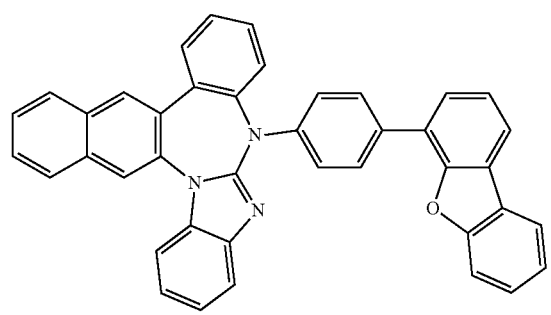
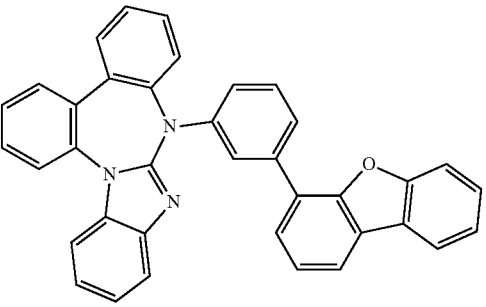
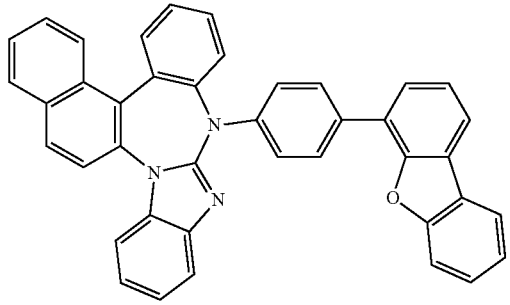
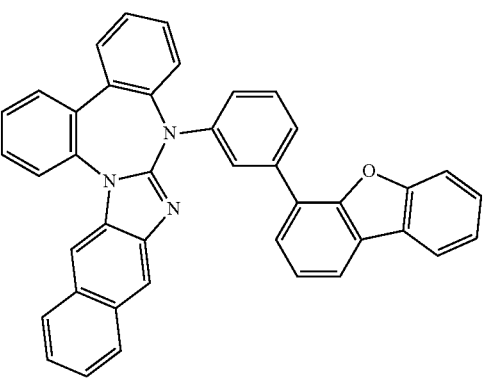
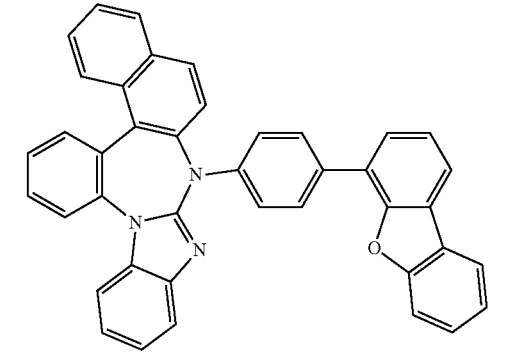 [SMILES: c1ccc2c(c1)-c1c(ccc3ccccc13)N(c1ccc(-c3cccc4c3oc3ccccc34)cc1)c1nc3ccccc3n1-2]
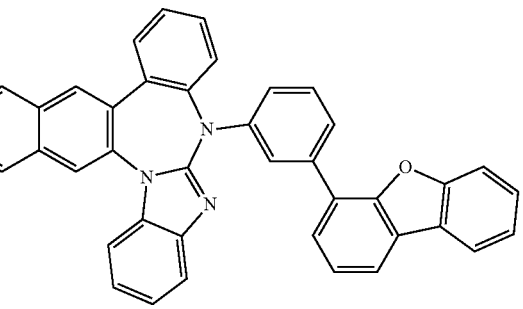
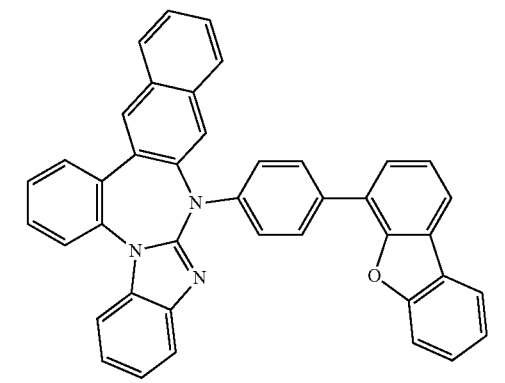
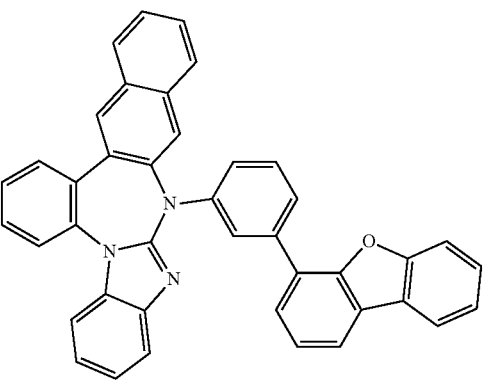

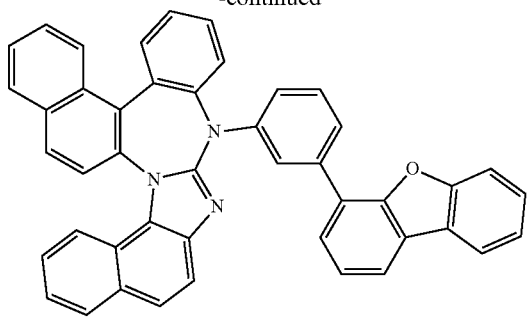
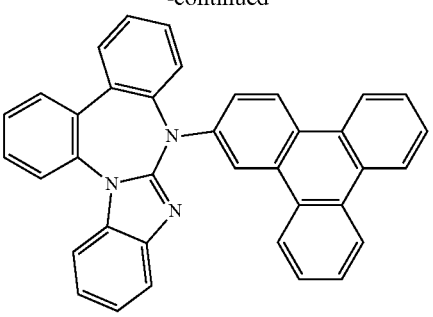
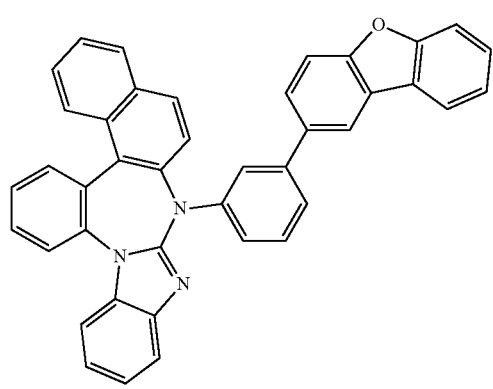
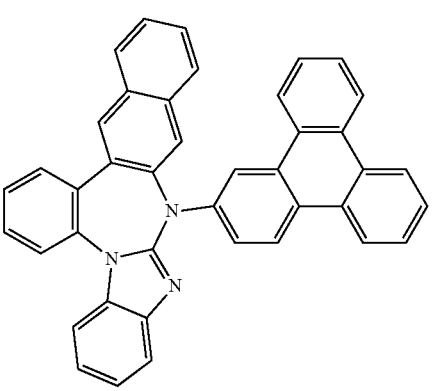
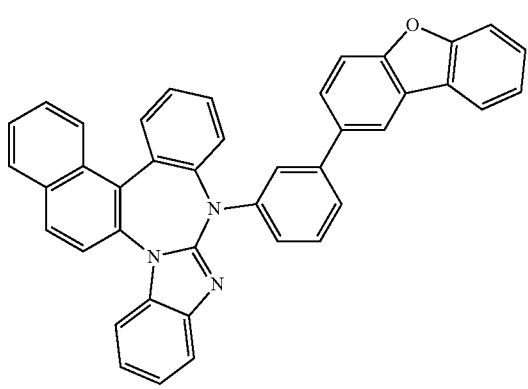
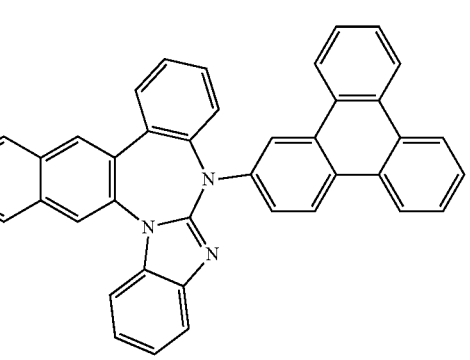
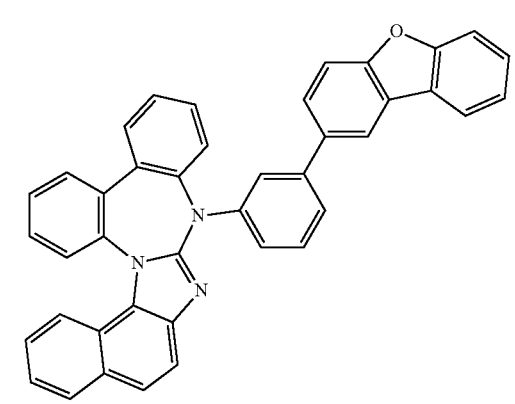
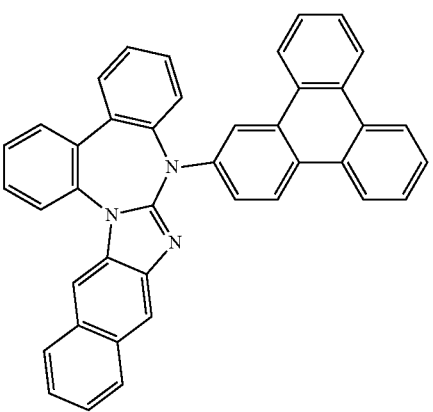

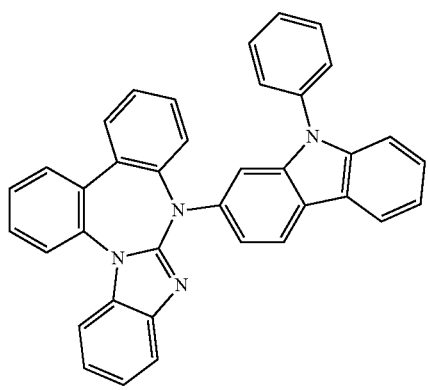
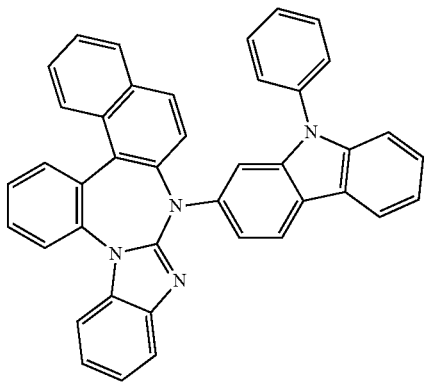
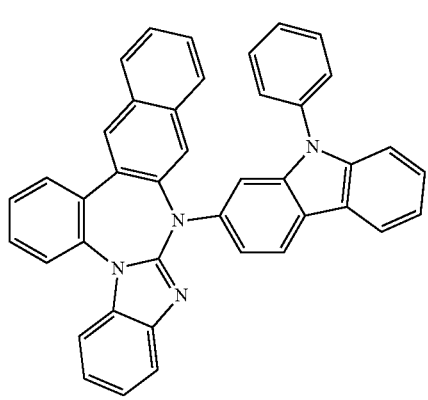
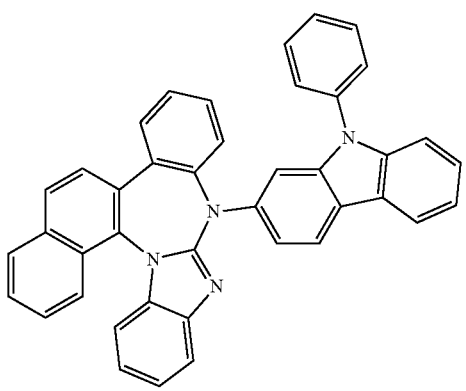
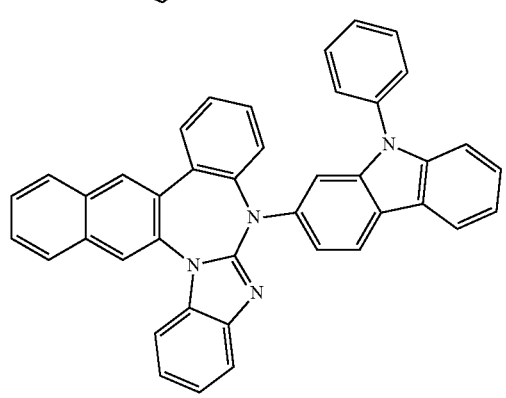
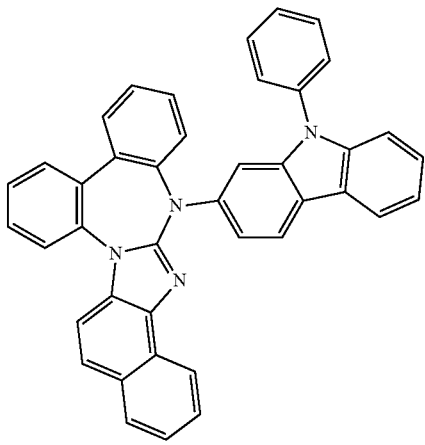
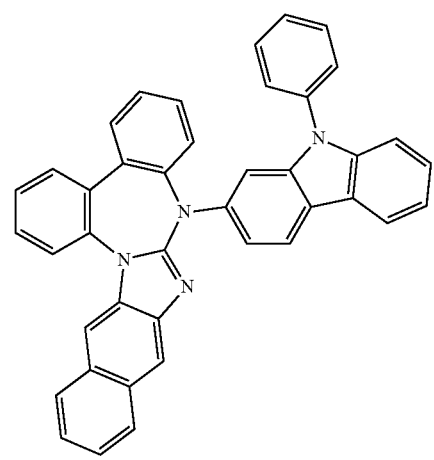
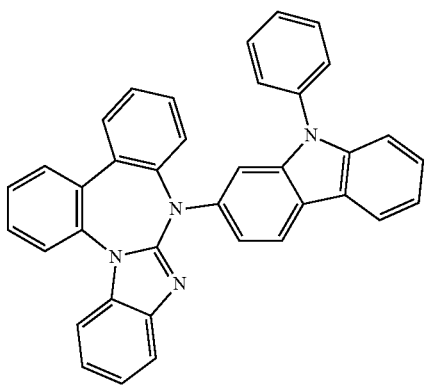

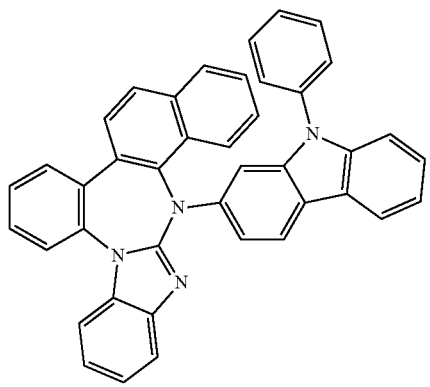
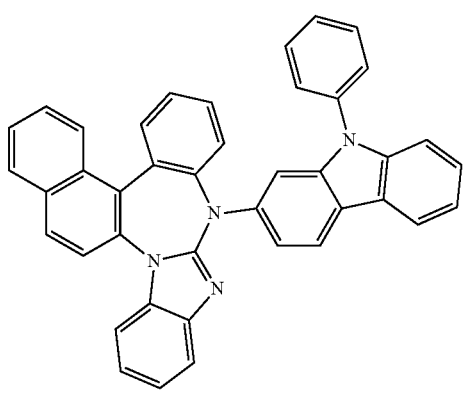
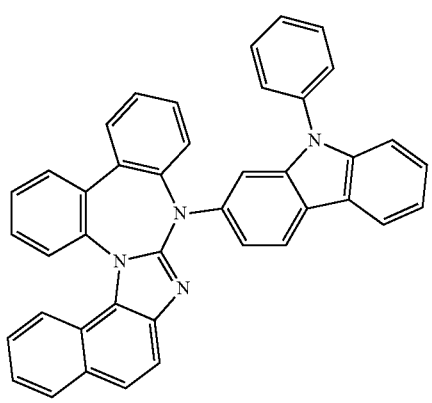
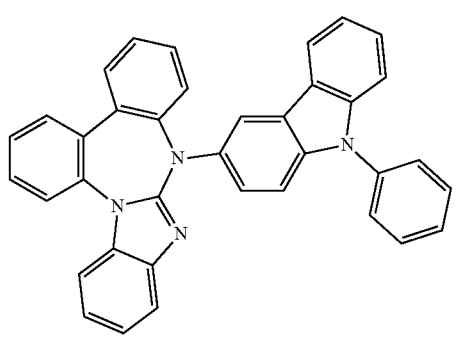
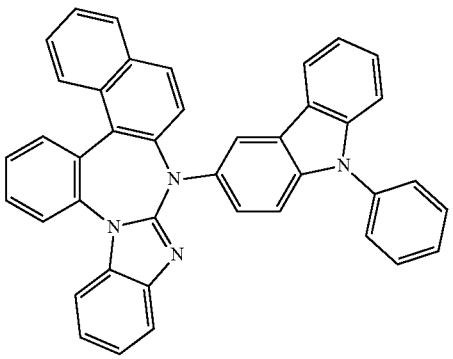
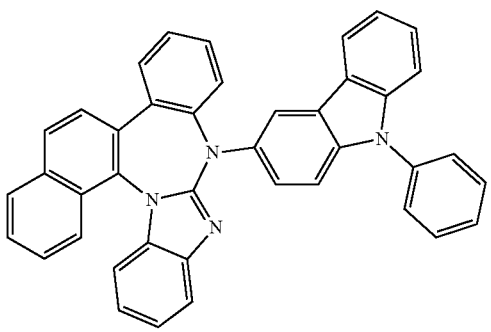
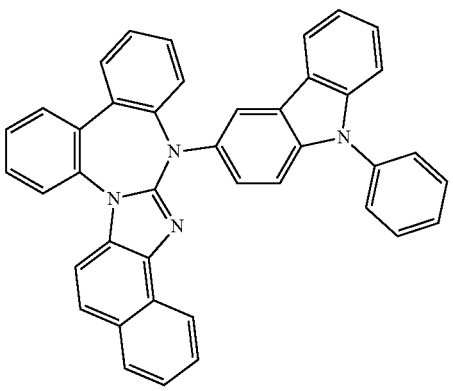
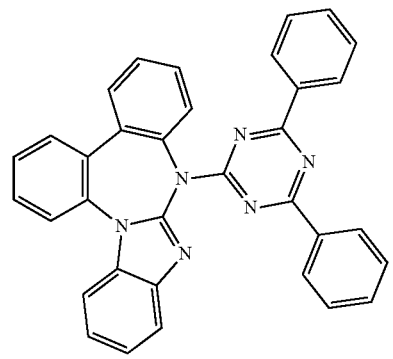

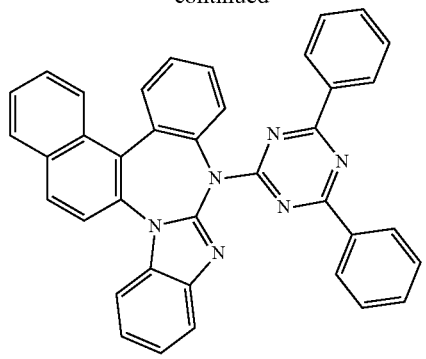
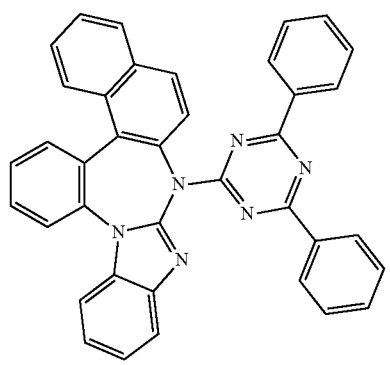
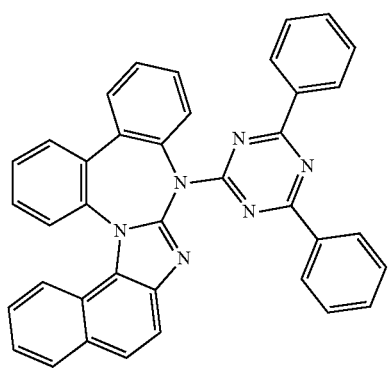
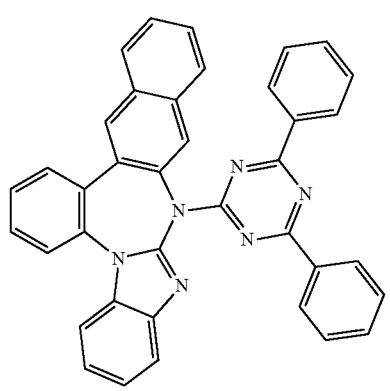
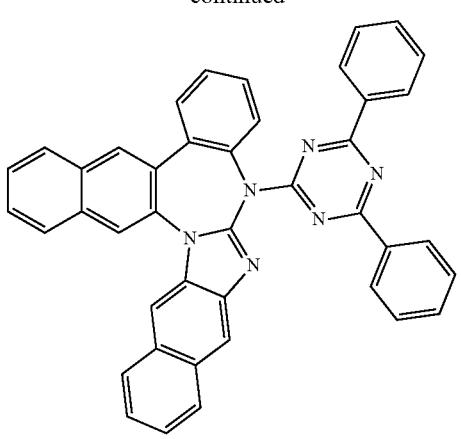
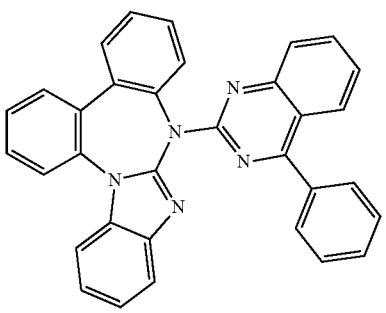
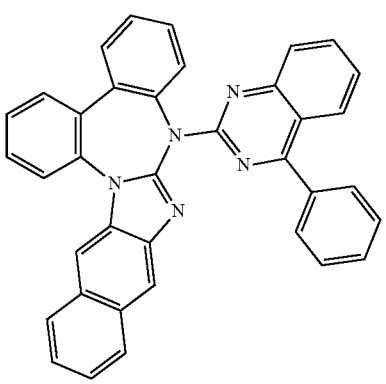
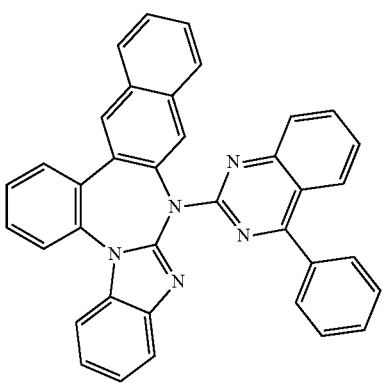

53
-continued
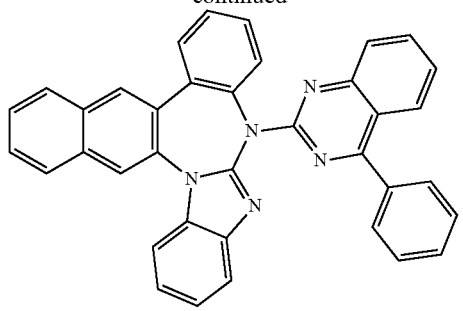
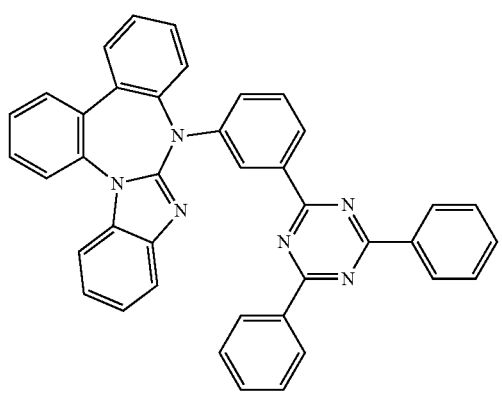
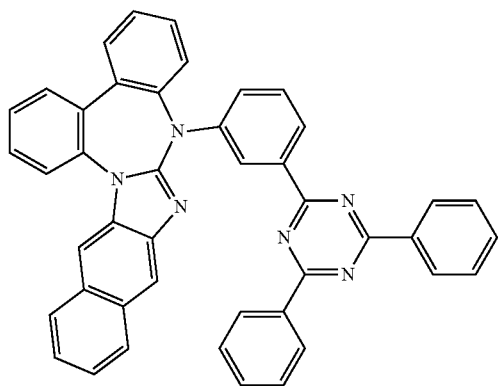
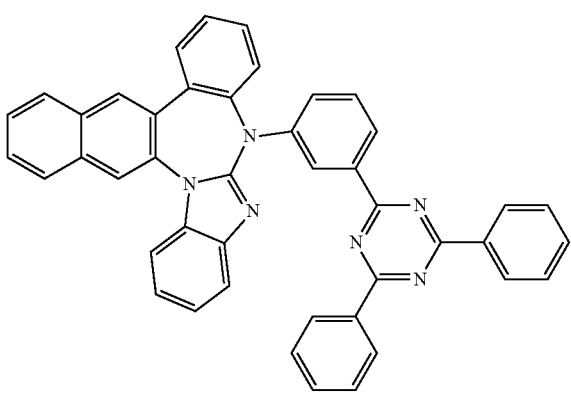
54
-continued
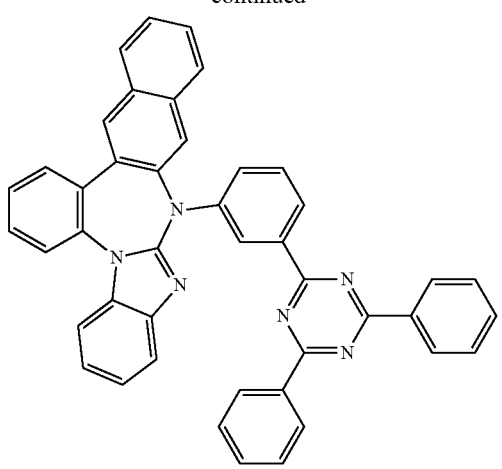
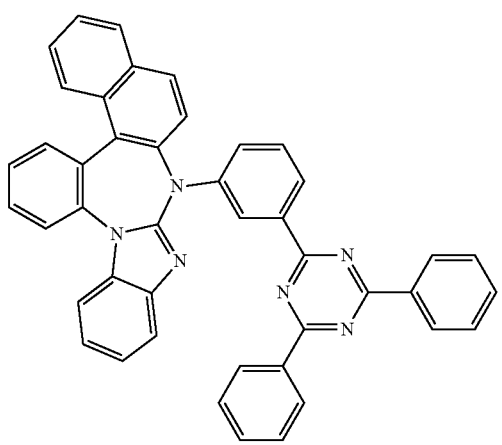
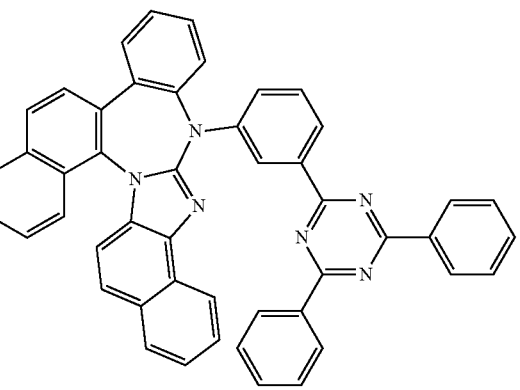
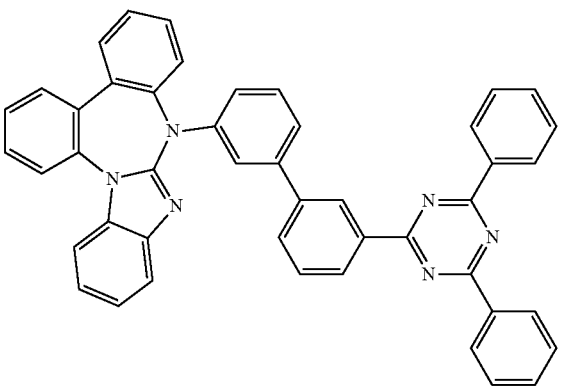

55
-continued
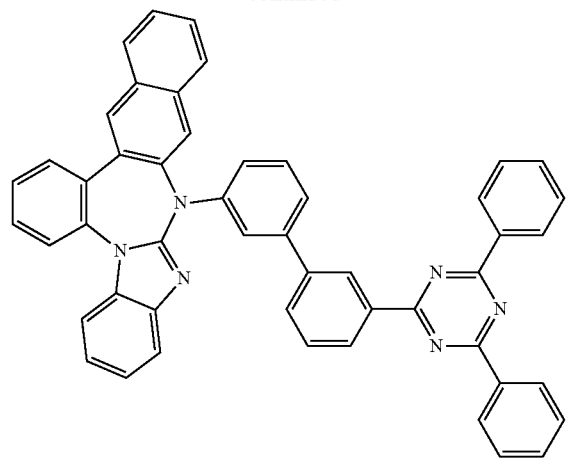
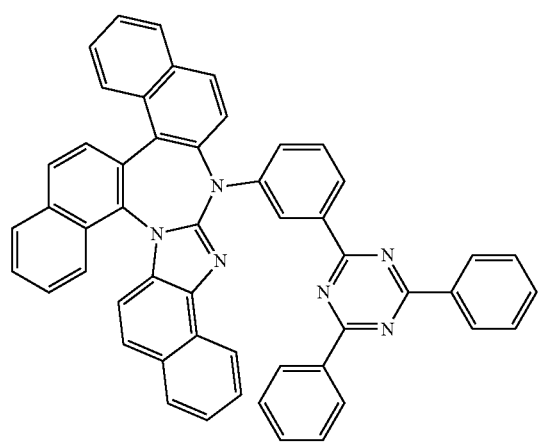
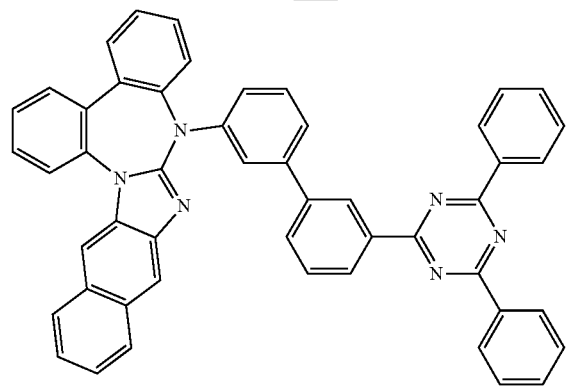
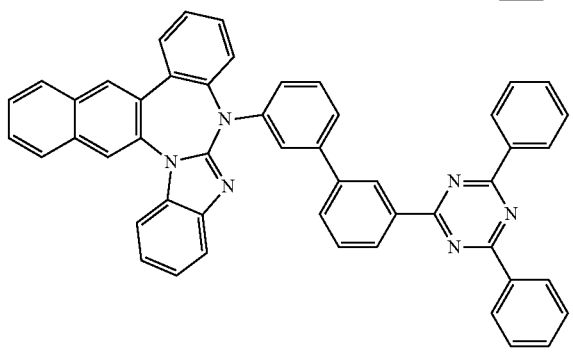
56
-continued
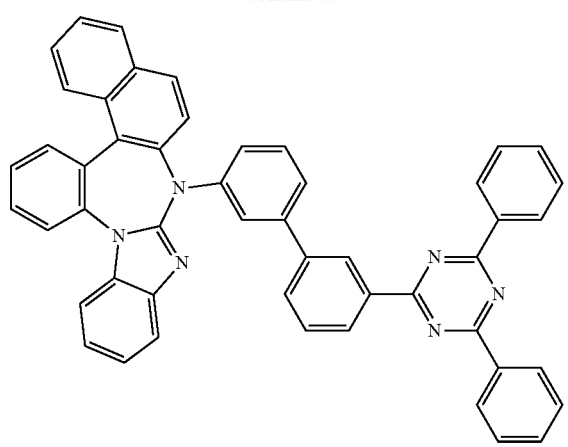
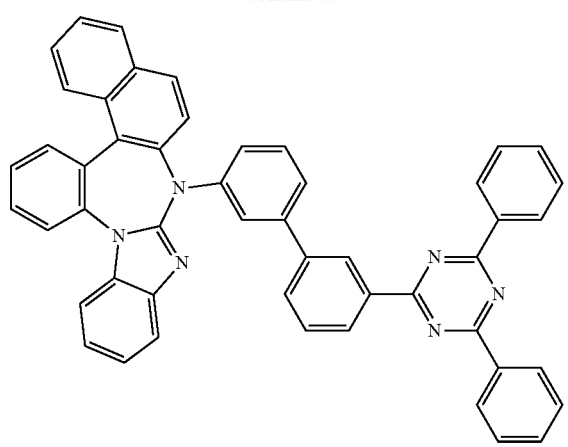
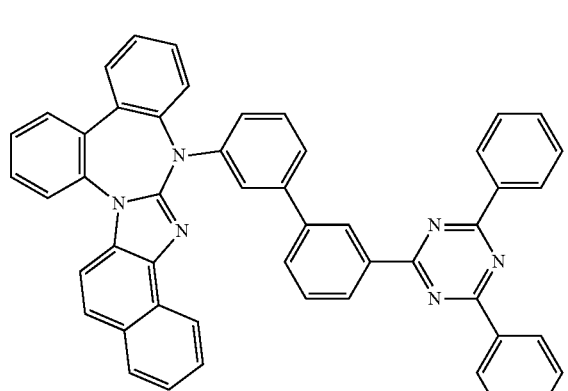
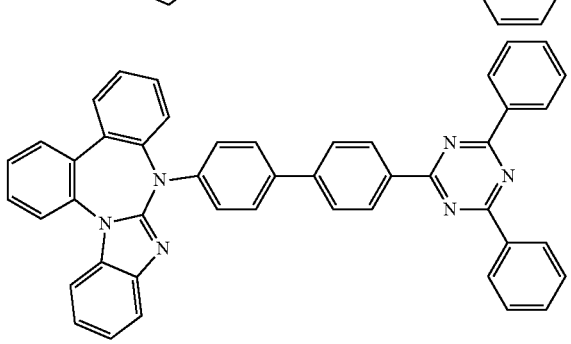

57
-continued
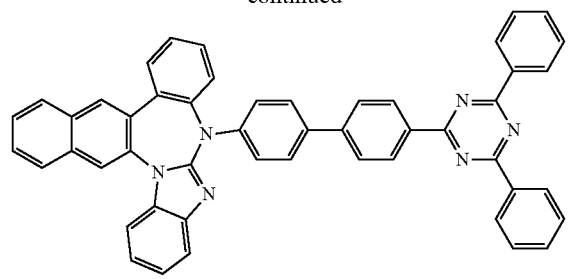
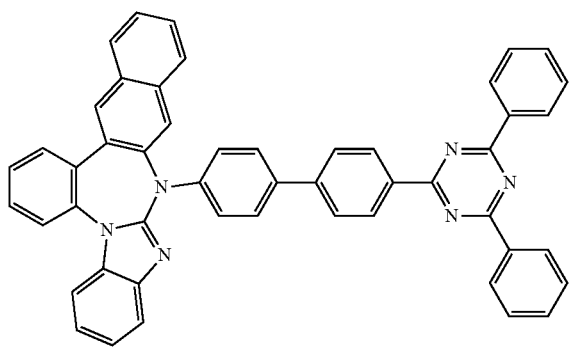
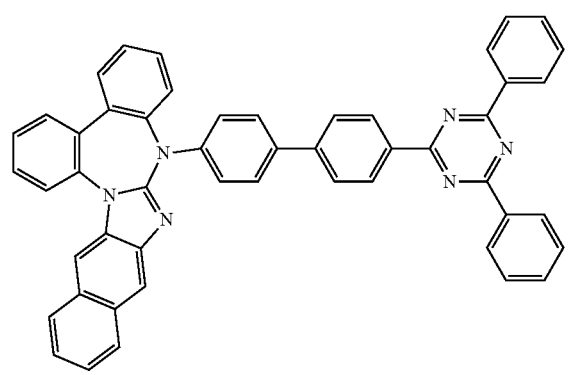
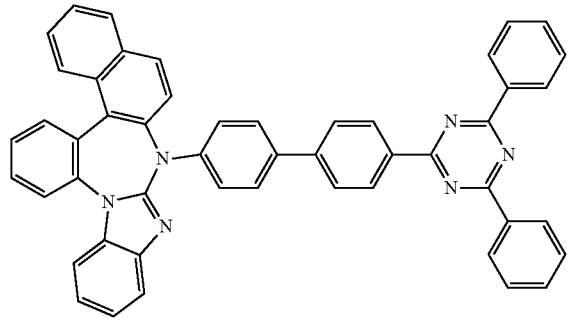
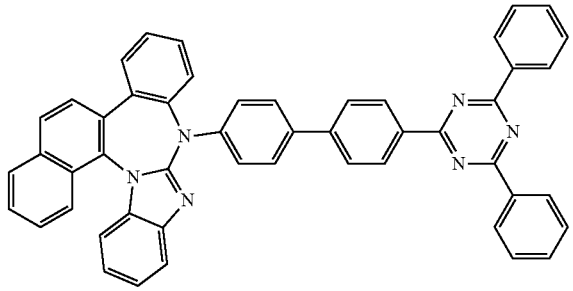
58
-continued
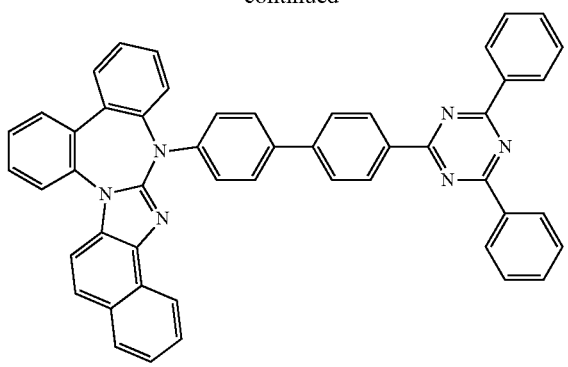
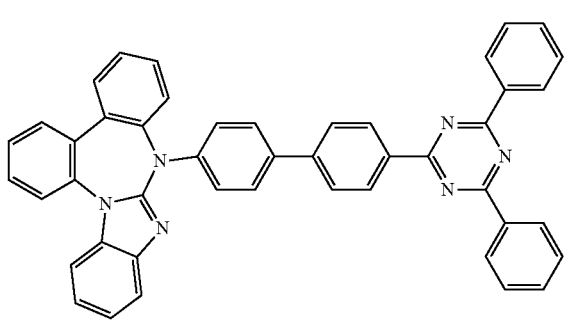
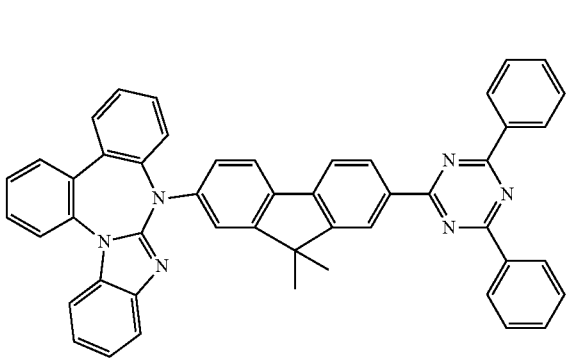
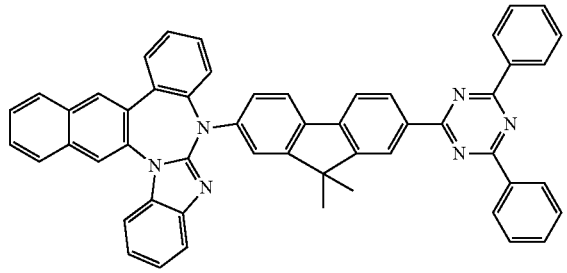
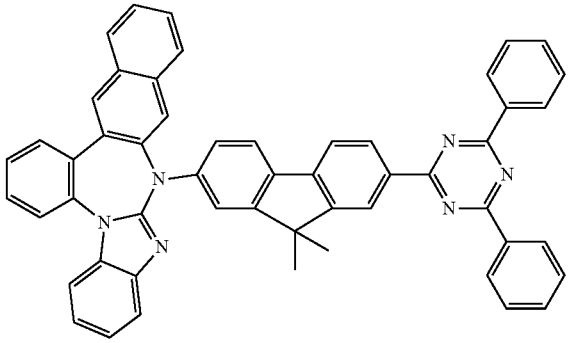

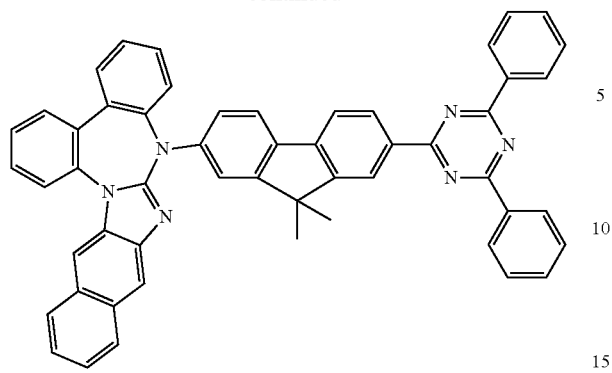
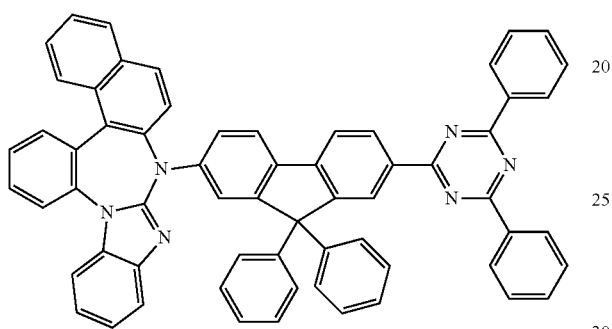
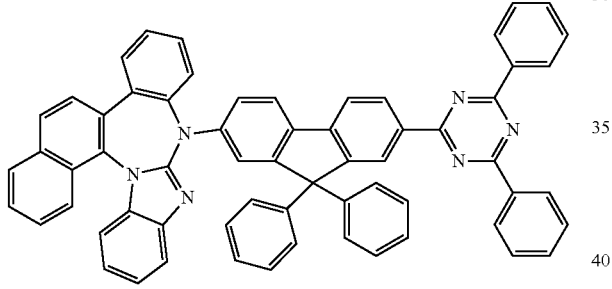
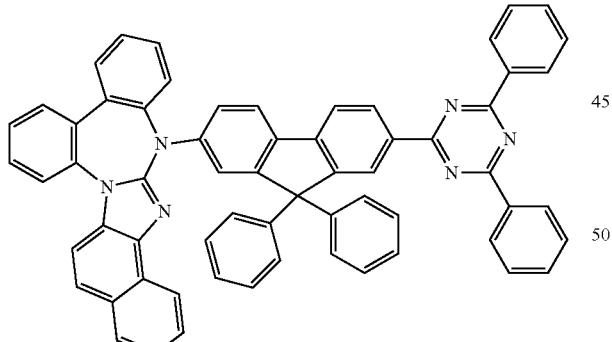
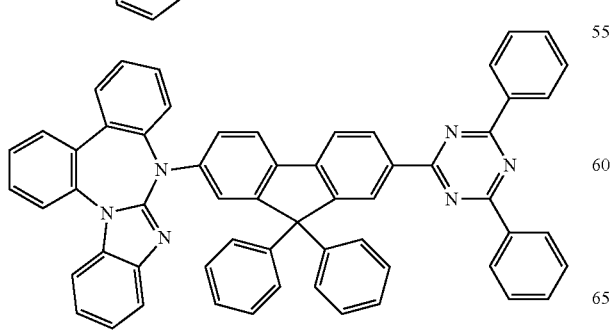
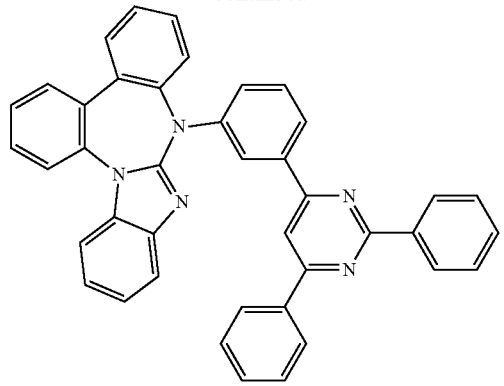
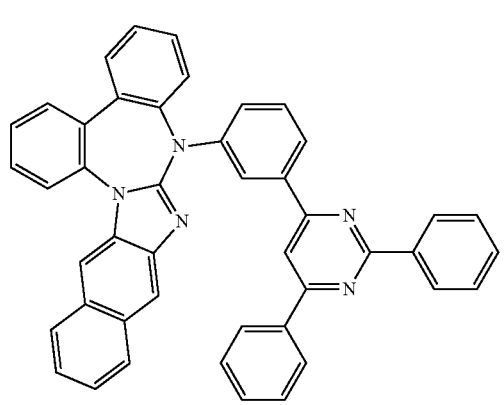
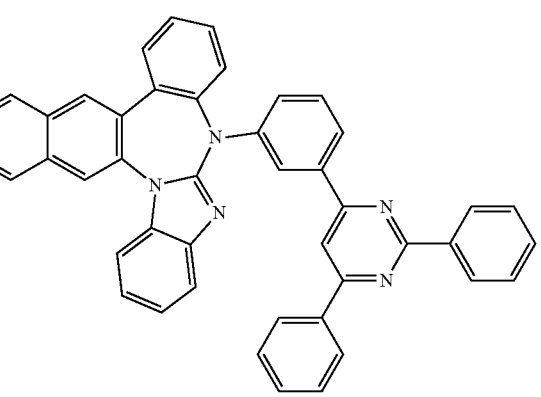
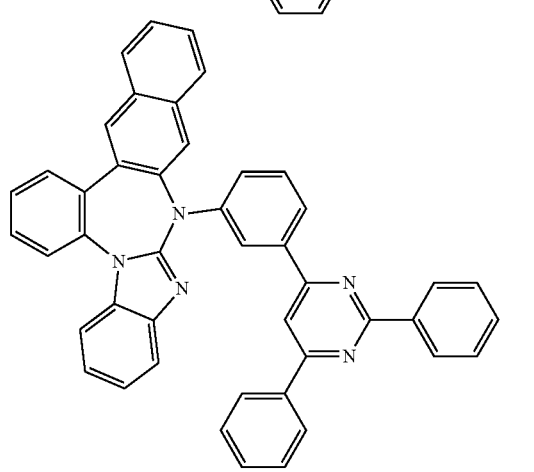

61
-continued
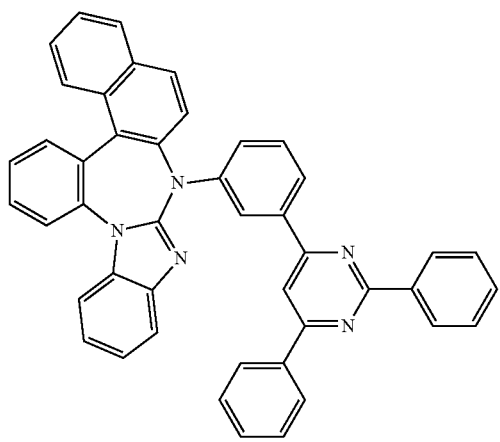
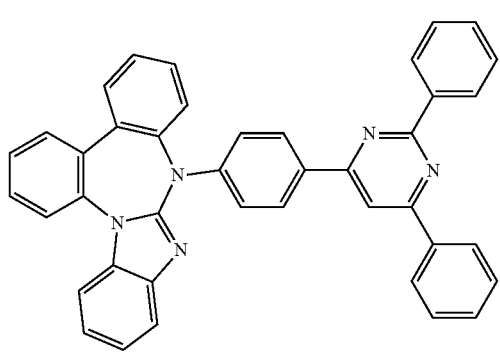
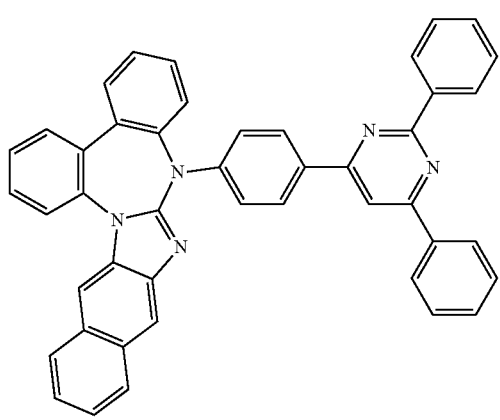
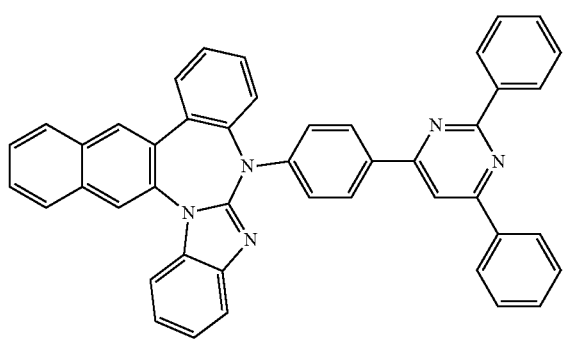
62
-continued
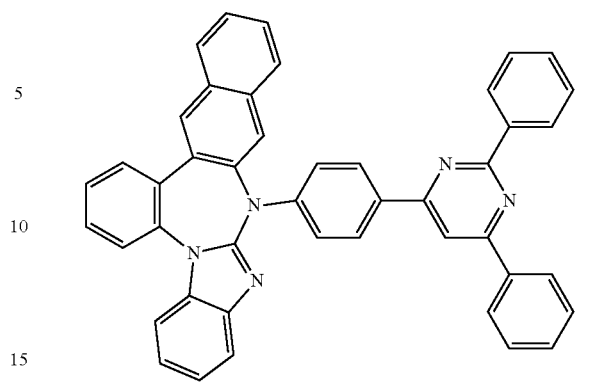
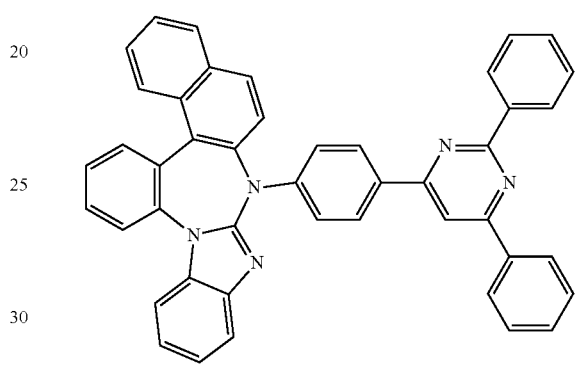
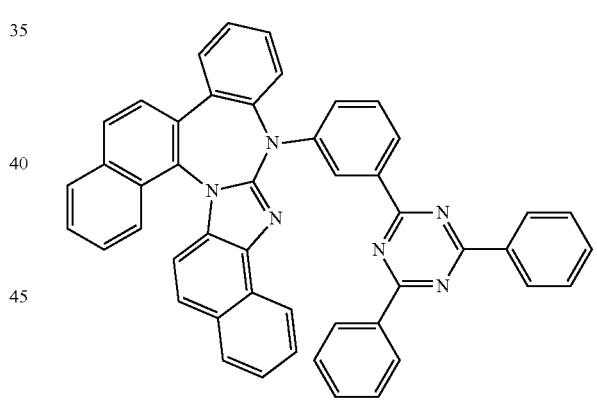
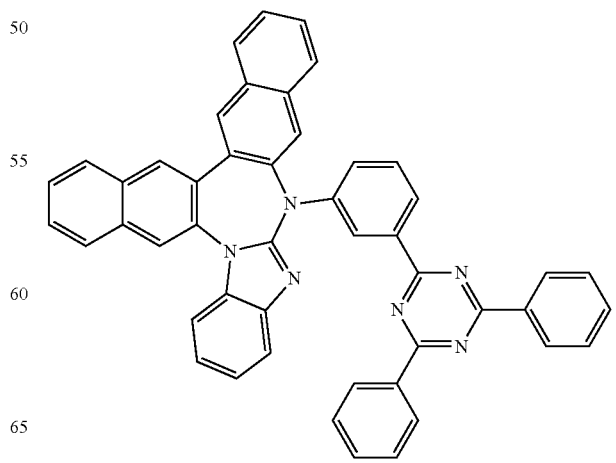

-continued
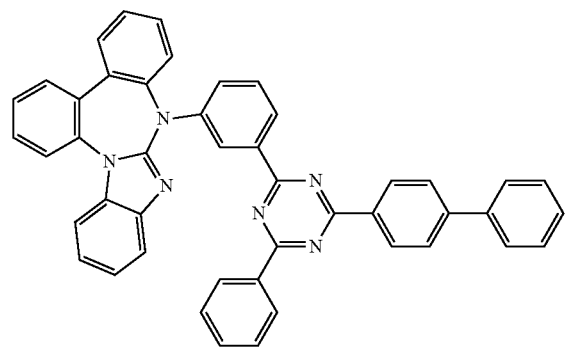
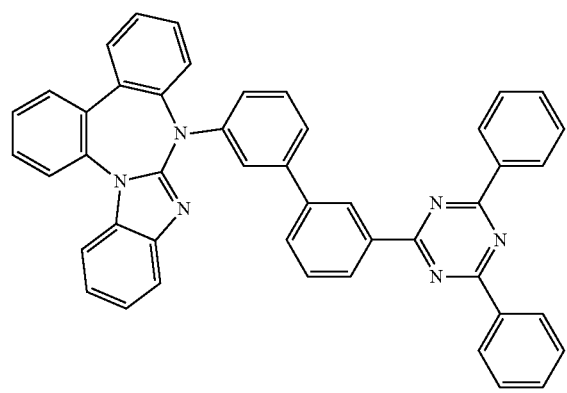
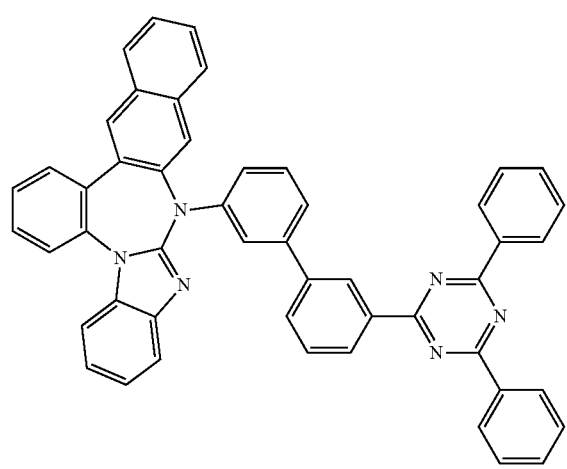
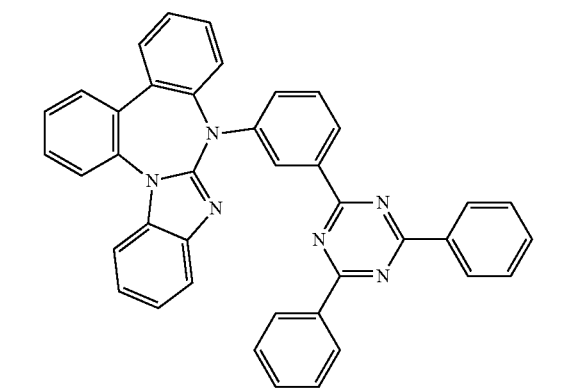
-continued
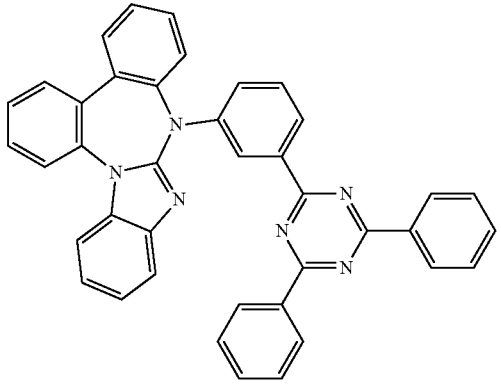
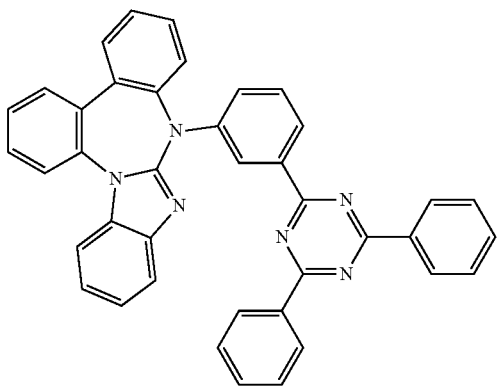
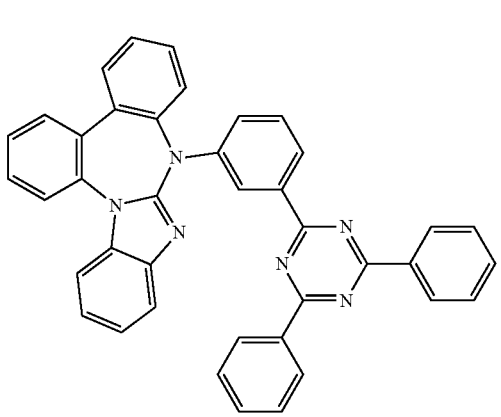
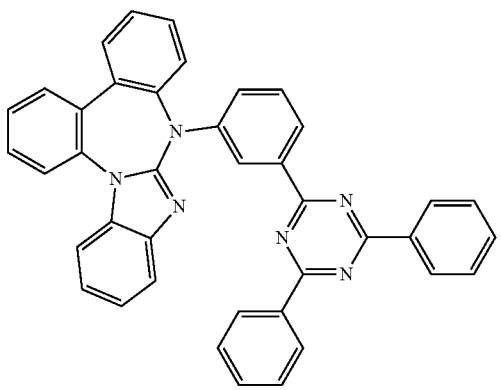

65
-continued
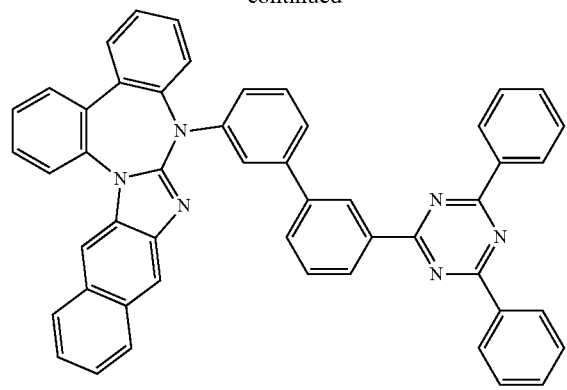
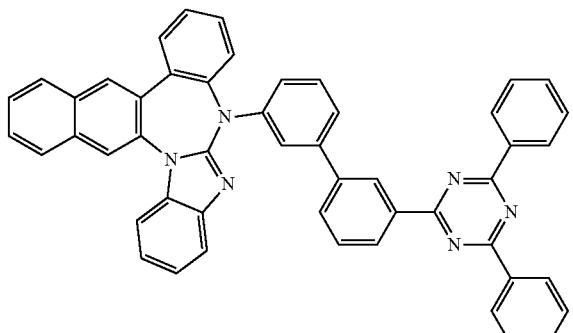
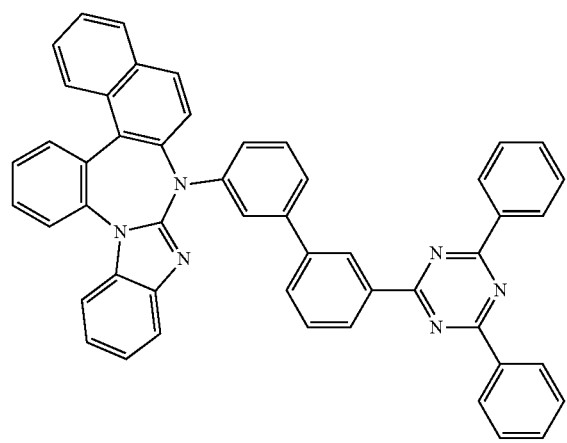
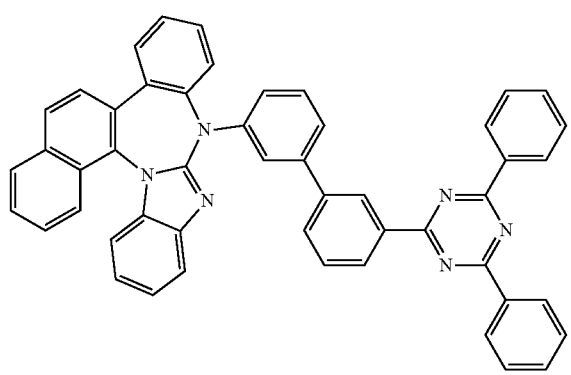
66
-continued
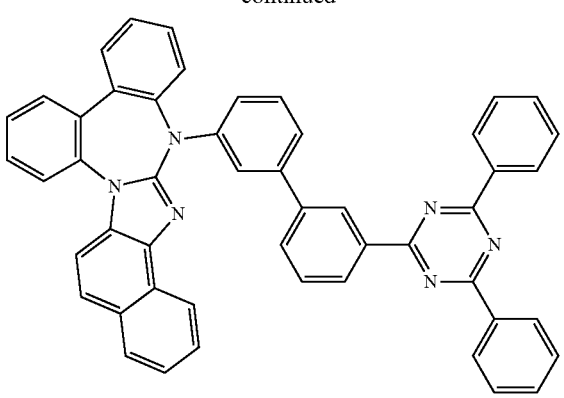
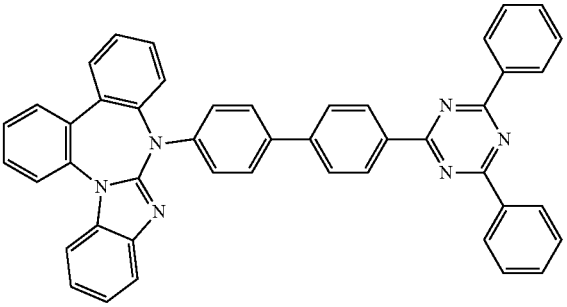
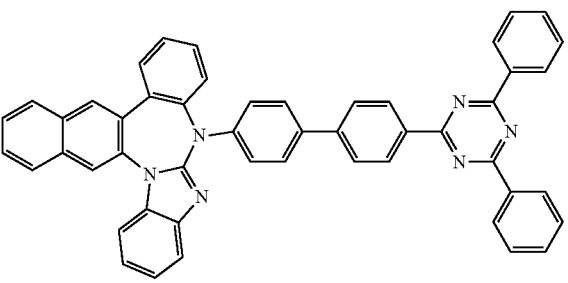
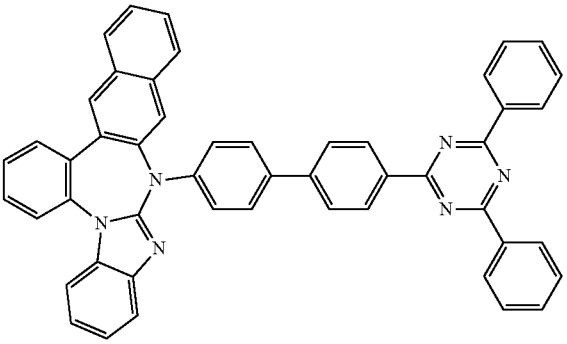
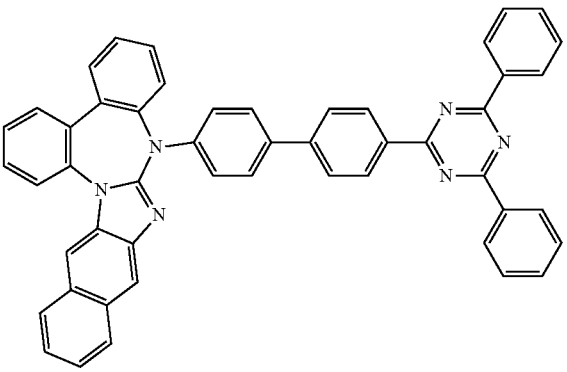

67
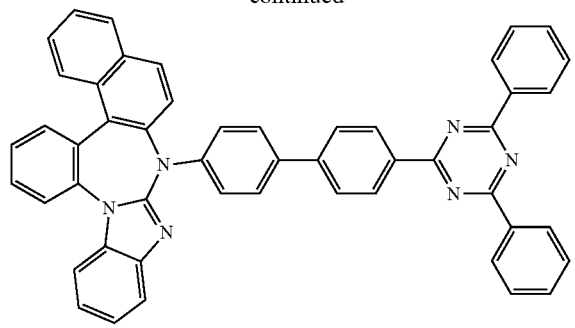
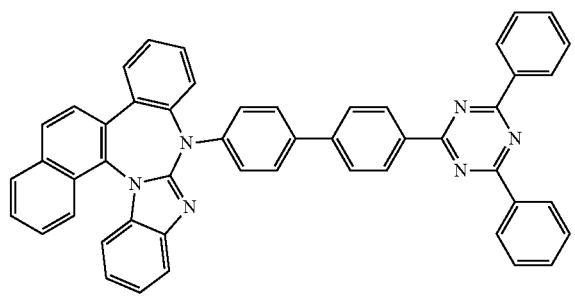
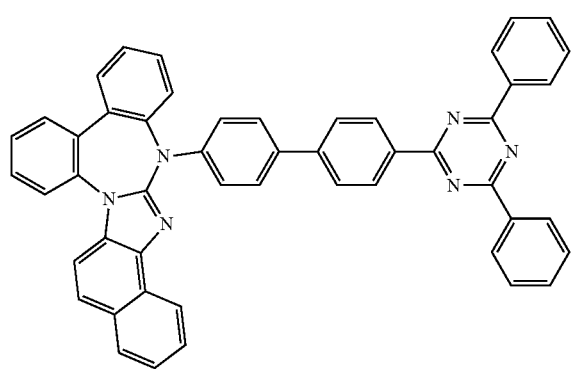
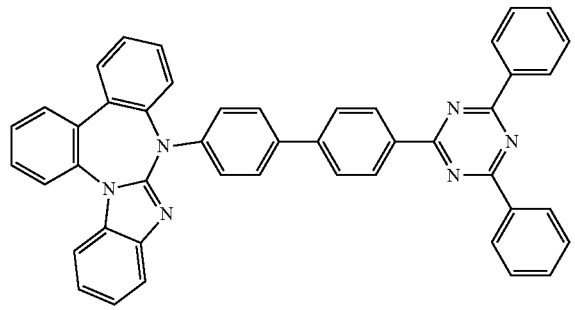
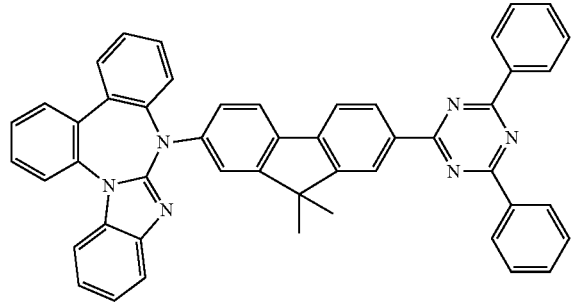
68
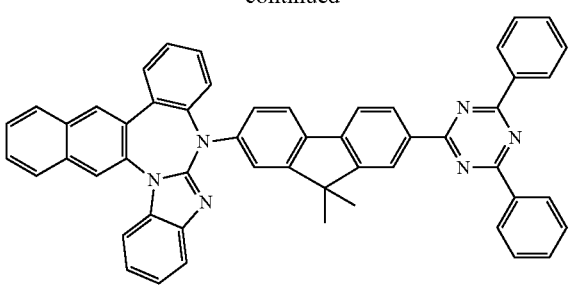
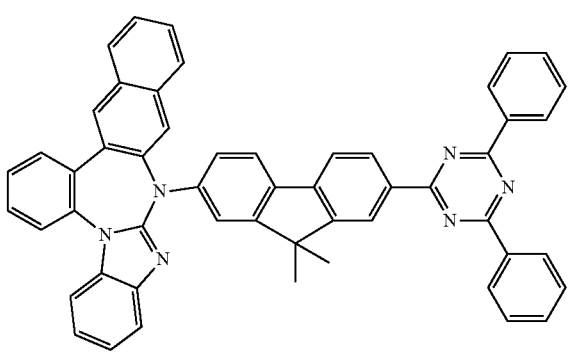
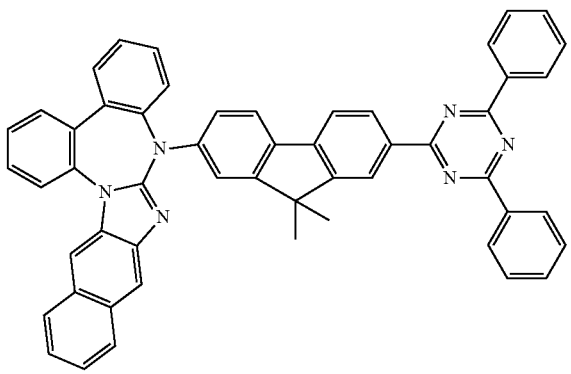
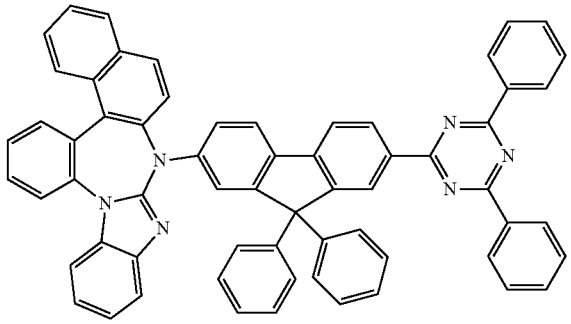
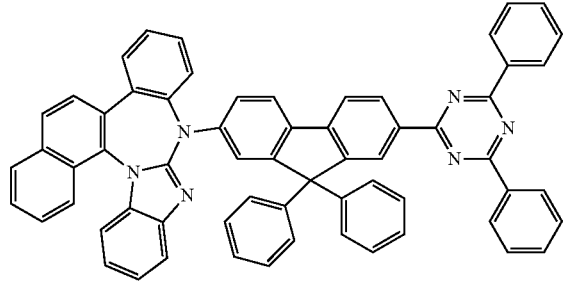

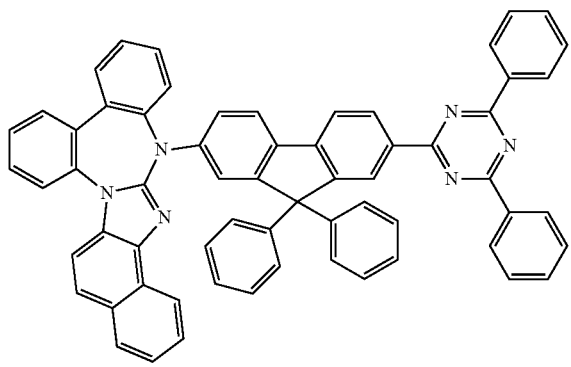
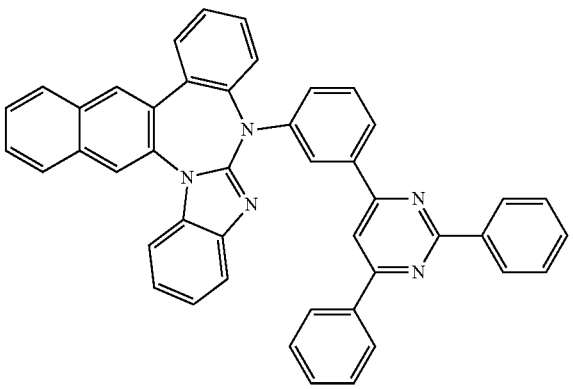
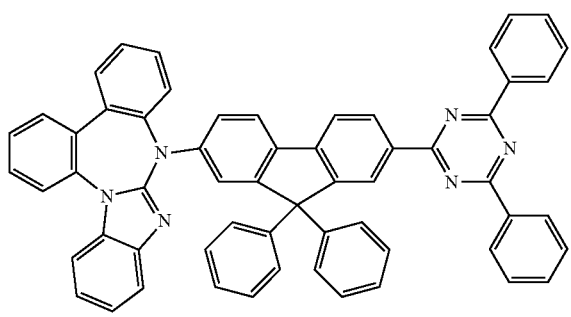
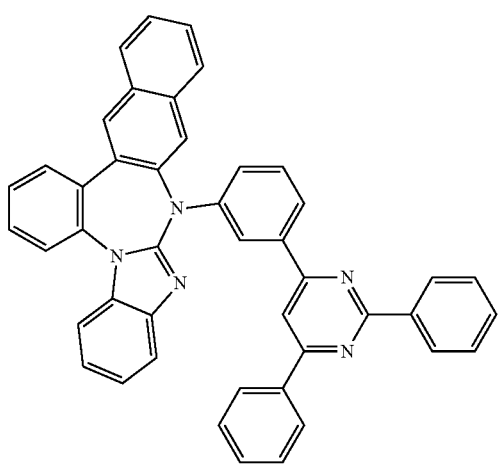
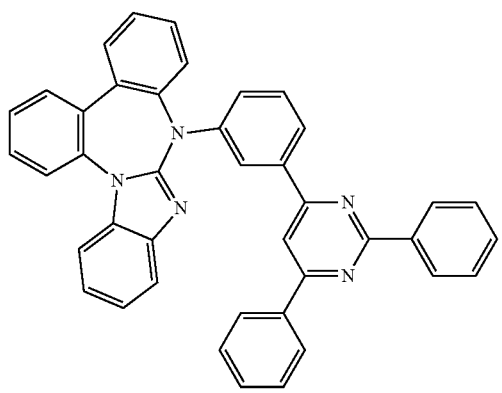
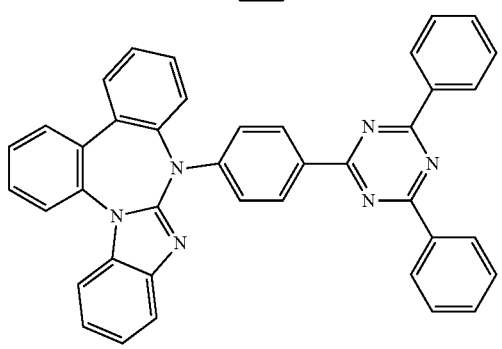

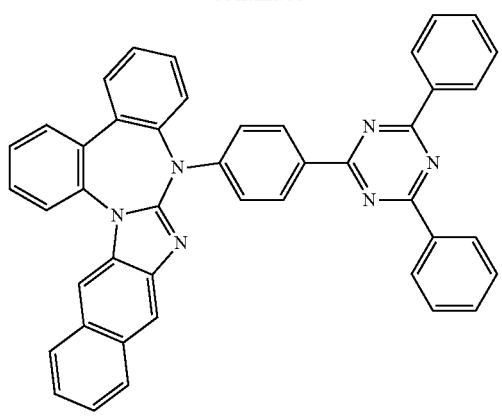
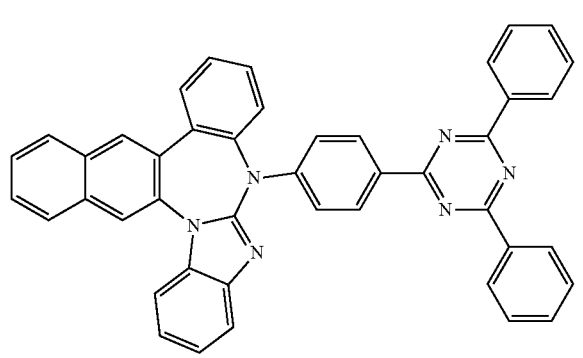
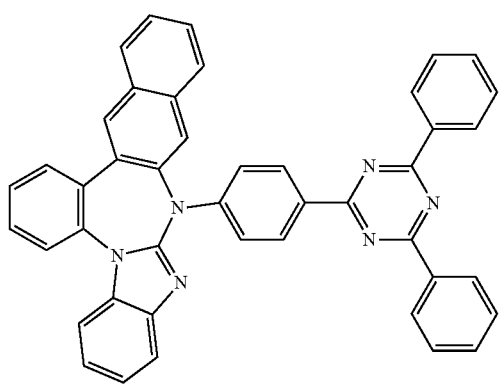
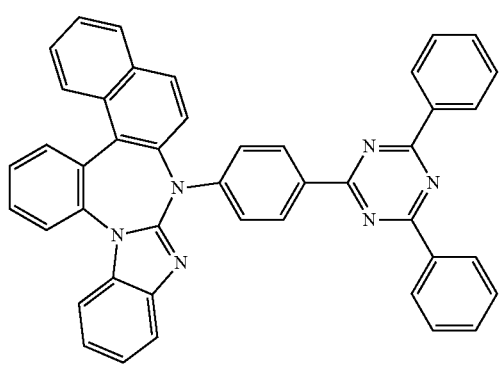
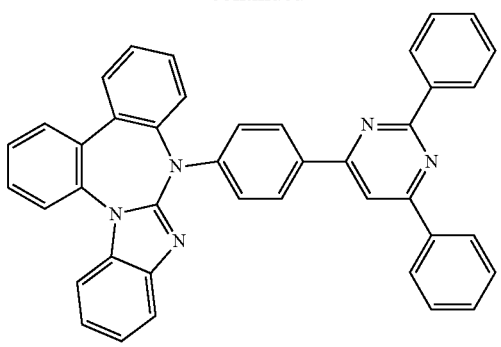
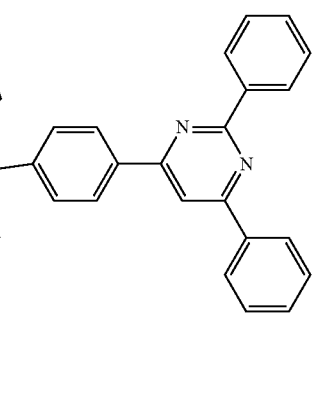
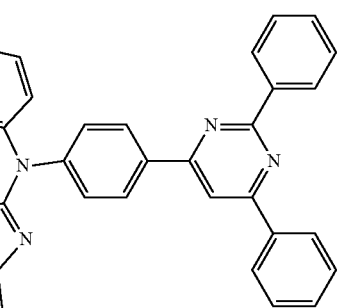
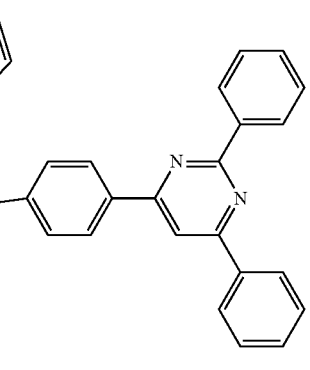

73
-continued
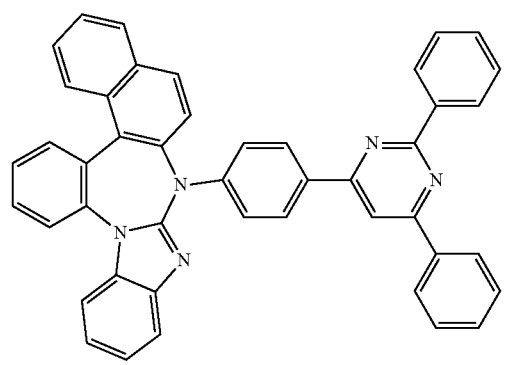
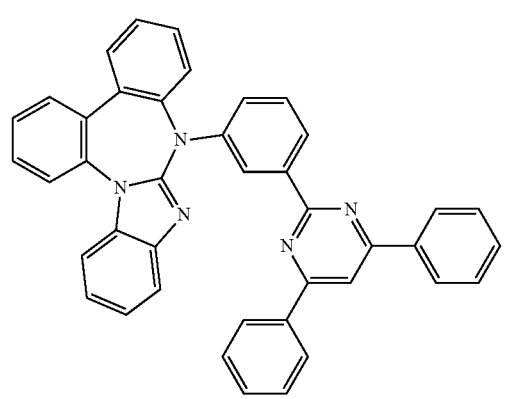
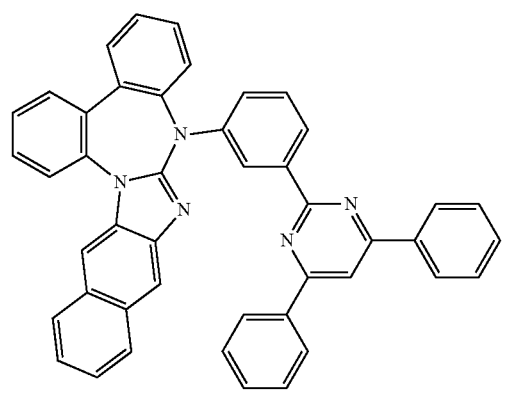
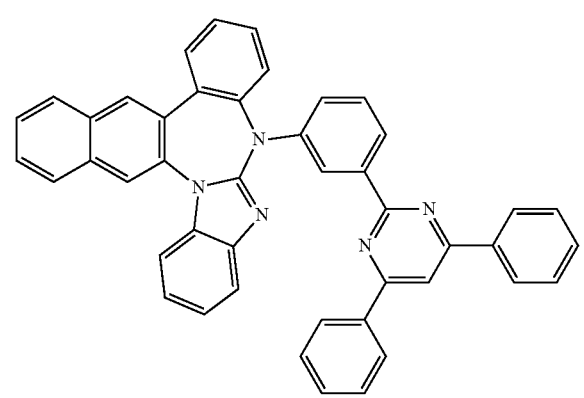
74
-continued
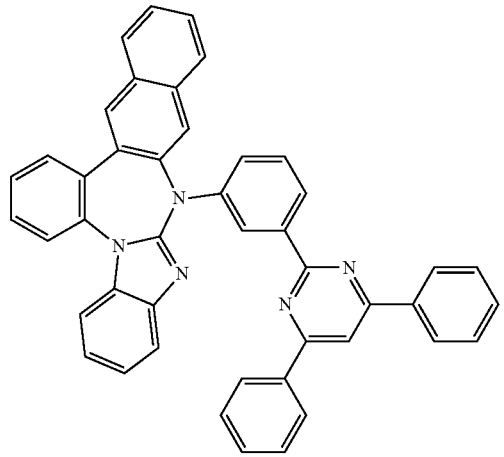
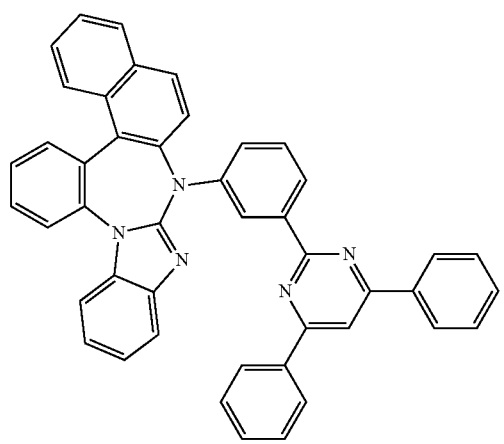
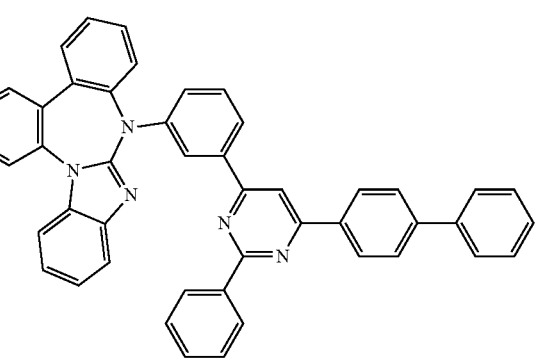
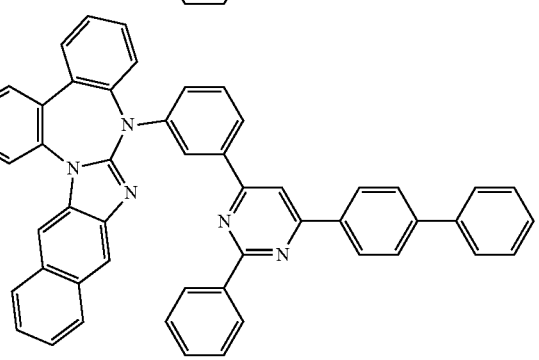

75
-continued
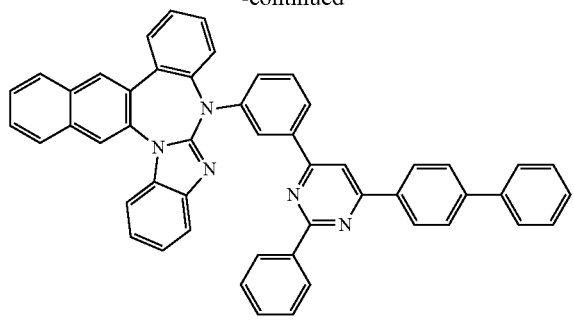
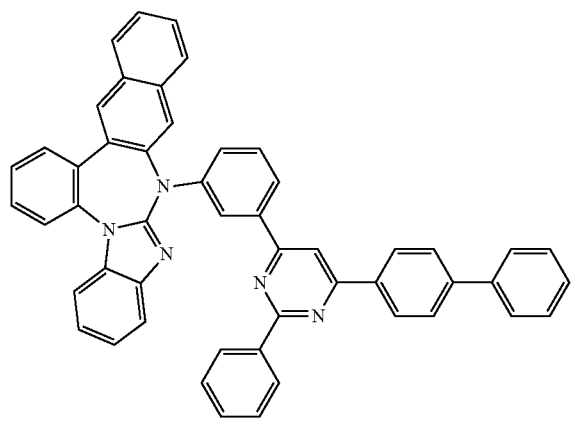
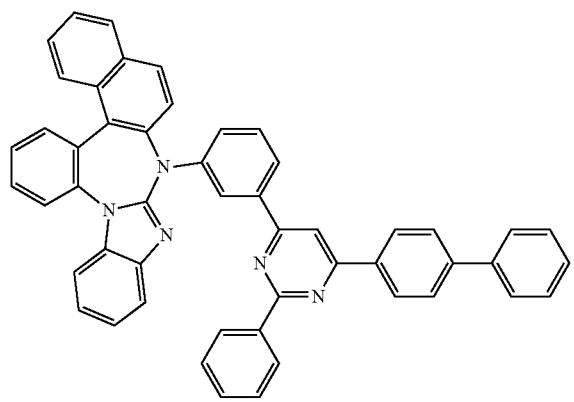
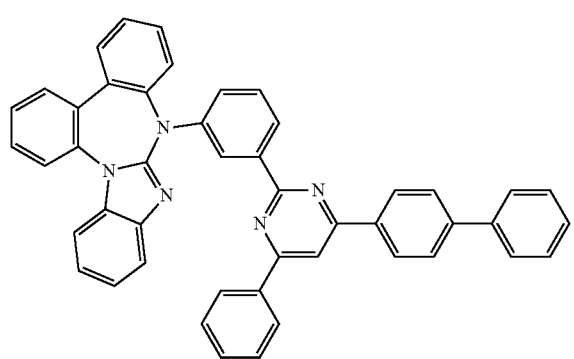 [SMILES: c1ccc(-c2ccc(-c3nc(-c4ccccc4)nc(-c4cccc(N5c6ccccc6-c6ccccc6-n6c5nc5ccccc56)c4)n3)cc2)cc1]
76
-continued
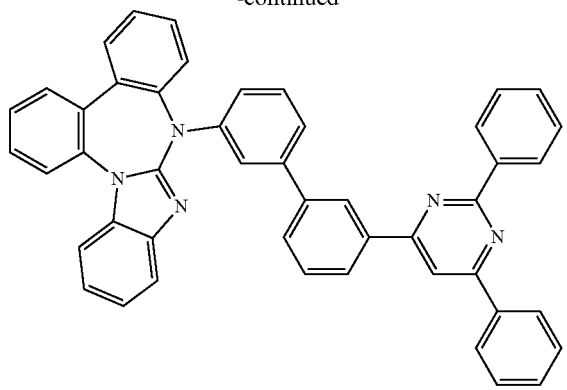
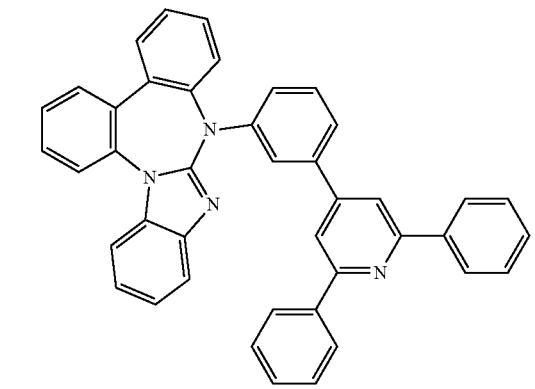
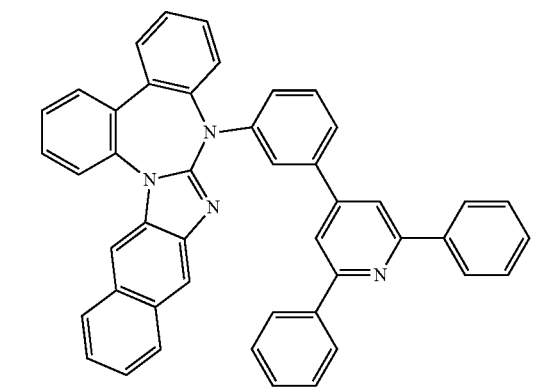
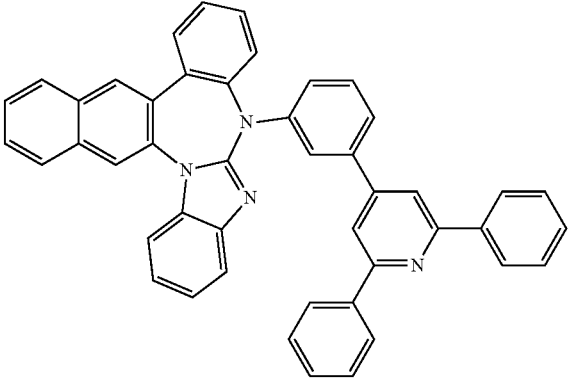

77
-continued
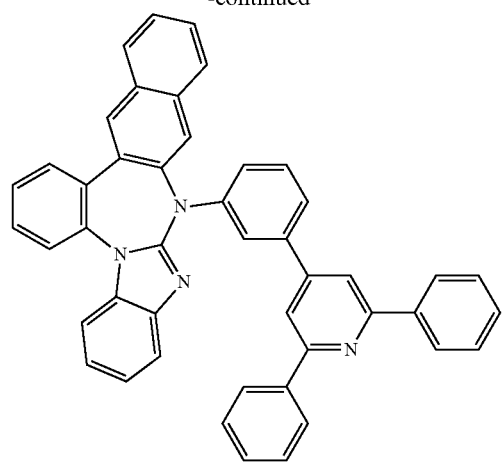
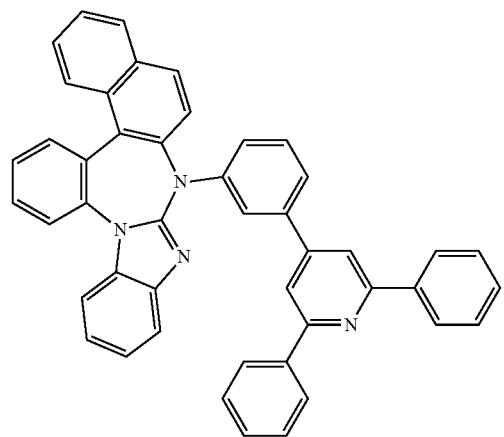
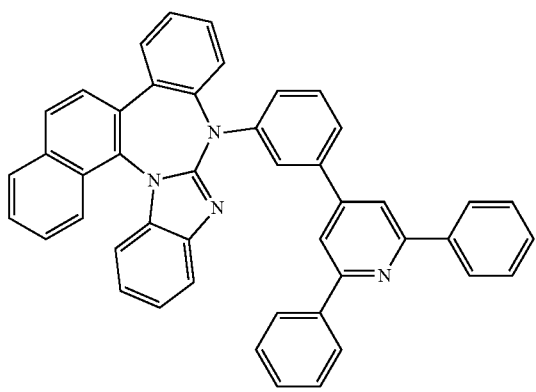
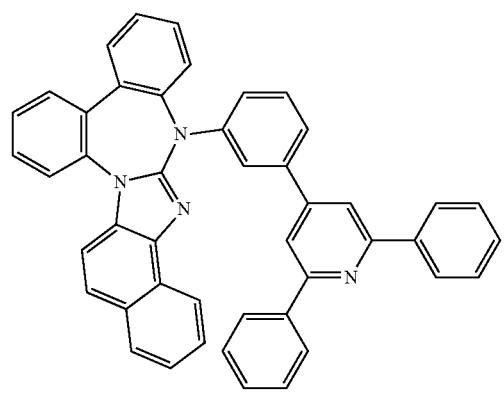
78
-continued
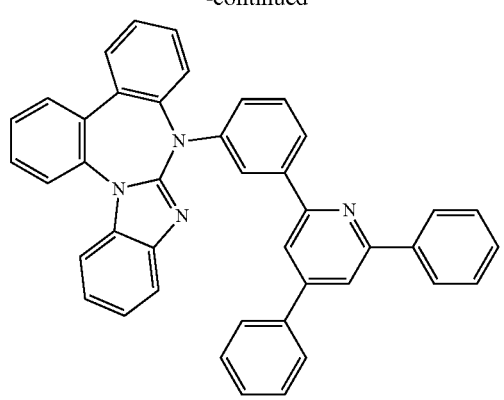
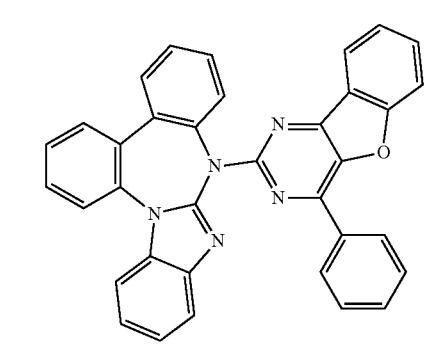
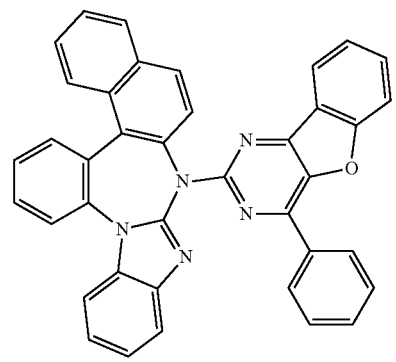
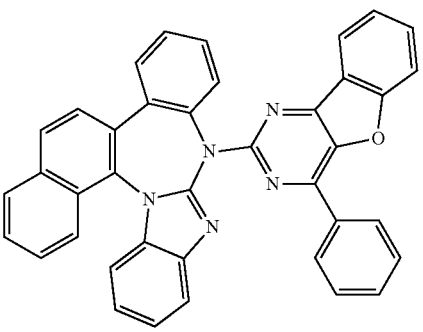

79
-continued
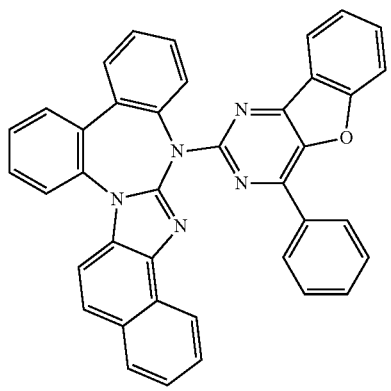
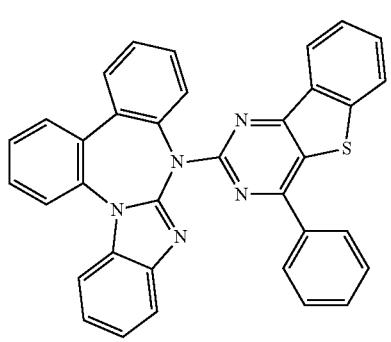
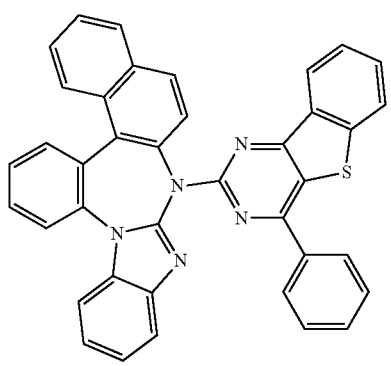
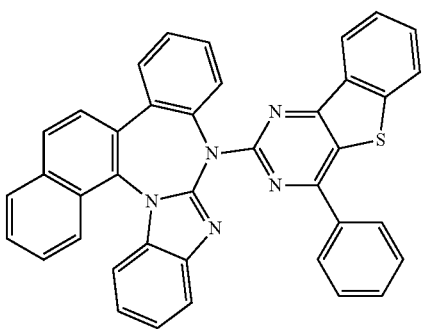
80
-continued
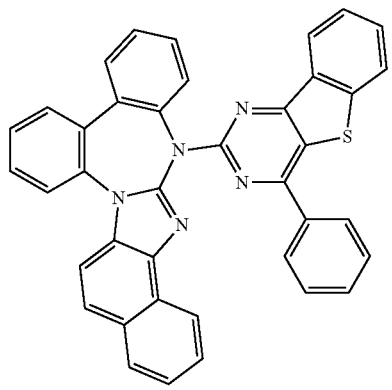
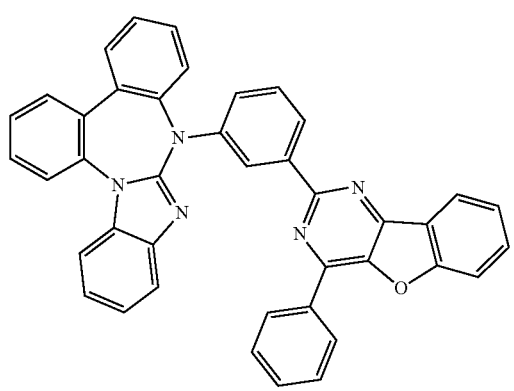
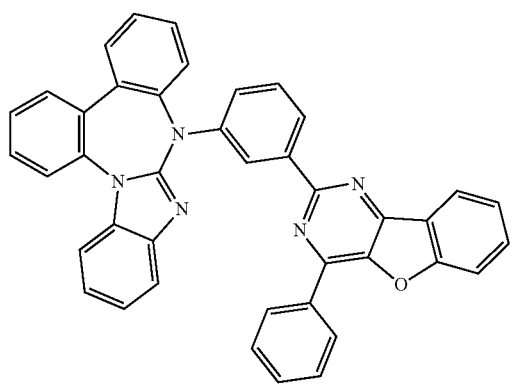
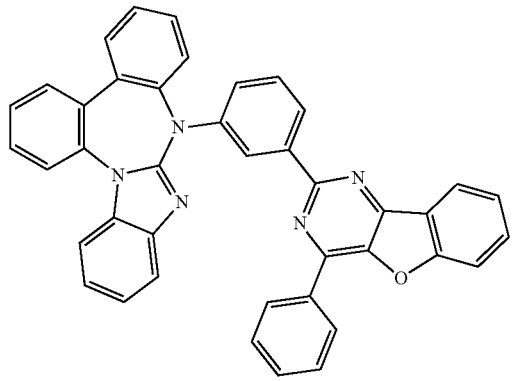

81
-continued
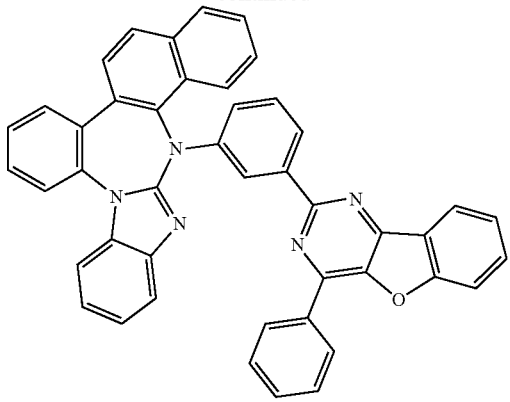
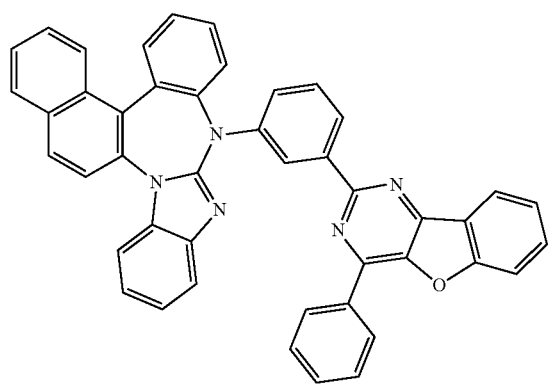
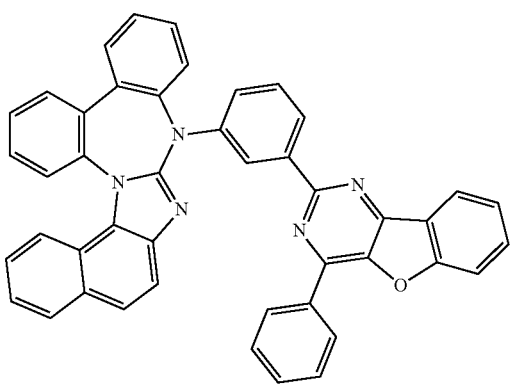
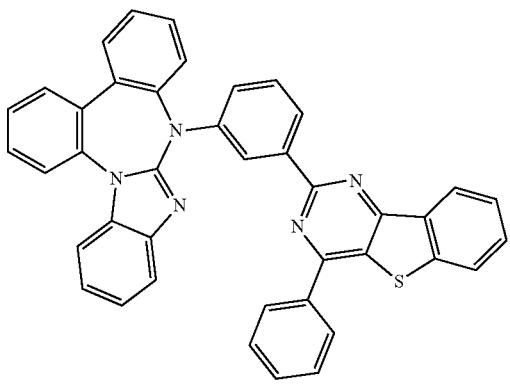
82
-continued
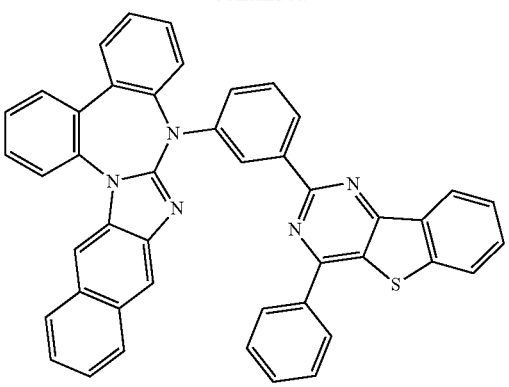
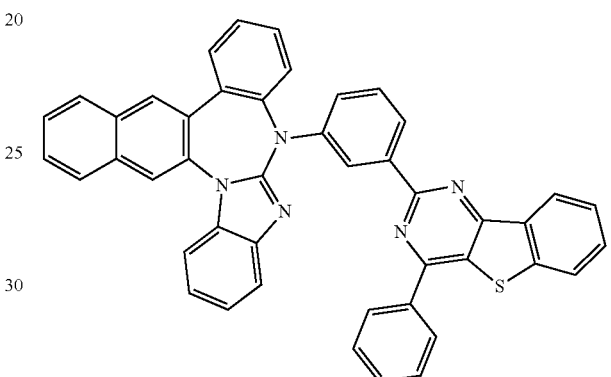
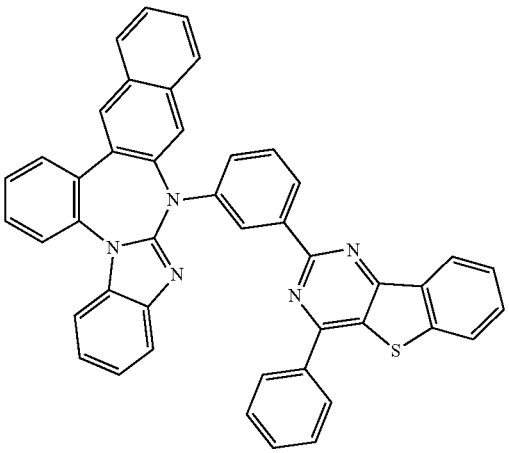
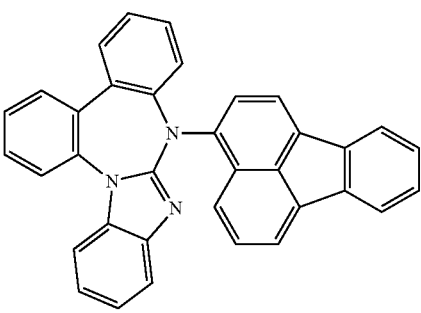

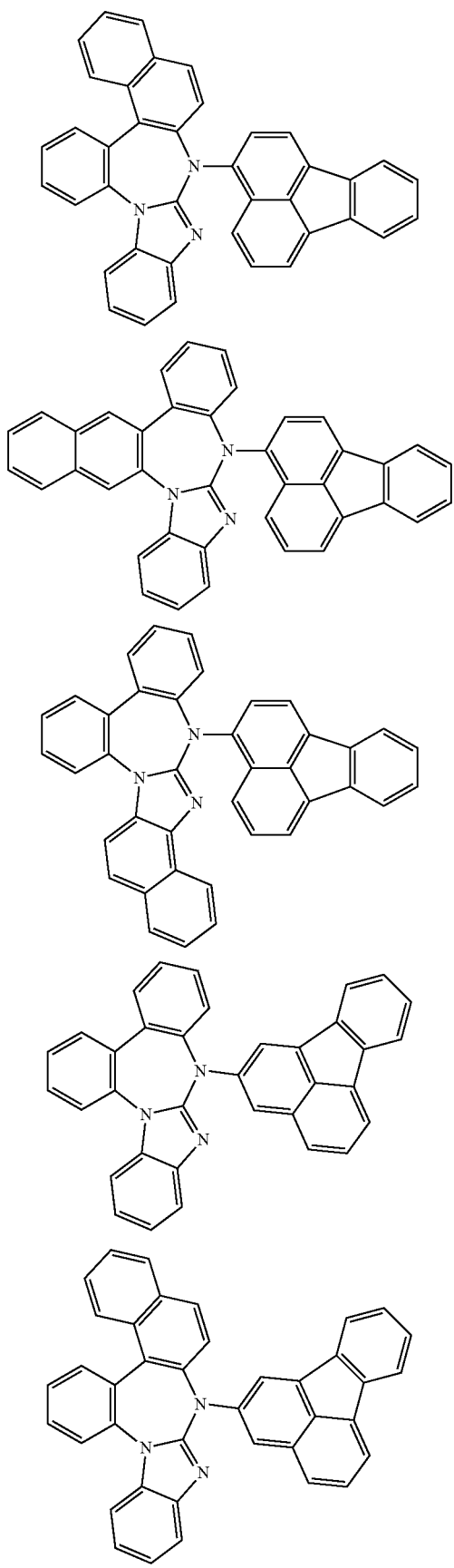
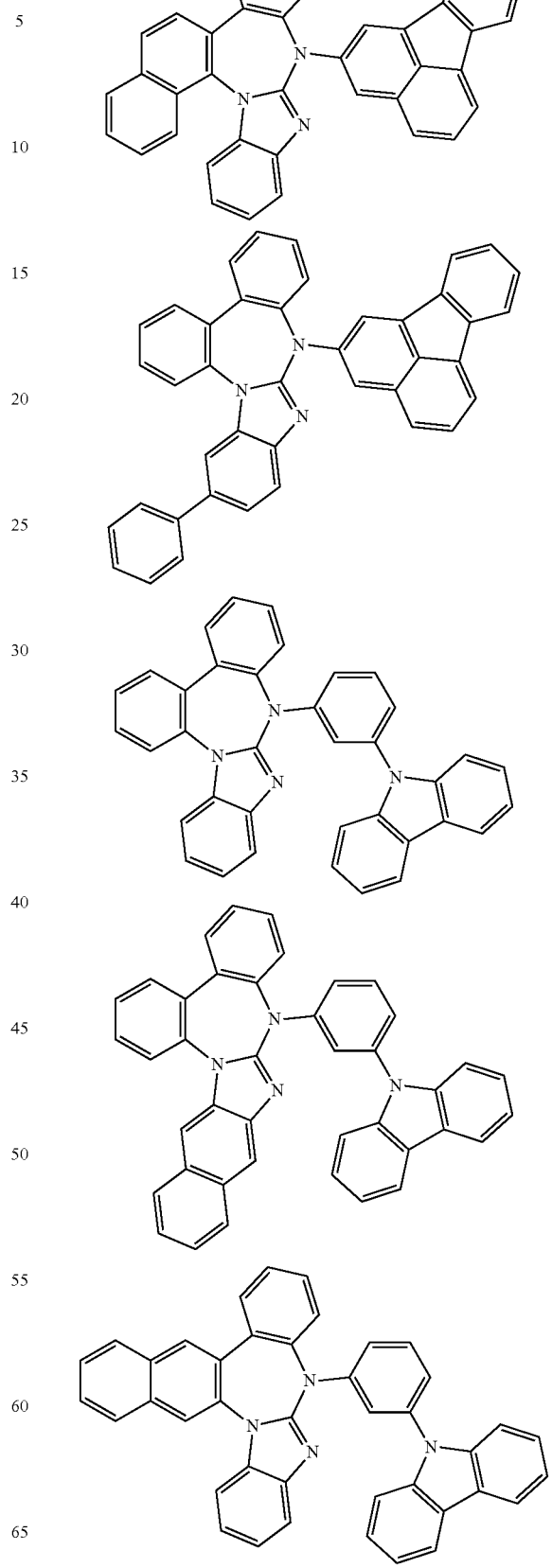

85
-continued
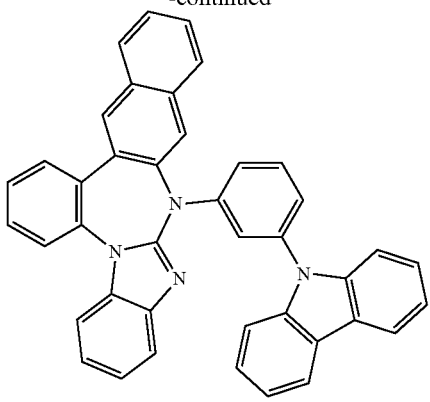
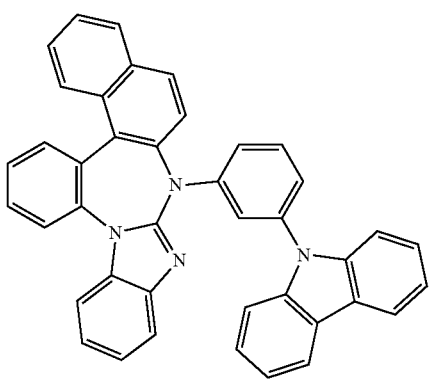
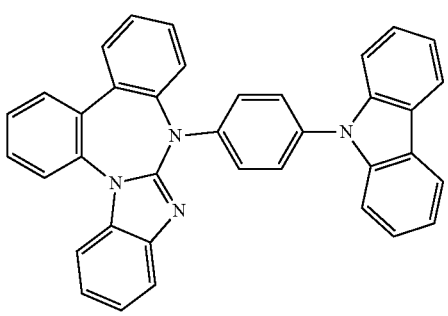
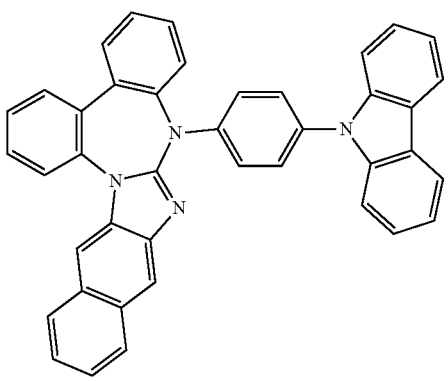
86
-continued
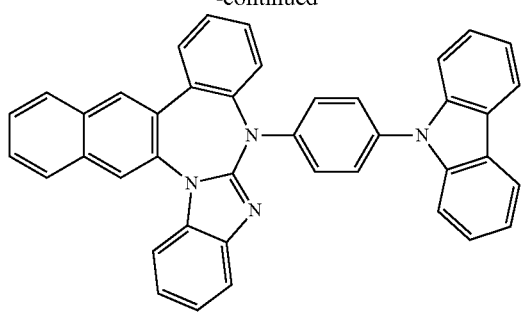
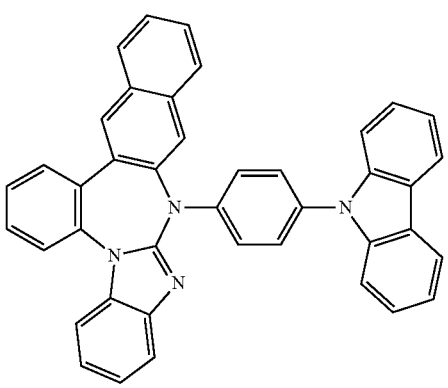
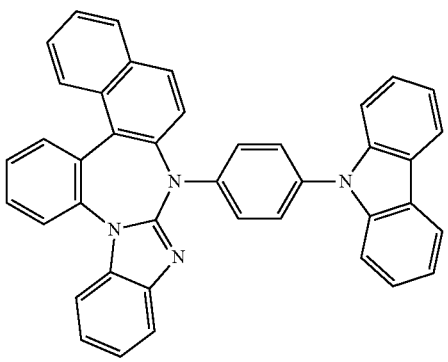
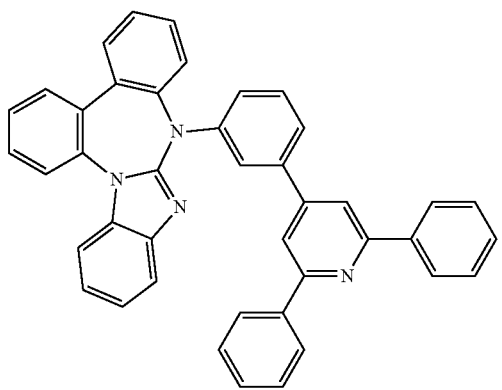

-continued
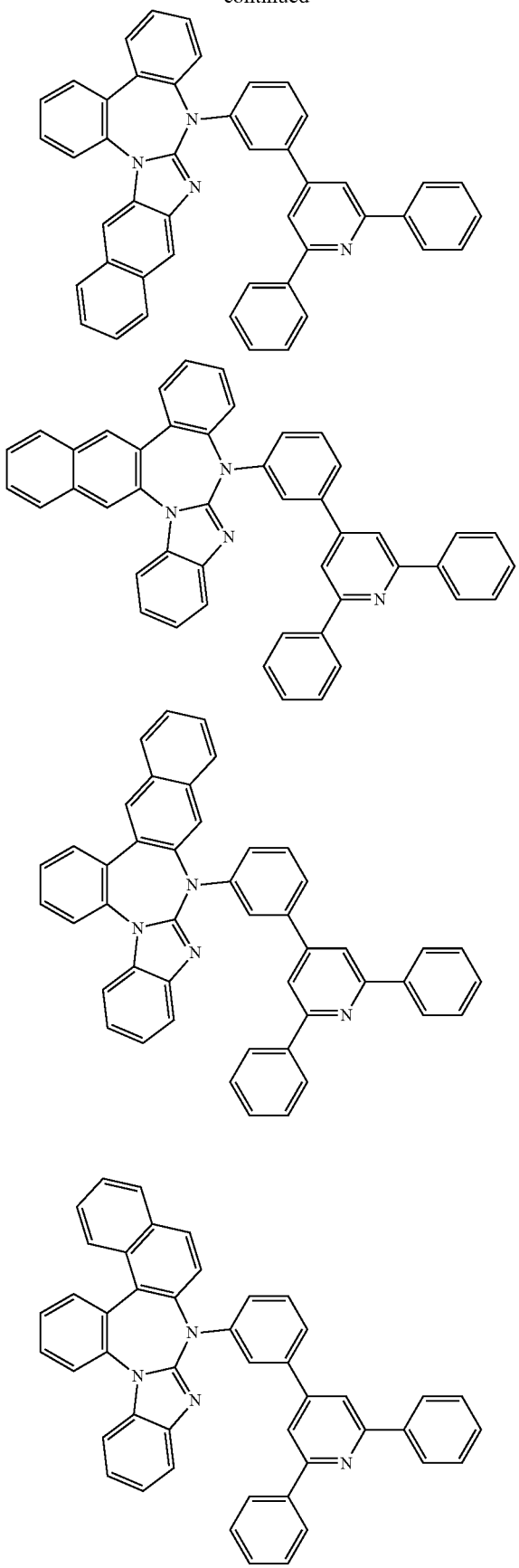
-continued
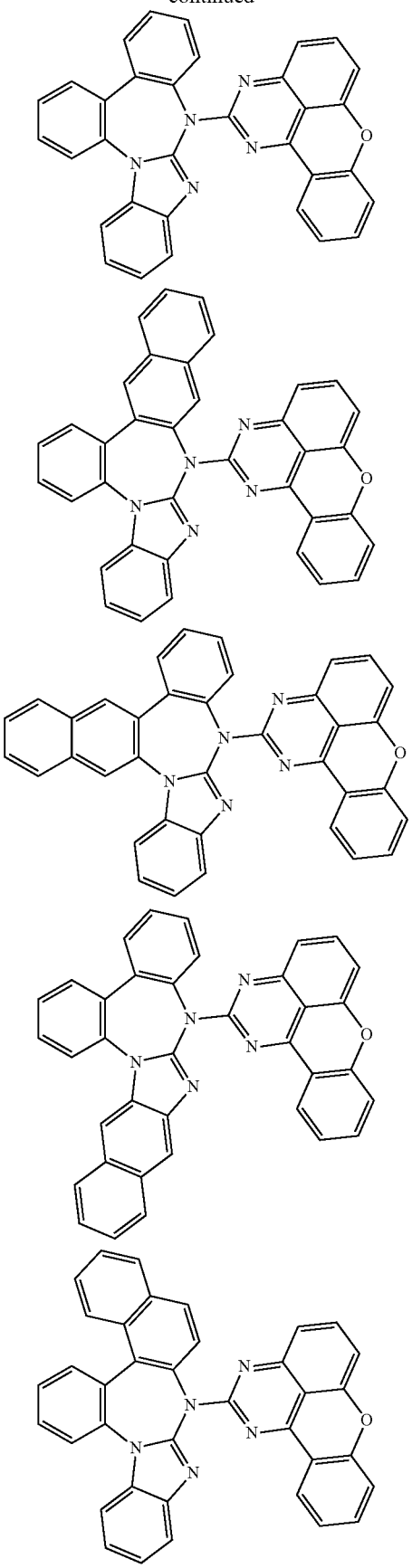

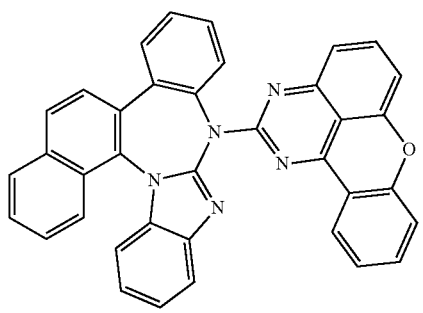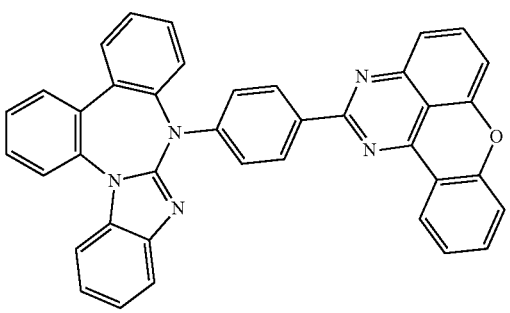

91
-continued
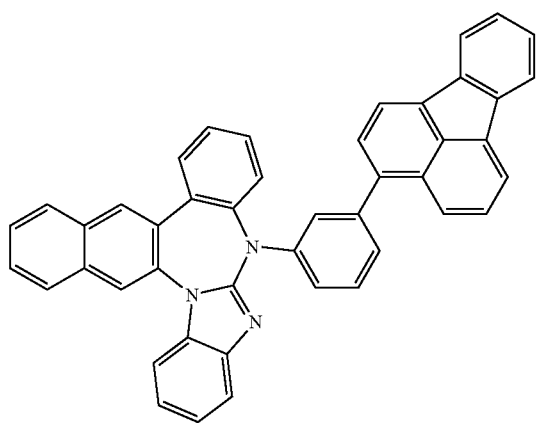
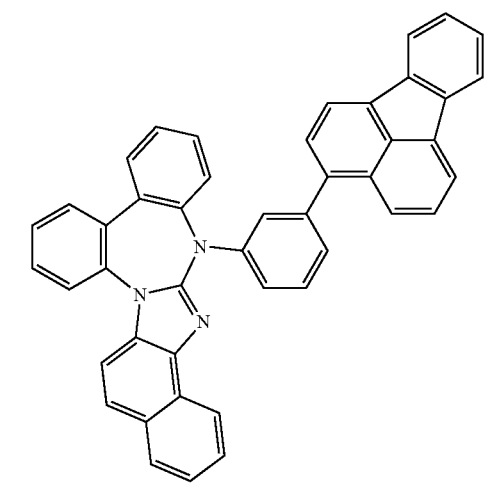
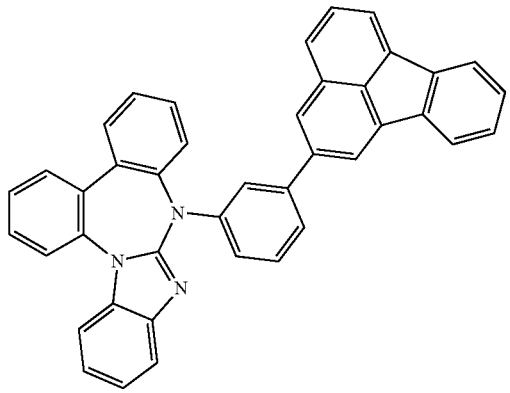
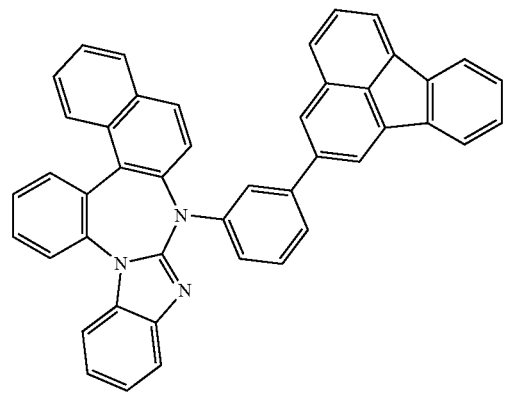
92
-continued
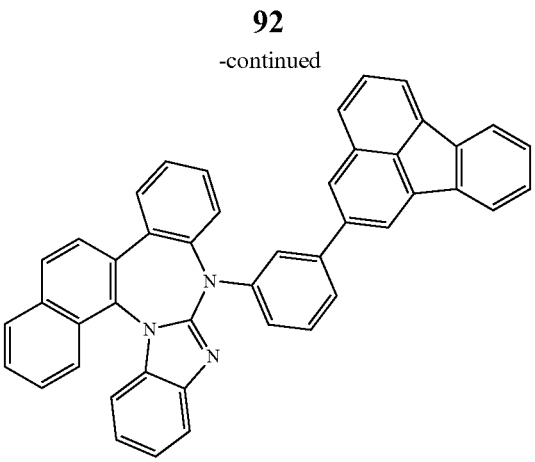
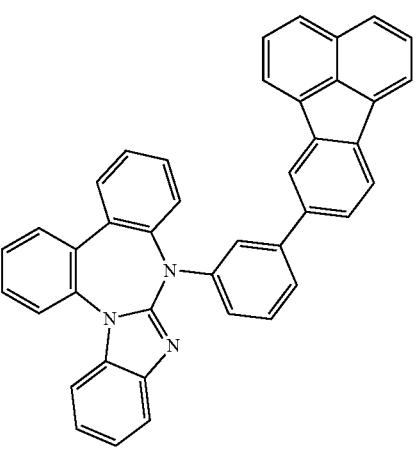
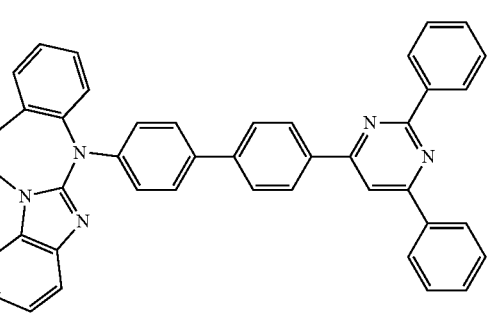
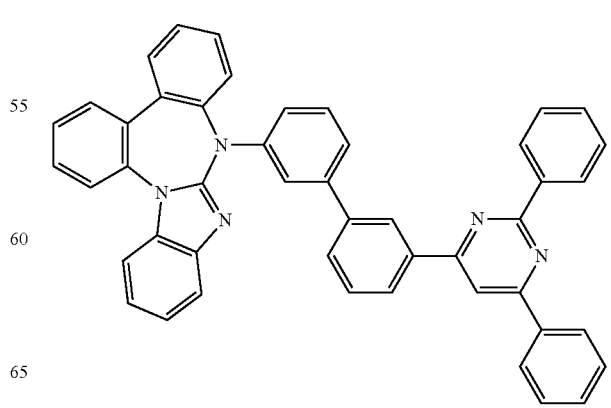

93
-continued
94
-continued
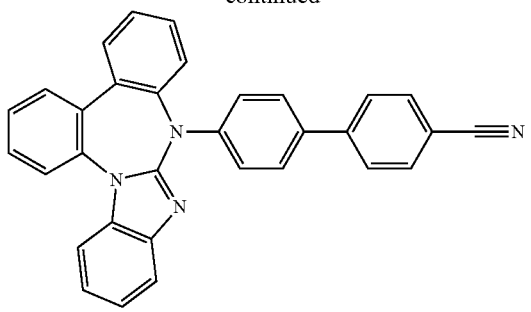
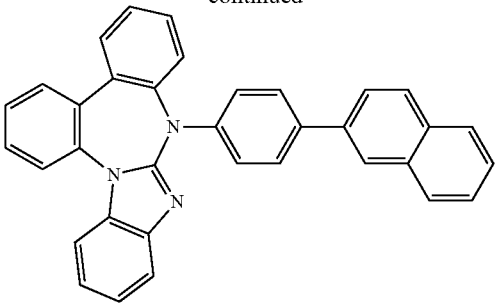
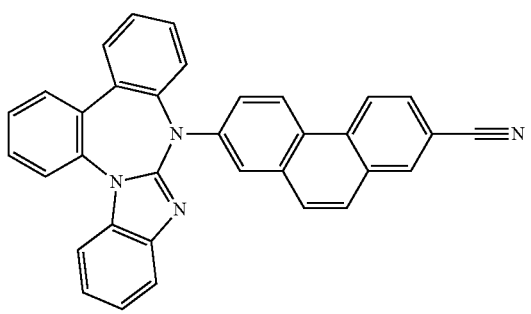
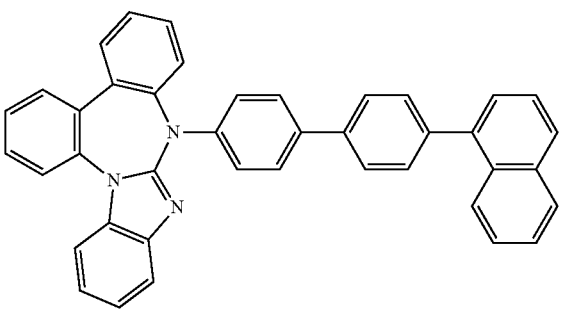
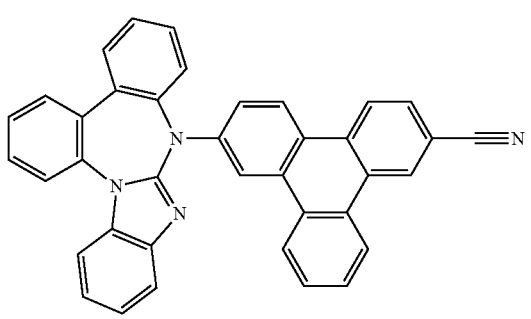
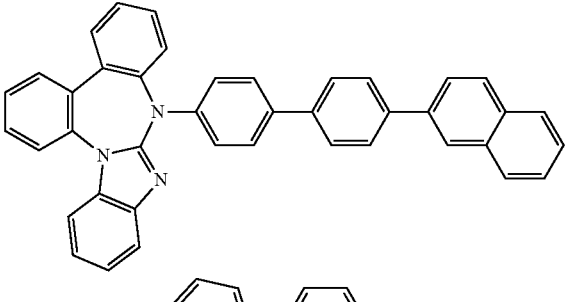
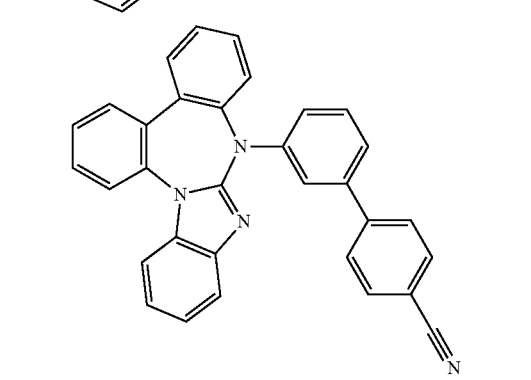
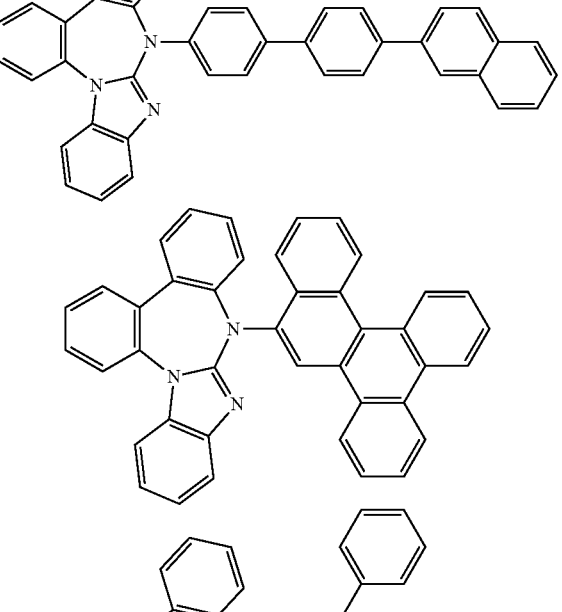
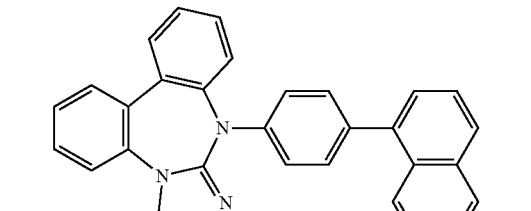

95
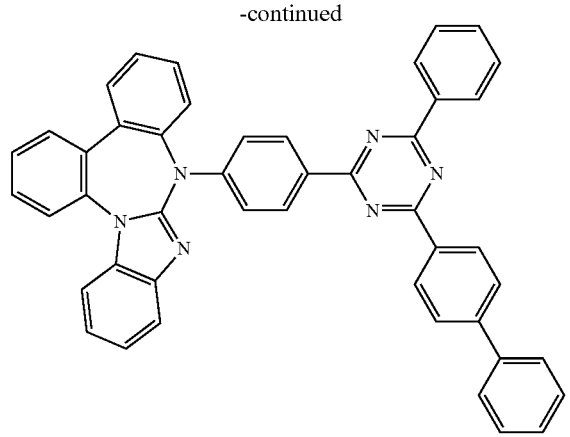
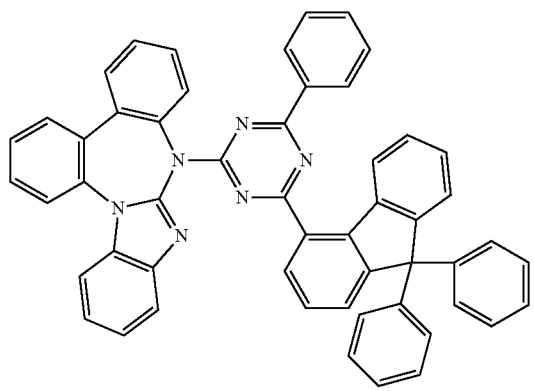
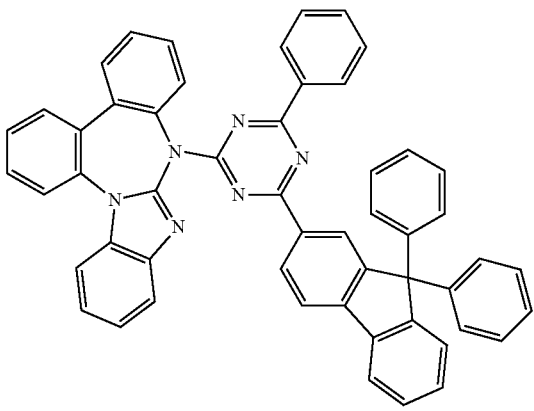
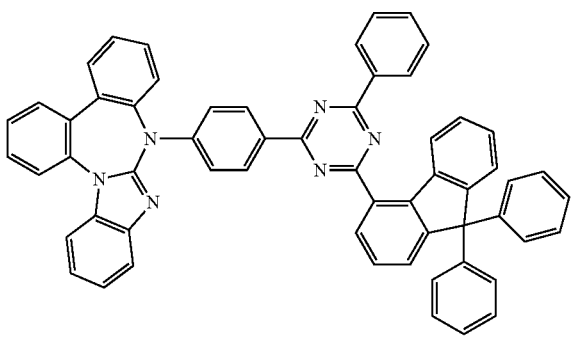
96
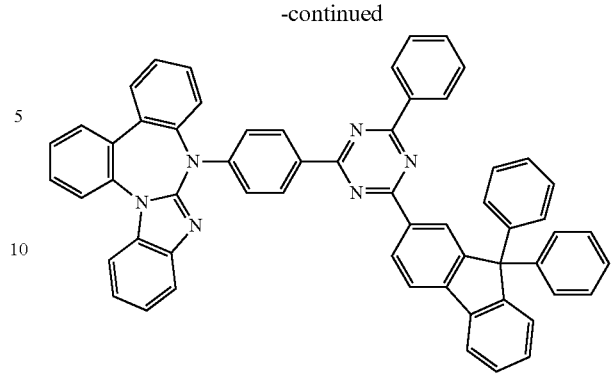
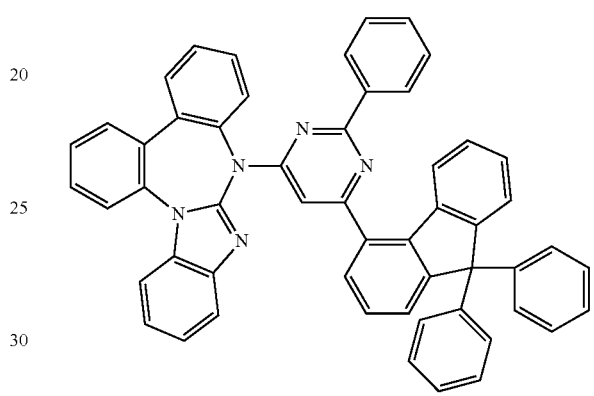
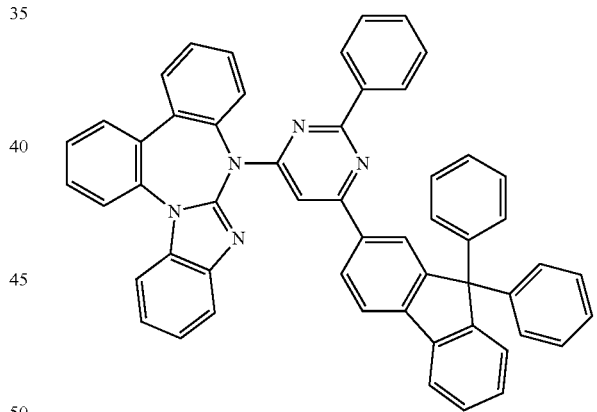
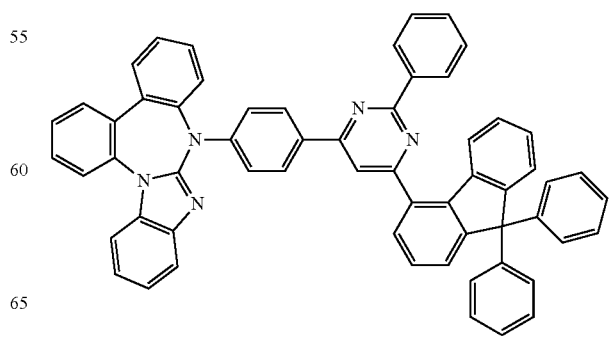

97
-continued
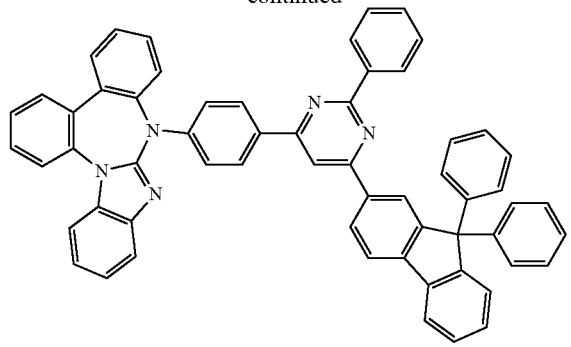
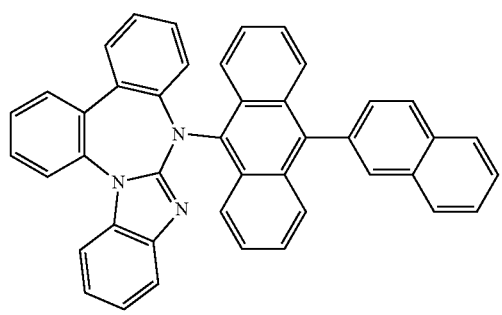
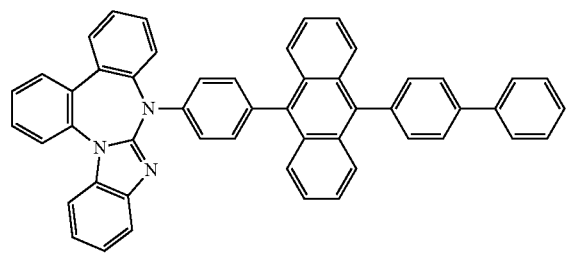
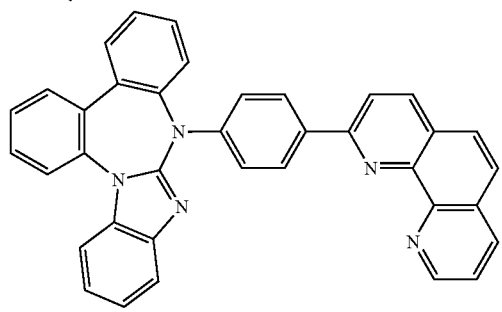
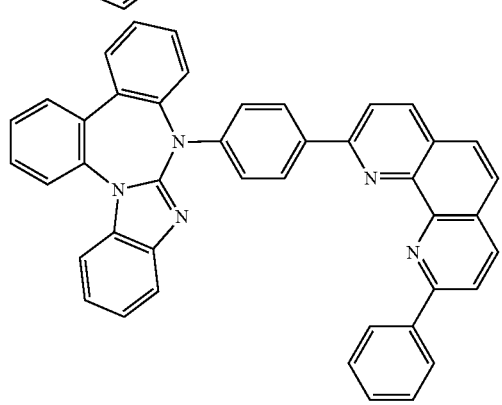
98
-continued
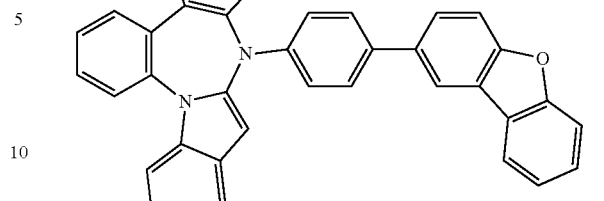
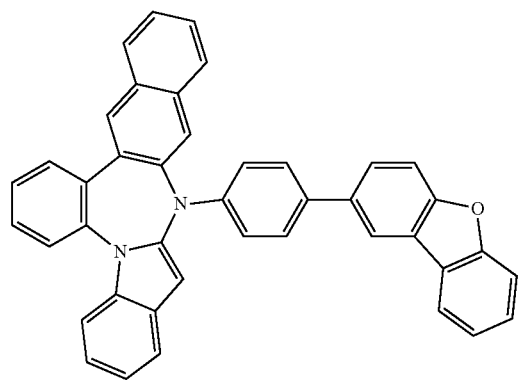
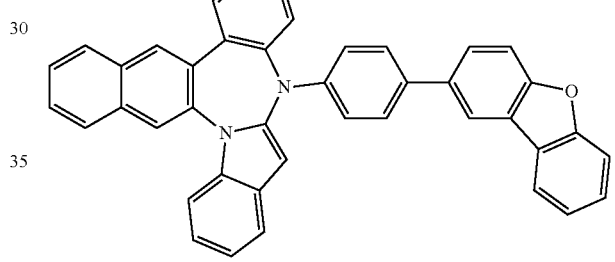
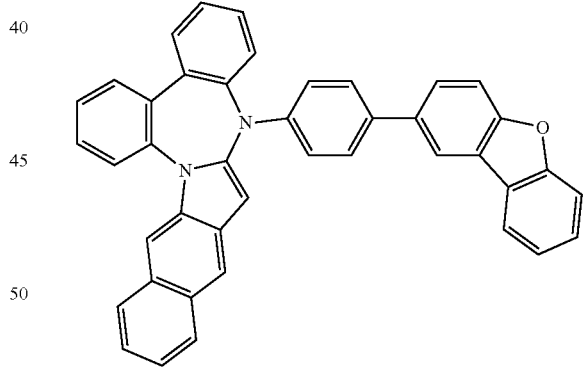
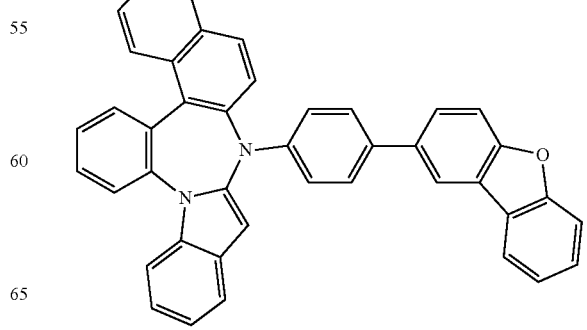

99
-continued

100
-continued

101
-continued
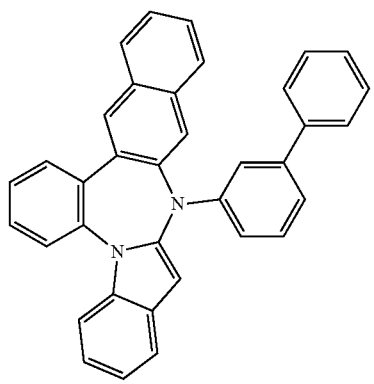
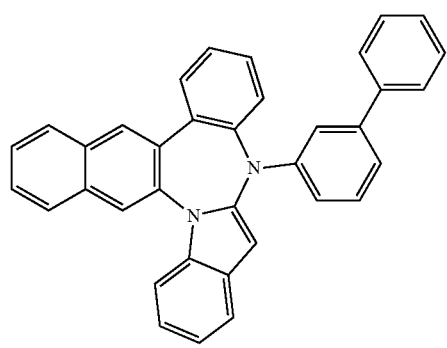
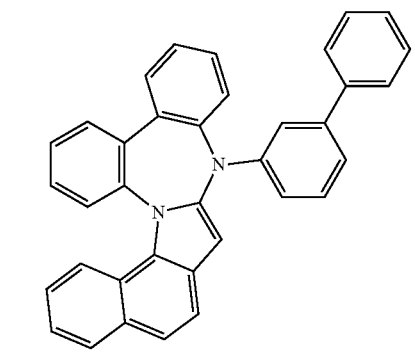
102
-continued
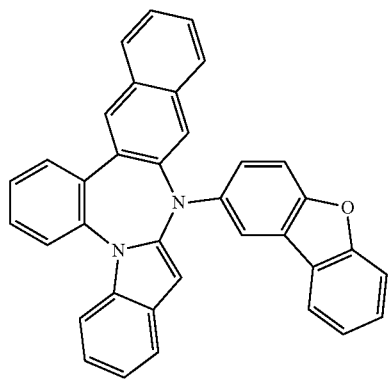
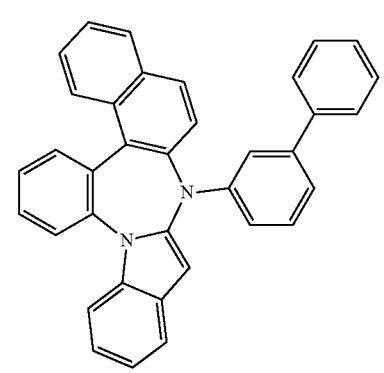
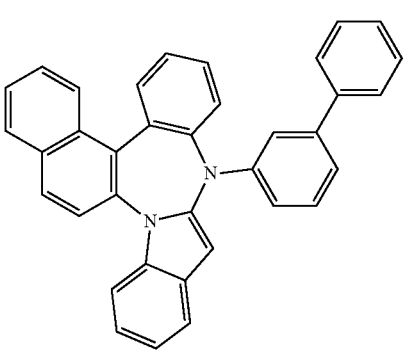
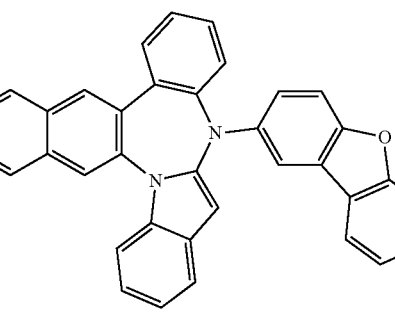

103
-continued
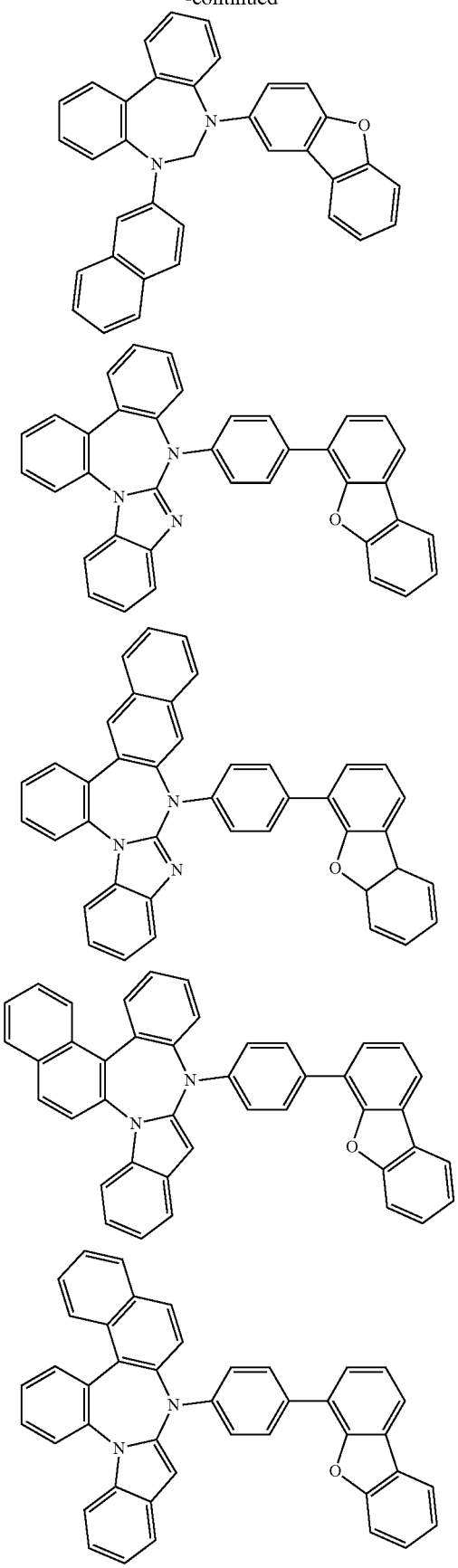
104
-continued
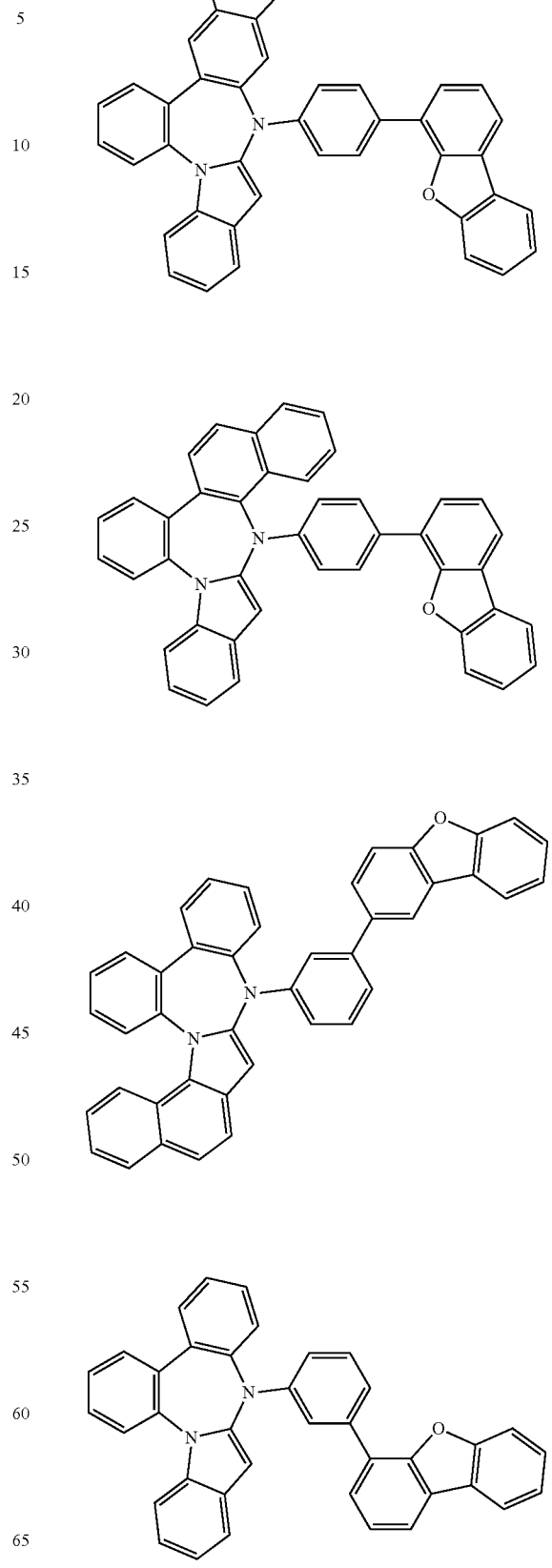

105
-continued
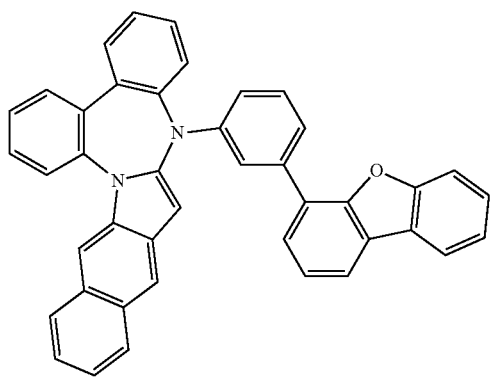
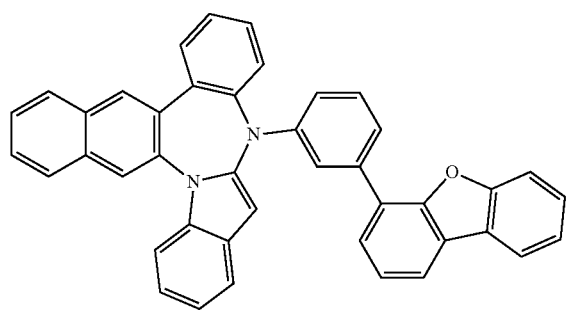
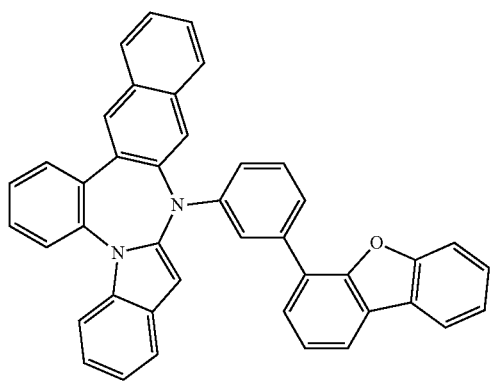
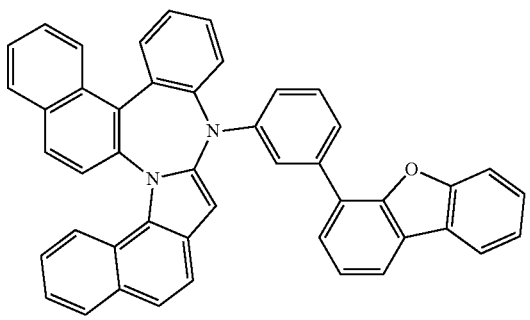
106
-continued
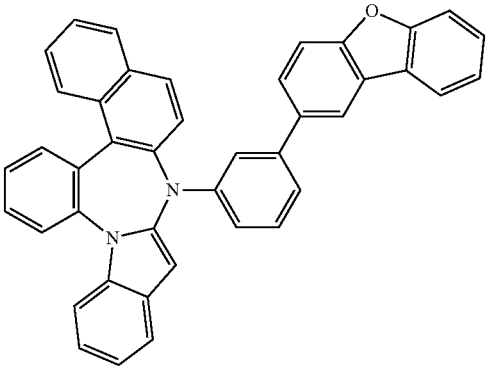
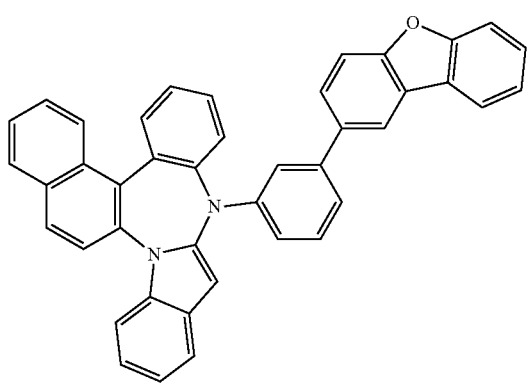
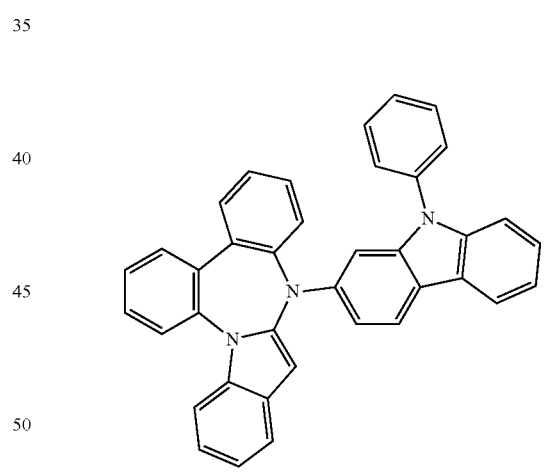
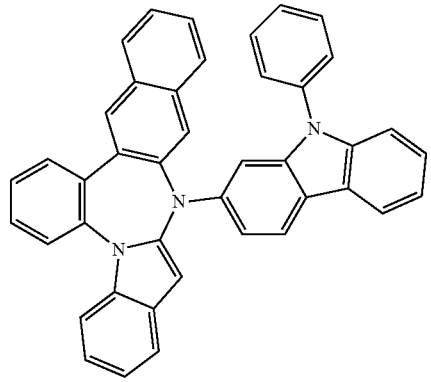

107
-continued
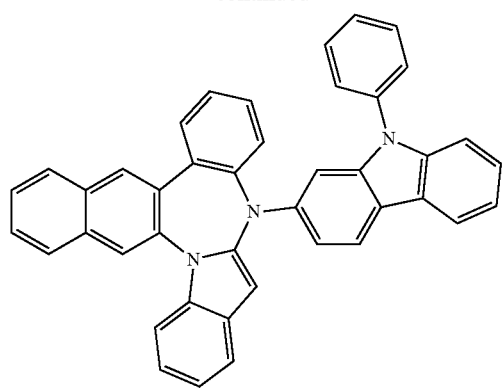
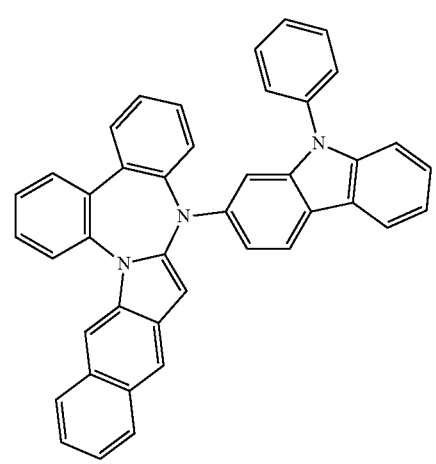
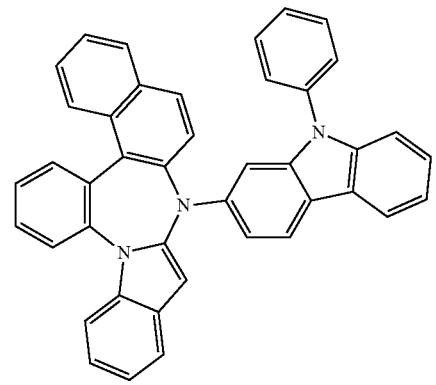
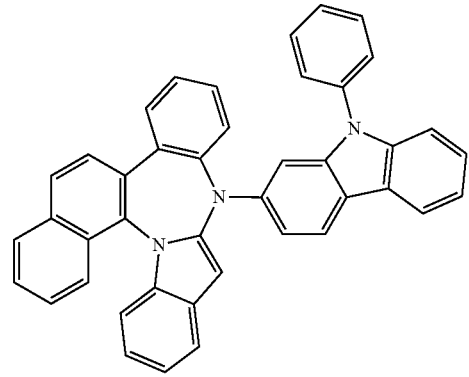
108
-continued
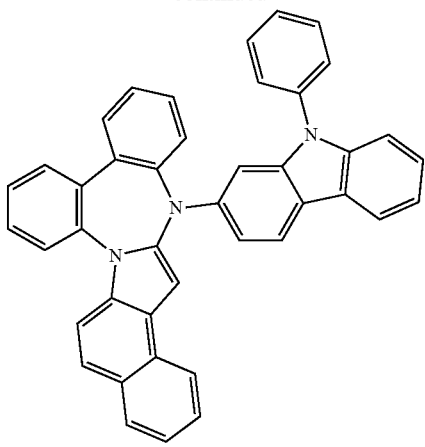
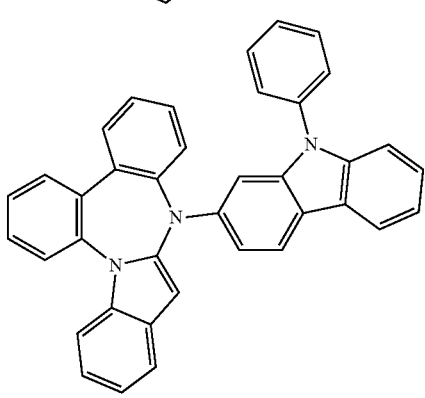
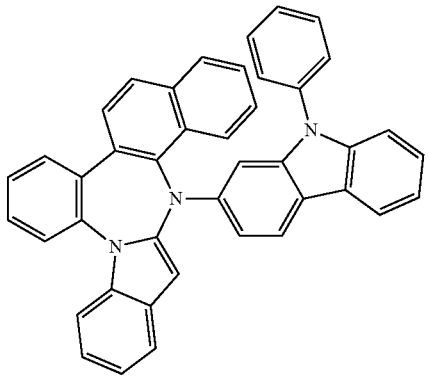
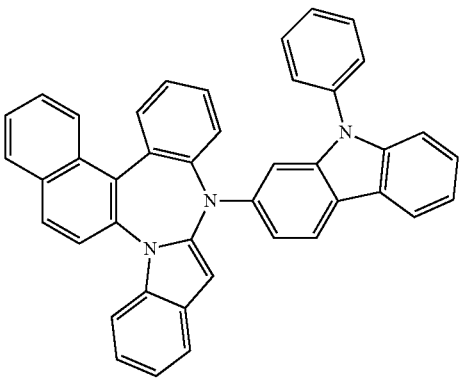

-continued
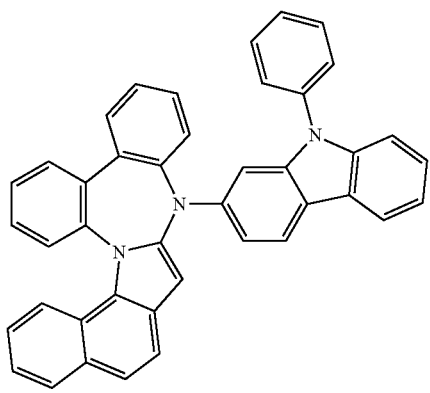
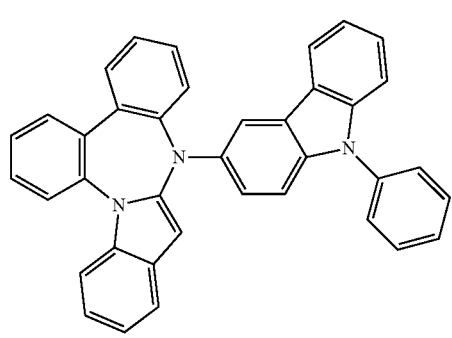
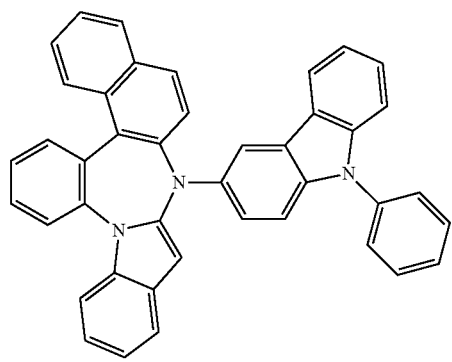
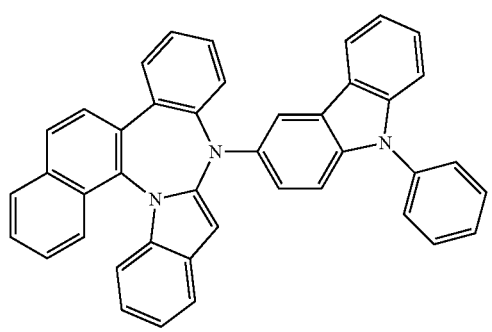
-continued
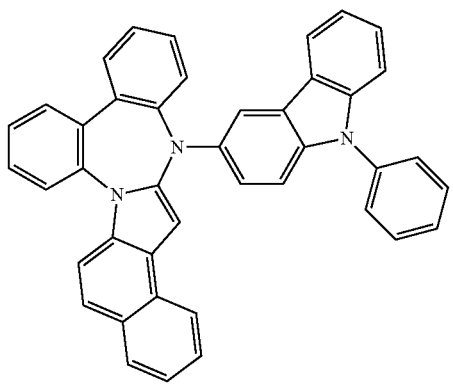
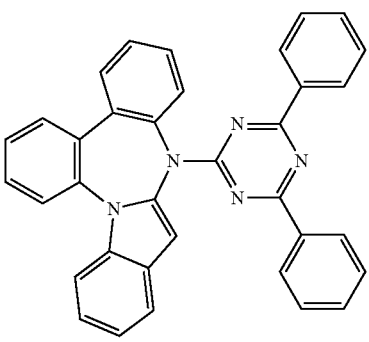
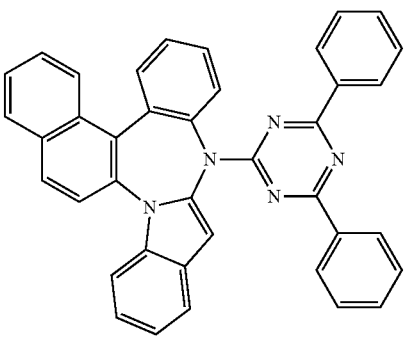
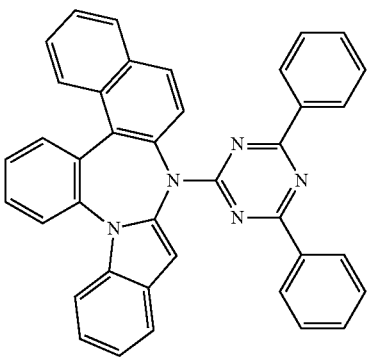

111
-continued
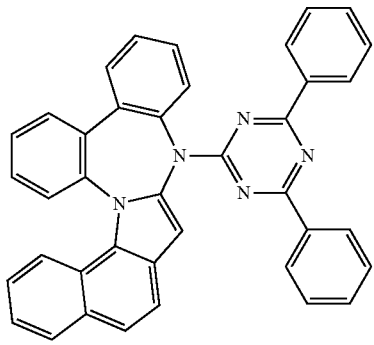
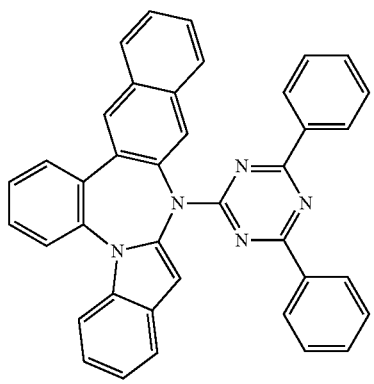
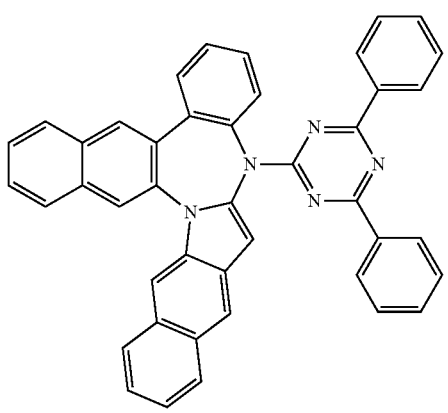
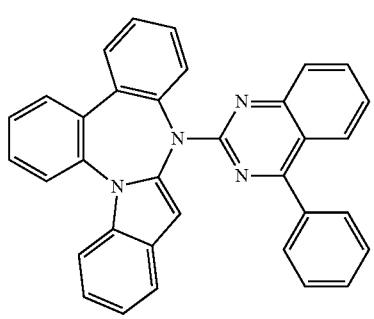
112
-continued
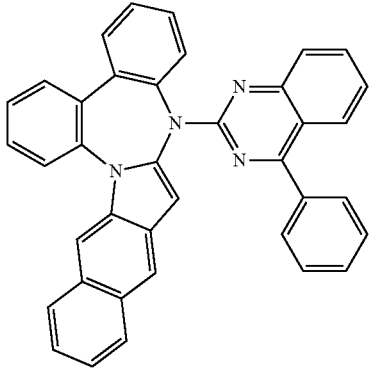
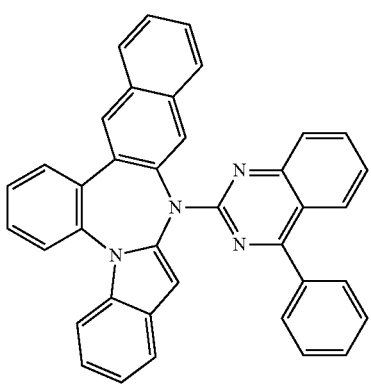
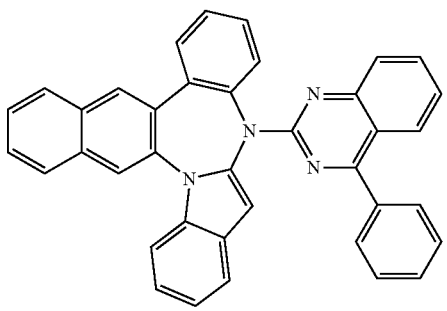
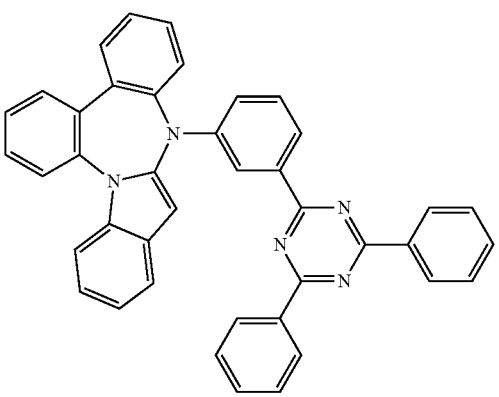

113
-continued
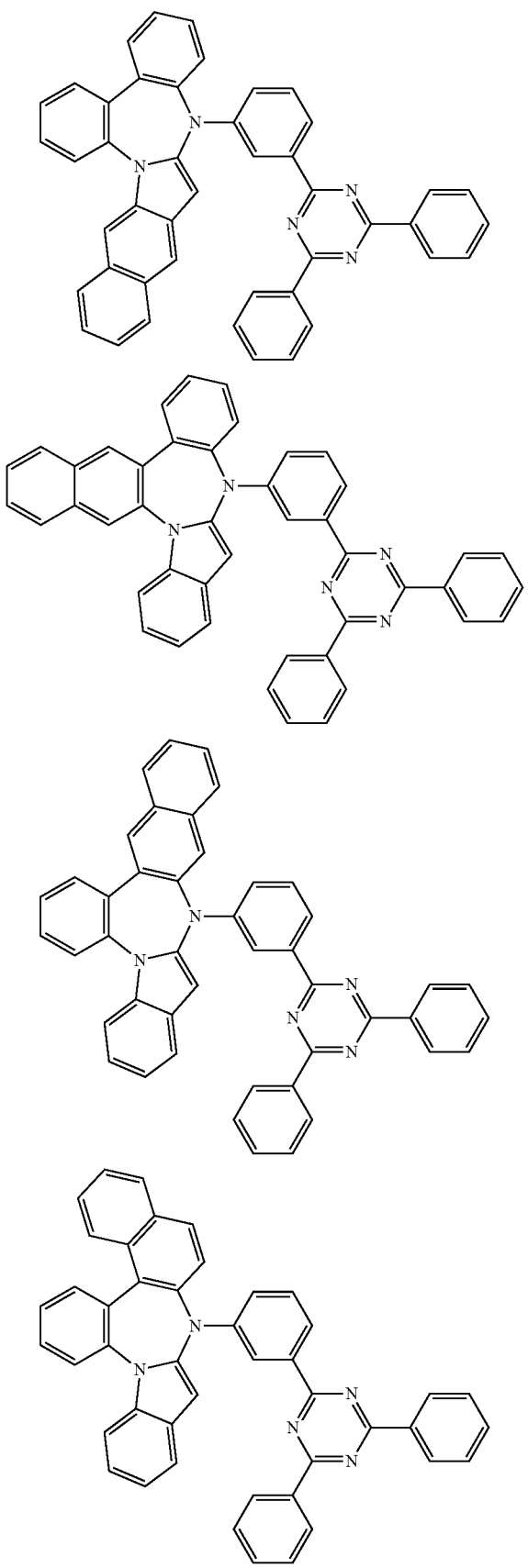
114
-continued
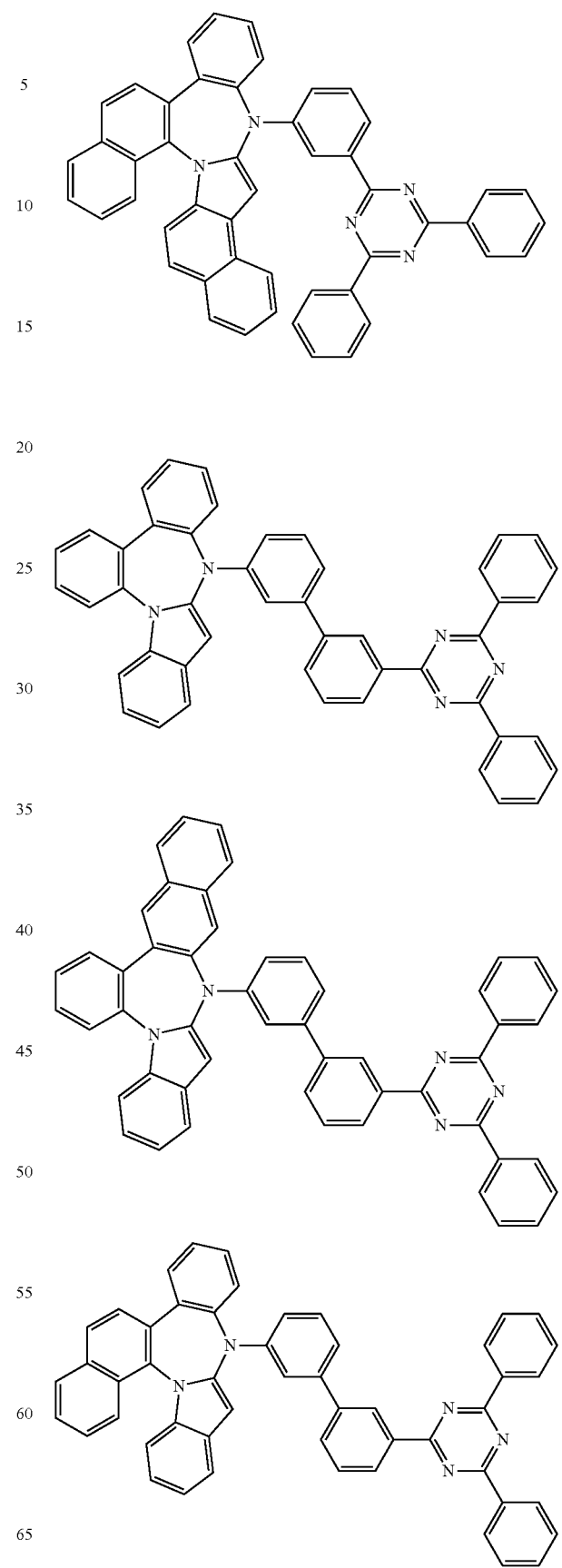

115
-continued
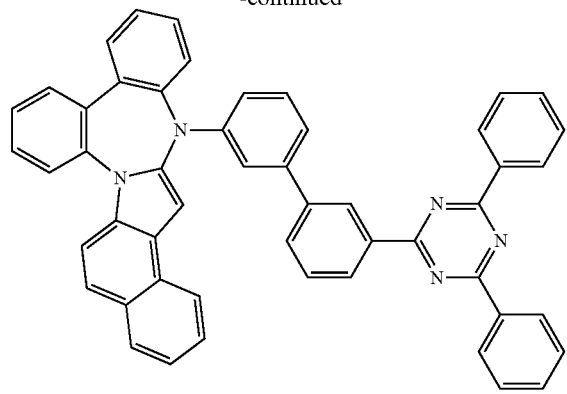
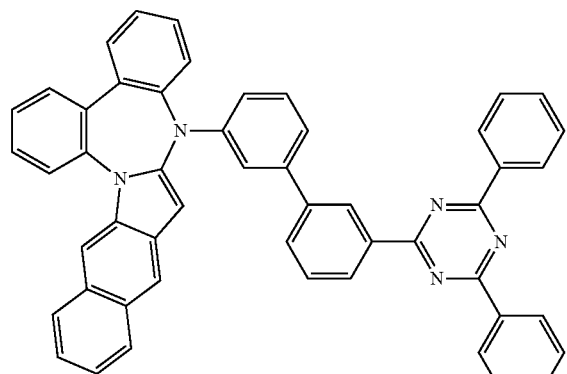
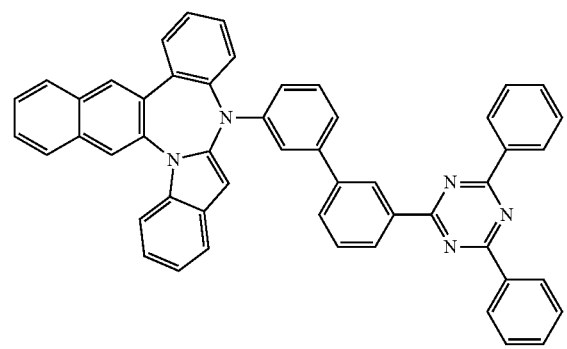
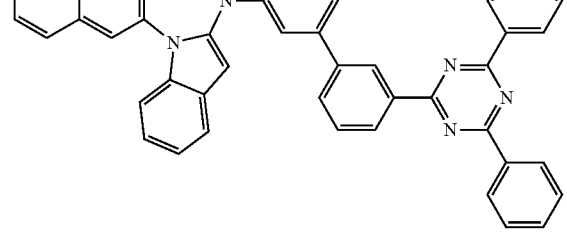
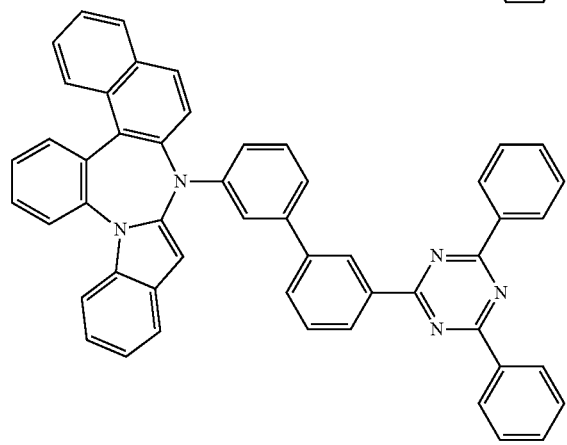
116
-continued
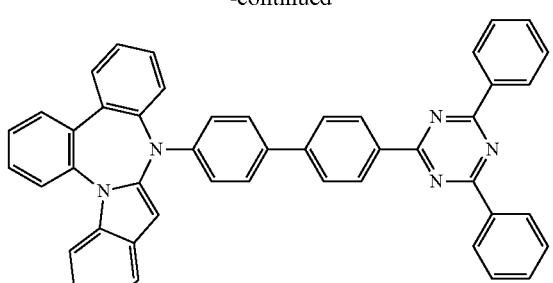
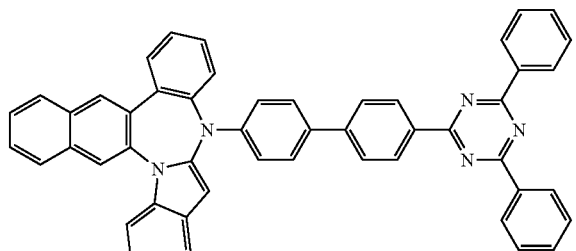
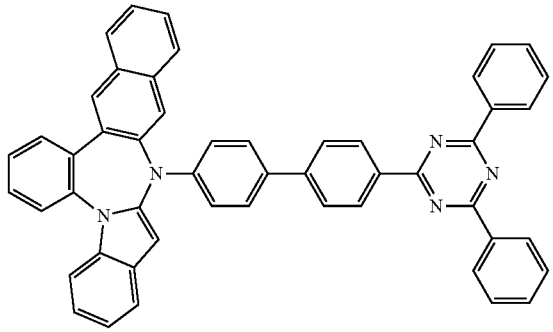
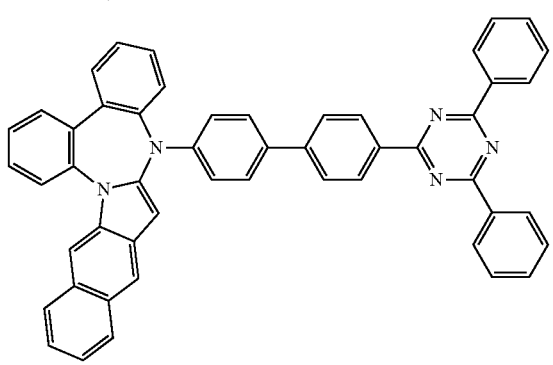
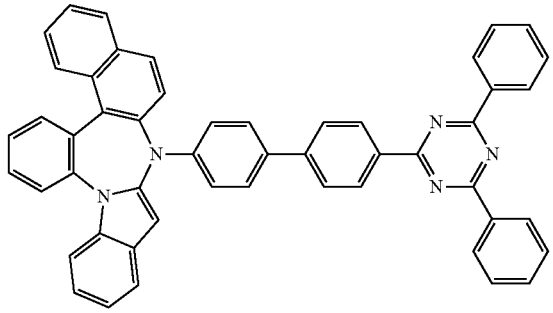

117
-continued
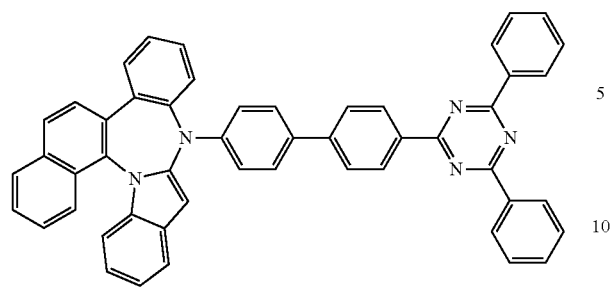
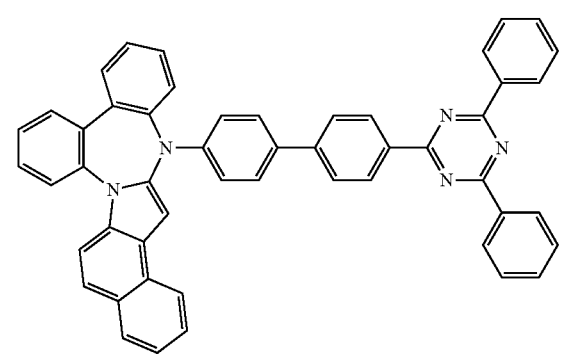
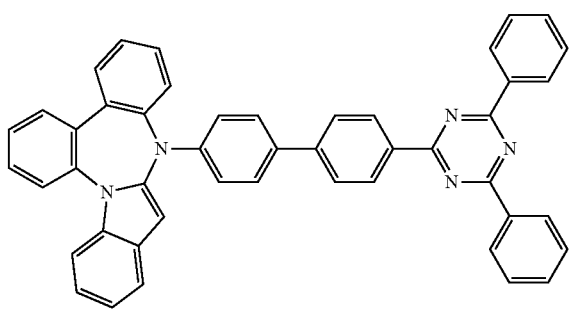
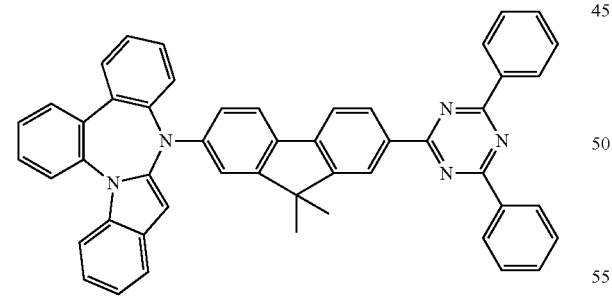
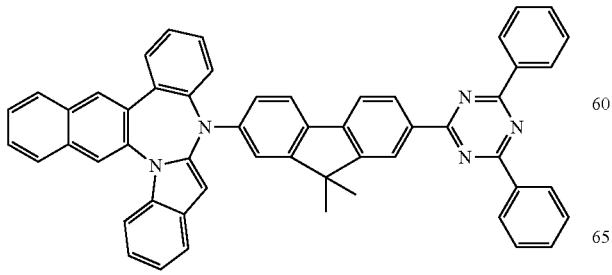
118
-continued
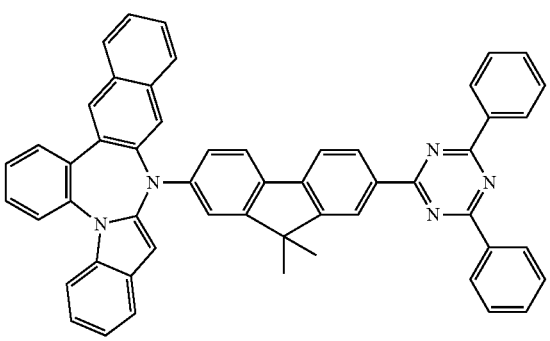
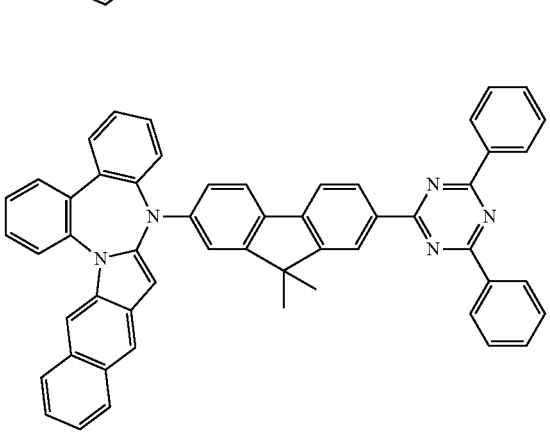
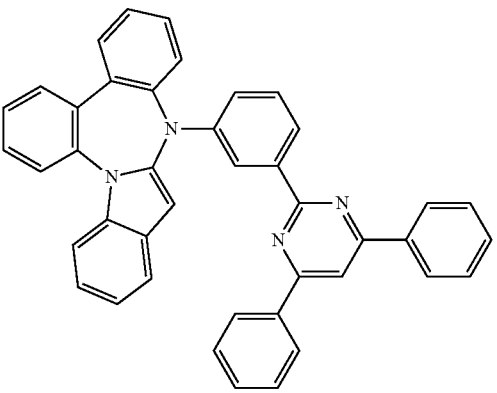
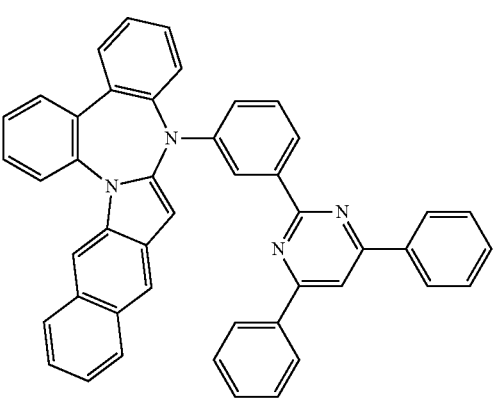

119
-continued
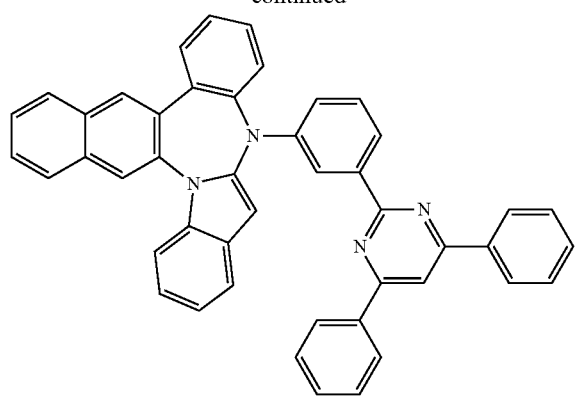
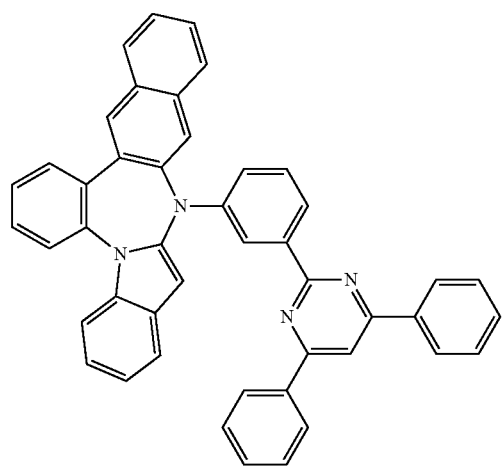
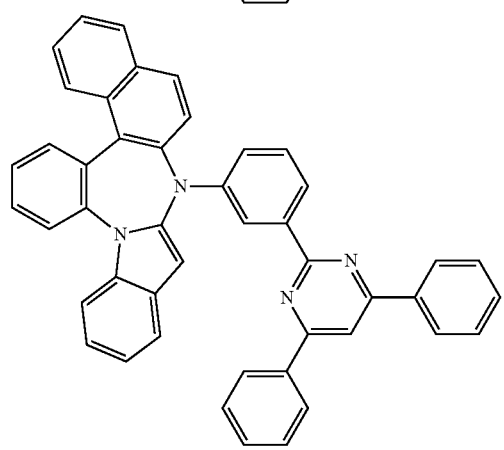
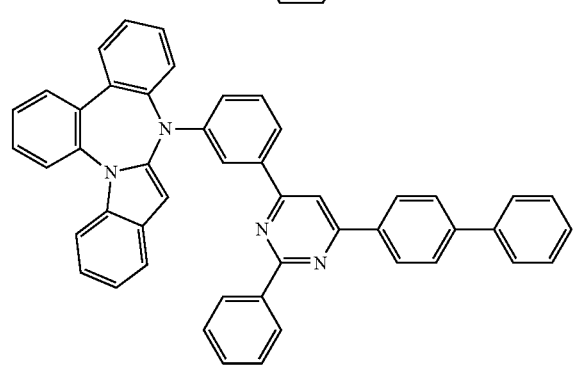
120
-continued
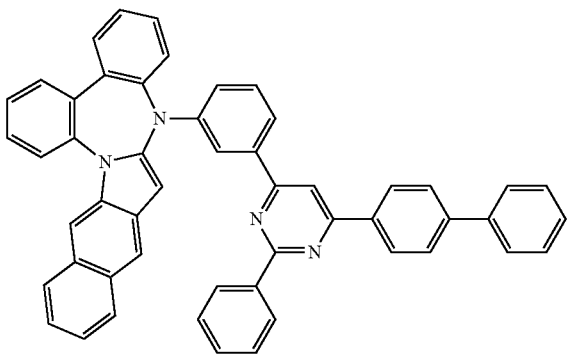
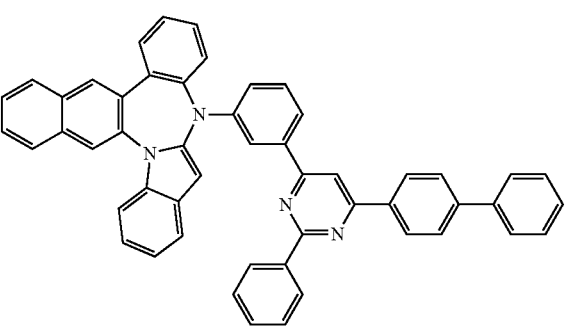
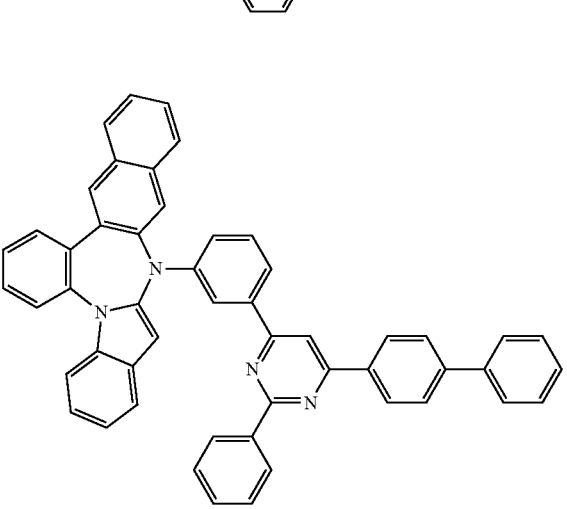
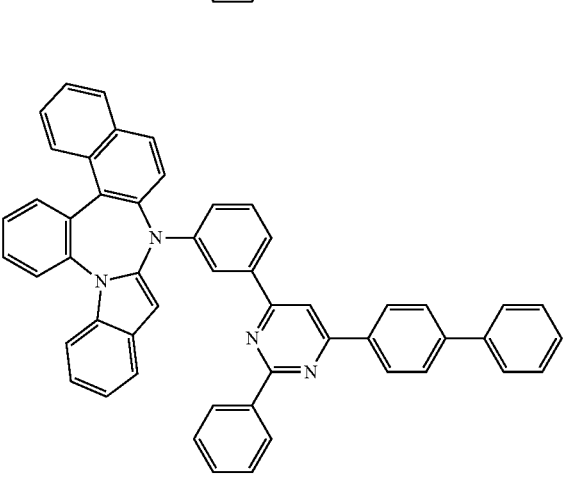

121
-continued
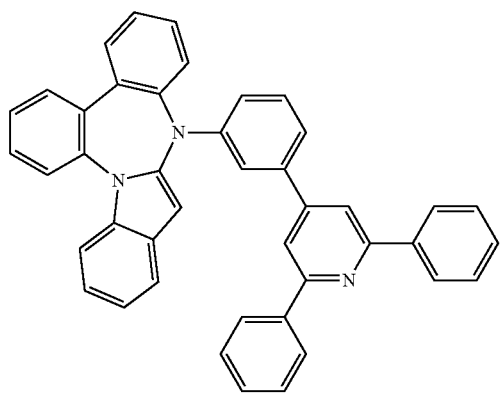
122
-continued
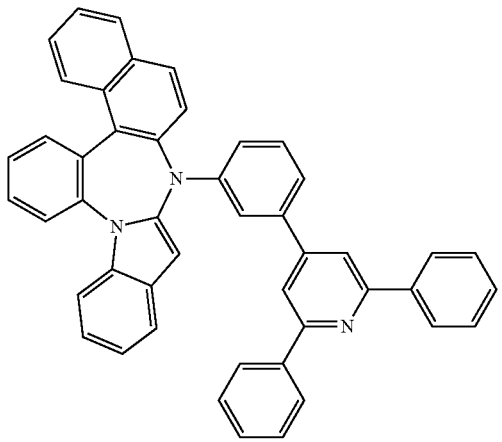
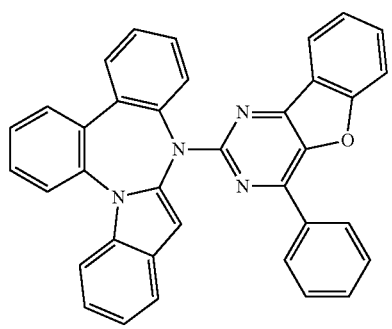
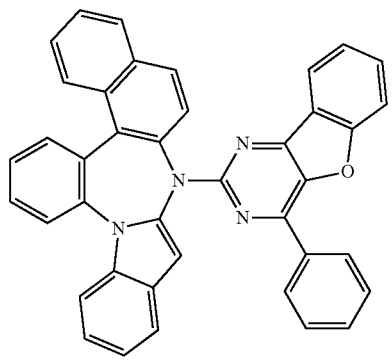

123
-continued
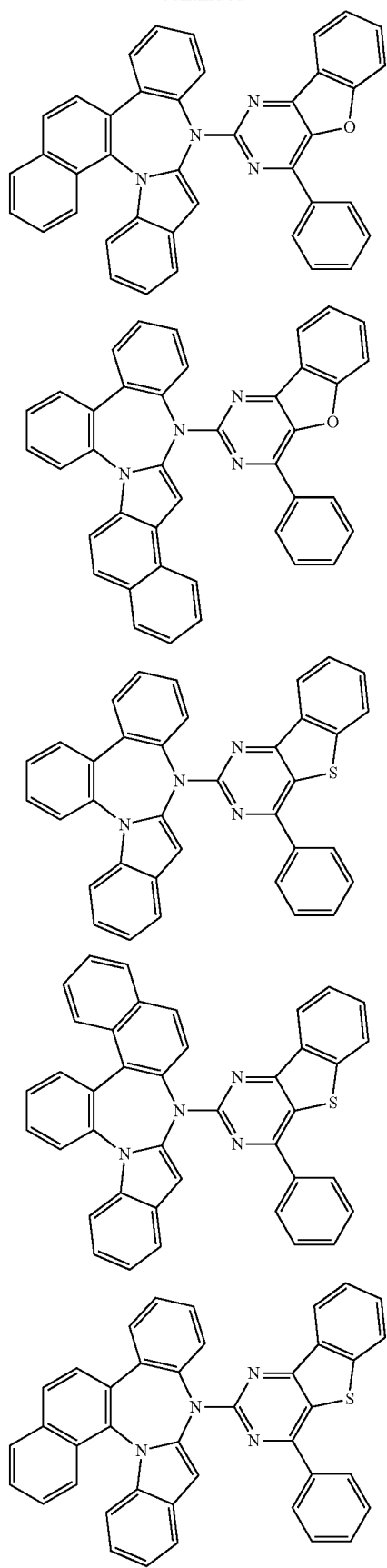
124
-continued
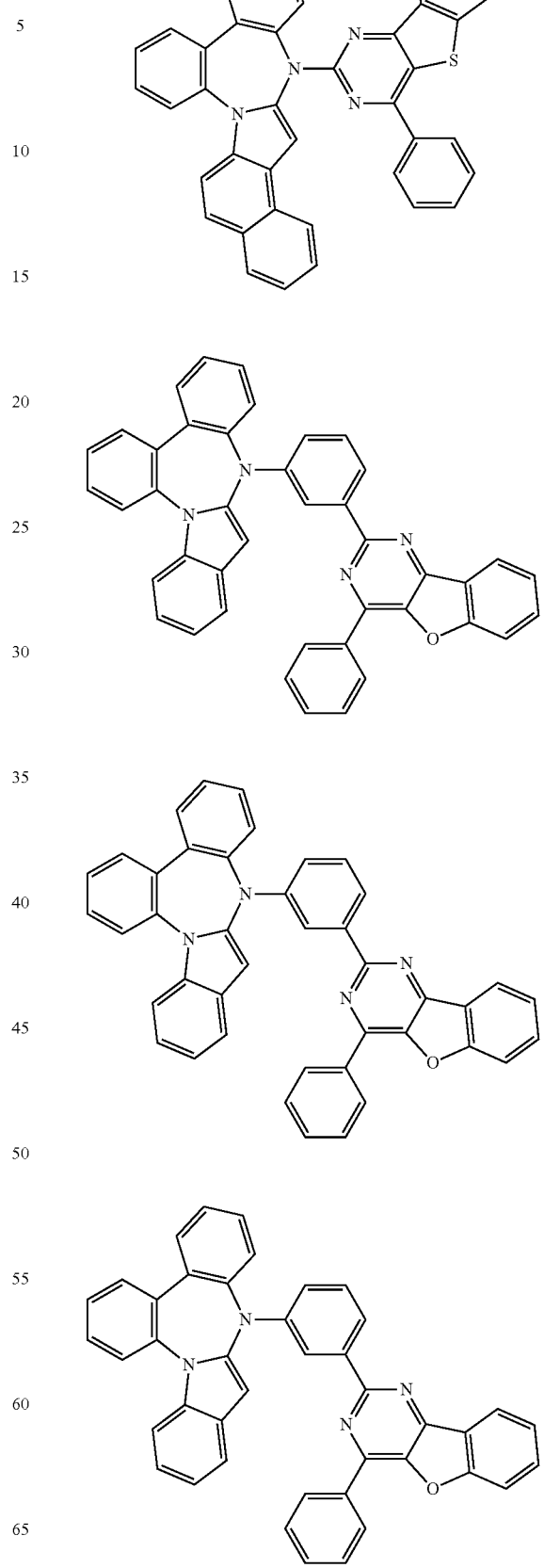

125
-continued
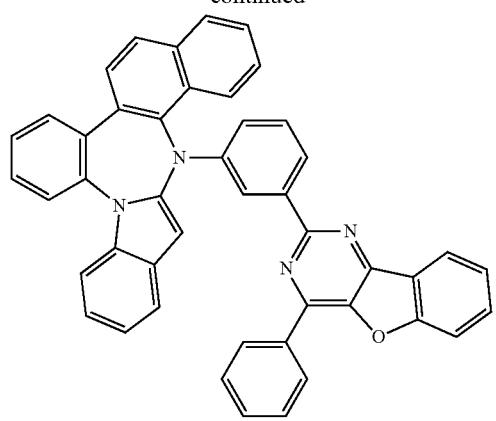
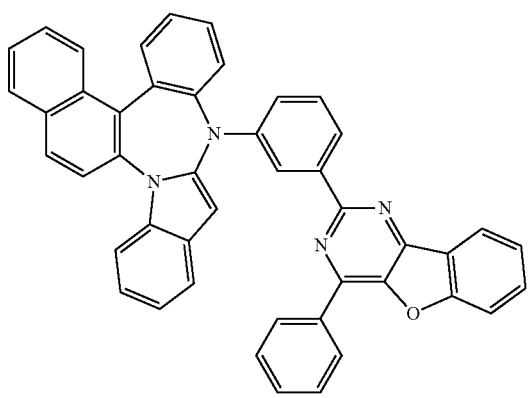
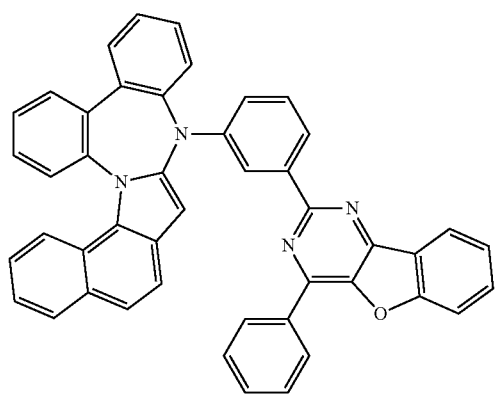
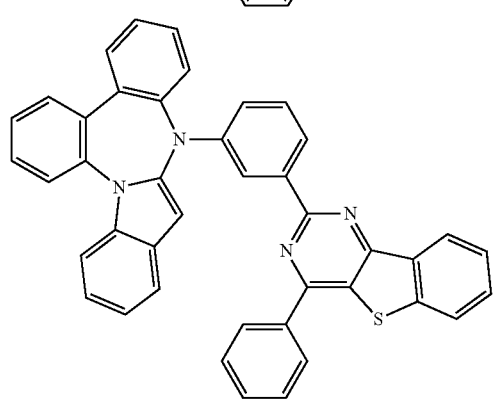
126
-continued
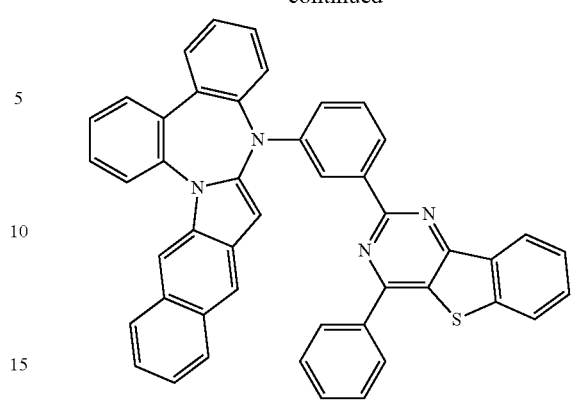
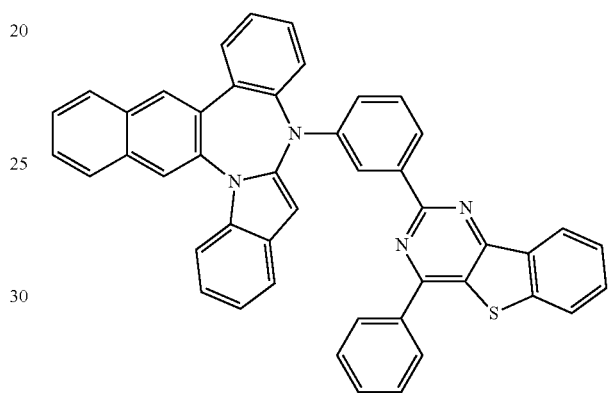
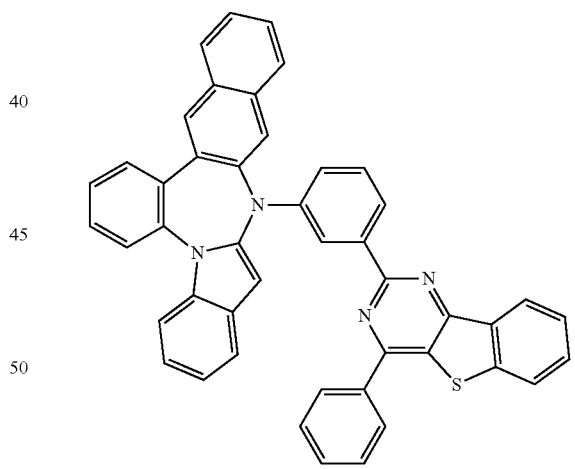
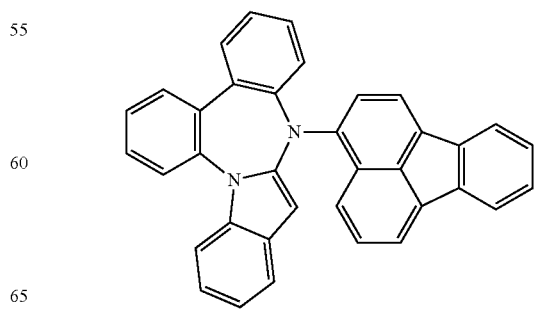

127
-continued
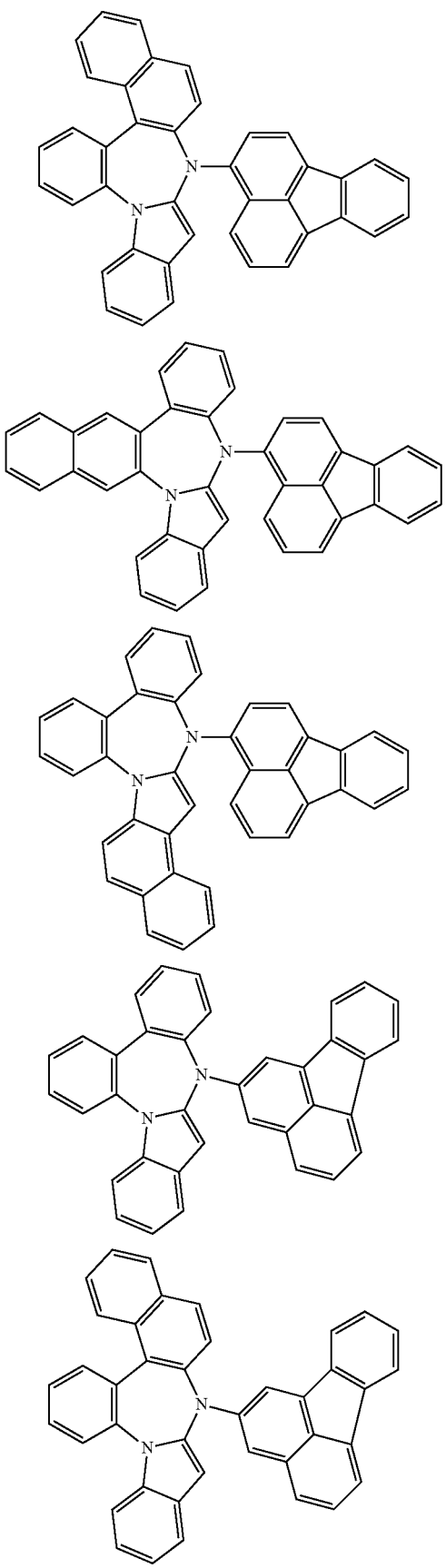
128
-continued
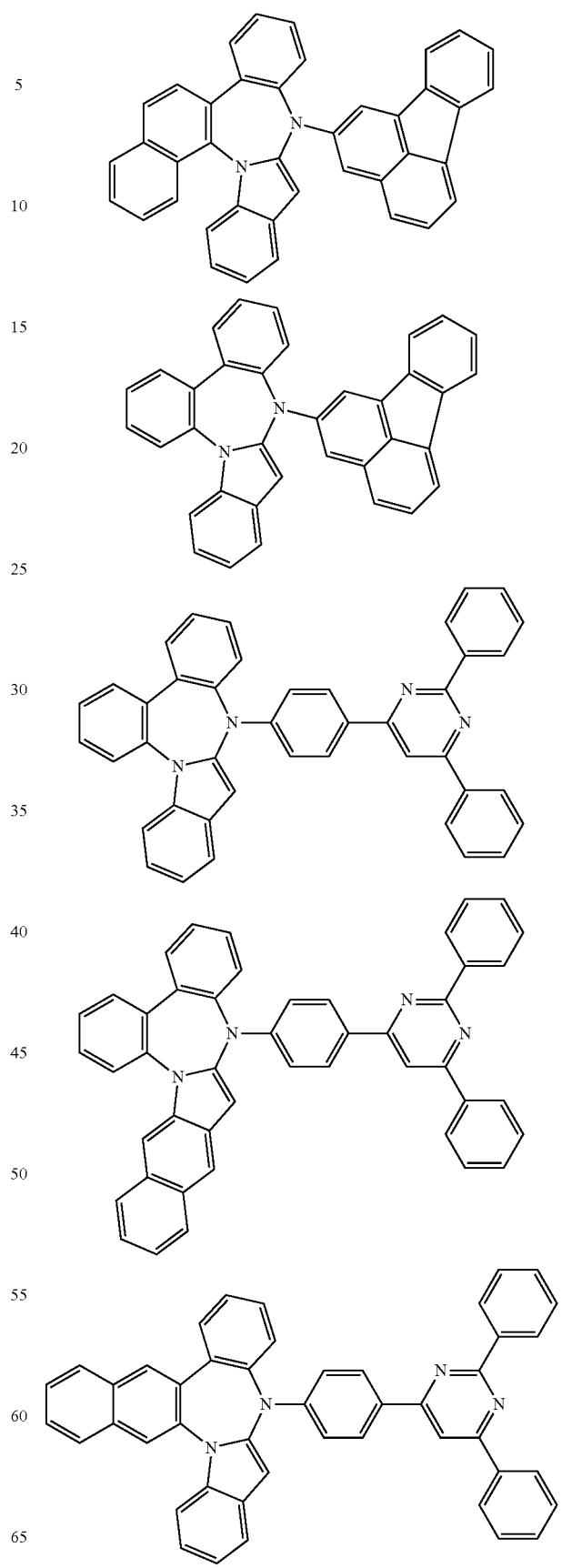

129
-continued
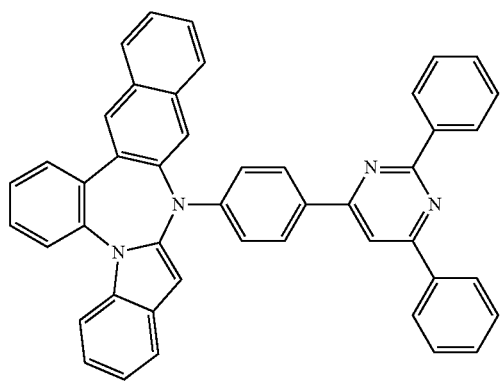
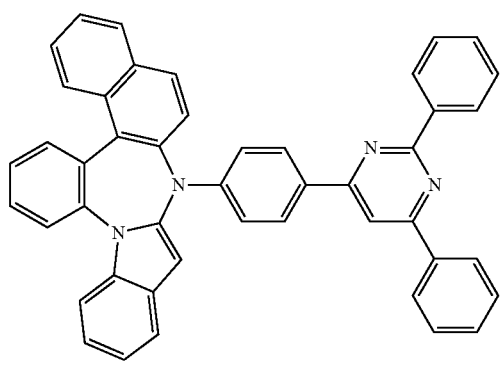
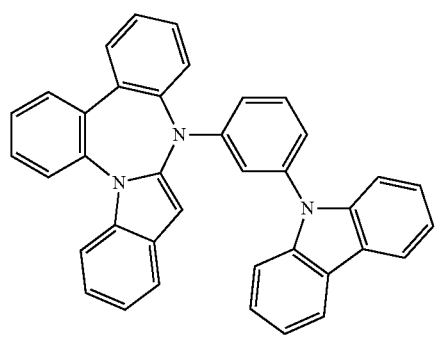
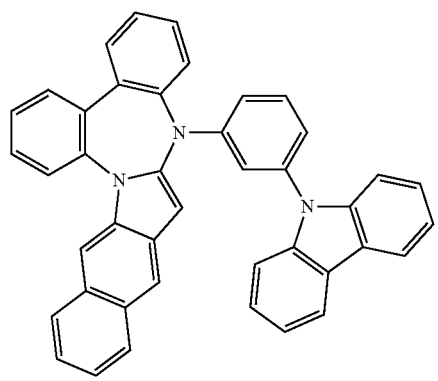
130
-continued
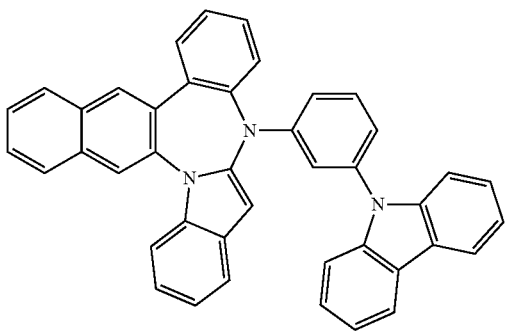
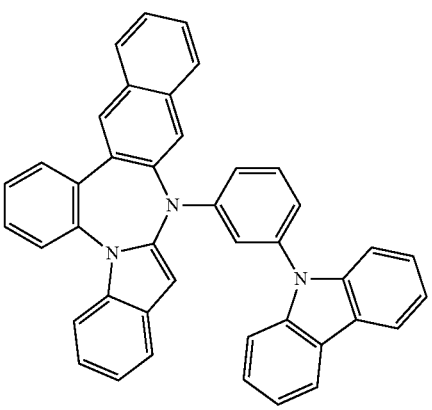
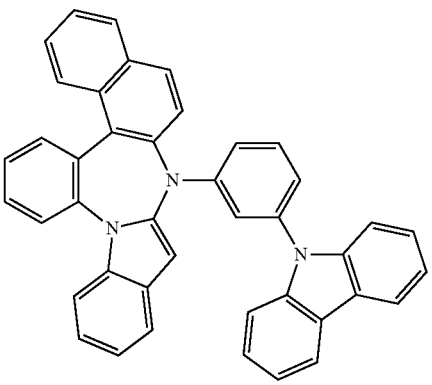
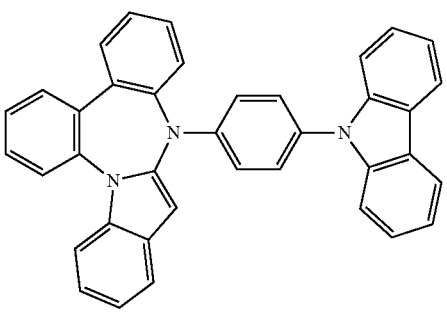

131
-continued
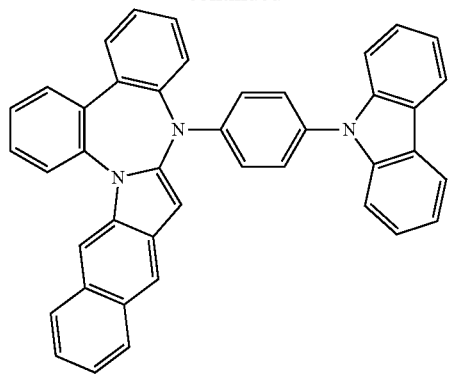
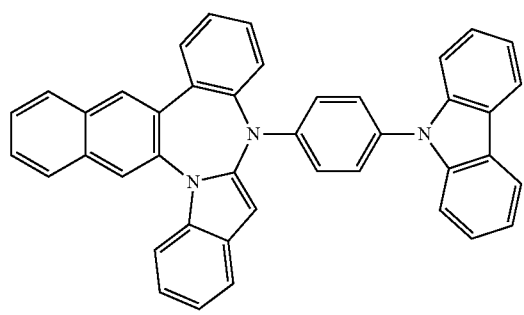
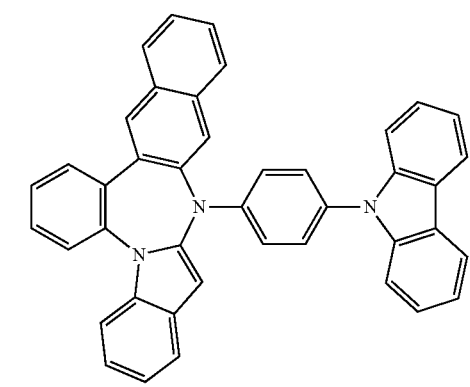
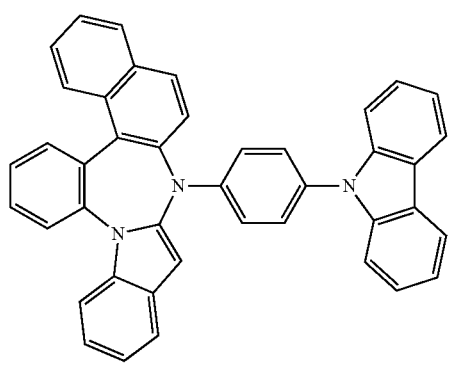
132
-continued
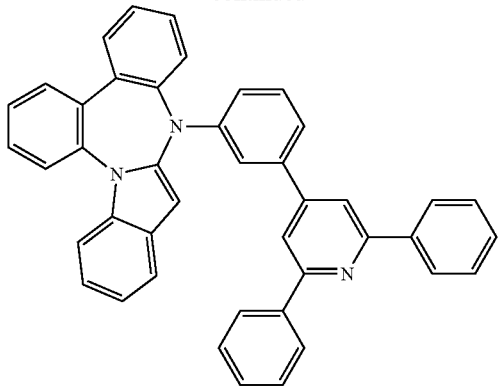
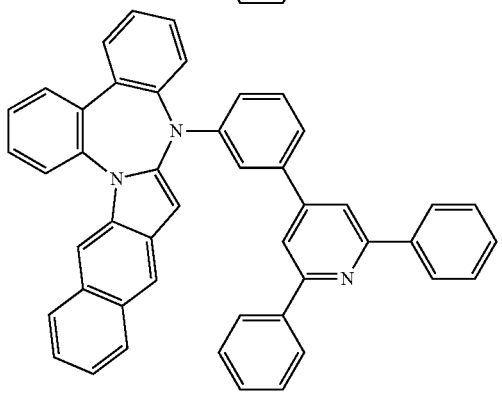
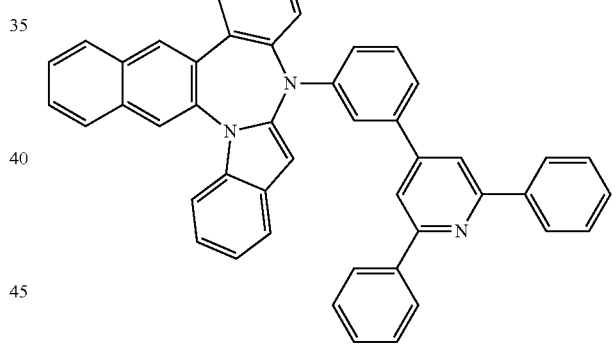
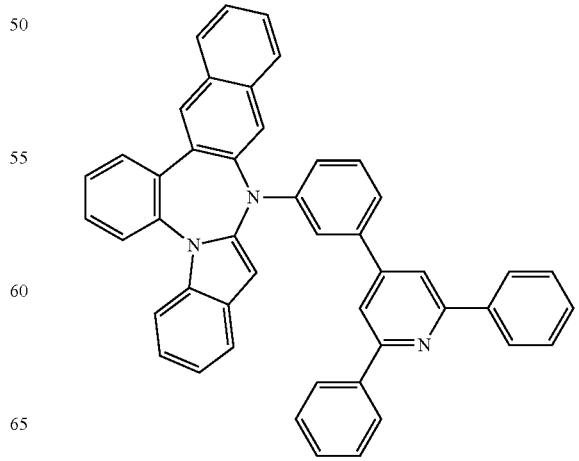

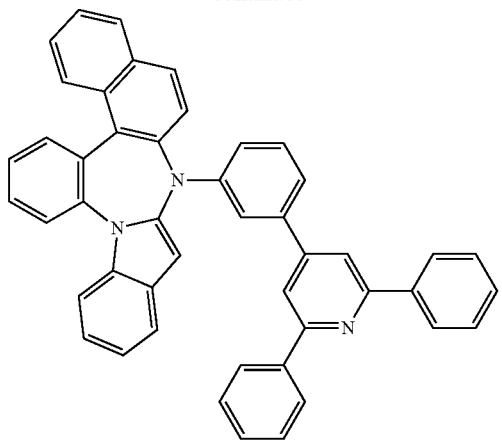
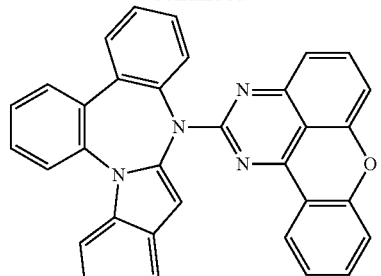
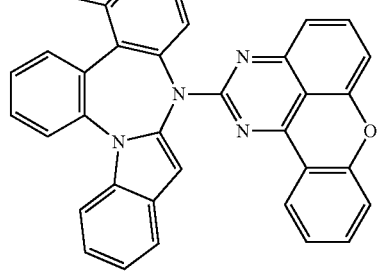
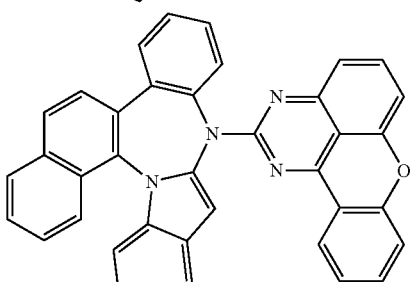
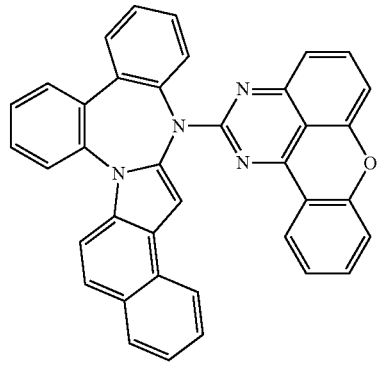
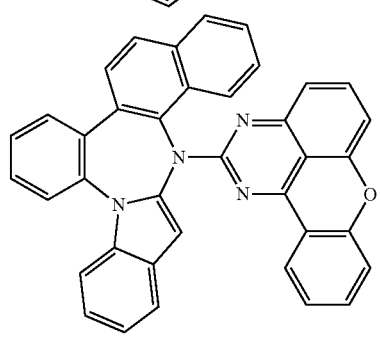

135
-continued
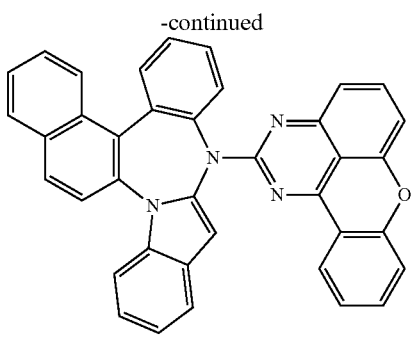
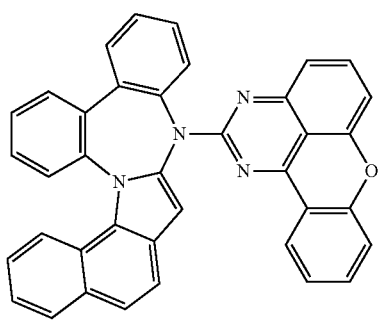
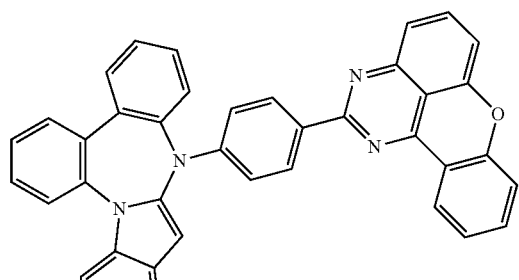
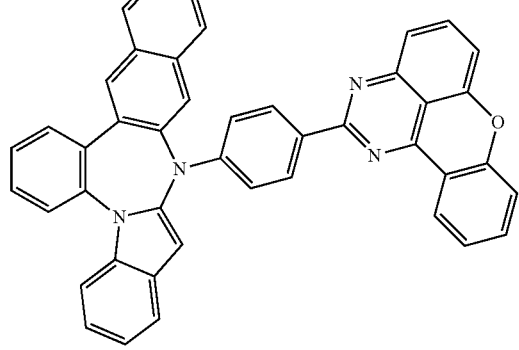
136
-continued
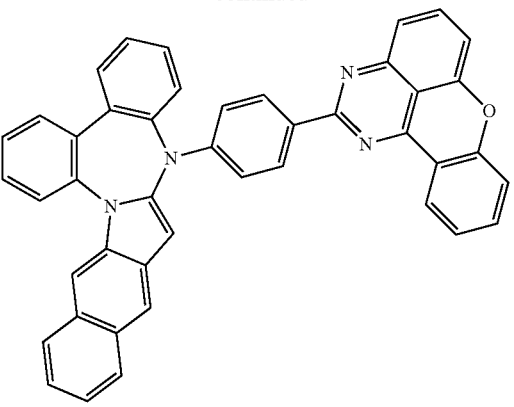
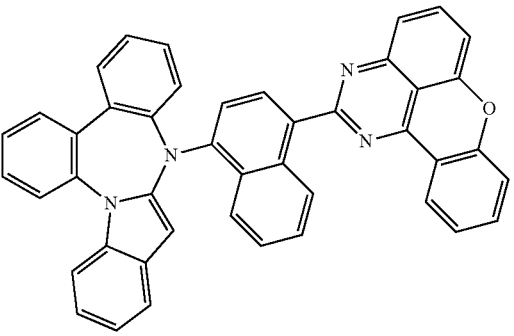
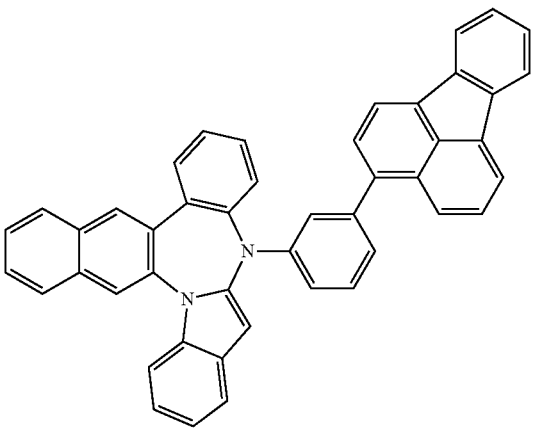
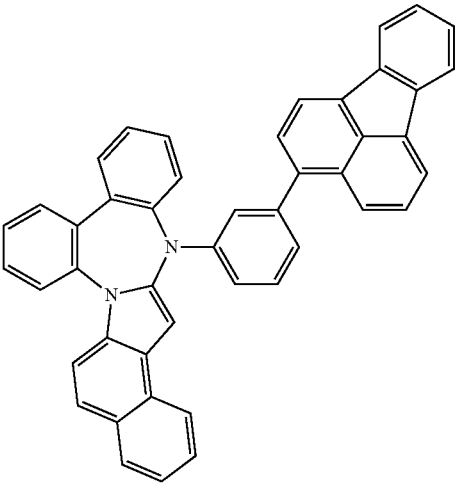

137
-continued
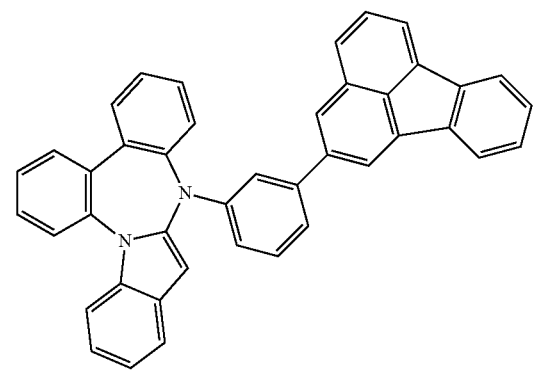
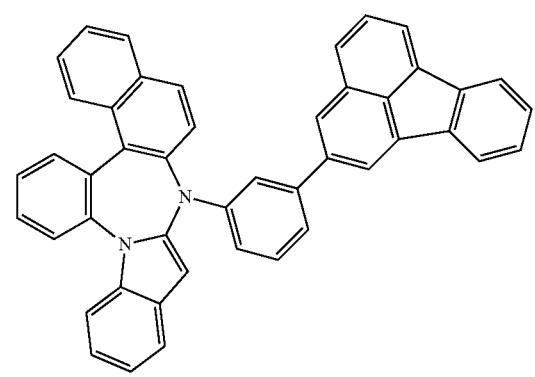
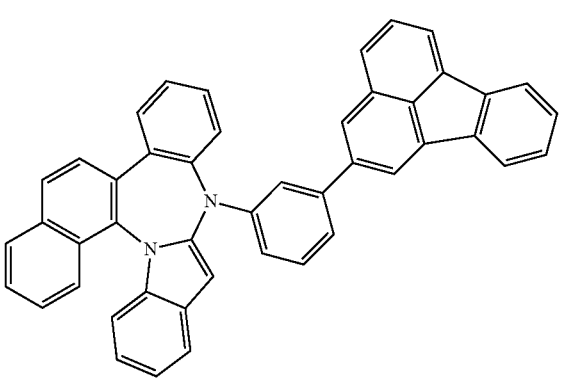
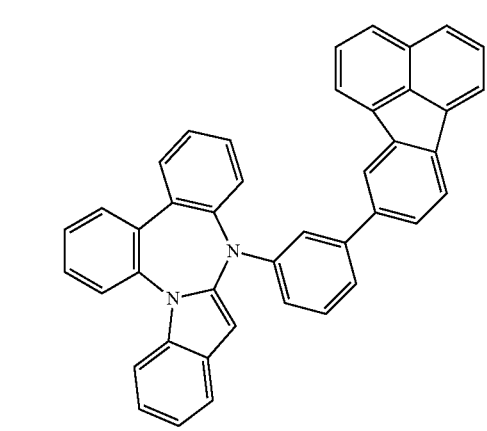
138
-continued
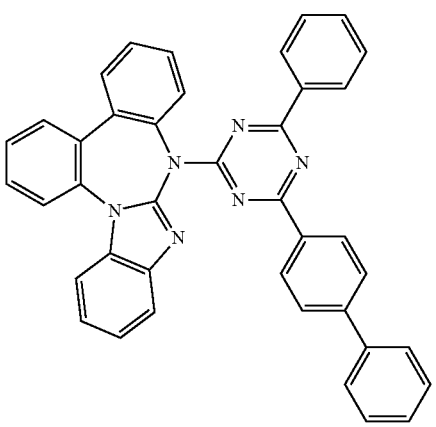
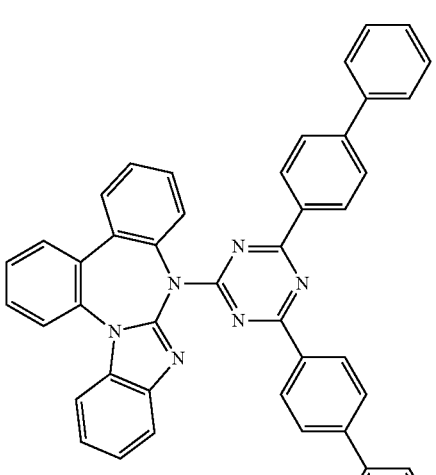
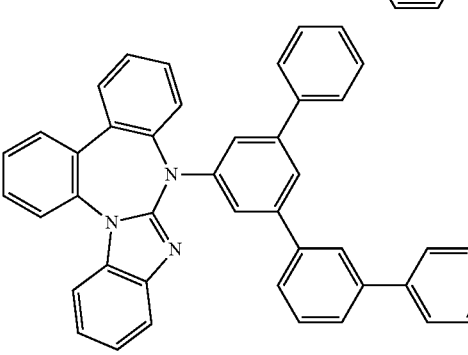
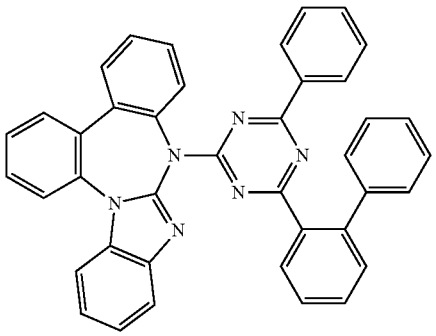

139
-continued
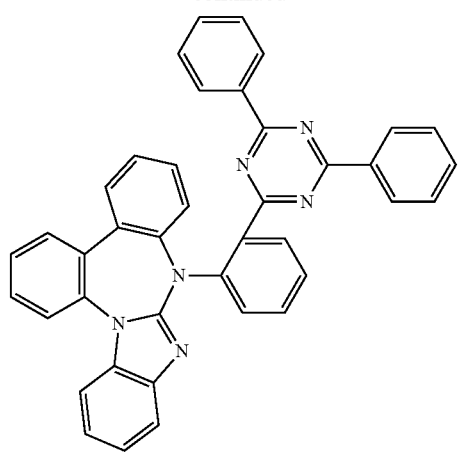
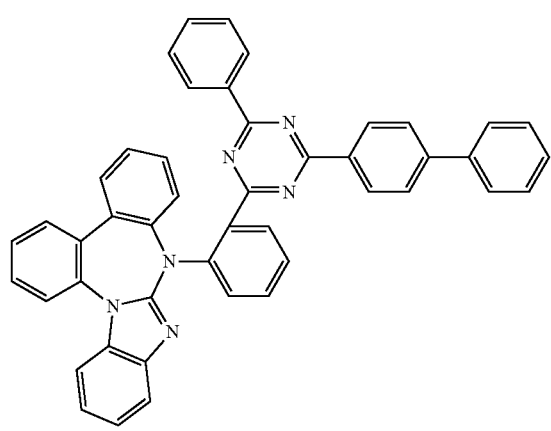
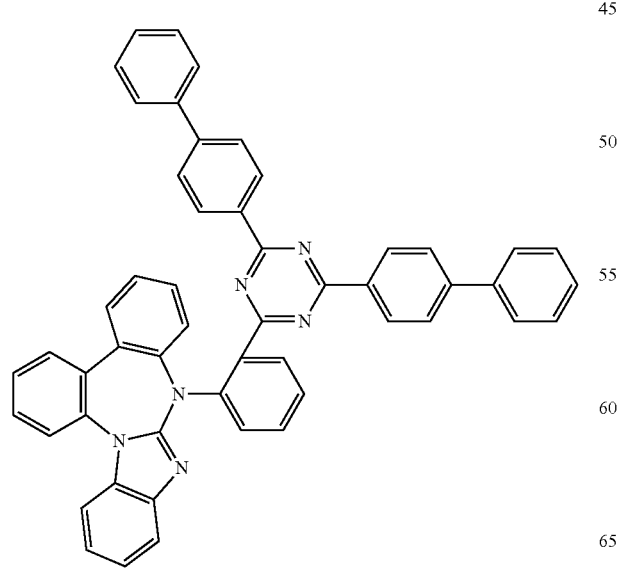
140
-continued
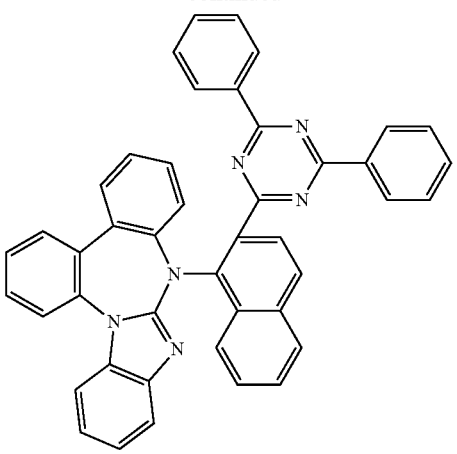
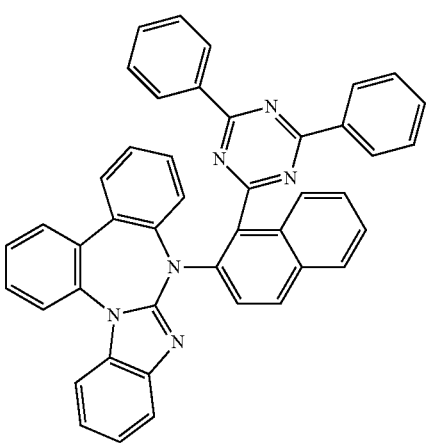
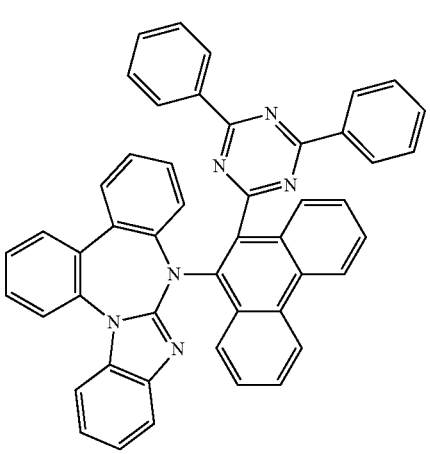

141
-continued
142
-continued
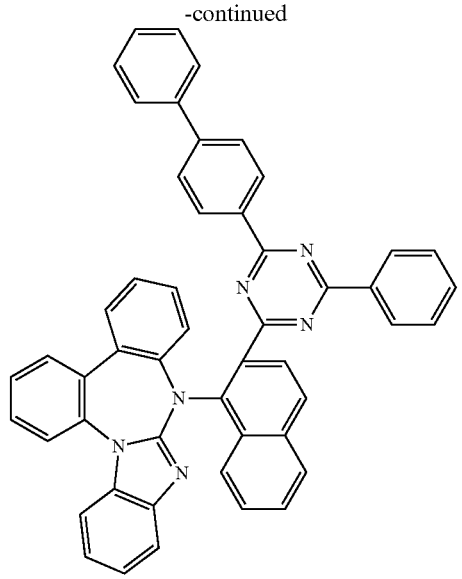
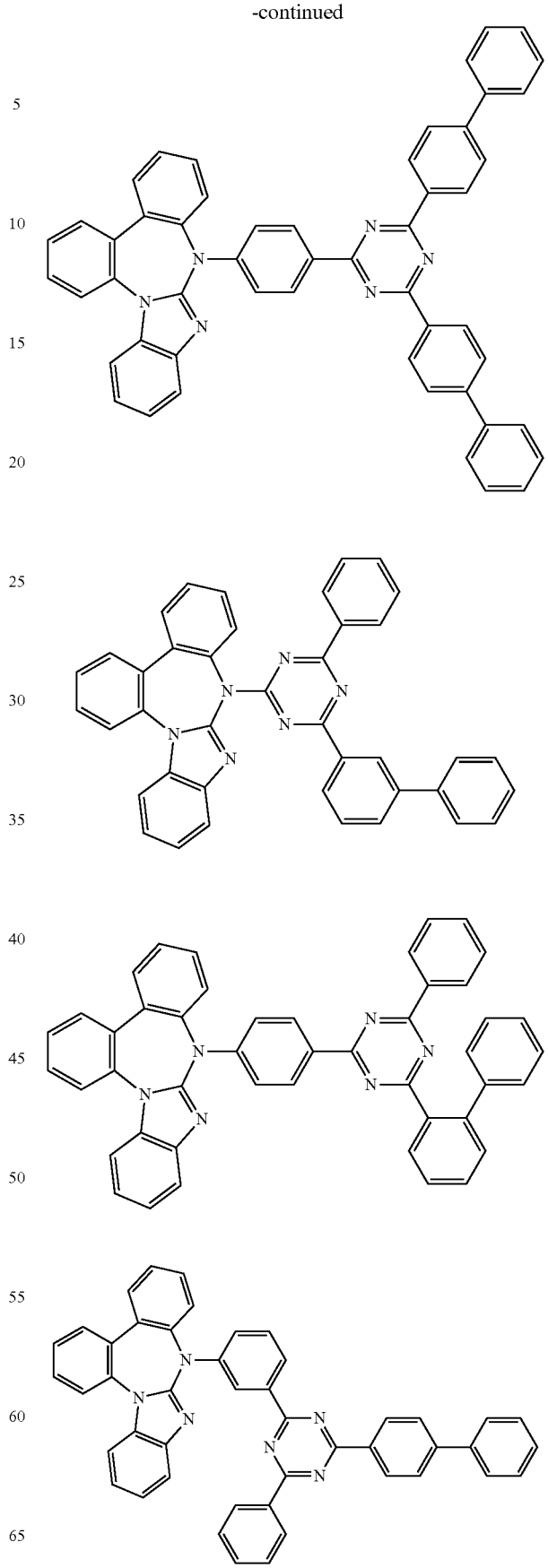

143
-continued
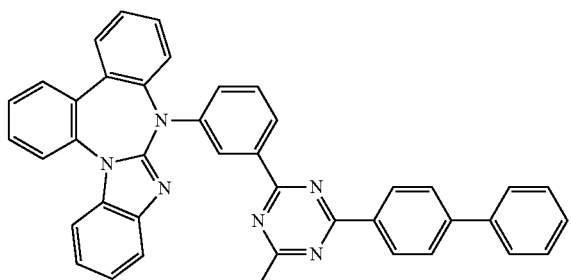
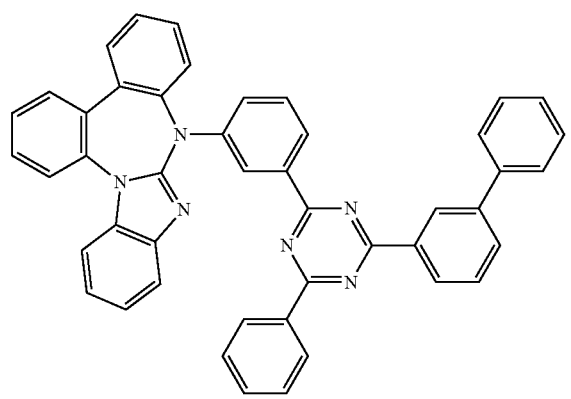
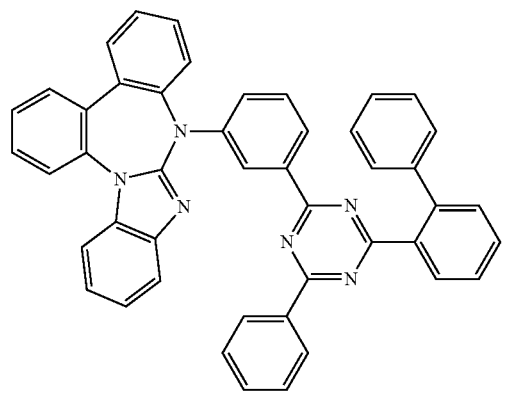
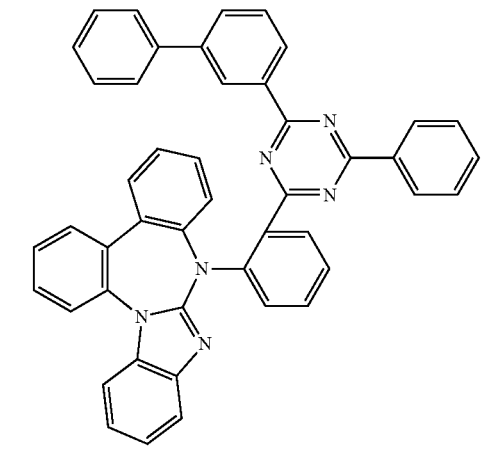
144
-continued
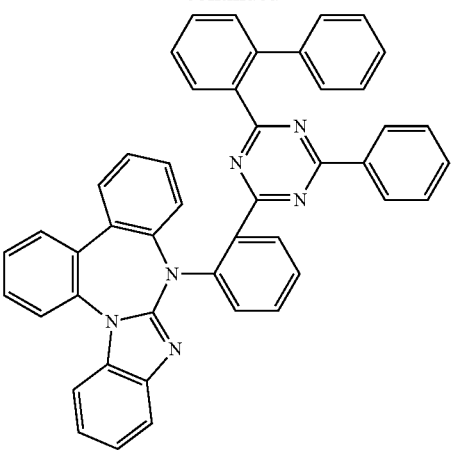
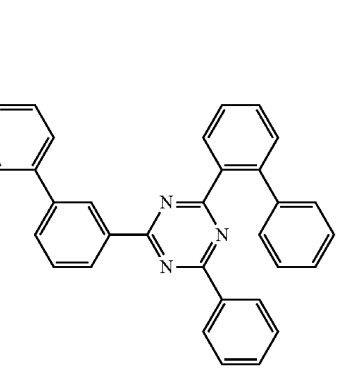
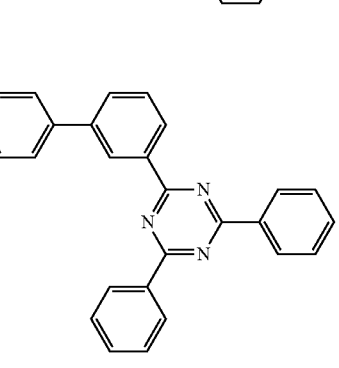
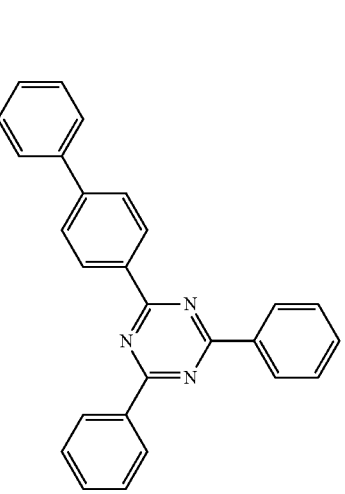

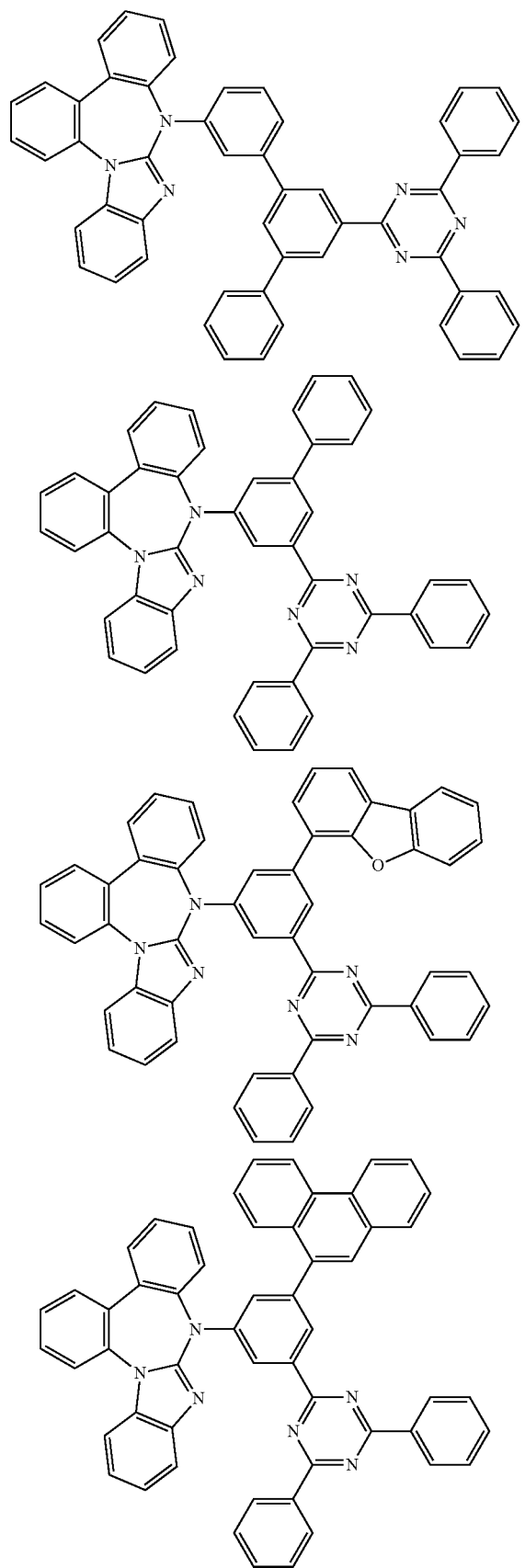
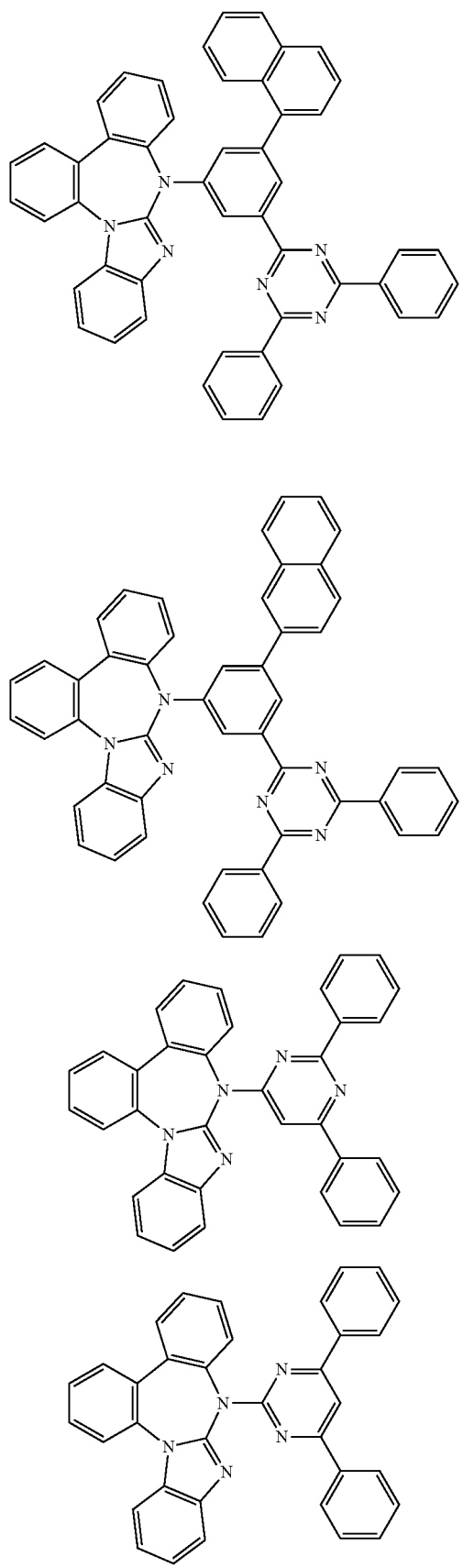

147
-continued
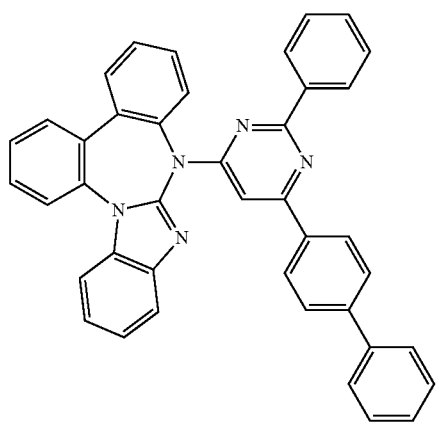
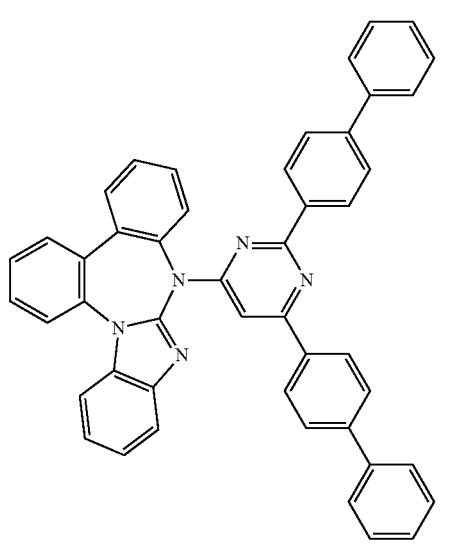
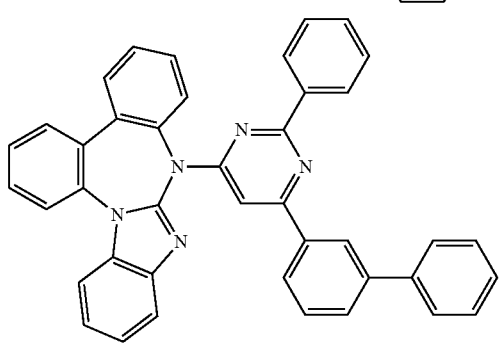
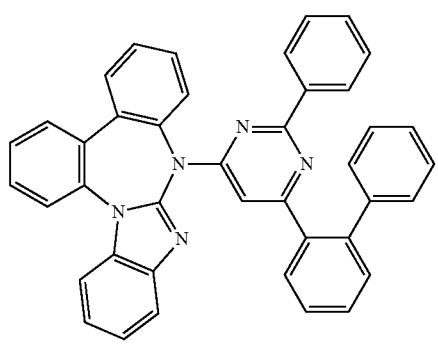
148
-continued
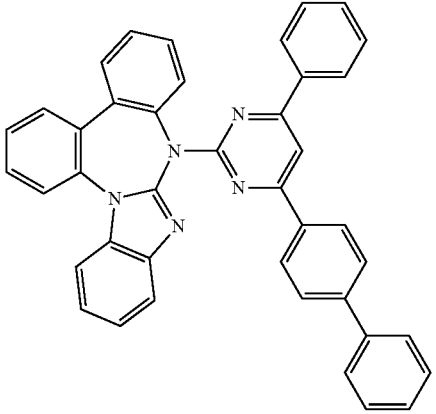
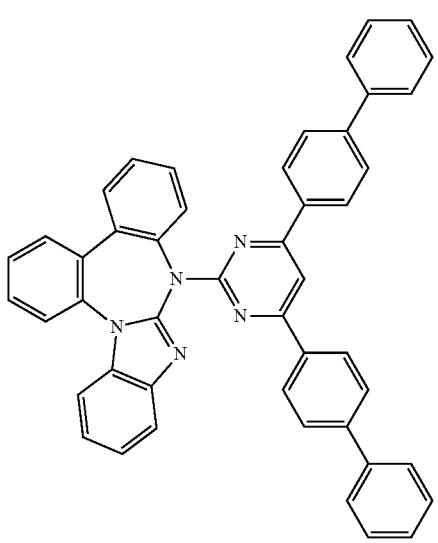
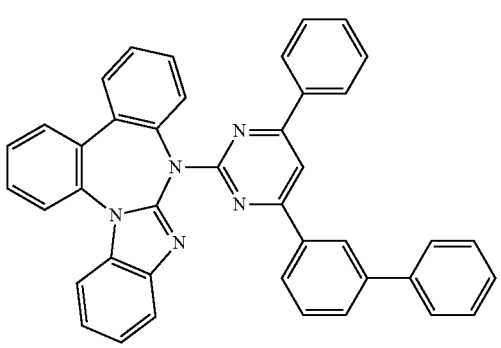
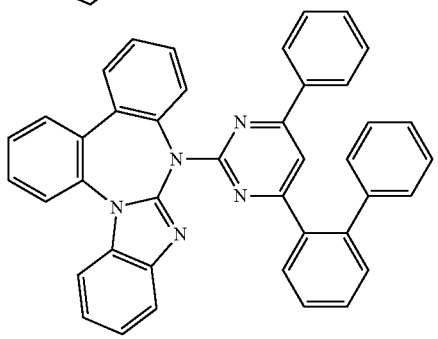

149
-continued
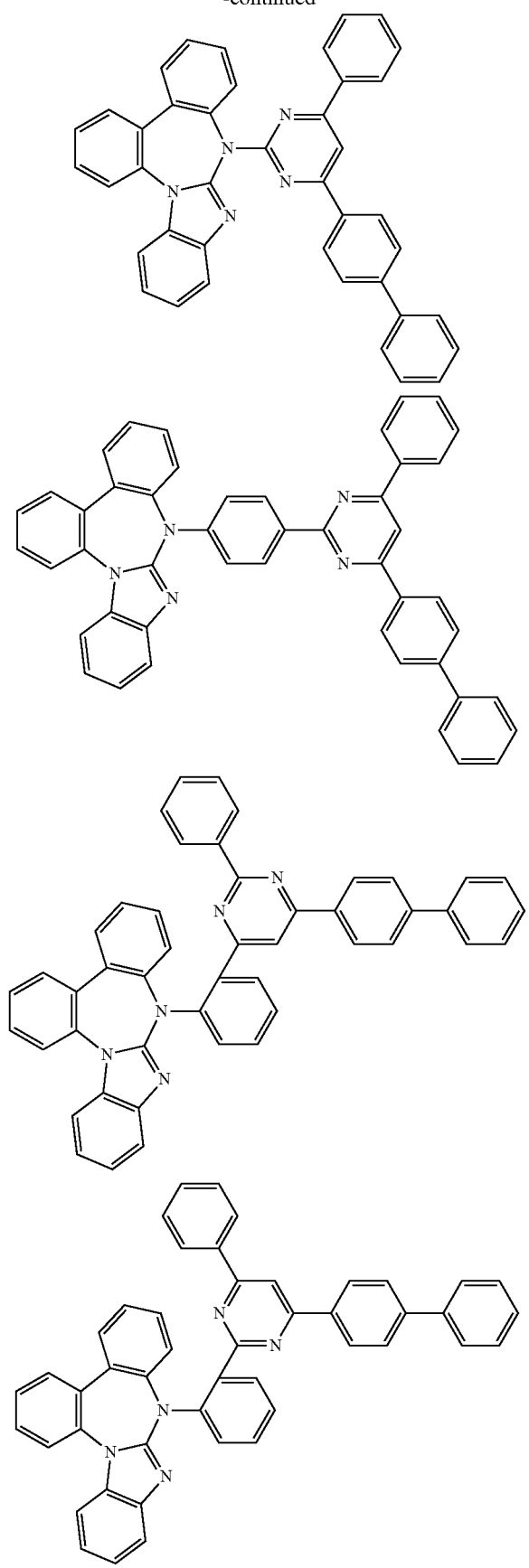
150
-continued
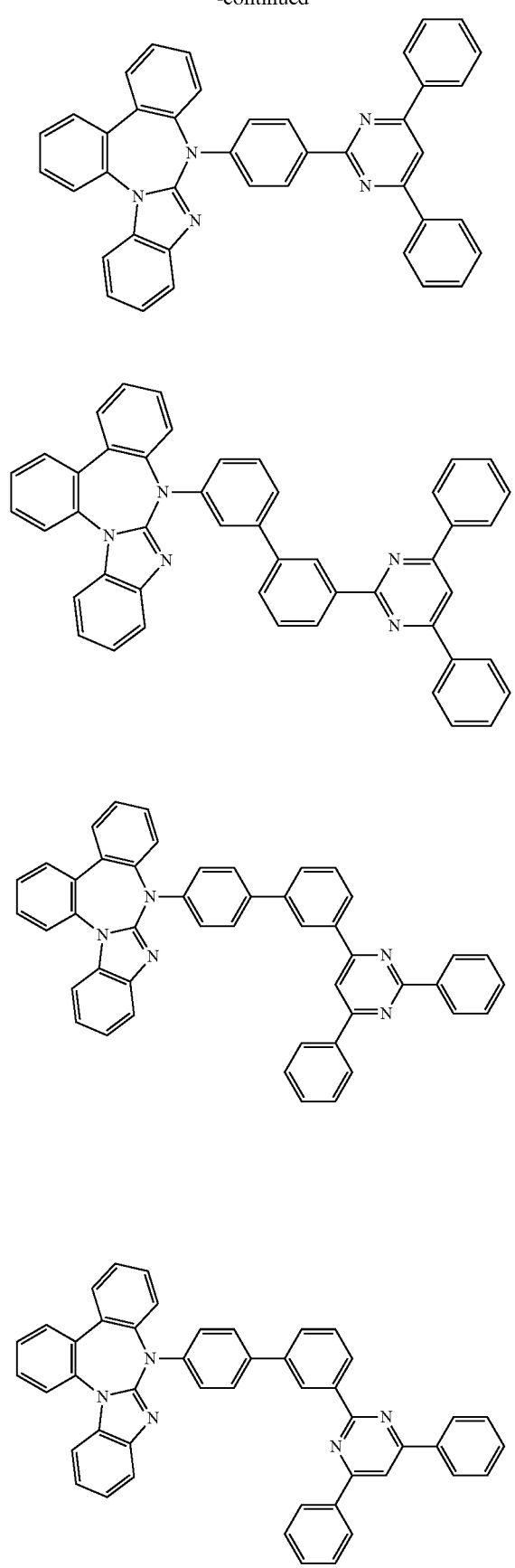

151
-continued
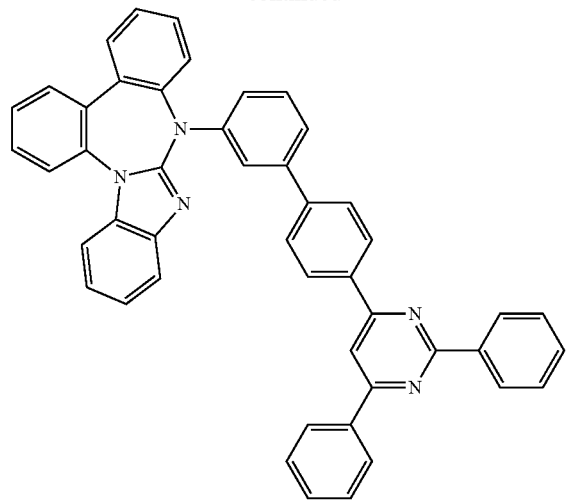
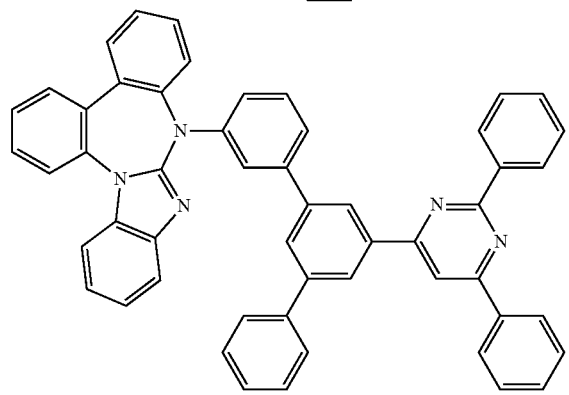
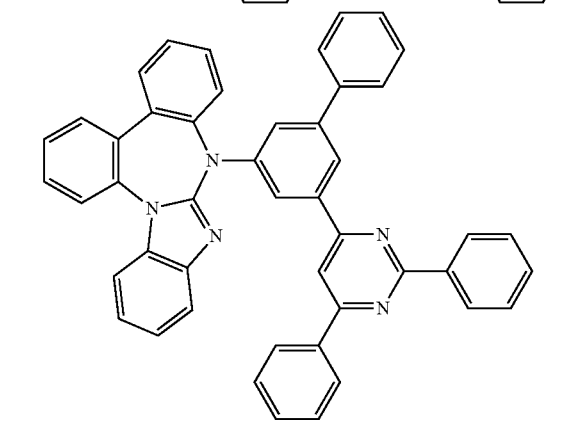
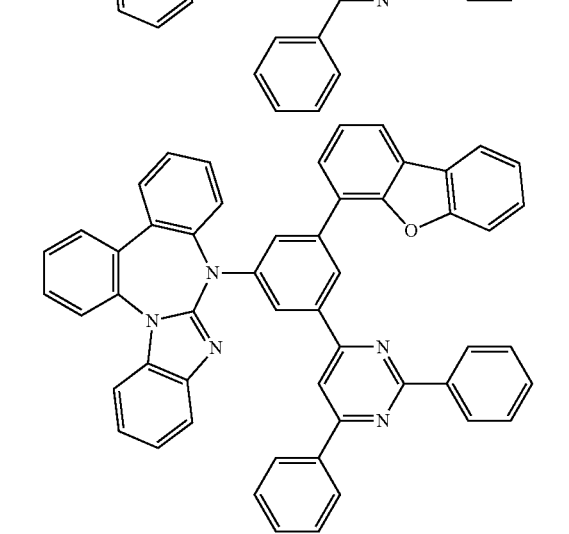
152
-continued
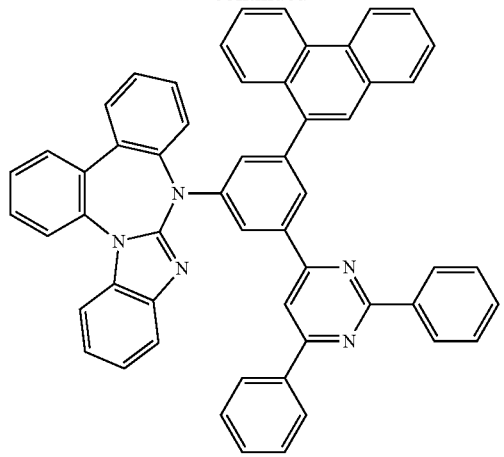
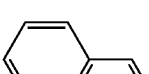
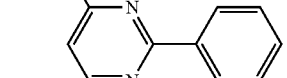
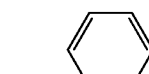

153
-continued
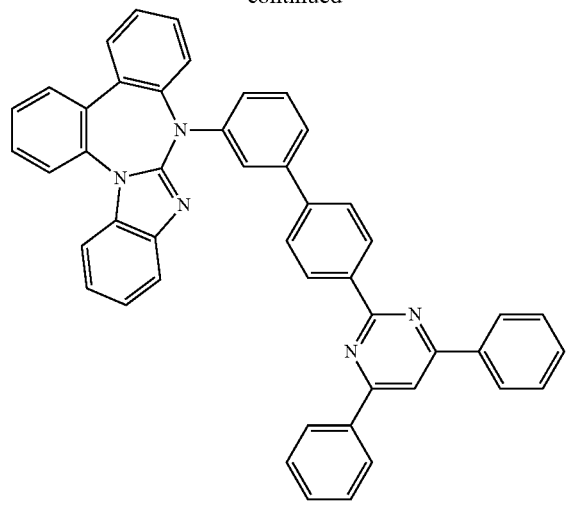
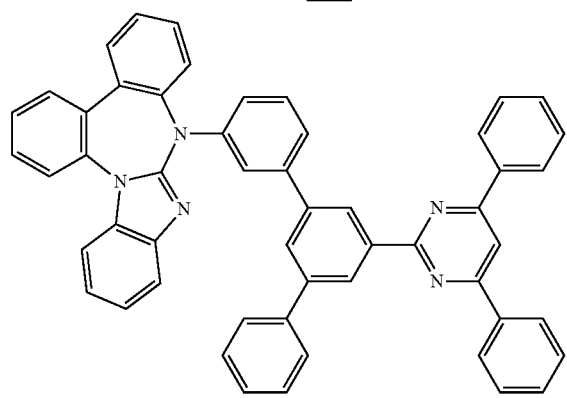
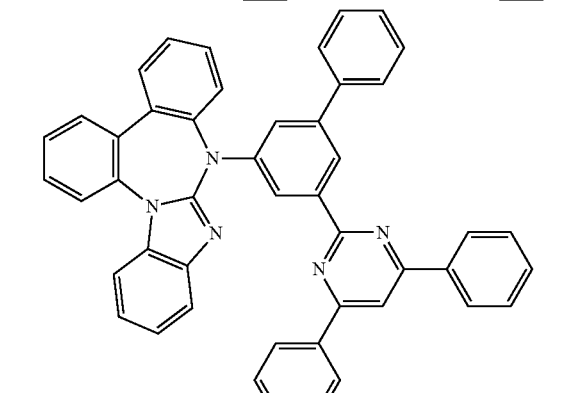
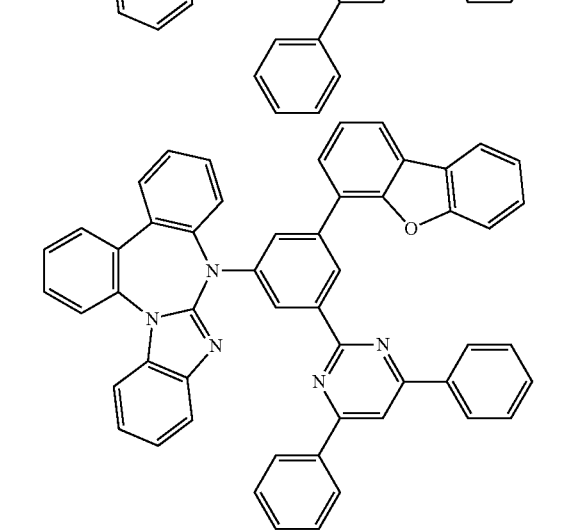
154
-continued
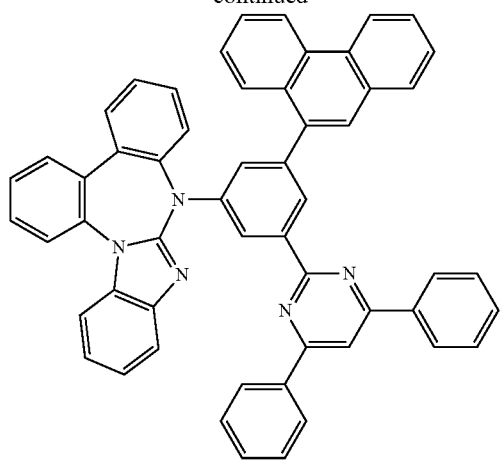
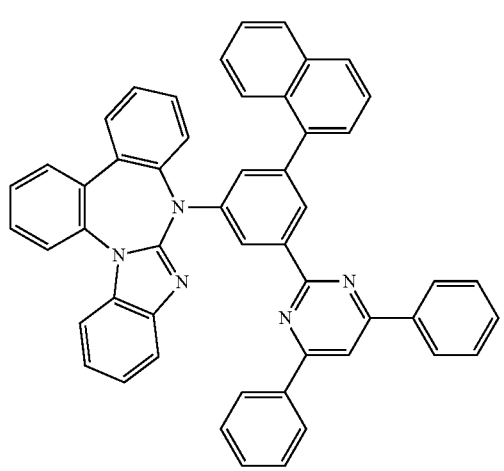
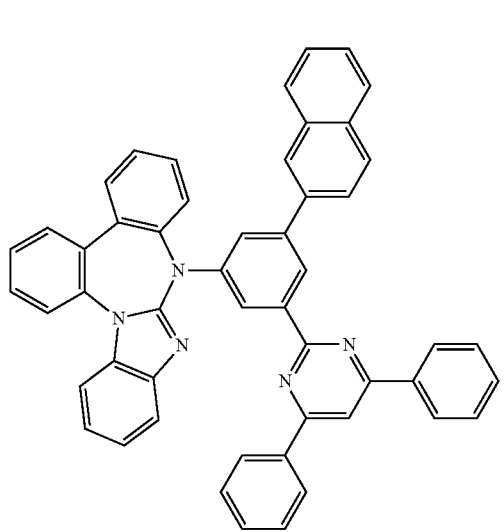

155
-continued
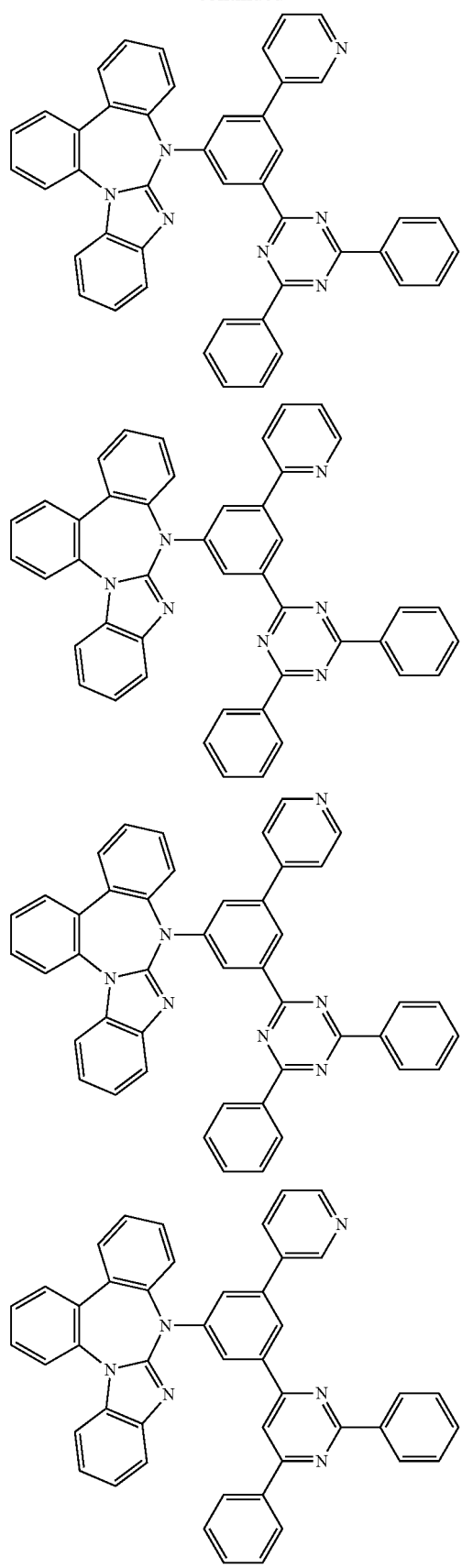
156
-continued
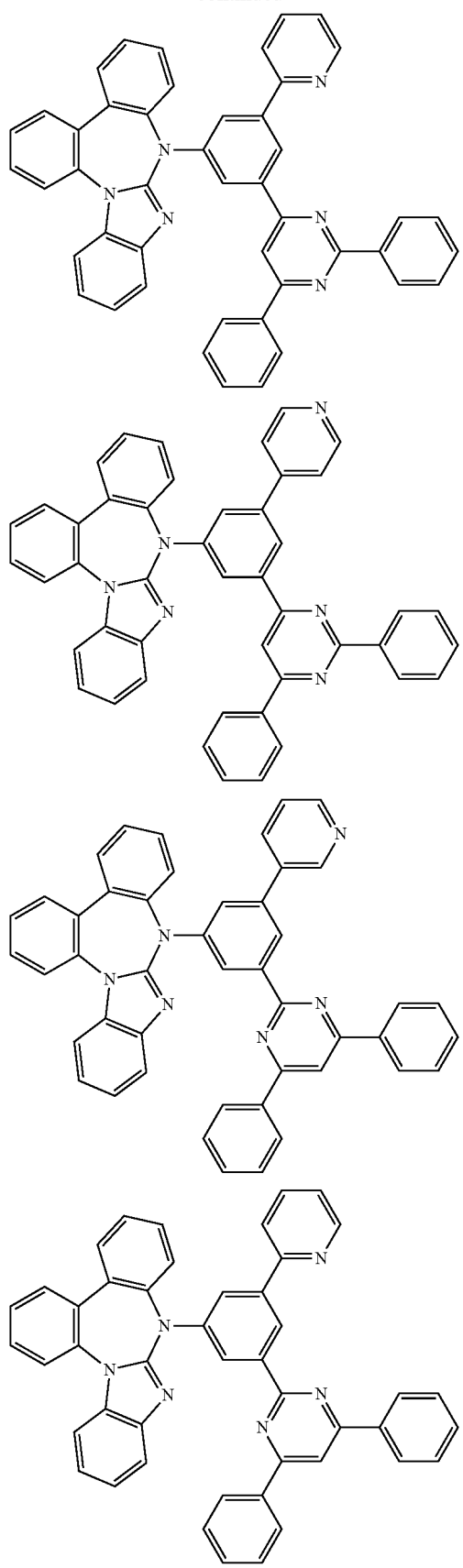

157
-continued
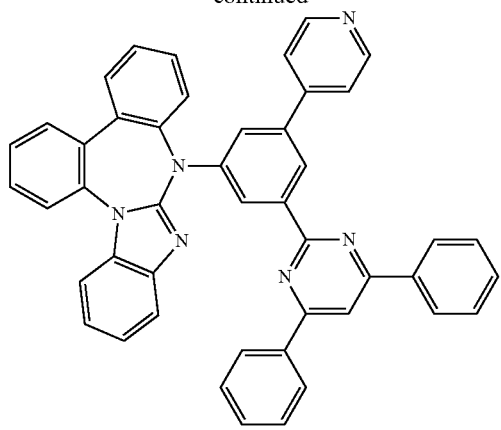
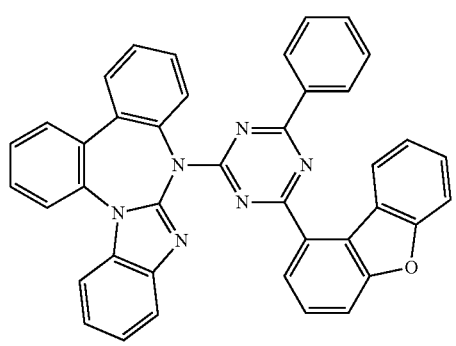
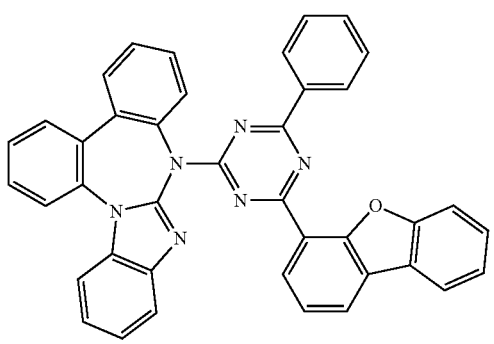
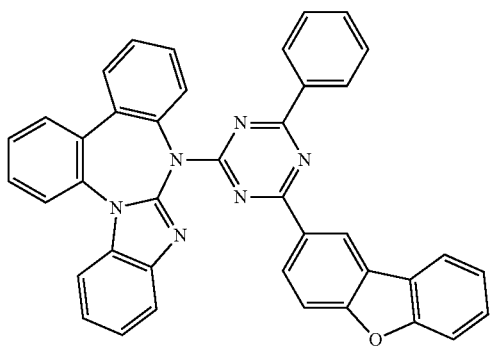
158
-continued
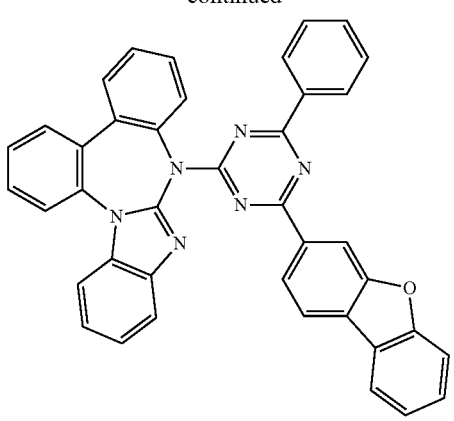
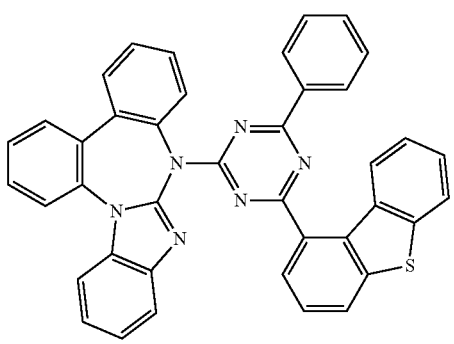
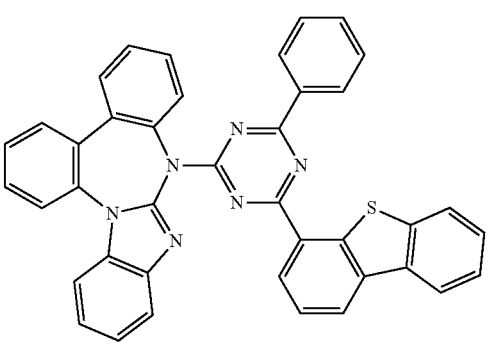
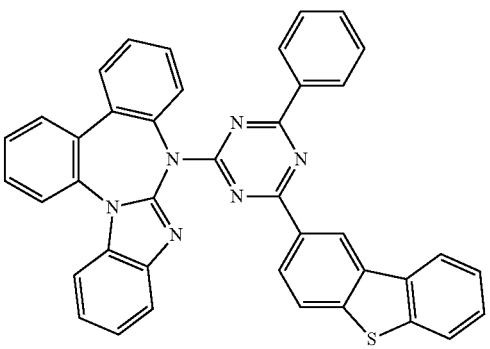

159
-continued
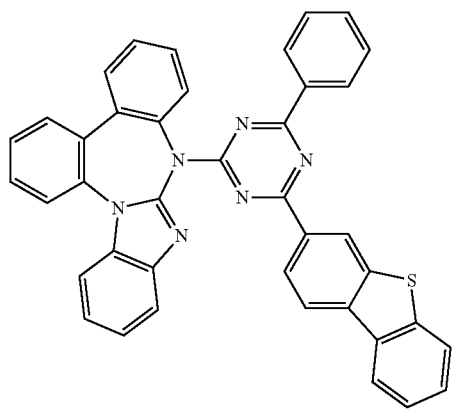
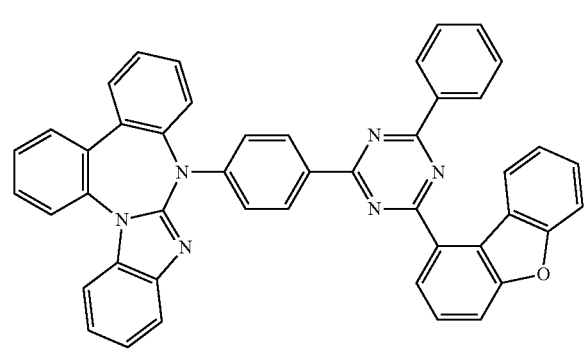
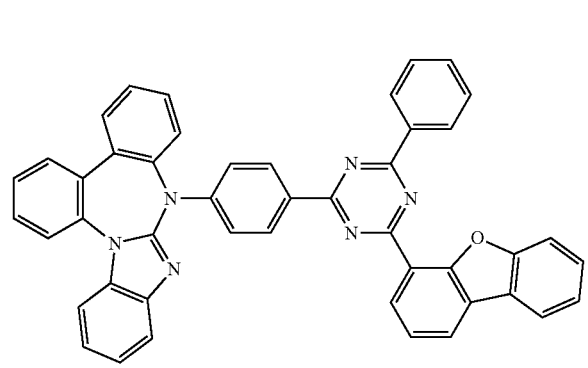
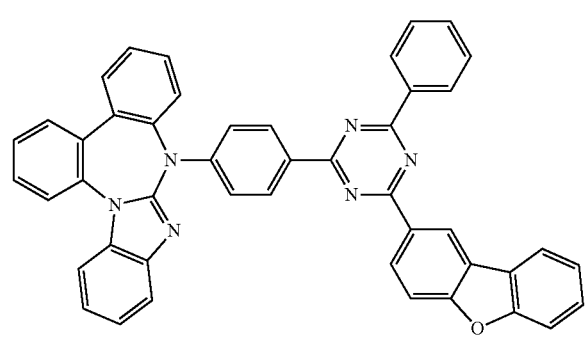
160
-continued
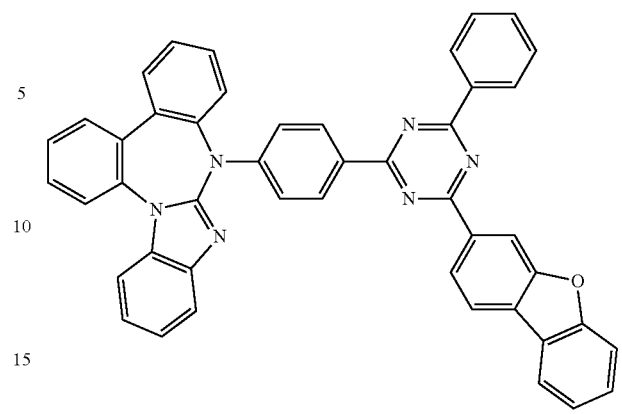
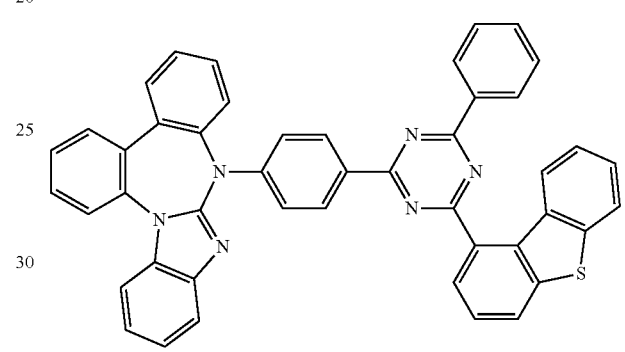
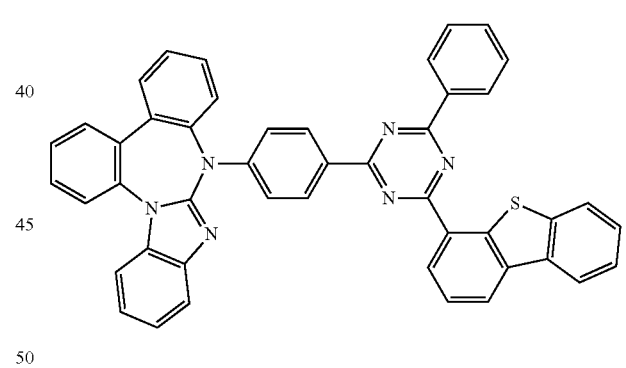
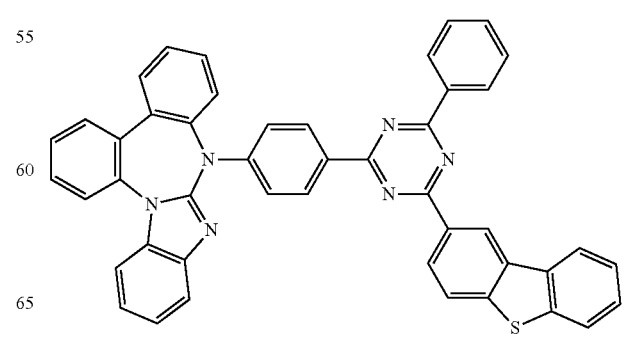

161
-continued
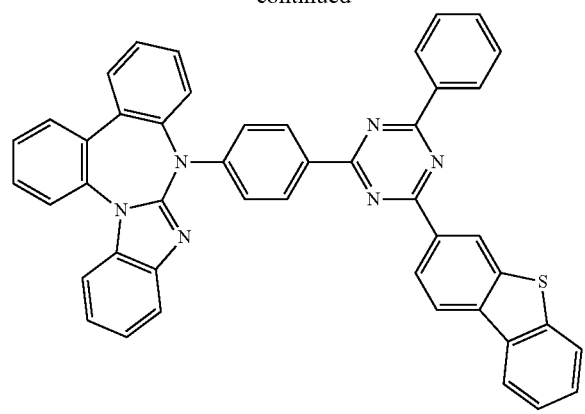
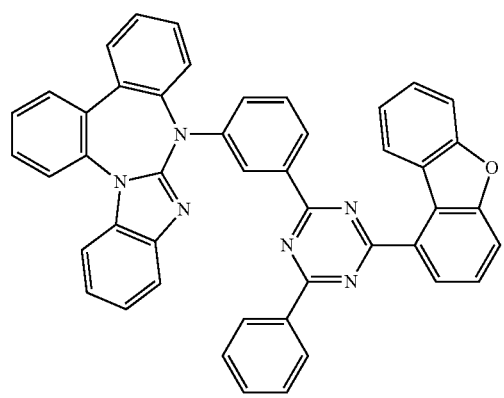
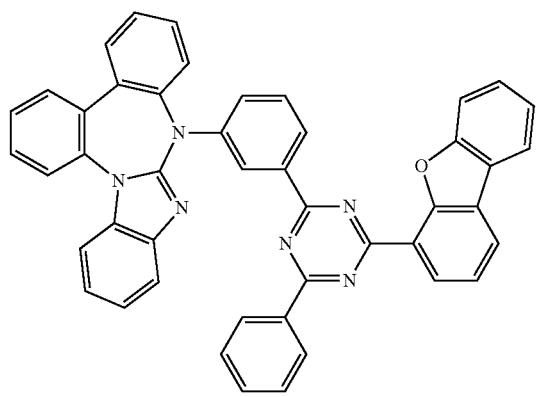
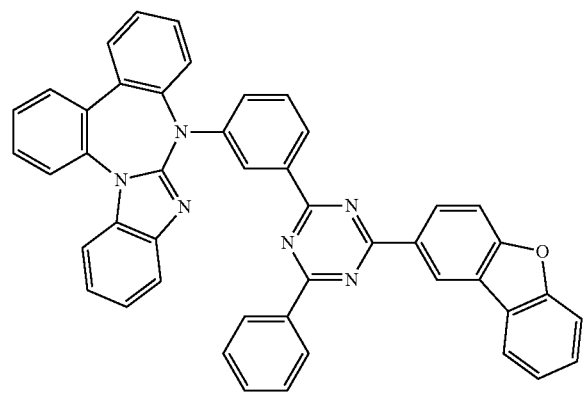
162
-continued
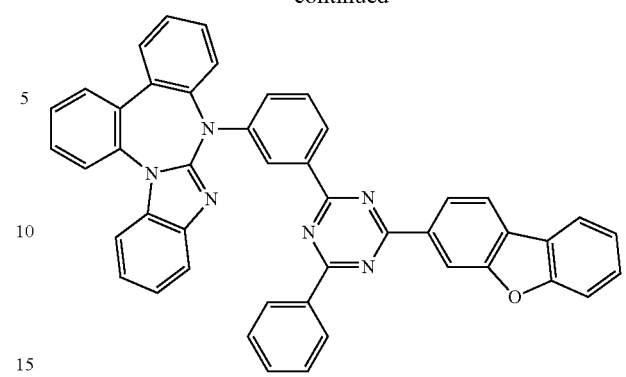
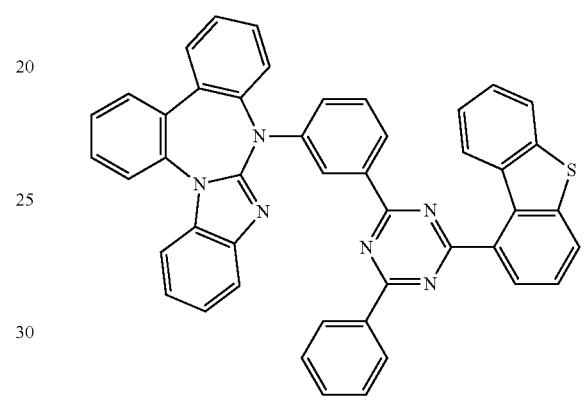
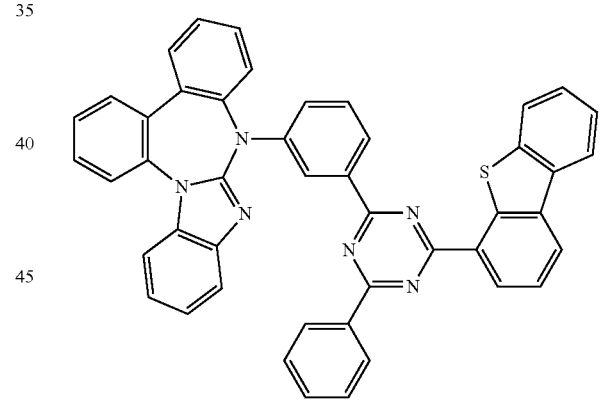
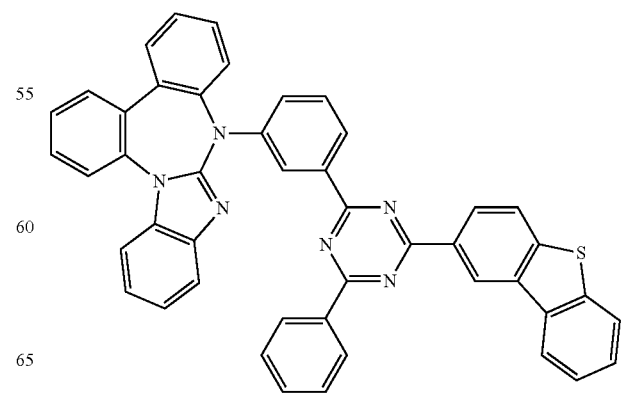

163
-continued
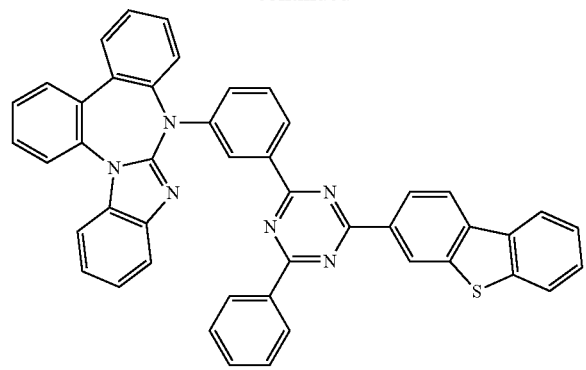
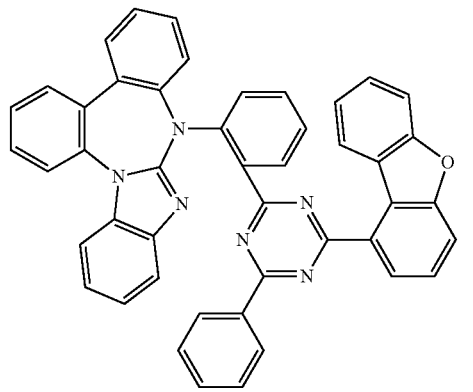
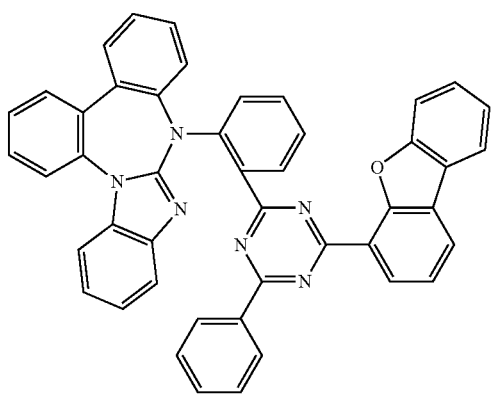
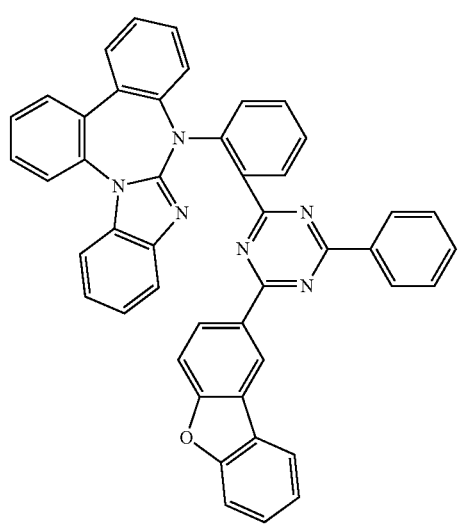
164
-continued
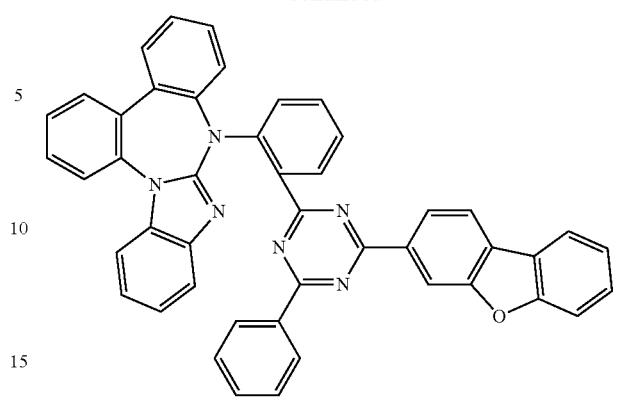
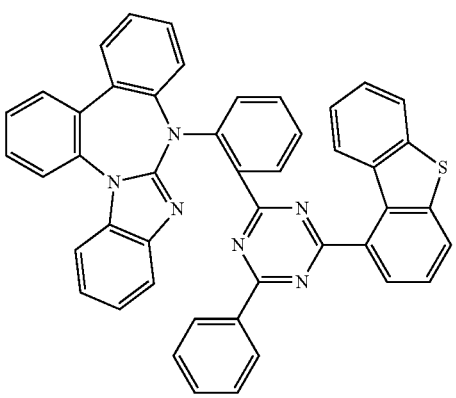
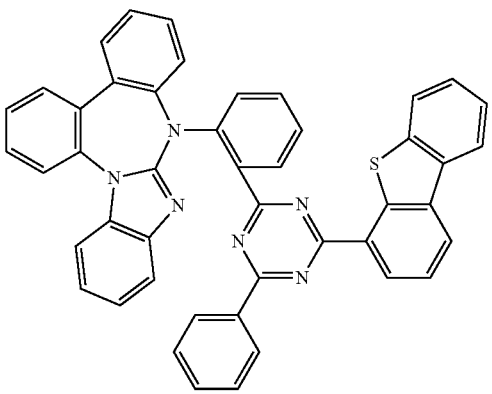
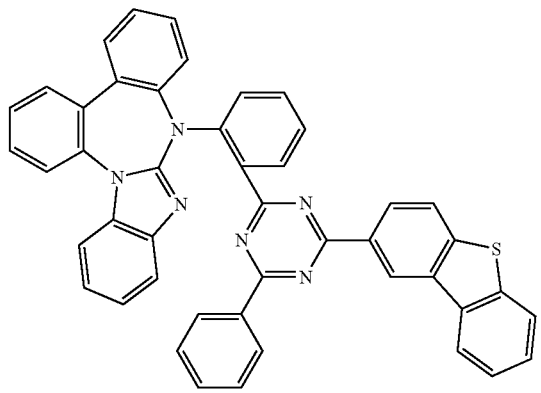

165
-continued
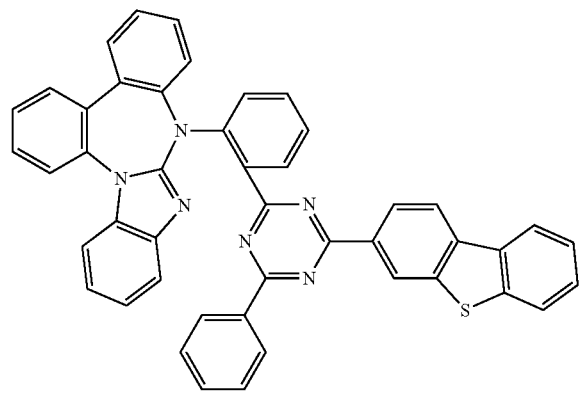
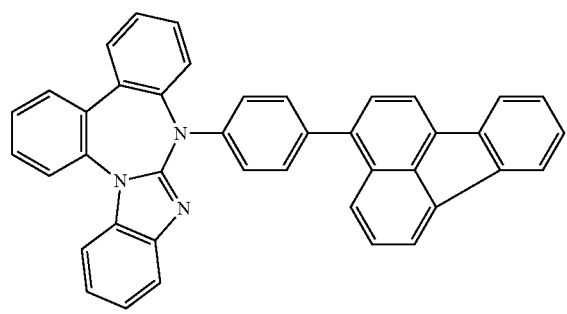
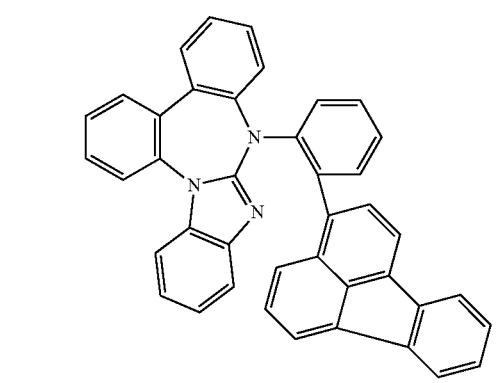
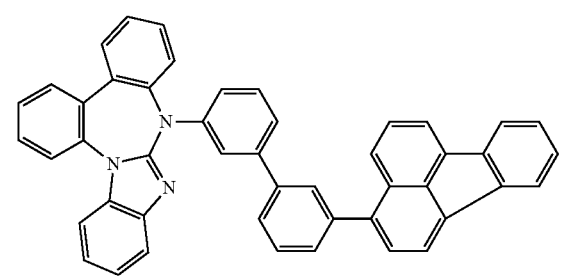
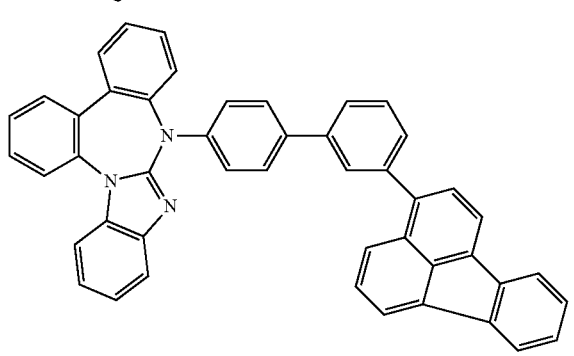
166
-continued
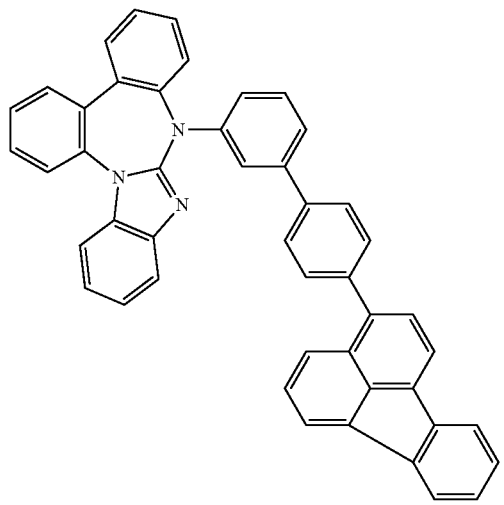
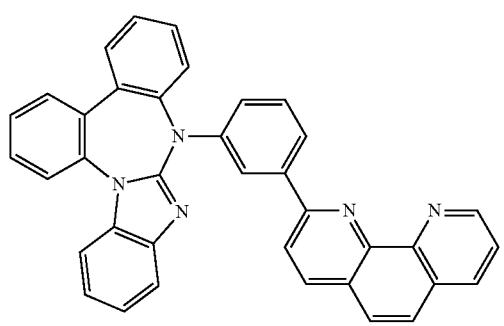
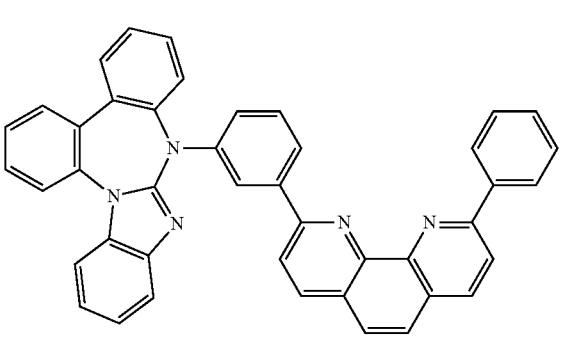
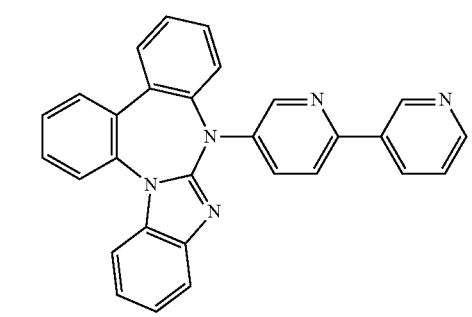

167
-continued
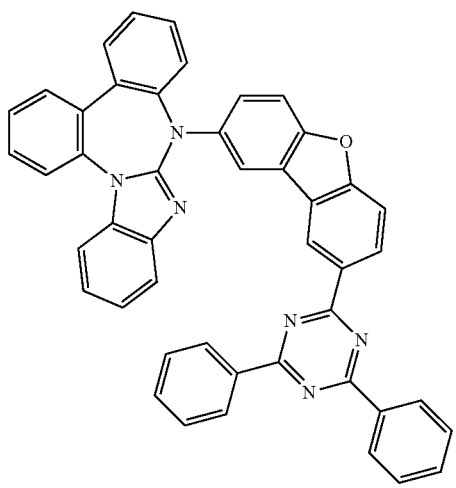
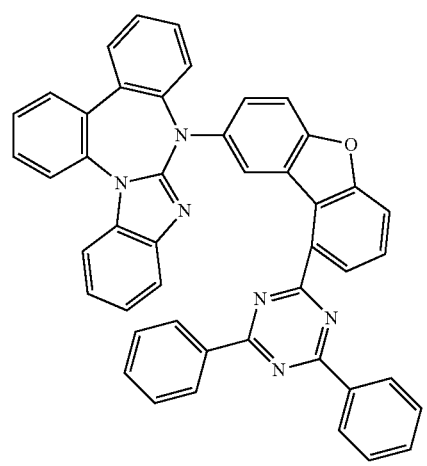
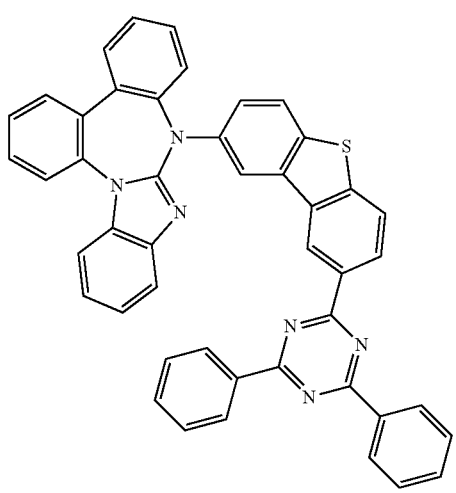
168
-continued
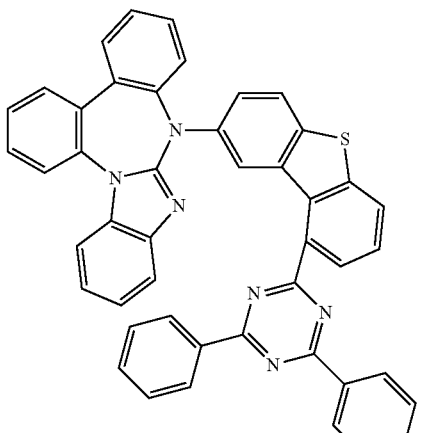
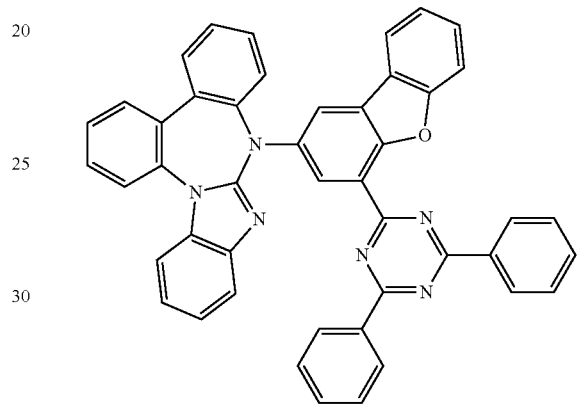
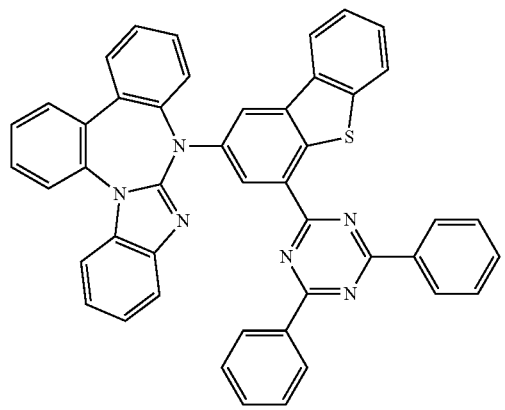

169
-continued
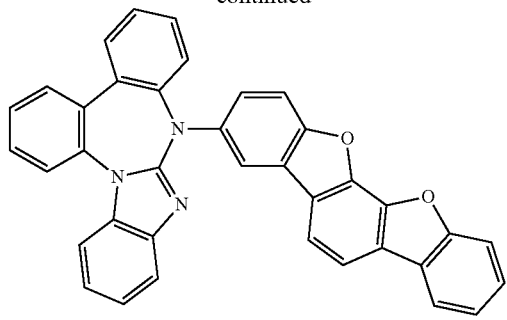
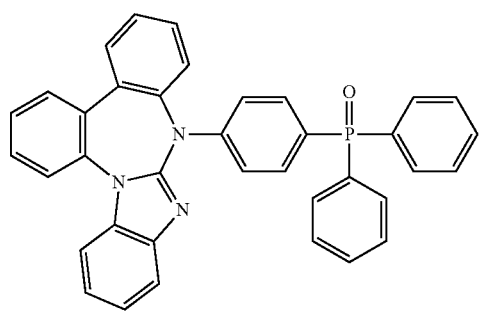
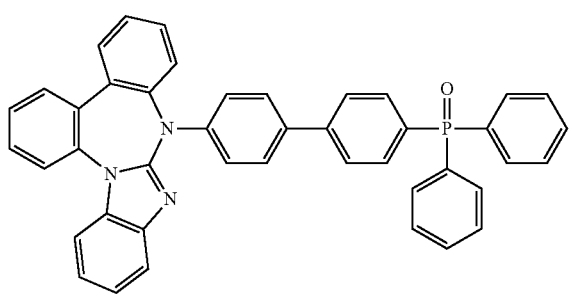
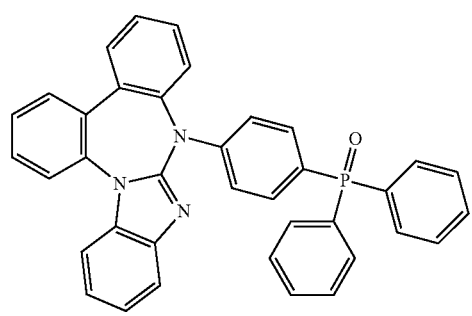
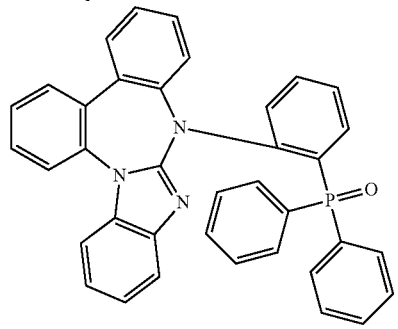
170
-continued
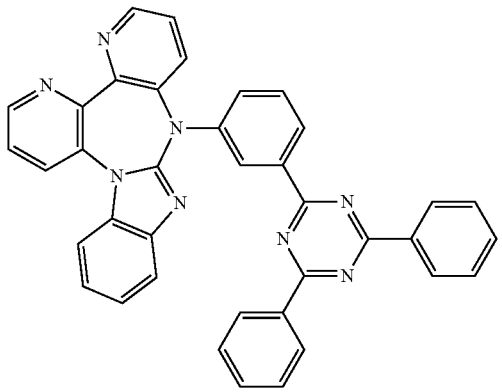
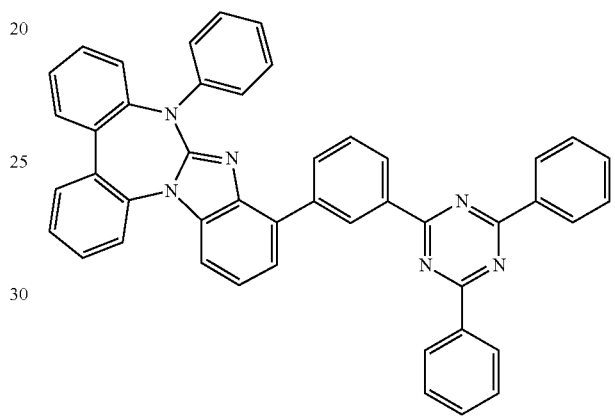
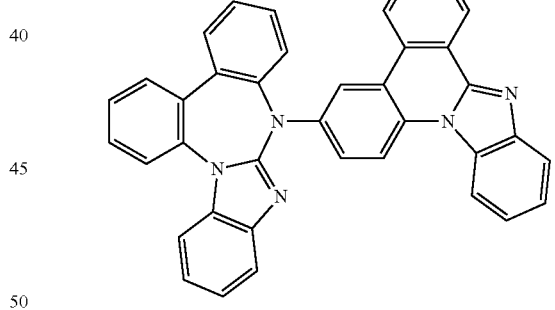
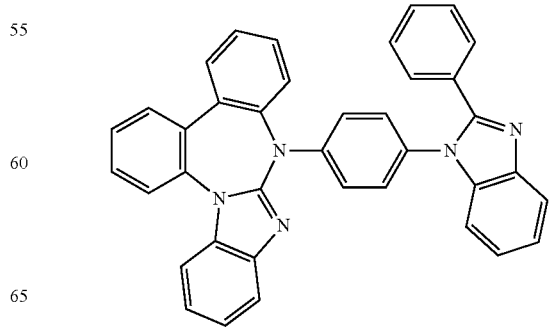

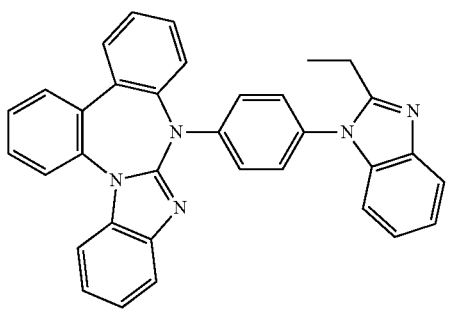
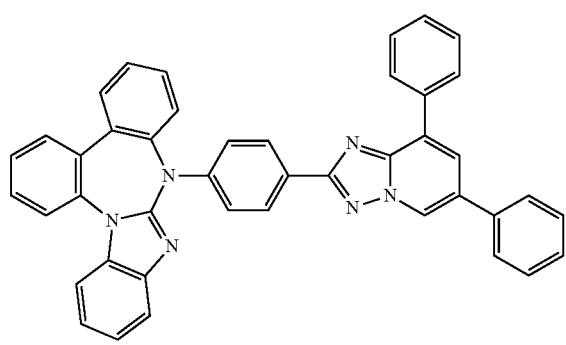
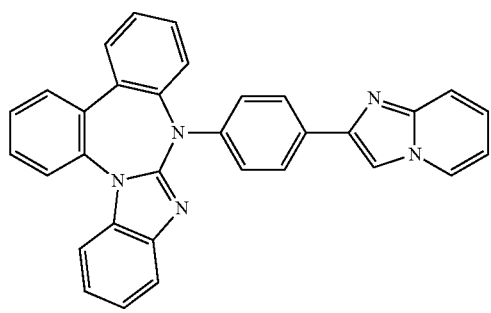
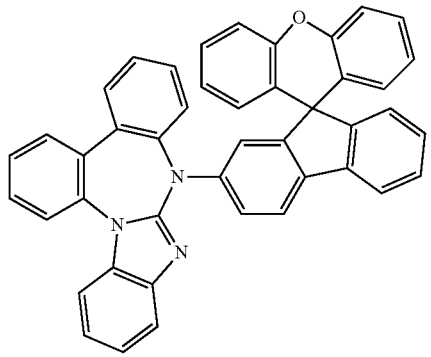
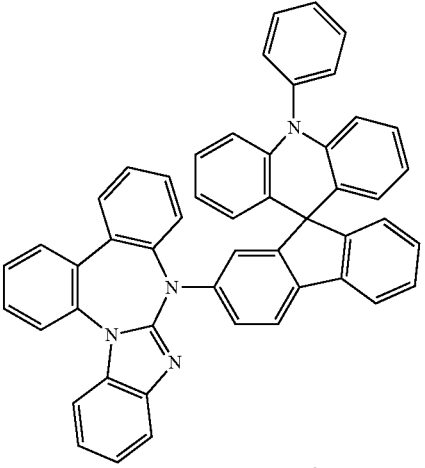
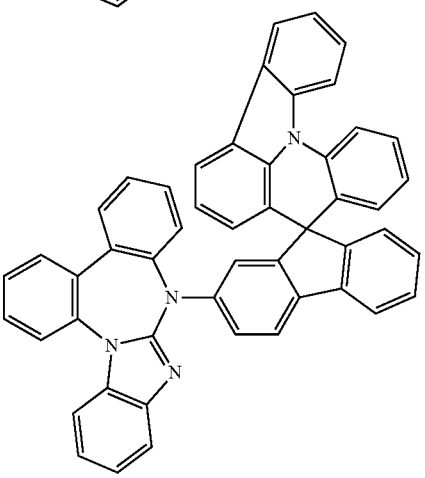
Synthesis of the Compounds of Formula (I)
The compounds of formula (I) are for example prepared by one of the following processes:
$Z_1$ is N
In the case that $Z_1$ is N, the process comprises the following steps
Ai) Reaction of a diamine (II) with an isothiocyanate (III) followed by cyclization with a carbodiimide (IV), whereby a seven membered heterocycle (V) is formed,
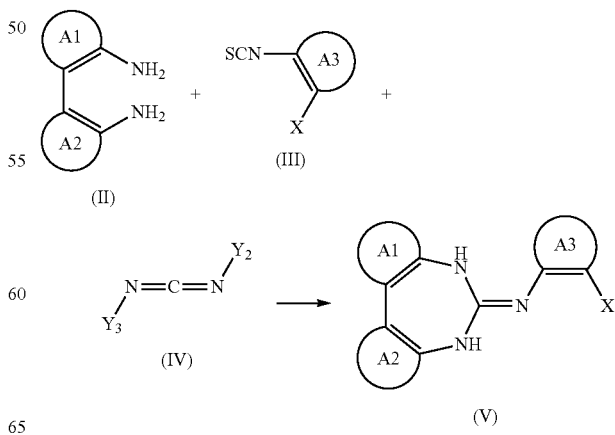

wherein $Y_2$ and $Y_3$ are each independently a substituted or unsubstituted alkyl group having 1 to 30 carbon atoms; a substituted or unsubstituted cycloalkyl group having 3 to 30 ring carbon atoms; a substituted or unsubstituted aromatic hydrocarbon group having 6 to 30 ring carbon atoms; or a substituted or unsubstituted heterocyclic group having 5 to 30 ring atoms; and X is a halogen, preferably Br or I; and Aii) Cyclization of the seven membered heterocycle (V) in the presence of a copper salt, whereby a heterocyclic system (VI) is formed

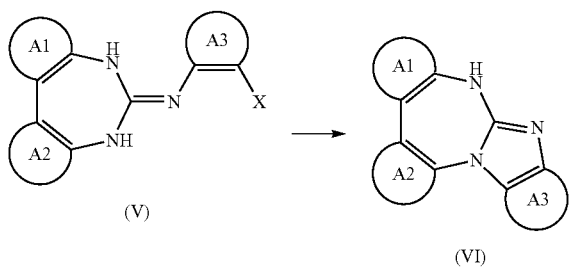

wherein $A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms.

Step Ai) Reaction of a Diamine (II) with an Isothiocyanate (III) Followed by Cyclization with a Carbodiimide (IV), Whereby a Seven Membered Heterocycle (V) is Formed Preparation of the Diamine (1):

i) Suzuki-Miyaura coupling catalysed by palladium, whereby the amino nitro compound C is formed:

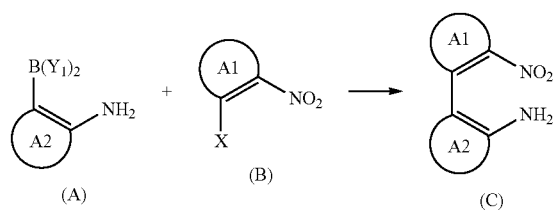

wherein $B(Y_1)_2$ represents a boronic acid or a boronic ester, X represents a halogen, preferably Cl, Br or I;

ii) Metal mediated reduction of the nitro group, whereby the diamine (II) is formed:

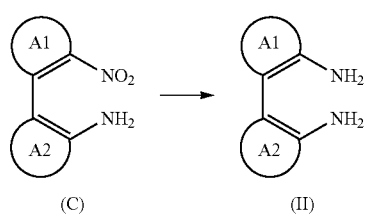

The metal mediated reduction of the nitro group is for example carried out with Pd/C in the presence of $H_2$ or Zn or Sn in the presence of a protic acid like HCl, AcOH or $NH_4Cl$.

The compounds (A) and (B) are prepared as known by a person skilled in the art.

Reaction of a Diamine (II) with an Isothiocyanate (iii) Followed by Cyclization with a Carbodiimide (IV), Whereby a Seven Membered Heterocycle (V) is Formed:

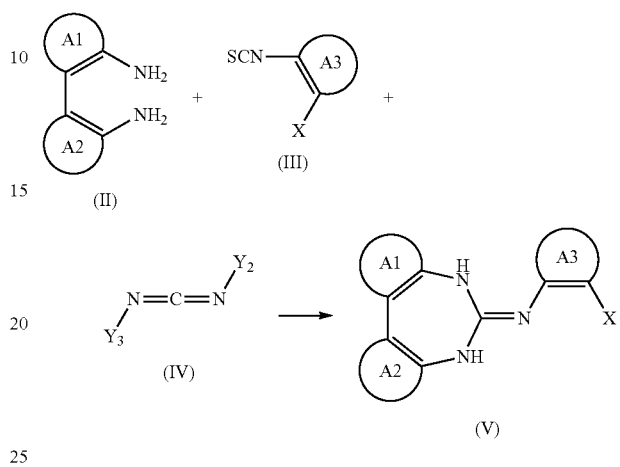

Reaction of the diamine (II) with an isothiocyanate (III) followed by cyclisation with a suitable carbodiimide (IV). Suitable residues $Y^2$ and $Y^3$ are mentioned above. Suitable carbodiimides are for example dicyclohexylcarbodiimide, diisopropylcarbodiimide or ethyl-3-(3-dimethylaminopropyl)carbodiimide hydrochloride; X is a halogen, preferably Cl, Br or I, more preferably Br or I.

Aii) Cyclization of the Seven Membered Heterocycle (V) in the Presence of a Copper Salt, Whereby a Heterocyclic System (VI) is Formed

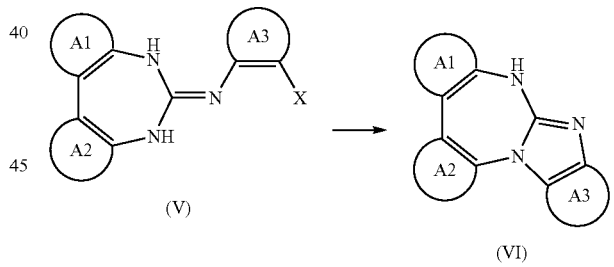

Cyclisation of (V) in the presence of a copper salt, e.g CuI, CuCl, CuBr, CuOAc and a diamine ligand, e.g 1,10-phenanthroline, 1,2-cyclohexyldiamine or ethylenediamine or an amino acid e.g. proline, sarcosine or glycine.

$A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms. Preferred groups $A_1$, $A_2$ and $A_3$ are mentioned above.

$Z_1$ is $CR^1$

In the case that $Z_1$ is $CR^1$, the process comprises the following step

Bi) Acid mediated ring closure of a compound of formula (VII) whereby a heterocyclic system of formula (VIII) is formed

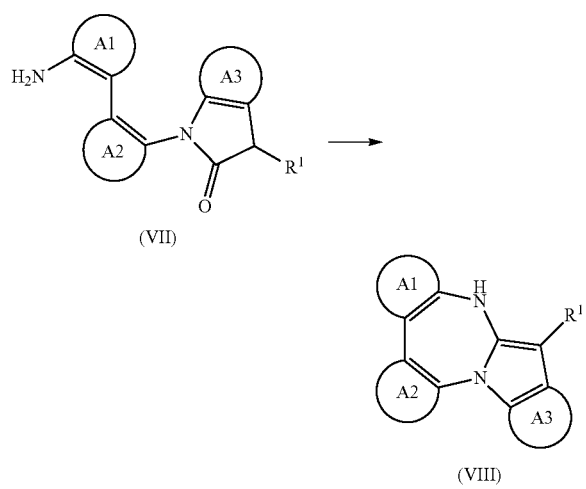

(VII)

(VIII)

wherein $A_1$, $A_2$ and $A_3$ each independently represent a substituted or unsubstituted aromatic hydrocarbon group having 6 to 30 ring carbon atoms or a substituted or unsubstituted heterocyclic group having 5 to 30 ring atoms, and $R^1$ is hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms.

Preparation of Compound (VIII).

i) Acylation of the Amino Nitro Compound (C)

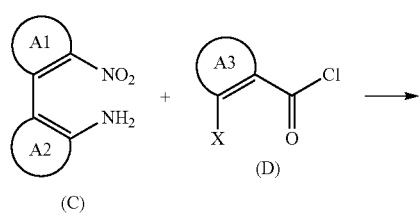

(C)  (D)

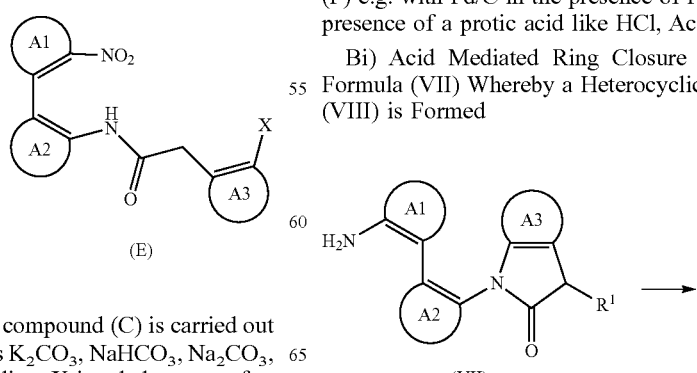

(E)

Acylation of the amino nitro compound (C) is carried out in the presence of a base such as $K_2CO_3$, $NaHCO_3$, $Na_2CO_3$, $NEt_3$, $NEt_2{}^iPr$, lutidine or pyridine. X is a halogen, preferably Cl, Br or I.

ii) Cyclisation of Compound (E)

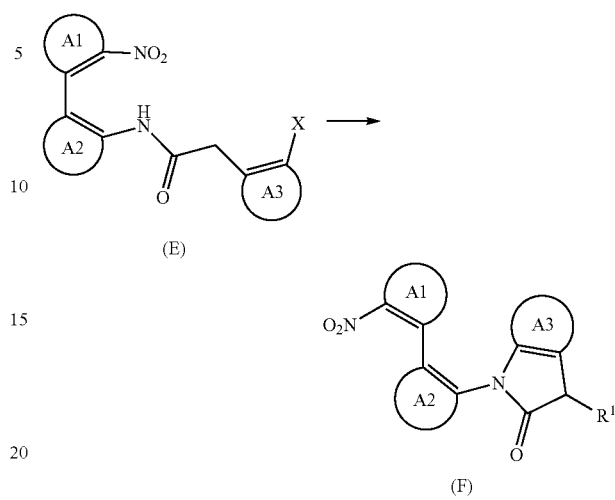

(E)

(F)

Cyclisation of compound (E) in the presence of a copper salt, e.g CuI, CuCl, CuBr or CuOAc and a diamine ligand, e.g 1,10-phenathroline, 1,2-cyclohexyldiamine or ethylenediamine or an amino acid, e.g. proline, sarcosine or glycine.

iii) Reduction of the Nitro Group in Compound (F), Whereby Compound (VII) is Formed

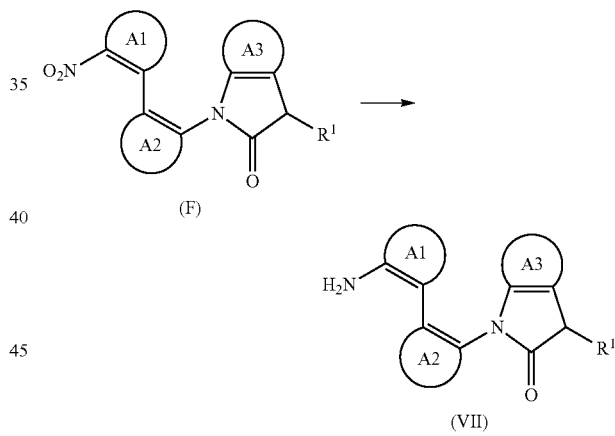

(F)

(VII)

Metal mediated reduction of the nitro group in compound (F) e.g. with Pd/C in the presence of $H_2$ or Zn or Sn in the presence of a protic acid like HCl, AcOH or $NH_4Cl$.

Bi) Acid Mediated Ring Closure of a Compound of Formula (VII) Whereby a Heterocyclic System of Formula (VIII) is Formed (VII)

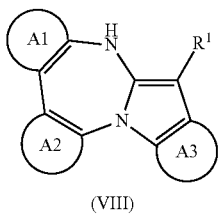

(VIII)

Acid mediated ring closure e.g with polyphosphoric acid, H₂SO₄ or CH₃SO₃H.

A₁, A₂ and A₃ each independently represent a substituted or unsubstituted aromatic hydrocarbon group having 6 to 30 ring carbon atoms or a substituted or unsubstituted heterocyclic group having 5 to 30 ring atoms, and R¹ is hydrogen, a substituted or unsubstituted alkyl group having 1 to 30 carbon atoms; a substituted or unsubstituted cycloalkyl group having 3 to 30 ring carbon atoms; a substituted or unsubstituted alkenyl group having 2 to 30 carbon atoms; a substituted or unsubstituted aromatic hydrocarbon group having 6 to 30 ring carbon atoms; a substituted or unsubstituted aralkyl group having 7 to 31 ring carbon atoms; or a substituted or unsubstituted heterocyclic group having 5 to 30 ring atoms.

Preferred groups A₁, A₂ and A₃ and preferred residues R¹ are mentioned above.

Functionalisation of the Heterocyclic Systems (VI) and (VIII) with -(L)ᵣ-B¹:

The functionalisation of the heterocyclic systems (VI) and (VIII) with -(L)ᵣ-B¹ is carried out as known by a person skilled in the art. Below, examples for suitable functionalisation methods are mentioned:

N-Arylation

The introduction of the group -(L)ᵣ-B¹ is generally carried out by reacting the heterocyclic systems (VI) and (VIII) with a group Hal-(L)ᵣ-B¹, wherein Hal is F, Cl, Br or I, preferably F, Br or I. Suitable groups -(L)ᵣ-B¹ are mentioned before.

The nucleophilic aromatic substitution (N-arylation) of the heterocyclic systems (VI) and (VIII) with a group Hal-(L)ᵣ-B¹ is generally performed in the presence of a base (Angew. Chem. 2012, 124, 8136-8140, Angew. Chem. Int. Ed. 2008, 47, 8104-8107). Suitable bases are known to those skilled in the art and are preferably selected from the group consisting of alkali metal and alkaline earth metal hydroxides such as NaOH, KOH, Ca(OH)₂, alkali metal hydrides such as NaH, KH, alkali metal amides such as NaNH₂, alkali metal or alkaline earth metal carbonates such as K₂CO₃ or Cs₂CO₃, alkaline metal phosphates such as K₃PO₄ alkaline metal fluorides such as KF, CsF and alkali metal alkoxides such as NaOMe, NaOEt. In addition, mixtures of the aforementioned bases are suitable. K₂CO₃ or Cs₂CO₃, K₃PO₄ are preferred.

The nucleophilic aromatic substitution (N-arylation) can be performed in solvent or in a melt. Preferably, the reaction is carried out in a solvent. Suitable solvents are, for example, (polar) aprotic solvents such as dimethyl sulfoxide (DMSO), dimethylformamide (DMF), N-methyl-2-pyrrolidone (NMP) or dimethylacetamide (DMA).

The reaction temperature is strongly dependent on the reactivity of the aryl fluoride. The reaction (N-arylation) is preferably carried out at a temperature of −10 to 220° C., more preferably 60 to 150° C.

Ullmann reaction (N-arylation) of the heterocyclic systems (VI) and (VIII) with a group Y-(L)ᵣ-B¹ (Y is Cl, Br, or I) is generally performed in the presence of a base and a catalyst.

Reaction conditions for Ullmann reactions are, for example, described in Angew Chem Int Ed Engl., 48 (2009) 6954-71 WO14009317, WO12130709, J. Am. Chem. Soc. 131 (2009) 2009-2251, J. Org. Chem, 70 (2005) 5165.

Typically the Ullmann coupling of the heterocyclic systems (VI) and (VIII) with a group Y-(L)ᵣ-B¹ (Y is Cl, Br, or I, especially Br, I very especially I) is done in the presence of copper, or a copper salt, such as, for example, CuI, CuBr, Cu₂O, or CuO, and a ligand, such as, for example, L-proline, trans-cyclohexane-1,2-diamine (DACH), 1,10-phenanthroline in a solvent, such as, for example, dimethylsulfoxide (DMSO), dimethylformamide (DMF), dimethylacetamide (DMA), N-methylpyrrolidone (NMP) and dioxane, or a solvent mixture. The reaction temperature is dependent on the reactivity of the starting materials, but is generally in the range of 25 to 200° C. If copper salt are used without a ligand the reaction temperatures are higher.

The N-arylation is, for example, disclosed in H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151.

Buchwald-Hartwig catalytic N-arylation can also be applied to the heterocyclic systems (VI) and (VIII) with a group Y-(L)ᵣ-B¹ (Y is Cl, Br, or I, especially Br, I very especially I). This is typically carried out in the presence of a catalytic amount of Pd(0) or Pd(II) salts such as for example Pd(OAc)₂, PdCl₂, Pd₂dba₃, [Pd allyl Cl]₂ in the presence of monophosphine ligands such as for example triphenylphosphine (PPh₃), tri(o-tolyl)phosphine (P(o-tol)₃), (tBu)₃P, tricyclohexylphosphine 2-dicyclohexylphosphino-2',6'-dimethoxybiphenyl (Sphos) or bidentate phosphine ligands such as (2,2'-bis(diphenylphosphino)-1,1'-binaphthyl) (BINAP), 4,5-bis(diphenylphosphino)-9,9-dimethylxanthene (xantphos), bis[(2-diphenylphosphino)phenyl] ether (DPEphos), 1,1'-bis(diphenylphosphino)ferrocene (DPPF), 2,2'-bis(diphenylphosphino)-6,6'-dimethoxy-1,1'-biphenyl (MeOBIPHEP) or N-heterocyclic carbene ligands like 1,3-bis(2,6-diisopropylphenyl)imidazolinium chloride, 1,3-bis(2,4,6-trimethylphenyl)imidazolinium chloride or 1,3-bis(2,6-diisopropylphenyl)imidazol-2-ylidene with a base such as Cs₂CO₃, K₂CO₃, K₃PO₄, NaOtBu, KOtBu; potassium hexamethyldisilazane (KHMDS) in solvents such as toluene, dioxane, dimethoxyethane (DME), N,N-dimehtylformamide (DMF), N,N-dimethylacetamide (DMAc) or n-butanol at temperatures from usually 40° C. to 200° C., preferably 70° C. to 150° C.

The N-arylation for example is disclosed in Louie, J.; Hartwig, J. F., Tetrahedron Letters, 36 (1995) 3609-3612; Guram, A. S.; Rennels, R. A.; Buchwald, S. L. Angewandte Chemie International Edition, 34 (1995), 1348-1350.

Details of the reaction steps and process conditions are mentioned above and in the examples of the present application.

Compounds of Formula (I) in Organic Electronics Applications

It has been found that the compounds of the formula (I) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The term organic EL device (organic electroluminescence device) is used interchangeable with the term organic light-emitting diode (OLED) in the following; i.e. both terms have the same meaning in the sense of the present application.

The present invention further relates to a material for an organic EL device comprising at least one compound of formula (I).

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (I).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (I).

The compounds of formula (I) are particularly suitable in OLEDs for use as matrix material (host material) in a light-emitting layer and/or as charge and/or exciton blocker material, i.e. as electron/exciton blocker material or as hole/exciton blocker material, and/or charge transport material, i.e. hole transport material or electron transport material, preferably as matrix material in a light-emitting layer and/or as electron transport material, especially in combination with a phosphorescence emitter.

In the case of use of the inventive compounds of formula (I) in OLEDs, OLEDs have good efficiencies. The inventive compounds of formula (I) are suitable especially for use as matrix and/or charge transport, i.e. hole or electron transport, and/or charge blocker material, i.e. hole or electron blocker material. Furthermore, the compounds of the formula (I) can be used as conductor/complementary materials in organic electronics applications selected from switching elements and organic solar cells. (In the sense of the present application, the terms matrix and host are used interchangeable).

Organic EL Device (OLED)

The organic EL device as one embodiment of the invention comprises one or more organic thin film layers including an emitting layer between a cathode and an anode, and at least one layer of the organic thin film layers comprises the compound of formula (I).

As examples of the organic thin film layers that comprise the compound of formula (I), an anode-side organic thin film layer (hole-transporting layer, hole-injecting layer, or the like), an emitting layer, a cathode-side organic thin film layer (electron-transporting layer, electron-injecting layer, or the like) provided between a cathode and an emitting layer, a spacing layer, a barrier layer or the like can be given. The examples are not limited thereto.

The compound of formula (I) may be contained in any of the abovementioned layers, and can be used as a host material or a dopant material in the emitting layer of a fluorescent emitting unit, a host material in the emitting layer of a phosphorescent emitting unit, a hole-transporting layer, an electron-transporting layer or the like of an emitting unit.

Preferably, the compounds of the formula (I) are used as matrix materials (host materials), preferably in an emitting layer of an OLED, more preferably in an emitting layer of an OLED comprising at least one compound of the formula (I) and at least one emitter material, wherein the emitter material is preferably a fluorescent or phosphorescent emitter material, more preferably a green or red fluorescent or phosphorescent emitter material.

According to the other embodiment, the compounds of the formula (I) are preferably used as electron transporting layer of an OLED.

The organic EL device of the invention may be a fluorescent or phosphorescent monochromatic emitting device or may be a fluorescent/phosphorescent hybrid white emitting device. It may be a simple emitting device having a single emitting unit or a tandem emitting device having plural emitting units. Among them, the organic EL device may preferably be a phosphorescent emitting device.

As the representative device structure of a simple type organic EL device, the following device configuration can be given.

(1) Anode/Emitting Unit/Cathode

The emitting unit mentioned above may be a stacked type emitting unit comprising plural phosphorescent emitting layers or plural fluorescent emitting layers. In this case, in order to prevent diffusion of excitons generated in the phosphorescent emitting layer to the fluorescent emitting layer, a spacing layer may be provided between the emitting layers. The representative layer configuration of the emitting unit is given below.

(a) Hole-transporting layer/Emitting layer (/Electron-transporting layer)

(b) Hole-transporting layer/First phosphorescent emitting layer/Second phosphorescent emitting layer (/Electron-transporting layer)

(c) Hole-transporting layer/Phosphorescent emitting layer/Spacing layer/Fluorescent emitting layer (/Electron-transporting layer)

(d) Hole-transporting layer/First phosphorescent emitting layer/Second phosphorescent emitting layer/Spacing layer/Fluorescent emitting layer (/Electron-transporting layer)

(e) Hole-transporting layer/First phosphorescent emitting layer/Spacing layer/Second phosphorescent emitting layer/Spacing layer/Fluorescent emitting layer (/Electron-transporting layer)

(f) Hole-transporting layer/Phosphorescent emitting layer/Spacing layer/First fluorescent emitting layer/Second fluorescent emitting layer (/Electron-transporting layer)

(g) Hole-transporting layer/Electron barrier layer/Emitting layer (/Electron-transporting layer)

(h) Hole-transporting layer/Emitting layer/Hole barrier layer (/Electron-transporting layer)

(i) Hole-transporting layer/Fluorescent emitting layer/Triplet barrier layer (/Electron-transporting layer)

The phosphorescent or fluorescent emitting layer as mentioned above can emit different colors of light. Specifically, in the stacked emitting layer (d), a layer configuration of the hole transporting layer/first phosphorescent emitting layer (red emission)/second phosphorescent emitting layer (green emission)/spacing layer/fluorescent emitting layer (blue emission)/electron transporting layer or the like can be given.

Between each emitting layer and the hole-transporting layer or the spacing layer, an electron barrier layer may be provided appropriately. Between each emitting layer and the electron transporting layer, a hole-barrier layer (a hole blocking layer) may be provided appropriately. Due to provision of an electron-barrier layer or a hole-barrier layer, electrons or holes can be confined within the emitting layer, whereby possibility of recombination of carriers in the emitting layer can be increased, and the life can be improved.

As the represented device configuration of a tandem organic EL device, the following device configuration can be given.

(2) Anode/First Emitting Unit/Intermediate Layer/Second Emitting Unit/Cathode

Here, as the first emitting unit and the second emitting unit, the same emitting units as those mentioned above can independently be given, for example.

In general, the intermediate layer is called an intermediate electrode, an intermediate conductive layer, a carrier-generating layer, an electron-withdrawing layer, and a known material configuration that supplies electrons to the first emitting unit and supplies holes to the second emitting unit can be used.

The FIGURE shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4. An electron-barrier layer may be provided on the anode 3 side of the emitting layer 5 and a hole-barrier layer may be provided on the cathode 4 side of the emitting layer 5.

Due to such configuration, electrons or holes can be confined in the emitting layer 5, whereby possibility of generation of excitons in the emitting layer 5 can be improved.

Herein, a host that is combined with a fluorescent dopant is referred to as a fluorescent host and a host that is combined with a phosphorescent dopant is referred to as a phosphorescent host. The fluorescent host and the phosphorescent host are not distinguished only by the molecular structure thereof. That is, the phosphorescent host means a material constituting a phosphorescent emitting layer that contains a phosphorescent dopant and does not mean a material that cannot be used as a material constituting a fluorescent dopant. The same can be applied to a fluorescent host.

Substrate

The organic EL device is usually formed on a transparent substrate. The transparent substrate is a substrate for supporting the organic EL device, and is preferably a flat and smooth substrate having a 400-to-700-nm-visible-light transmittance of 50% or more. Specific examples thereof include glass plates and polymer plates. Examples of the glass plate include those obtained by using as raw materials soda-lime glass, barium/strontium-containing glass, lead glass, aluminosilicate glass, borosilicate glass, barium borosilicate glass, quartz, or the like. Examples of the polymer plate include those obtained by using as raw materials polycarbonate, acrylic polymer, polyethylene terephthalate, polyethersulfide, polysulfone, or the like.

Anode

The anode of the organic EL device plays a role for injecting holes into its hole-transporting layer or emitting layer. It is effective to use one having a work function of 4.5 eV or more. As specific examples of the anode material, indium tin oxide alloy (ITO), tin oxide (NESA), indium zinc oxide, gold, silver, platinum, copper, and the like can be given. The anode can be formed by forming these electrode materials into a thin film by vapor deposition, sputtering or the like. In the case where emission from the emitting layer is taken out through the anode, the transmittance of the anode to the emission is preferably more than 10%. The sheet resistance of the anode is preferably several hundred $\Omega/\square$ or less. The film thickness of the anode, which varies depending upon the material thereof, is usually from 10 nm to 1 μm, preferably from 10 to 200 nm.

Cathode

The cathode plays a role for injecting electrons into its electron-injecting layer, electron-transporting layer or emitting layer. The cathode is preferably formed of a material having a small work function. The cathode material is not particularly restricted. As specific examples of the cathode material, indium, aluminum, magnesium, a magnesium-indium alloy, a magnesium-aluminum alloy, an aluminum-lithium alloy, an aluminum-scandium-lithium alloy, a magnesium-silver alloy or the like can be given. As in the case of the anode, the cathode can be formed by forming the materials into a thin film by a deposition method, a sputtering method or the like. If necessary, emission can be outcoupled from the cathode side.

Emitting Layer

The present invention relates—in one embodiment—to an organic electroluminescence device, wherein the light emitting layer comprises at least one compound of formula (I).

The emitting layer is an organic layer having an emitting function, and where a doping system is used, it usually comprises a host material and a dopant material.

The host material has a function of accelerating recombination of electrons and holes and confining excitons within the emitting layer. The dopant material has a function of emitting efficiently excitons obtained by recombination.

In the case of a phosphorescent device, the host material has a function of confining excitons mainly generated by a dopant within the emitting layer.

Here, in the emitting layer, a double host (also referred to as a host/cohost) that adjusts the carrier balance in the emitting layer may be used by combining an electron-transporting host and a hole-transporting host or by other methods. It is preferred that the emitting layer comprise a first host material and a second host material and that at least one component of the first host material and the second host material is the compounds of the formula (I) according to the invention.

Double dopant may be used in which two or more types of dopant materials having a high quantum yield are incorporated, and each dopant emits light. Specifically, by allowing a host, a red dopant and a green dopant to be co-deposited, yellow emission from the common emitting layer, whereby yellow emission is realized.

As for the emitting layer, by allowing plural emitting layers to be a stacked body, electrons and holes are accumulated in the interface of the emitting layers, whereby the recombination region is concentrated in the interface of the emitting layers. As a result, the quantum efficiency is improved.

The relative ease of injection of holes to the emitting layer and ease of injection of electrons to the emitting layer may differ. Further, the hole-transporting performance and the electron transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like. The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

In a more preferred embodiment, the light-emitting layer is formed from 0.1 to 70% by weight, preferably 1 to 30% by weight, of at least one of the emitter materials and 30 to 99.9% by weight, preferably 70 to 99% by weight, of at least one of the matrix materials mentioned in the specification—in one embodiment at least one compound of the formula (I)—where the sum total of the emitter material and of the matrix material adds up to 100% by weight.

(1) Phosphorescent Emitting Layer

The phosphorescent emitting layer usually comprises at least one emitter material and at least one host material. The phosphorescent host is a compound which confines the triplet energy of the phosphorescent dopant efficiently in the light emitting layer to cause the phosphorescent dopant to emit light efficiently.

A host material for phosphorescent emitting layer is usually selected from known phosphorescent host materials. Specific examples of the preferable phosphorescent host are, nitrogen-containing heteroaromatics, such as, indole derivatives, carbazole derivatives, pyridine derivatives, pyrimidine derivatives, triazine derivatives, quinoline derivatives, isoquinoline derivatives, quinazoline derivatives, nitrogenated-dibenzothiophene derivatives, nitrogenated-dibenzofuran derivatives, imidazole derivatives, such as benzimidazole derivatives, imidazopyridine derivatives, Benzimidazophenanthridine derivatives, benzimidzobenzimidazole derivatives; oxygen or sulfur containing heteroaromatics, such as thiophene derivatives, furan derivatives, benzothiophene derivatives, benzofuran derivatives, dibenzothiophene derivatives, dibenzofuran derivatives; aryl or heteroaryl substituted amine derivatives; metal complexes; aromatic hydrocarbon derivatives, such as benzene derivatives naphthalene derivatives, phenanthrene derivatives, triphenylene derivatives, fluorene derivatives, and so on, preferably, nitrogen containing heteroaromatics, the most preferably, the compounds of the formula (I).

According to one embodiment, the light-emitting layer comprises at least one emitter material and at least two matrix materials, wherein one of the matrix materials is a compound of the formula (I) and the other matrix material(s) is/are used as co-host(s). Suitable other host materials than the compounds of formula (I) (co-hosts) are mentioned below.

However, it is also possible to use two or more different compounds of formula (I) as host material in the light-emitting layer in an OLED of the present application.

Said second host material is selected from general phosphorescent host materials. Specific examples are selected from above mentioned derivatives, preferably, nitrogen containing heteroaromatics, more preferably, following general formula (N-1). The present invention therefore further relates to an organic electroluminescence device, wherein the light emitting layer comprises a heterocyclic derivative represented by the general formula (N-1) and preferably at least one compound of formula (I).

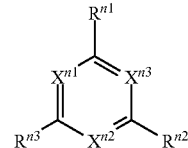

(N-1)

$X^{n1}$ to $X^{n3}$ each independently represents $CR^{n4}$ or N, $R^{n1}$ to $R^{n4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{n1}$ to $X^{n3}$ represent $CR^{n4}$, two or more substituents selected among $R^{n1}$ to $R^{n4}$ may be bonded to each other to form a ring structure.

In one embodiment of the present invention, preferable heteroaromatics for the second host are specific nitrogen containing heteroaromatics with electron donating nitrogen atom(s), such as pyrrole derivatives, indole derivatives, carbazole derivatives, acridine derivatives, phenoxadine derivatives, phenothiazine derivatives, imidazole derivatives, benzimidazole derivatives, benzimidazobenzimidazole derivatives and so on, which may have additional substituents and additional fused ring structures, preferably carbazole derivatives, more preferably following general formula (P-1).

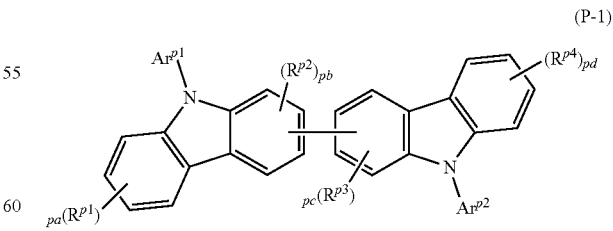

(P-1)

$Ar^{p1}$ and $Ar^{p2}$ each independently represents a substituted or unsubstituted aryl group having 6 to 24 carbon atoms, preferably, phenyl group, biphenyl group, terphenyl group, quarterphenyl group, naphthyl group, phenanthryl group or triphenylenyl group, or a substituted or unsubstituted heterocyclic group having 5 to 30 cyclic atoms, preferably, carbazoyl group, dibenzofuranyl group or dibenzothiophenyl group, or a substituent which consists of a substituted or unsubstituted aryl group and substituted or unsubstituted heteroaryl group, preferably, aryl group and dibenzofuran group, aryl group and dibenzothiophene group or aryl group and carbazole group.

$R^{p1}$ to $R^{p4}$ each independently represents a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, a substituted phosphoryl group or a cyano group, or $R^{50}$ and $R^{51}$ may be bonded to each other to form a substituted or unsubstituted aryl group having 6 to 24 carbon atoms.

pa and pd each independently represents 0 to 4.

pb and pc each independently represents 0 to 3.

In one embodiment of the present invention, aryl or heteroaryl substituted amine derivatives can be preferably used for the second host material. Latter mentioned materials for hole transporting layer can be preferably used as a second host material.

In one embodiment of the present invention, fused aryl derivatives or fused heteroaryl derivatives are preferable for the second host material.

According to another embodiment, the light-emitting layer comprises at least one emitter material and at least two matrix materials (host materials), wherein one of the matrix materials is a material selected from the above mentioned known host materials and the other matrix material(s) is/are used as co-host(s). Suitable other host material(s) is/are selected from before mentioned general host materials.

In said embodiment, the light-emitting layer is formed from 0.1 to 70% by weight, preferably 1 to 30% by weight, of the at least one emitter material and 30 to 99.9% by weight, preferably 70 to 99% by weight, of a first host and the further matrix material, where the sum total of the at least one emitter material, the further matrix materials adds up to 100% by weight.

The content ratio of the compound of the first host material and the second matrix material as co-host in the light emitting layer is not particularly limited and may be selected accordingly, and the ratio of first host material: second host material is preferably 1:99 to 99:1, more preferably 10:90 to 90:10, each based on mass.

A phosphorescent dopant (phosphorescent emitting material) that forms the emitting layer is a compound that can emit light from triplet excited state. The phosphorescent dopant is not limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex, with an ortho-metalated complex being more preferable. Among them, an iridium complex and a platinum complex are more preferable, and an ortho-metalated iridium complex is particularly preferable.

The phosphorescent host is a compound having a function of allowing a phosphorescent dopant to emit light efficiently by efficiently confining the triplet energy of the phosphorescent dopant in the emitting layer. The material for an organic EL device according to the invention is preferable as the phosphorescent host. The emitting layer may comprise one kind of the material for an organic EL device according to the invention or may comprise two or more kinds of the material for an organic EL device according to the invention.

When the material for an organic EL device according to the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to the invention as the host material and by forming an emitting layer by doping the phosphorescent dopant having such an emission wavelength, it is possible to obtain a long-lived organic EL device.

In the organic EL device according to the invention, other compounds than the material for an organic EL device according to the invention can appropriately be selected as the phosphorescent host according to the above-mentioned purpose.

The material for an organic EL device according to the invention and other compounds may be used in combination as the phosphorescent host material in the same emitting layer. When plural emitting layers are present, as the phosphorescent host material for one of these emitting layers, the material for an organic EL device according to the invention is used, and as the phosphorescent host material for one of other emitting layers, other compounds than the material for an organic EL device according to the invention may be used. The material for an organic EL device according to the invention can be used in an organic layer other than the emitting layer. In that case, as the phosphorescent host of the emitting layer, other compounds than the material for an organic EL device according to the invention may be used.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Suitable metal complexes (dopants, especially phosphorescent dopants) for use in the inventive OLEDs, preferably as emitter material, are described as following general formula (E-1).

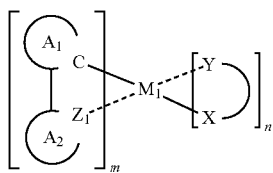

(E-1)

Wherein $M_1$ is a metal having an atomic weight greater than 40, preferably, Ir, Pt, Pd, Rh, Re, Ru, Os, Tl, Pb, Bi, In, Sn, Sb, Te, Au, or Ag, more preferably Ir, Pt, or Os, most preferably Ir, $A_1$ represents aryl group having 6 to 24 carbon atoms or heterocyclic group having 3 to 24 cyclic atoms, preferably above mentioned substituents which may have additional substituents, $A_2$ represents nitrogen containing heterocyclic group having 3 to 24 cyclic atoms, preferably above mentioned substituents which may have additional substituents, Z represents C or N, preferably N, (X—Y) is an ancillary ligand, preferably acetylacetonate derivatives, picolinate derivatives, more preferably acetylacetonate derivatives, m is a value from 1 to the maximum number of ligands that may be attached to the metal; and m+n is the maximum number of ligands that may be attached to the metal.

If m or n is more than 2, two or more ligands may be the same or different in each occurrence.

According to one embodiment, a metal complex represented by the following general formula (E-2) is more preferable especially for green and yellow emitter,

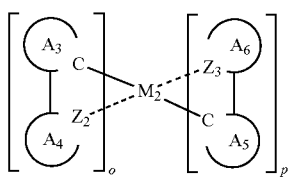

(E-2)

Wherein $M_2$ is a metal having an atomic weight greater than 40, preferably, Ir, Pt, Pd, Rh, Re, Ru, Os, Tl, Pb, Bi, In, Sn, Sb, Te, Au, or Ag, more preferably Ir, Pt, or Os, most preferably Ir, $A_3$, $A_5$ each independently represents aryl group having 6 to 24 carbon atoms or heterocyclic group having 3 to 24 cyclic atoms, preferably above mentioned substituents which may have additional substituents, $A_4$, $A_6$ each independently represents nitrogen containing heterocyclic group having 3 to 24 cyclic atoms, preferably above mentioned substituents which may have additional substituents, $Z_2$, $Z_3$ each independently represents C or N, preferably N, o is a value from 1 to the maximum number of ligands that may be attached to the metal; and o+p is the maximum number of ligands that may be attached to the metal.

If o or p is more than 2, two or more ligands may be the same or different in each occurrence.

A metal complex represented by the following general formula (T) or (β) is more preferable.

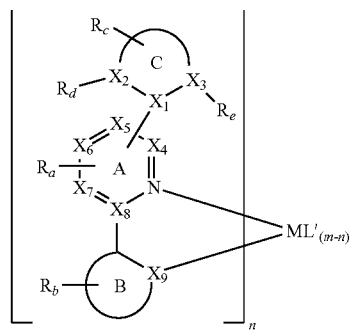

(T)

M represents the above mentioned metal atom,

B, C each independently represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, A represents a nitrogen containing 6 membered ring structure which may have additional substituents, preferably pyridine, pyrimidine, more preferably pyridine, X4 to X8 each represents C or N, preferably C, m represents oxidation state of the metal M, n is 1 or greater than 1, L' represents following chemical structure,

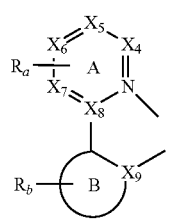

(L')

wherein A represents nitrogen containing 6 membered ring structure which may have additional substituents, preferably pyridine, pyrimidine, more preferably pyridine, B represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, X9 represents C or N, preferably, N.

Ra, Rb, Rc or Rd each independently represents hydrogen, a substituted or unsubstituted alkyl group having 1 to 25 carbon atoms, a substituted or unsubstituted alkoxy group having 1 to 25 carbon atoms, a substituted or unsubstituted amino group, a substituted or unsubstituted alkenyl group having 2 to 25 carbon atoms, a substituted or unsubstituted alkynyl group having 2 to 25 carbon atoms, a substituted or unsubstituted aralkyl group having 7 to 24 carbon atoms, a substituted or unsubstituted aryl group having 6 to 24 carbon atoms or a substituted or unsubstituted heterocyclic group having 5 to 30 cyclic atoms,

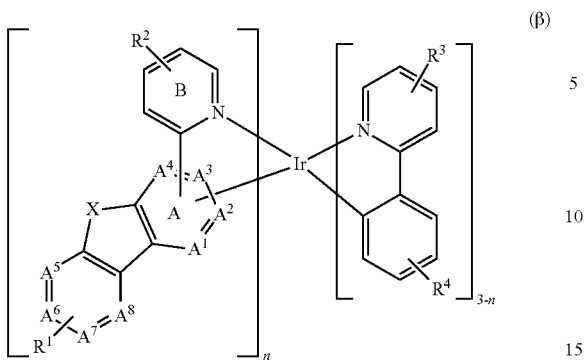
(β)

Wherein X represents NR, oxygen atom, sulfur atom, BR or Selenium atom,

R represents hydrogen atom, a substituted or unsubstituted alkyl group having 1 to 25 carbon atoms, $A^1$ to $A^8$ independently represents CH, $CR^5$ or N, preferably CH or $CR^5$, $R^1$ to $R^5$ each independently represents a substituted or unsubstituted alkyl group having 1 to 25 carbon atoms, a substituted or unsubstituted aryl group having 6 to 24 ring carbon atoms, n is 1, 2 or 3, preferably 1.

In another embodiment, a metal complex represented by any one of the following general formula (V), (X), (Y), (Z) can be used.

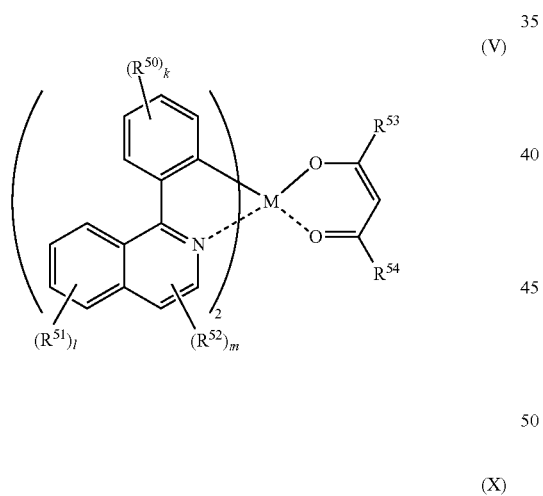
(V)

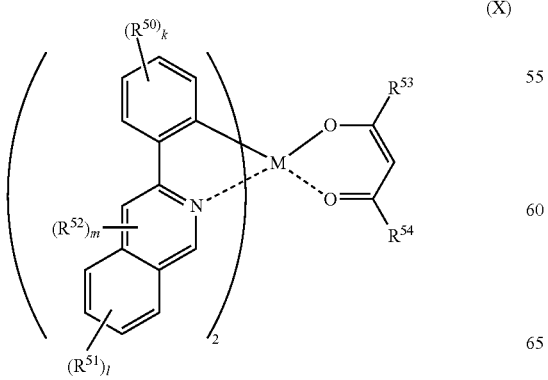
(X)

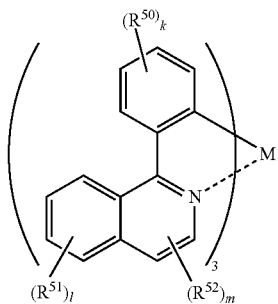
(Y)

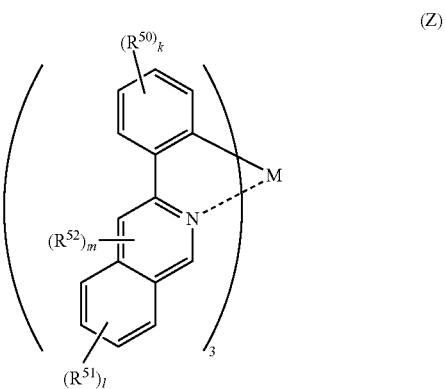
(Z)

Wherein $R^{50}$ to $R^{52}$ each represents a substituted or unsubstituted alkyl group having 1 to 25 carbon atoms, a substituted or unsubstituted aryl group having 6 to 24 ring carbon atoms, k is 0, 1, 2, 3 or 4, m is 0, 1 or 2, l is 0, 1, 2, 3 or 4, M represents iridium atom (Ir), osmium atom (Os) or platinum atom (Pt).

Formula (V) is preferably represented by formula (V-1). Formula (X) is preferably represented by formula (X-1) or (X-2).

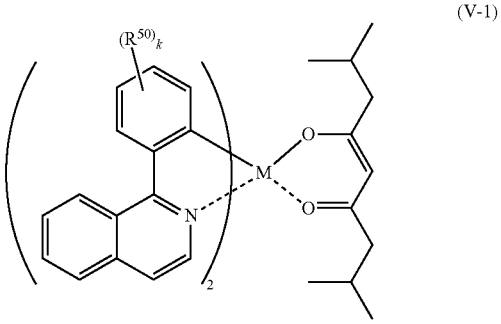
(V-1)

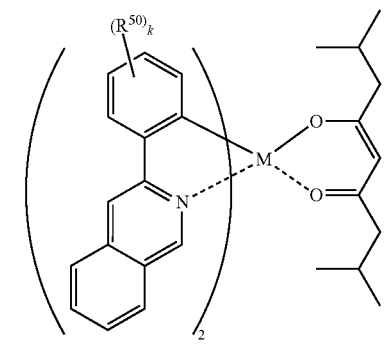

(X-1)

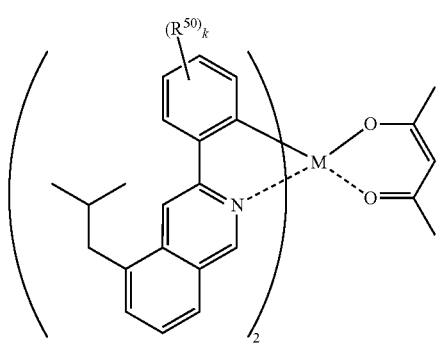

(X-2)

Wherein $R^{50}$, M and k are as defined in formula (V) and (X).

(2) Fluorescent Emitting Layer

The fluorescent emitting layer usually comprises at least one emitter material and at least one host material.

A host material for fluorescent emitting layer is usually selected from general host materials, which preferably have wider band-gap than the emitter material to get highly efficient light emission from the emitter through energy transfer mechanism from the excited host to the emitter. Specific examples of the preferable fluorescent host are, substituted or unsubstituted above mentioned heterocyclic compounds; or substituted or unsubstituted aromatic hydrocarbon compounds, such as oligo-phenylene derivatives, naphthalene derivatives, fluorene derivatives, fluoranthene derivatives, anthracene derivatives, phenanthrene derivatives, pyrene derivatives, triphenylene derivatives, benzanthracene derivatives, chrysene derivatives, benzphenanthrene derivatives, naphthacene derivatives, benzochrysene derivatives, and so on, preferably anthracene derivatives, pyrene derivatives and naphthacene derivatives, more preferably, anthracene derivatives represented by following general formula (X) especially for fluorescent blue or green device.

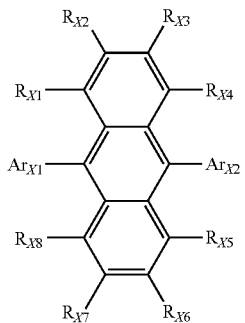

(X)

$Ar_{X1}$ and $Ar_{X2}$ are independently a substituted or unsubstituted aryl group including 6 to 50 ring carbon atoms, preferably phenyl group, biphenyl group, naphthyl group, phenanthryl group, fluorenyl group, fluoranthenyl group, anthryl group, pyrenyl group, benzphenanthryl group, triphenylenyl group, benzanthryl group, benzochrysenyl group, or a heterocyclic group including 5 to 50 ring atoms, preferably, benzofuranyl group, benzothiophenyl group, indolyl group, dibenzothiophenyl group, dibenzofuranyl group, carbazolyl group, benzocarbazoryl group, dibenzocarbazoryl group, indolophenanthryl group, naphthobenzofuranyl group, naphthobenzothiophenyl group, dinaphthofuranyl group, dinaphthothiophenyl group, benzophenanthlofuranyl group, benzophenanthlothiophenyl group, benzofurodibenzofuranyl group, benzothiodibenzothiophenyl group, benzofurodibenzotihiophenyl group, benzothiodibenzofuranyl group, more preferably oxygen or sulfur containing heteroaromatics, such as furan or thiophene containing heteroaromatics in one of the part of the heteroaromatics.

$R_{X1}$ to $R_{X8}$ are independently a hydrogen atom, a substituted or unsubstituted aryl group including 6 to 50 ring carbon atoms, a substituted or unsubstituted heterocyclic group including 5 to 50 ring atoms, an alkyl group including 1 to 50 carbon atoms, a substituted or unsubstituted alkoxy group including 1 to 50 carbon atoms, a substituted or unsubstituted aralkyl group including 7 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, a substituted or unsubstituted silyl group, a carboxy group, a halogen atom, a cyano group, a nitro group or a hydroxyl group.

An emitter material for fluorescent emitting layer is usually selected from general emitter materials or fluorescent dyes, which preferably have high absorption co-efficiency and high quantum efficiency to get highly efficient light emission from the emitter. Specific examples of the preferable fluorescent emitter are, aromatic hydrocarbon derivatives, such as oligo-phenylene derivatives, naphthalene derivatives, fluorene derivatives, fluoranthenyl group, fused fluoranthenyl group, anthracene derivatives, phenanthrene derivatives, pyrene derivatives, triphenylene derivatives, benzanthracene derivatives, chrysene derivatives, benzphenanthrene derivatives, naphthacene derivatives, benzochrysene derivatives, and so on; aromatic or heterocyclic amine derivatives represented by following general formula (Y); organic boron derivatives represented by general formula (Z),

(Y)

$Y_1$ is a substituted or unsubstituted aromatic hydrocarbon group including 6 to 50 ring carbon atoms, preferably fused aromatic hydrocarbon group, or substituted or unsubstituted heterocyclic group having 5 to 50 cyclic atoms.

$Ar_{y1}$ and $Ar_{y2}$ are independently a substituted or unsubstituted aryl group including 6 to 50 ring carbon atoms or a substituted or unsubstituted heterocyclic ring group including 5 to 50 ring atoms, preferably, oxygen or sulfur containing heterocyclic group.

Specific examples of $Y_1$ include the above-mentioned fused aryl group. $Y_1$ is preferably a substituted or unsubstituted anthryl group; a substituted or unsubstituted pyrenyl group; a substituted or unsubstituted chrysenyl group; substituted or unsubstituted fluorenyl group, especially substituted or unsubstituted mono-, di-, or tri-benzofuro-fused fluorene, or substituted or unsubstituted mono-, di-, or tri-benzothio-fused fluorene; substituted or unsubstituted dibenzofuran containing heterocyclic group; substituted or unsubstituted dibenzothiophene containing heterocyclic group.

n is an integer of 1 to 4, preferably 1 or 2.

Electron-Transporting Layer

The electron-transporting layer is an organic layer that is formed between the emitting-layer and the cathode and has a function of transporting electrons from the cathode to the emitting layer. When the electron-transporting layer is formed of plural layers, an organic layer that is nearer to the cathode is often defined as the electron-injecting layer. The electron-injecting layer has a function of injecting electrons from the cathode efficiently to the organic layer unit.

According to one embodiment, it is preferred that an electron-transporting layer further comprises the other one or more layer(s) than electron injection layer to enhance efficiency and lifetime of the device, preferably between an electron injection layer and an emitting layer as a hole blocking layer, an exciton blocking layer or a triplet blocking layer.

A compound of the formula (I) is also preferable as all the use of the electron transporting layer, such as an electron transporting layer, an electron-injecting layer, a hole blocking layer, a exciton blocking layer or a triplet blocking layer.

According to one embodiment, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable. Examples of the alkaline earth metal compound include BaO, SrO, CaO, and mixtures thereof such as $Ba_xSr_{1-x}O$ (0<x<1) and $Ba_xCa_{1-x}O$ (0<x<1). Among them, BaO, SrO and CaO are preferable. Examples of the rare earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline; phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound: the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component: electron-donating dopant=5:1 to 1:5 in terms of molar ratio, more preferably 2:1 to 1:2.

As the electron-transporting material used in the electron-transporting layer other than a compound of the formula (I), an aromatic heterocyclic compound having one or more hetero atoms in the molecule may preferably be used. In particular, a nitrogen containing heterocyclic derivative is preferable.

According to one embodiment, it is preferable that the electron-transporting layer comprises a nitrogen containing heterocyclics metal chelate, such as 8-hydroxyquinolinolato aluminum, which is generally called as Alq$_3$.

According to the other embodiment, it is preferable that the electron-transporting layer comprising substituted or unsubstituted nitrogen containing heterocyclic derivative. Specific examples of the preferable heterocyclic derivative for the elecrtron-transporting layer are, 6-membered azine derivatives; such as pyridine derivatives, pyrimidine derivatives, triazine derivatives, pyrazine derivatives, preferably pyrimidine derivatives or triazine derivatives; 6-membered fused azine derivatives, such as quinolone derivatives, isoquinoline derivatives, quinoxaline derivatives, quinazoline derivatives, phenanthroline derivatives, benzoquinoline derivatives, benzoisoquinoline derivatives, dibenzoquinoxaline derivatives, preferably quinolone derivatives, isoquinoline derivatives, phenanthroline derivatives; 5-membered heterocyclic derivatives, such as imidazole derivatives, oxazole derivatives, oxadiazole derivatives, triazole derivatives, thiazole derivatives, thiadiazole derivatives; fused imidazole derivatives, such as benzimidazole derivatives, imidazopyridine derivatives, naphthoimidazole derivatives, benzimidazophenanthridine derivatives, benzimidzobenzimidazole derivatives, preferably benzimidazole derivatives, imidazopyridine derivatives or benzimidazophenanthridine derivatives.

According to the other embodiment, it is preferable the electron-transporting layer comprises phosphine oxide derivative represented as $Ar_{p1}Ar_{p2}Ar_{p3}P=O$.

$Ar_{p1}$ to $Ar_{p3}$ are the substituents of phosphor atom and each independently represent substituted or unsubstituted above mentioned aryl group or substituted or unsubstituted above mentioned heterocyclic group.

According to the other embodiment, it is preferable that the electron-transporting layer comprises aromatic hydrocarbon derivatives.

Specific examples of the preferable aromatic hydrocarbon derivatives for the electron-transporting layer are, oligophenylene derivatives, naphthalene derivatives, fluorene derivatives, fluoranthenyl group, anthracene derivatives, phenanthrene derivatives, pyrene derivatives, triphenylene derivatives, benzanthracene derivatives, chrysene derivatives, benzphenanthrene derivatives, naphthacene derivatives, benzochrysene derivatives, and so on, preferably anthracene derivatives, pyrene derivatives and fluoranthene derivatives.

The present invention therefore relates to an organic electroluminescence device, wherein an electron transporting layer is provided between the cathode and the light emitting layer, and the electron transporting layer comprises at least one compound of formula (I).

The present invention therefore further relates to an organic electroluminescence device, wherein a hole blocking layer is provided between the electron transporting layer and the light emitting layer, and the hole blocking layer comprises at least one compound of formula (I). According to one embodiment, it is preferred that the other electron transporting region is further comprised between the hole blocking layer comprising the compound of general formula (I) and cathode. Said electron transporting region generally comprises one or more electron transporting layer(s).

Above mentioned electron injection materials, such as alkali metal compound or alkali metal complex, preferably comprising as one of electron transporting layer at the interface of cathode. Second electron transporting layer preferably comprises between hole blocking layer and said electron transporting layer comprising electron injection material.

Above mentioned heterocyclic derivatives or fused aromatic derivatives are preferably used for second electron transporting layer, more preferably heterocyclic derivatives represented by general formulae (ET-1), (ET-2), (ET-3) or (ET-4).

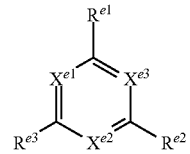

(ET-1)

$X^{e1}$ to $X^{e3}$ each independently represents $CR^{e4}$ or N, preferably more than two of $X^{e1}$ to $X^{e3}$ are N, $R^{e1}$ to $R^{e4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{e1}$ to $X^{e3}$ represent $CR^{e4}$, two or more substituents selected among $R^{e1}$ to $R^{e4}$ may be bonded to each other to form a ring structure.

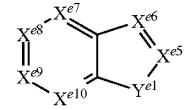

(ET-2)

$X^{e6}$ to $X^{e10}$ each independently represents $CR^{e5}$ or N, preferably at least $X^{e6}$ is N, $Y^{e1}$ represents oxygen atom, sulfur atom, $CR^{e6}R^{e7}$ or $NR^{e7}$, $R^{e5}$ to $R^{e8}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, two or more substituents selected among $R^{e5}$ to $R^{e8}$ may be bonded to each other to form a ring structure.

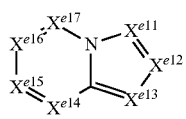

(ET-3)

$X^{e11}$ to $X^{e17}$ each independently represents $CR^{e9}$ or N, preferably at least one selected from $X^{e11}$, $X^{e12}$ and $X^{e13}$ is N, $R^{e9}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, two or more substituents selected among $R^{e9}$ may be bonded to each other to form a ring structure.

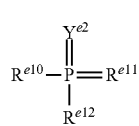

(ET-4)

$R^{e10}$ to $R^{e12}$ each independently represents a substituted or unsubstituted aryl group having 6 to 24 carbon atoms, a substituted or unsubstituted heterocyclic group having 5 to 30 cyclic atoms, two or more substituents selected among $R^{e10}$ to $R^{e1}2$ may be bonded to each other to form a ring structure, preferably at least one of $R^{e10}$ to $R^{e1}2$ have additional substituted or unsubstituted aryl group having 6 to 24 carbon atoms, or substituted or unsubstituted heterocyclic group having 5 to 30 cyclic atoms, $Y^{e2}$ represents oxygen atom or sulfur atom.

Hole-Transporting Layer

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

Said hole injection layer is generally used for stabilizing hole injection from anode to hole transporting layer which is generally consist of organic materials.

Organic material having good contact with anode or organic material with p-type doping is preferably used for the hole injection layer.

Acceptor materials, or fused aromatic hydrocarbon materials or fused heterocycles which have high planarity, are preferably used, acceptor materials are more preferably used for the hole injection layer.

Specific examples for acceptor materials are, the quinone derivatives with one or more electron withdrawing groups, such as $F_4TCNQ$(2,3,5,6-tetrafluoro-7,7,8,8-tetracyanoquinodimethane), 1,2,3-Tris[(cyano)(4-cyano-2,3,5,6-tetrafluorophenyl)methylene]cyclopropane, and so on; hexa-azatriphenylene derivatives with one or more electron withdrawing groups, such as hexa-azatriphenylene-hexanitrile; aromatic hydrocarbon derivatives with one or more electron withdrawing groups; aryl boron derivatives with one or more electron withdrawing groups, and so on.

p-doping is usually consist of one or more p-dopant materials and one or more matrix materials. Matrix materials preferably have shallower HOMO level and p-dopant preferably have deeper LUMO level to enhance the carrier density of the layer. Aryl or heteroaryl amine derivatives are preferably used as the matrix materials. Specific examples for the matrix material are the same as that for hole transporting layer which is explained at the later part. Specific examples for p-dopant are the above mentioned acceptor materials, preferably the quinone derivatives with one or more electron withdrawing groups, such as $F_4TCNQ$, 1,2,3-Tris[(cyano)(4-cyano-2,3,5,6-tetrafluorophenyl)methylene]cyclopropane.

The ratio of the p-type dopant is preferably less than 20% of molar ratio, more preferably less than 10%, such as 1%, 3%, 5% and so on.

Hole transporting layer is generally used for injecting and transporting holes efficiently, and aromatic or heterocyclic amine derivatives are preferably used.

Specific examples for hole transporting layer are represented as general formula (H),

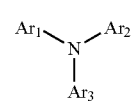

(H)

$Ar_1$ to $Ar_3$ each independently represents substituted or unsubstituted aryl group having 5 to 50 carbon atoms or substituted or unsubstituted heterocyclic group having 5 to 50 cyclic atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar^1$ to $Ar^3$ may be bonded to each other to form a ring structure, such as carbazole ring structure, acridane ring structure and so on.

According to one embodiment, it is preferable that at least one of $Ar_1$ to $Ar_3$ have additional one aryl or heterocyclic amine substituent, more preferably $Ar_1$ has an additional aryl amino substituent, at the case of that it is preferable that $Ar_1$ represents substituted or unsubstituted biphenylene group, substituted or unsubstituted fluorenylene group.

A second hole transporting layer is preferably inserted between the first hole transporting layer and the emitting layer to enhance device performance by blocking excess electrons or excitons. Specific examples for second hole transporting layer is the same as the first hole transporting layer. It is preferably that second hole transporting layer have higher triplet energy to block triplet exciton especially for phosphorescent green device, such as bicarbazole derivatives, biphenylamine derivatives, triphenylenyl amine derivatives, fluorenyl amine derivatives, carbazole substituted arylamine derivatives, dibenzofuran substituted arylamine derivatives, dibenzothiophene substituted arylamine derivatives, and so on.

Spacing Layer

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

Barrier Layer

It is preferred that the organic EL device according to the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules in the electron-transporting layer other than the emitting dopant by confining the triplet excitons within the emitting layer.

When the triplet barrier layer is provided, in the phosphorescent emitting device, the following is considered. The triplet energy of the phosphorescent emitting dopant is taken as $E^T_d$ and the triplet energy of the compound used as the triplet barrier layer is taken as $E^T_{TB}$. If the energy relationship $E^T_d < E^T_{TB}$ is satisfied, in respect of energy, the triplet excitons of the phosphorescent emitting dopant is confined (i.e. the triplet excitons cannot be moved to other molecules), whereby the energy deactivation route other than emission on the dopant is cut off, leading to efficient emission. However, even when the relationship $E^T_d < E^T_{TB}$ is established, if the energy difference $\Delta E^T = E^T_{TB} - E^T_d$ is small, it is thought that, in an environment at around room temperature where the device is actually driven, due to thermal energy of the surrounding area, the triplet excitons can move to other molecules by endothermically overcoming this energy difference $\Delta E^T$. In particular, in the case of phosphorescent emission that has a longer exciton life as compared with fluorescent emission, effects of the endothermic move of excitons relatively tend to appear. Relative to the thermal energy at room temperature, a larger energy difference $\Delta E^T$ is preferable. The energy difference $\Delta E^T$ is further preferably 0.1 eV or more, and particularly preferably 0.2 eV or more. On the other hand, in a fluorescent device, as the triplet barrier layer of the TTF device configuration disclosed in WO2010/134350A1, the inventive compounds of formula (I) can be used.

The electron mobility of the material constituting the triplet barrier layer is desirably $10^{-6}$ cm$^2$/Vs or more in a field intensity range of 0.04 to 0.5 MV/cm. As the method for measuring the electron mobility of an organic material, several methods that include the Time of Flight method are known. Here, the electron mobility means an electron mobility that is determined by the impedance spectroscopy.

The electron mobility of the electron-injecting layer is desirably $10^{-6}$ cm$^2$/Vs or more in a field intensity range of 0.04 to 0.5 MV/cm. The reason is that, by this electron mobility, injection of electrons from the cathode to the electron-transporting layer is promoted, and as a result, injection of electrons to adjacent barrier layer and emitting layer is promoted, enabling the device to be driven at a lower voltage.

The present invention further relates to an electronic equipment comprising the organic electroluminescence device according to the present invention.

The organic EL device using the inventive compounds of formula (I) can be used as an emitting device in a panel module used in various displays.

The organic EL device using the inventive compounds of formula (I) can be used as a display element of a TV, a mobile phone and a PC; or an electronic apparatus such as lightings or the like.

The OLEDs (organic EL devices) can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

I Preparation Examples

Example 1

Example 1.1

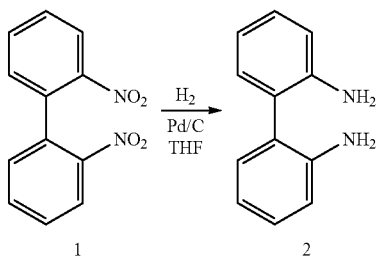

2,2'-Dinitrobiphenyl (15 g, 61.5 mmol) was dissolved in THF (500 mL) and 5% Pd/C (1.5 g) was added. The reaction was degassed with Ar and then pressurised with $H_2$ (3 bar) and allowed to stir at room temperature maintaining the pressure at 3 bar. The reaction was allowed to continue overnight. The reaction was then degassed with Ar and the catalyst filtered over a pad of celite washing through with THF. The solvent was evaporated and the crude diamine (11 g) was isolated as a pale brown solid and was used without further purification. 1H NMR (400 MHz, Chloroform-d) δ 7.26-7.12 (m, 4H), 6.91-6.78 (m, 4H), 3.70 (br s, 4H). m/z; 185 (M+1).

Example 1.2

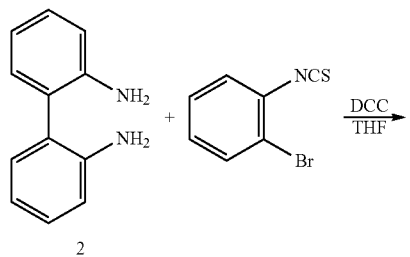

2,2'-Biphenyldiamine (10 g, 54 mmol) was combined with 2-bromophenylisothiocyanate (7.3 mL, 54 mmol) in THF (200 mL) and allowed to stir at room temperature for 2 hours. Dicyclohexylcarbodiimide (11.1 g, 54 mmol) was added to the reaction and the resulting solution stirred at an oil bath temperature of 70° C. overnight. The crude reaction mixture was cooled to room temperature and the solvent evaporated. The crude residue was suspended in methanol and stirred at room temperature for 2 hours. The white precipitate was filtered and dried (17.4 g, 89% yield) and used without further purification. 1H NMR (400 MHz, Chloroform-d) δ 7.68 (m, 1H), 7.53 (m, 2H), 7.36 (m, 1H), 7.27 (m, 4H), 7.12-6.96 (m, 3H), 6.72 (m, 1H), 6.58 (br s, 1H), 5.75 (br s, 1H). m/z; 364 (M+1).

Example 1.3

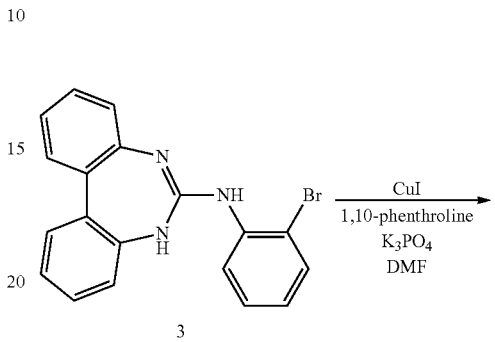

Compound 3 (17.4 g, 47.8 mmol) was combined with CuI (0.91 g, 4.8 mmol), 1,10-phenathroline (1.73 g 9.6 mmol) and $K_3PO_4$ (30.4 g, 143.4 mmol) and DMF (100 mL) added. The reaction mixture was degassed with $N_2$ and then heated at an oil bath temperature of 70° C. overnight. The reaction was cooled to room temperature and poured into water. The precipitate was filtered and washed with water and dried. The precipitate was dissolved in $CHCl_3$ and adsorbed onto silica gel. The desired product was purified by eluting the silica with EtOAc to give 4 as an off white solid (9.7 g, 71% yield). 1H NMR (400 MHz, DMSO-d6) δ 9.12 (s, 1H), 7.70 (m, 1H), 7.67-7.41 (m, 6H), 7.37 (m, 1H), 7.28 (m, 1H), 7.28-7.15 (m, 2H), 7.20-7.11 (m, 1H). m/z 273 (M+1).

Example 1.4

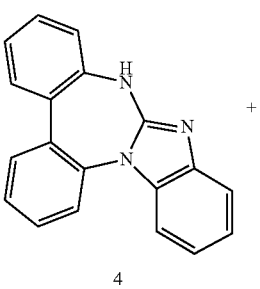

-continued

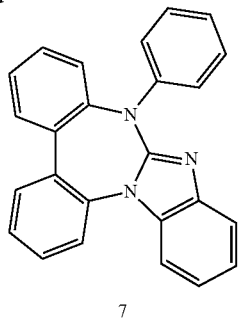

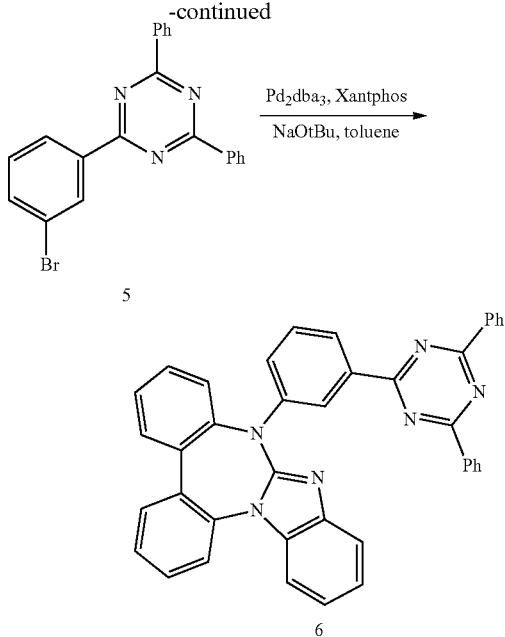

Compound 4 (2.5 g, 8.8 mmol) was combined with compound 5 (3.4 g, 8.8 mmol) in the presence of Pd₂dba₃ (0.16 g, 0.17 mmol), Xantphos (0.3 g, 0.5 mmol) and NaOtBu (1.7 g, 17.6 mmol) in toluene (44 mL) under N₂ atmosphere. The reaction mixture was heated at an oil bath temperature of 110° C. overnight. The reaction was then cooled to room temperature and solvent evaporated. The crude material was dissolved in CHCl₃ and washed with water, dried over anhydrous MgSO₄ and filtered directly over a pad of celite, washing through with CHCl₃. The solvent was evaporated and the crude residue was suspended in acetone and stirred at room temperature for 1 hour. The precipitate was filtered. The product was recrystallized from chlorobenzene to give 2.66 g (51% yield) of pure product 6. 1H NMR (400 MHz, Chloroform-d) δ 9.13 (m, 1H), 8.79-8.71 (m, 4H), 8.33 (m, 1H), 7.96 (m, 1H), 7.84 (m, 2H), 7.76 (m, 1H), 7.68 (m, 2H), 7.67-7.52 (m, 7H), 7.57-7.46 (m, 3H), 7.50-7.32 (m, 3H). m/z 591 (M+1).

Example 2

Example 2.1

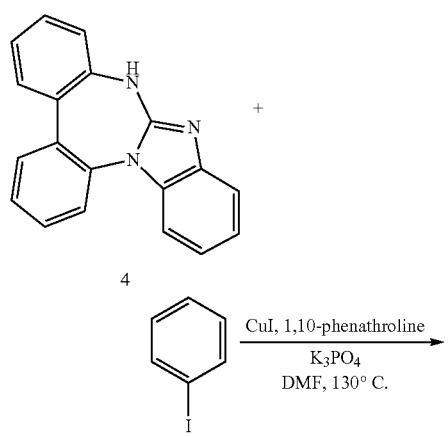

-continued

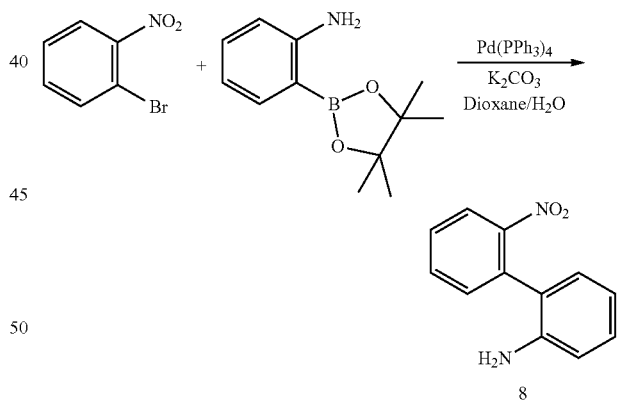

Compound 4 (see example 1.3) (0.48 g, 1.76 mmol) was combined with iodobenzene (0.4 mL, 3.5 mmol) in the presence of CuI (0.13 g, 0.7 mmol), 1,10-phenanthroline (0.25 g, 1.4 mmol) and K₂CO₃ (0.75 g, 0.35 mmol) and DMF (5 mL) was added. The reaction mixture was degassed with N₂ and then stirred at an oil bath temperature of 135° C. overnight. The reaction mixture was cooled to room temperature and diluted with water. The insoluble precipitate was filtered and washed well with water. The crude product was then suspended in MeOH and stirred at room temperature for 1 hour. The product was then purified by chromatography on silica using toluene as eluant. 0.25 g (40% yield) was thus isolated. 1H NMR (400 MHz, DMSO-d6) δ 7.92-7.72 (m, 4H), 7.67-7.51 (m, 5H), 7.47 (m, 1H), 7.38-7.31 (m, 2H), 7.30-7.10 (m, 4H), 6.95-6.86 (m, 1H). m/z 360 (M+1).

Example 3

Example 3.1

2-bromo-nitrobenzene (11.7 g, 58 mmol) was combined with 2-(4,4,5,5-Tetramethyl-1,3,2-dioxaborolan-2-yl)aniline (13 g, 61 mmol), Pd(PPh₃)₄ (0.7 g, 0.58 mmol) and K₂CO₃ (16 g, 116 mmol) in Dioxane/water (400 mL, 4:1) and the resulting mixture was degassed with N₂. The reaction was then heated at an oil bath temperature of 90° C. After 2 hours, the reaction was stopped and allowed to cool to room temperature. The reaction solution was concentrated under reduced pressure. The residue was diluted with CH₂Cl₂ and washed with water and brine, dried over anhydrous MgSO₄ and solvent evaporated. The crude product was then purified by chromatography on silica using 20-30% EtOAc in heptane as eluant. 7 g (56% yield) of 8 was this obtained. 1H NMR (400 MHz, Chloroform-d) δ 7.99 (dd, J=8.1, 1.3 Hz, 1H), 7.68 (td, J=7.5, 1.3 Hz, 1H), 7.59-7.46 (m, 2H), 7.24 (ddd, J=8.0, 7.4, 1.6 Hz, 1H), 7.02 (dd, J=7.6, 1.6 Hz, 1H), 6.92-6.79 (m, 2H), 3.85 (br m, 2H). m/z 215 (M+1).

Example 3.2

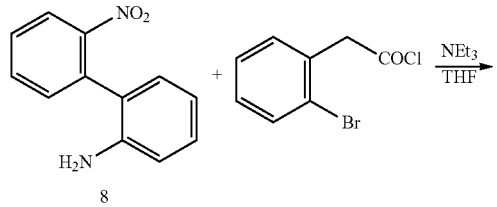

8

Example 3.3

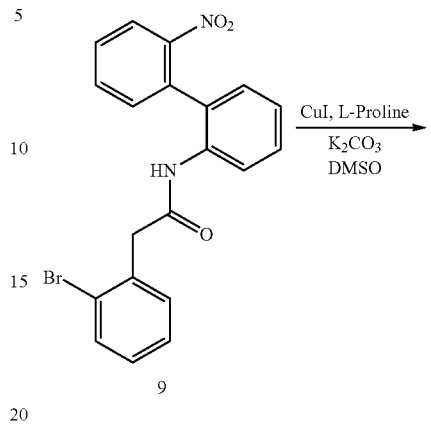

9

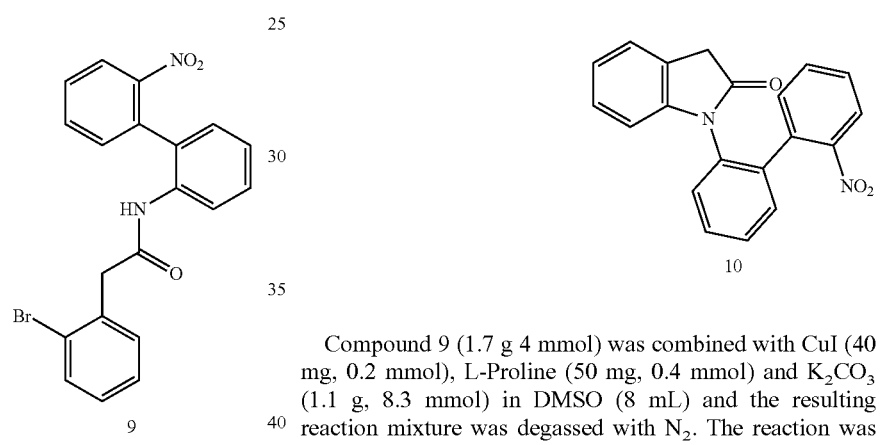

10

Compound 9 (1.7 g 4 mmol) was combined with CuI (40 mg, 0.2 mmol), L-Proline (50 mg, 0.4 mmol) and K₂CO₃ (1.1 g, 8.3 mmol) in DMSO (8 mL) and the resulting reaction mixture was degassed with N₂. The reaction was heated at an oil bath temperature of 70° C. overnight. The reaction was allowed to cool to room temperature and diluted with water and stirred at room temperature for 1 hour. The precipitate was filtered and allowed to dry. The crude product was taken up in CH₂Cl₂ and washed with 2.5% aqueous NH₃ and water, dried over anhydrous MgSO₄. The crude reaction solution was passed through a plug of silica to give the target compound 10 (1 g, 73% yield) which was used without further purification. HPLC MS m/z 331 (M+1).

Example 3.4

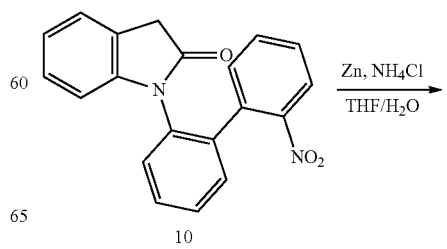

10

Compound 8 (7 g, 33 mmol) was combined with (2-bromophenyl)acetyl chloride (5.6 mL, 39 mmol) in THF (60 mL) under an atmosphere of N₂ and cooled to 0° C. NEt₃ (5.4 mL, 39 mmol) was added dropwise and the resulting mixture was allowed to warm to room temperature and stirred for 2 hours at room temperature. The reaction was then stopped and worked up by evaporating the solvent under reduced pressure, and redissolving the crude in CH₂Cl₂, washed with water and brine and dried over anhydrous MgSO₄. The solvent was evaporated under reduced pressure. The crude product was recrystallized from EtOH/H₂O and 10.7 g was thus obtained (82% yield). This was used without further purification. 1H NMR (400 MHz, Chloroform-d) δ 8.16 (d, J=8.4 Hz, 1H), 7.86 (dd, J=7.3, 2.2 Hz, 1H), 7.60-7.48 (m, 2H), 7.43 (td, J=7.8, 1.6 Hz, 1H), 7.39-7.35 (m, 1H), 7.26-6.98 (m, 5H), 6.85 (s, 1H), 3.75 (d, J=2.8 Hz, 2H). m/z 411 (M+1).

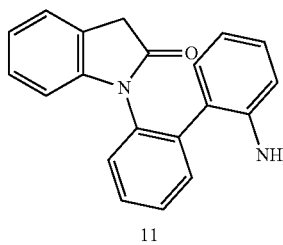

Compound 10 (1 g, 3 mmol) was taken up in THF/H$_2$O (50 mL, 1:1) and Zn (2 g, 30 mmol) and NH$_4$Cl (1.6 g, 30 mmol) were added. The reaction mixture was stirred at an oil bath temperature of 70° C. for 4 hours. The reaction was then cooled to room temperature and filtered through a pad of celite washing through with EtOAc. The aqueous phase was separated and dried over anhydrous MgSO$_4$ and solvent evaporated. Compound 11 was confirmed by HPLC MS (m/z 301, M+1) thus obtained and used without further purification. 1H NMR (300 MHz, Chloroform-d) δ 7.85 (d, J=8.1 Hz, 1H), 7.68-7.36 (m, 7H), 7.33-7.12 (m, 4H), 7.02 (t, J=7.5 Hz, 1H), 6.75 (d, J=7.9 Hz, 1H), 3.67-3.19 (m, 2H).

Example 3.5

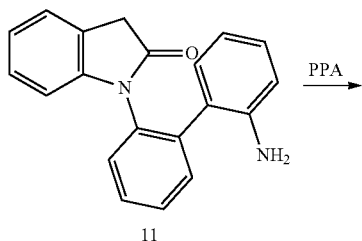

Compound 11 (0.5 g, 1.7 mmol) was suspended in polyphosphoric acid (5 g) and the resulting mixture was heated at an oil bath temperature of 120° C. for 2 hours. The reaction was cooled to room temperature and quenched with ice water. The precipitate was filtered rapidly and used without further purification. HPLC MS m/z 283 (M+1).

The N functionalization of compound 12 is carried out as for example described in examples 1.4 and 2.1.

Example 4

Example 4.1

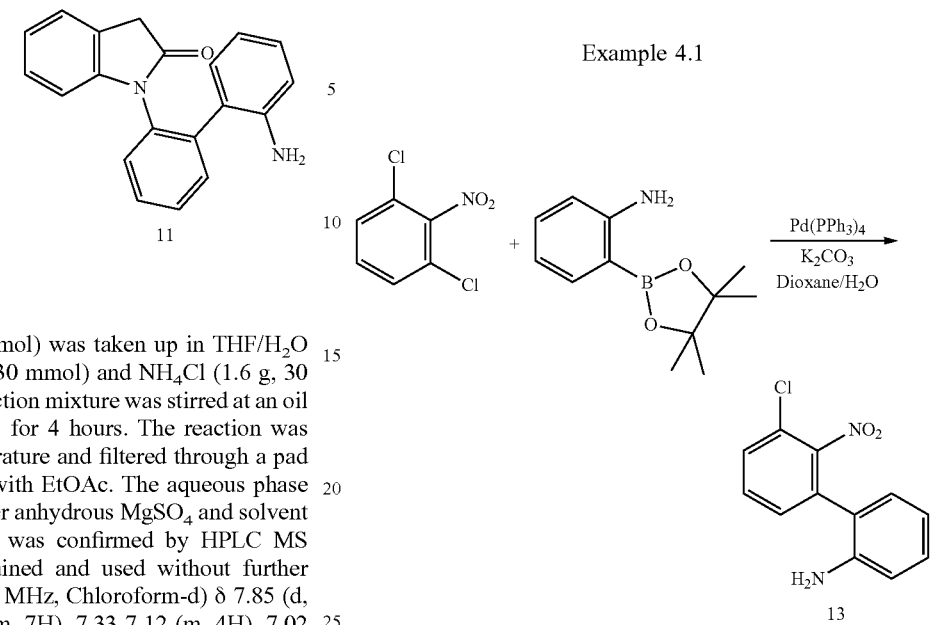

2,6-dichloronitrobenzene (6.5 g 34 mmol) was combined with 2-(4,4,5,5-Tetramethyl-1,3,2-dioxaborolan-2-yl)aniline (5 g, 22.6 mmol) in the presence of Pd(PPh$_3$)$_4$ (0.5 g, 0.45 mmol) and K$_2$CO$_3$ (6.25 g, 45 mmol) in Dioxane/water (100 mL, 4:1) and the resulting mixture was degassed with N$_2$. The reaction was stirred at an oil bath temperature of 90° C. overnight. The solvent was evaporated under reduced pressure and the crude residue dissolved in CH$_2$Cl$_2$, washed with water and dried over anhydrous MgSO$_4$. The product was purified by chromatography on silica using 20% EtOAc in heptane as eluant. Compound 13 (5 g, 90% yield) was thus obtained. The product was confirmed by HPLC MS m/z 249 (M+1).

Example 4.2

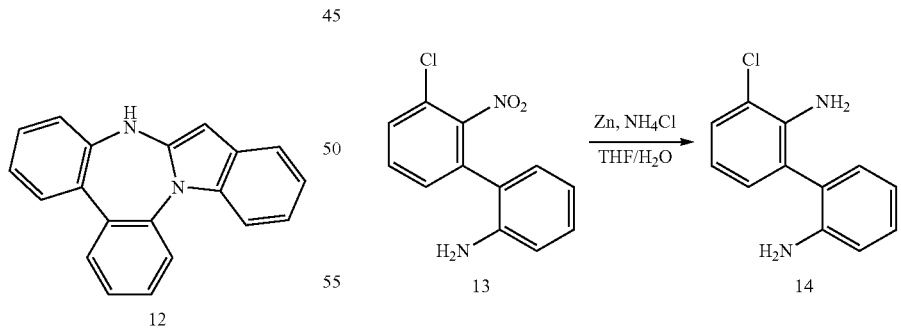

Compound 13 (5 g, 20 mmol) was treated with Zn (13 g, 200 mmol), NH$_4$Cl (10.7 g, 200 mmol) in THF/H$_2$O (1:1, 100 mL) and the reaction was heated at an oil bath temperature of 70° C. overnight. The reaction was then cooled to room temperature and the solids filtered over a pad of celite. The organic phase was diluted with MTBE and the aqueous phase separated. The organic phase was then dried over anhydrous MgSO$_4$ and the solvent evaporated. The product (4.2 g, 96%) was confirmed by HPLC MS (m/z 219, M+1) and was used without further purification.

Example 4.3

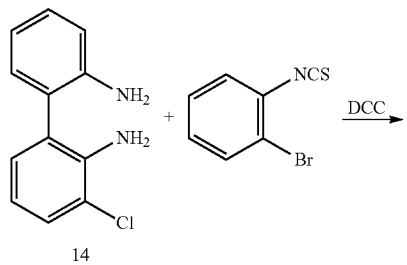

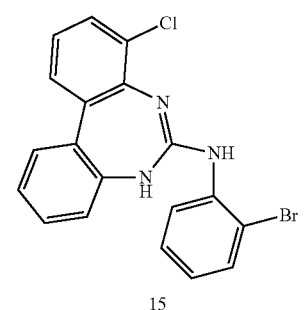

Compound 14 (4.2 g, 19.2 mmol) was combined with 2-bromophenylisothiocyanate (2.6 mL, 19.2 mmol) in THF (100 mL) at room temperature under $N_2$ for 1 hour. Dicyclohexylcarbodiimide (3.9 g, 19.2 mmol) was then added and the reaction mixture was heated at an oil bath temperature of 60° C. for 6 hours. The reaction was cooled to room temperature and solvent was evaporated. The crude product was suspended in methanol and stirred at room temperature for 2 hours. The precipitate 15 was filtered washing through with methanol. $^1$H NMR (400 MHz, DMSO-d6) δ 9.04 (s), 8.69 (d), 8.10 (m), 7.69-6.88 (m), 6.60 (s). HPLC MS m/z 398 (M+1).

Example 4.4

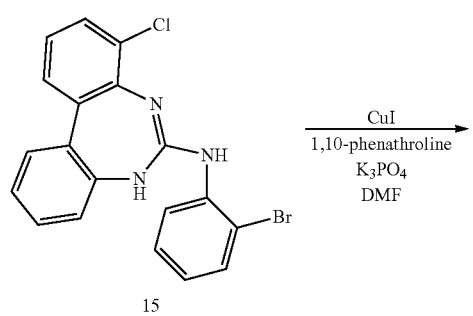

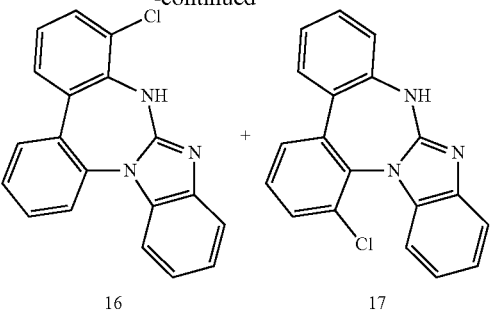

Compound 15 (0.2 g, 0.5 mmol) was combined with CuI (10 mg, 0.05 mmol), 1,10-phenathroline (18 mg, 0.1 mmol) and $K_3PO_4$ (0.32 g 1.5 mmol) in DMF (5 mL) and the resulting mixture was degassed with $N_2$: The reaction was heated at an oil bath temperature of 80° C. under an atmosphere of $N_2$ for 2 hours. The target compounds were formed in a 2:1 mixture of isomers and confirmed by HPLC MS (m/z 318, M+1).

The N functionalization of compounds 16 and 17 is carried out as for example described in examples 1.4 and 2.1. The functionalization at Cl in the compounds of formulae 16 and 17 can be carried out as known in the art.

Example 5

Example 5.1

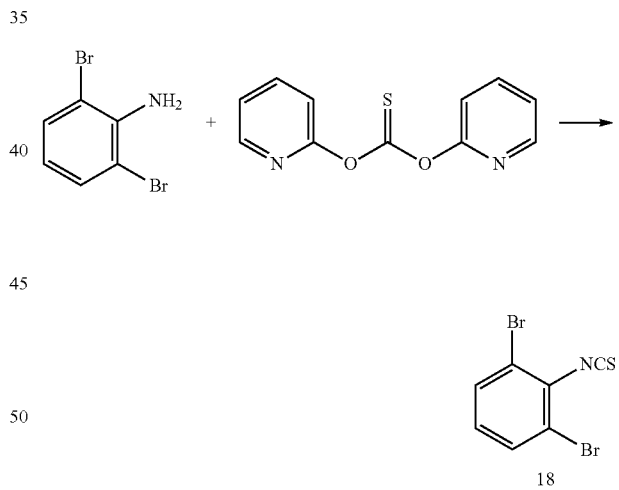

2,6-dibromoaniline (5.7 g, 22.7 mmol) was combined with O,O-Di-2-pyridinyl carbonothioate (5.3 g, 22.7 mmol) in chlorobenzene (100 mL) and the reaction was heated at an oil bath temperature of 140° C. for 3 hours. The solvent was evaporated and the crude material was adsorbed onto silica. The silica was then flushed with heptane and the solvent evaporated under reduced pressure to give the desired isothiocyanate 18 (6 g, 90%). 1H NMR (300 MHz, Chloroform-d) δ 7.56 (d, 2H), 7.05-6.95 (m, 1H).

Example 5.2

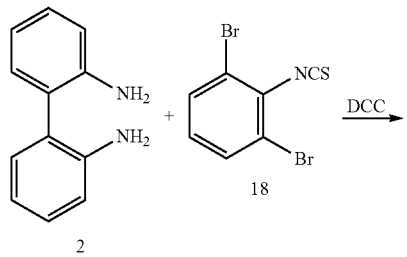

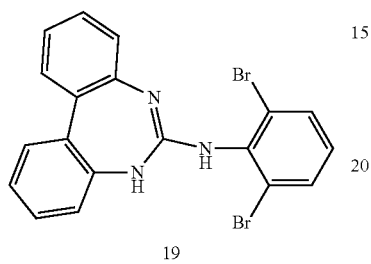

Diamine 2 (4.4 g, 24 mmol) was combined with thioisocyanate 18 (7 g, 24 mmol) in THF (100 mL) at room temperature and allowed to stir for 4 hours. Dicyclohexylcarbodiimide (5 g, 24 mmol) was then added and the reaction mixture was heated at an oil bath temperature of 70° C. overnight. The reaction was then cooled to room temperature and the solvent evaporated under reduced pressure. The crude product was suspended in methanol and allowed to stir at room temperature for 2 hours. The precipitate was filtered and washed with methanol to give the desired product 19 (8.5 g, 75%). 1H NMR (300 MHz, Chloroform-d) δ 7.63 (d, 2H), 7.53 (dd, 2H), 7.39-7.19 (m, 4H), 7.11 (s, 1H), 6.87 (1H), 6.72 (s, 2H), 5.52 (s, 1H).

Example 5.3

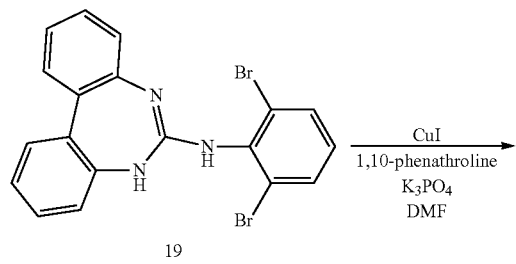

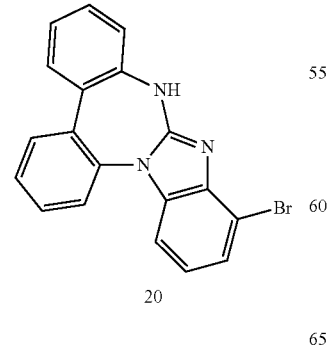

Compound 19 (8.5 g, 19.2 mmol) was combined with CuI (0.36 g, 1.92 mmol), 1,10-phenathroline (0.69 g, 180 mmol) and K₃PO₄ (8 g, 38.4 mmol) in DMF (40 mL) and degassed with N₂. The reaction mixture was heated at an oil bath temperature of 70° C. After 1.5 hours, the reaction was stopped and cooled to room temperature, poured into water and stirred at room temperature and the precipate was filtered and dried. The product was purified by soxhlet extraction with CHCl₃ to give 20 (5 g, 72%). 1H NMR (400 MHz, DMSO-d6) δ 9.49 (s, 1H), 7.73-7.47 (m, 6H), 7.40 (m, 2H), 7.34-7.22 (m, 2H), 7.11 (m, 1H). HPLC MS m/z 363 (M+1). The N functionalization of compound 20 is carried out as for example described in examples 1.4 and 2.1. The functionalization at Br in the compound of formula 20 can be carried out as known in the art.

Example 6

Example 6.1

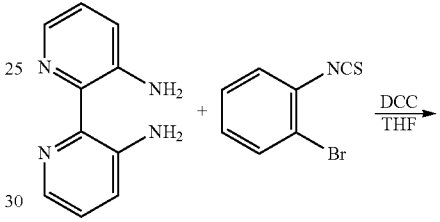

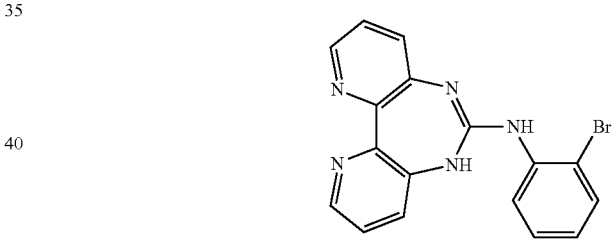

The compound 21 was synthesized in the same manner as in Example 1.2 (synthesis of compound 3) except for using 2-(3-amino-2-pyridyl)pyridin-3-amine in place of 2,2'-Biphenyldiamine (72% yield).

Example 6.2

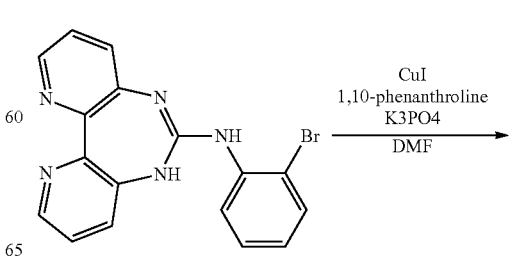

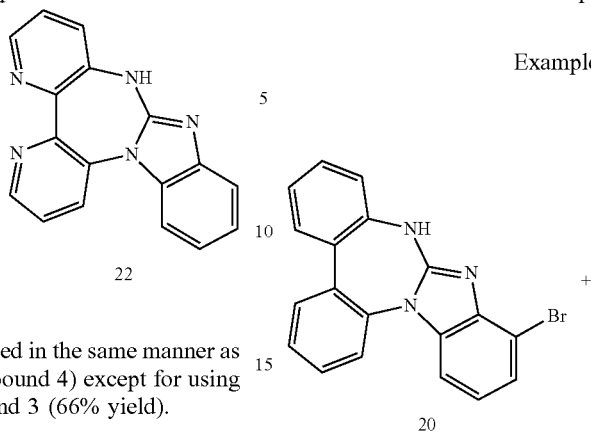

The compound 22 was synthesized in the same manner as in Example 1.3 (synthesis of compound 4) except for using compound 21 in place of compound 3 (66% yield).

Example 6.3

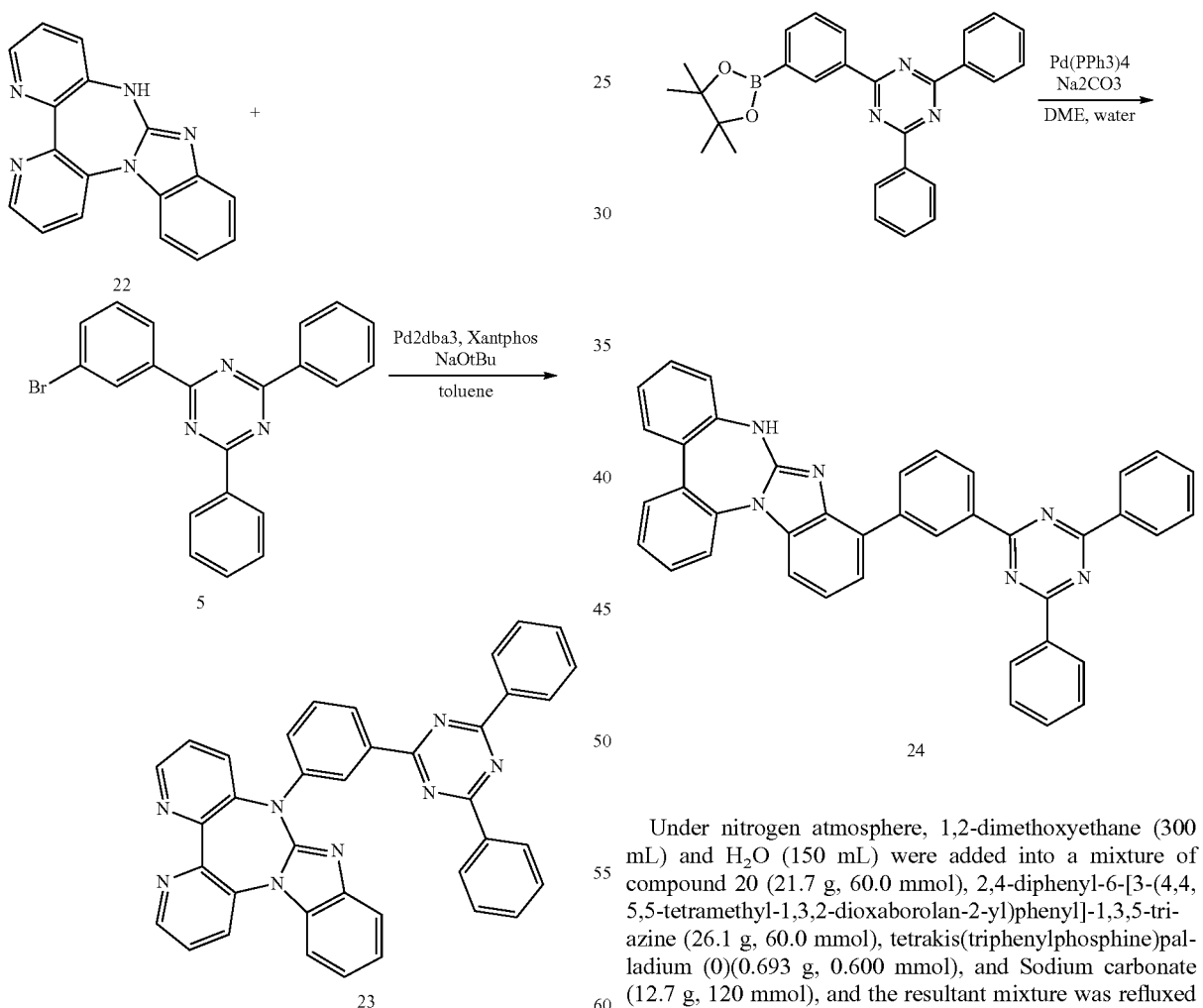

The compound 23 was synthesized in the same manner as in Example 1.4 (synthesis of compound 6) except for using compound 22 in place of compound 4 (60% yield). Identification of compound 23 (Exact mass: 592.21) was made by the result of mass spectrometry (m/e=592).

Example 7

Example 7.1

Under nitrogen atmosphere, 1,2-dimethoxyethane (300 mL) and H$_2$O (150 mL) were added into a mixture of compound 20 (21.7 g, 60.0 mmol), 2,4-diphenyl-6-[3-(4,4,5,5-tetramethyl-1,3,2-dioxaborolan-2-yl)phenyl]-1,3,5-triazine (26.1 g, 60.0 mmol), tetrakis(triphenylphosphine)palladium (0)(0.693 g, 0.600 mmol), and Sodium carbonate (12.7 g, 120 mmol), and the resultant mixture was refluxed under heating for 8 hours. After cooling the reaction to room temperature, the insolubles were removed by filtration and an organic layer was concentrated under reduced pressure. The resultant mixture was dissolved in dichloromethane and purified by chromatography on silica. The resultant solution was concentrated under reduced pressure to give compound 24 (25.1 g, 42.6 mmol, 71% yield).

Example 7.2

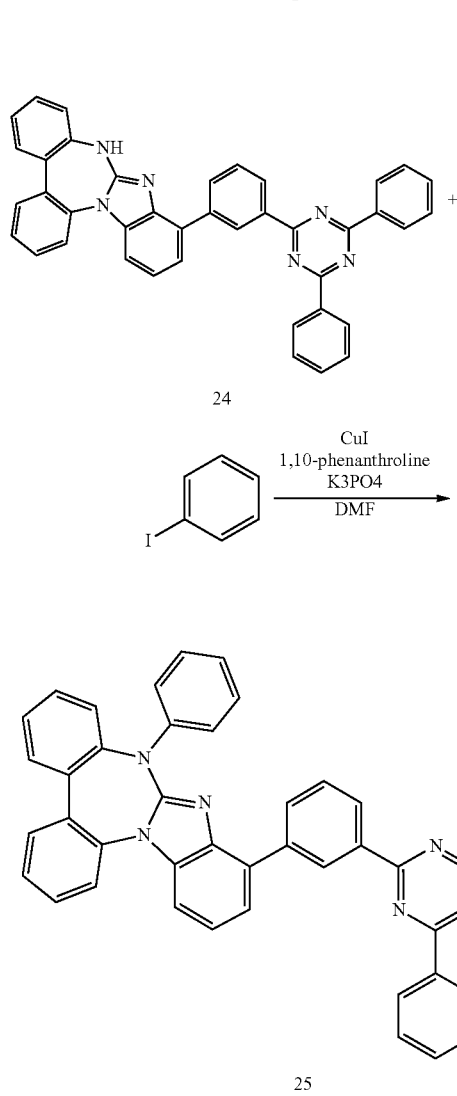

24

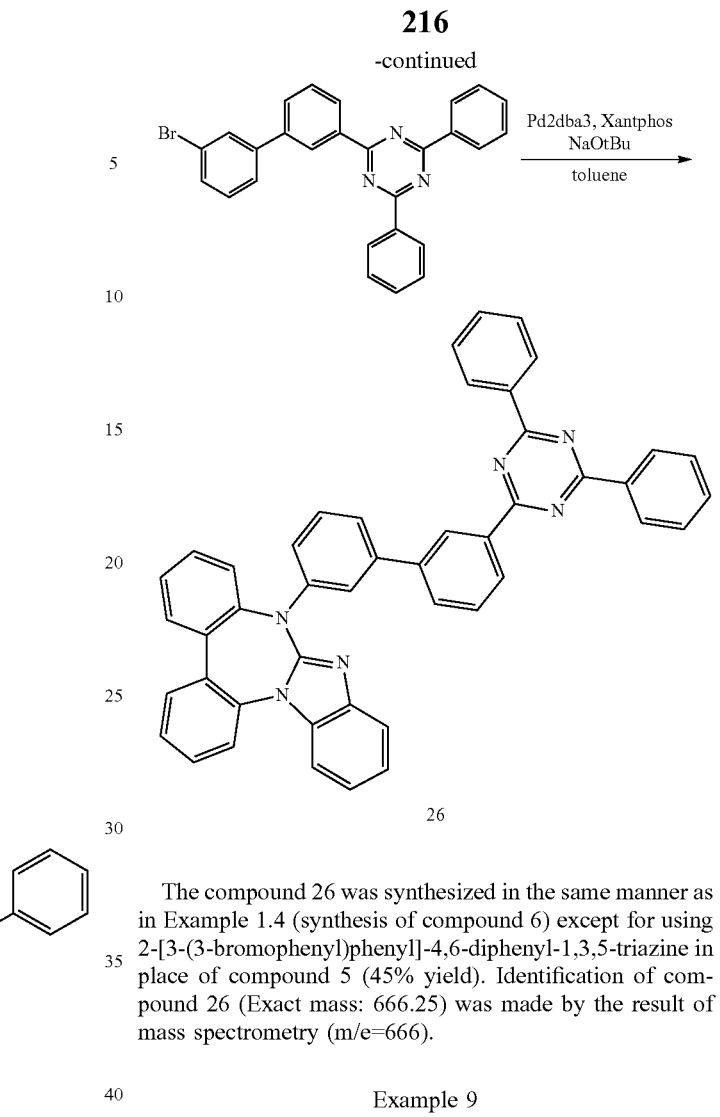

26

The compound 26 was synthesized in the same manner as in Example 1.4 (synthesis of compound 6) except for using 2-[3-(3-bromophenyl)phenyl]-4,6-diphenyl-1,3,5-triazine in place of compound 5 (45% yield). Identification of compound 26 (Exact mass: 666.25) was made by the result of mass spectrometry (m/e=666).

Example 9

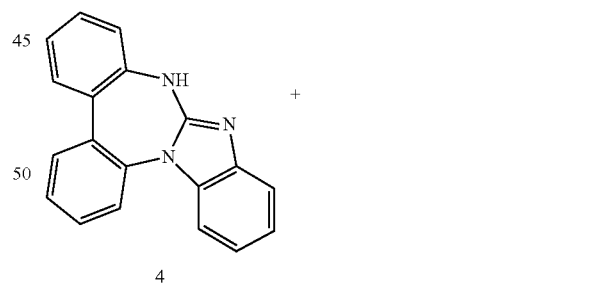

4

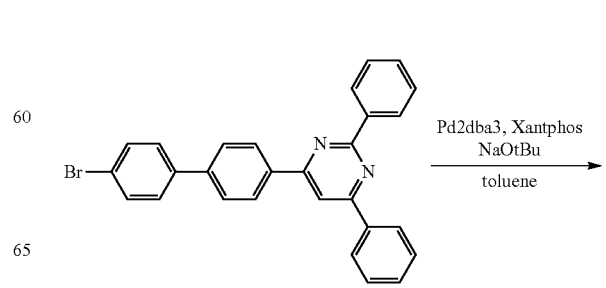

25

The compound 25 was synthesized in the same manner as in Example 2.1 (synthesis of compound 7) except for using compound 24 in place of compound 4 (15% yield). Identification of compound 25 (Exact mass: 666.25) was made by the result of mass spectrometry (m/e=666).

Example 8

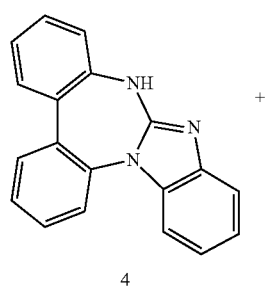

4

-continued

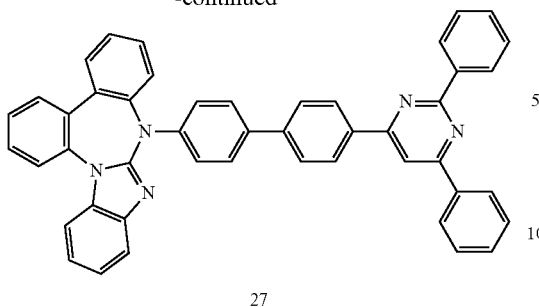

27

The compound 27 was synthesized in the same manner as in Example 1.4 (synthesis of compound 6) except for using 4-[4-(4-bromophenyl)phenyl]-2,6-diphenyl-pyrimidine in place of compound 5 (11% yield). Identification of compound 27 (Exact mass: 666.26) was made by the result of mass spectrometry (m/e=666).

Example 10

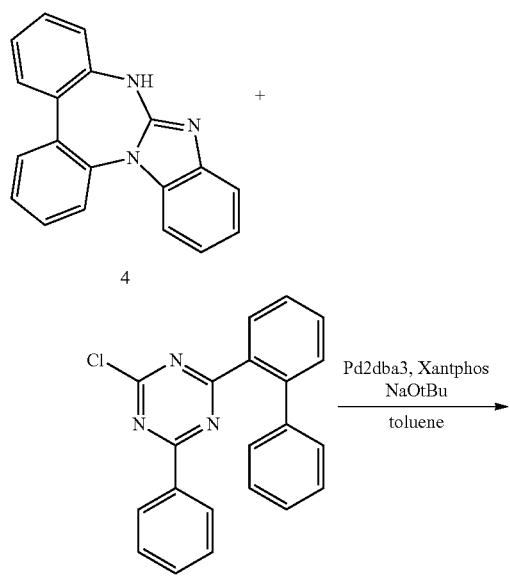

28

The compound 28 was synthesized in the same manner as in Example 1.4 (synthesis of compound 6) except for using 2-chloro-4-phenyl-6-(2-phenylphenyl)-1,3,5-triazine in place of compound 5 (75% yield). Identification of compound 28 (Exact mass: 590.22) was made by the result of mass spectrometry (m/e=590).

Example 11

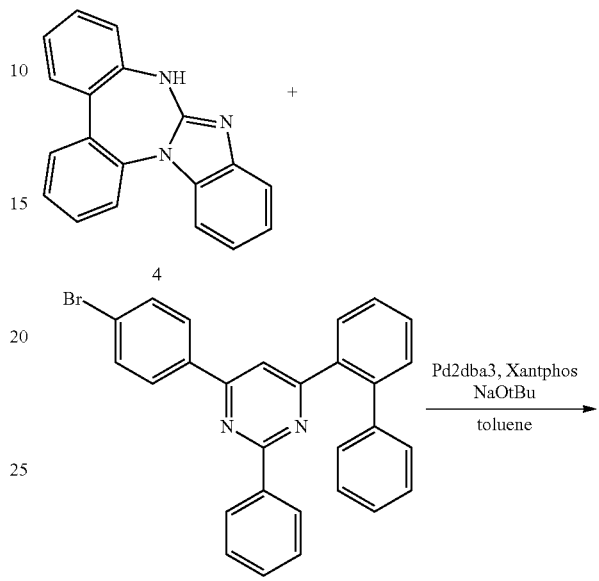

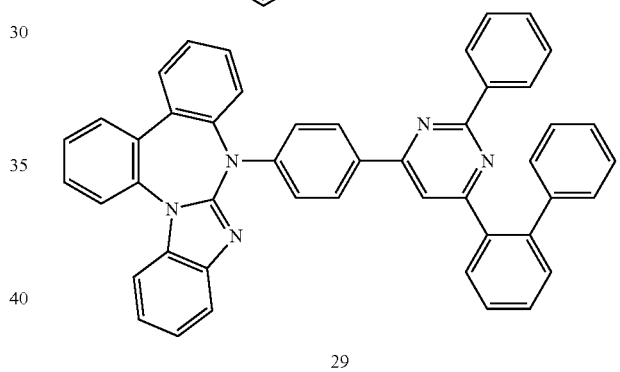

29

The compound 29 was synthesized in the same manner as in Example 1.4 (synthesis of compound 6) except for using 4-(4-bromophenyl)-2-phenyl-6-(2-phenylphenyl)pyrimidine in place of compound 5 (23% yield). Identification of compound 29 (Exact mass: 665.26) was made by the result of mass spectrometry (m/e=666).

Example 12

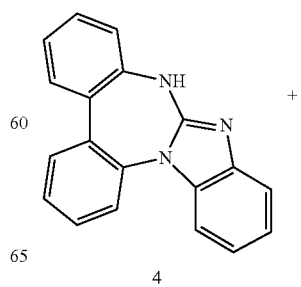

4

-continued

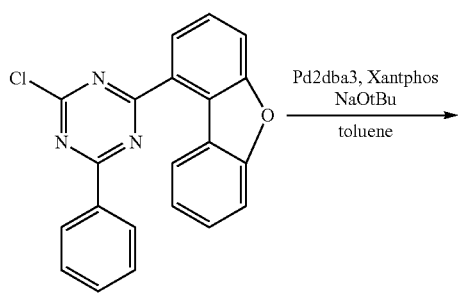

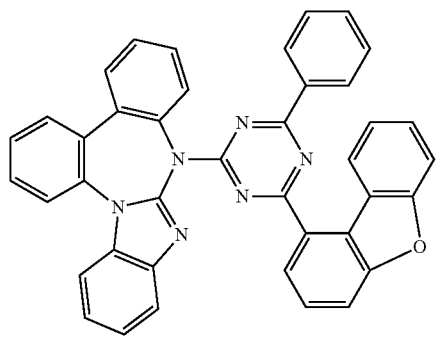

30

The compound 30 was synthesized in the same manner as in Example 1.4 (synthesis of compound 6) except for using 2-chloro-4-dibenzofuran-1-yl-6-phenyl-1,3,5-triazine in place of compound 5 (67% yield). Identification of compound 30 (Exact mass: 604.20) was made by the result of mass spectrometry (m/e=604).

Example 13

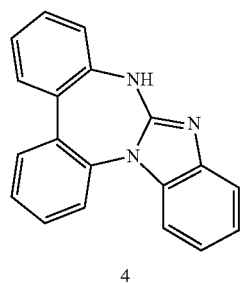

4

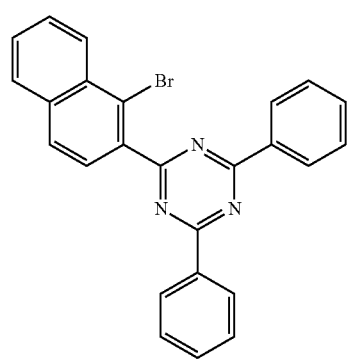

-continued

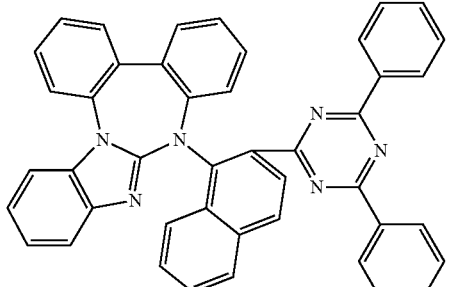

31

The compound 31 was synthesized in the same manner as in Example 1.4 (synthesis of compound 6) except for using 2-(1-bromo-2-naphthyl)-4,6-diphenyl-1,3,5-triazine in place of compound 5 (16% yield). Identification of compound 31 (Exact mass: 640.24) was made by the result of mass spectrometry (m/e=640).

Example 14

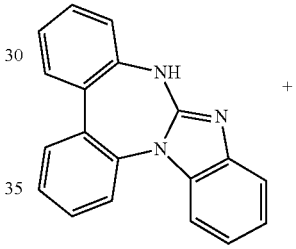

+

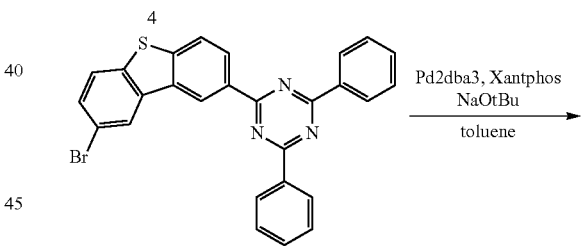

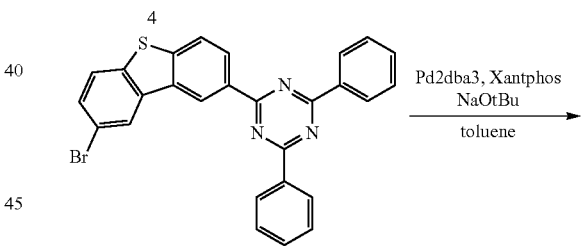

32

The compound 32 was synthesized in the same manner as in Example 1.4 (synthesis of compound 6) except for using 2-(8-bromodibenzothiophen-2-yl)-4,6-diphenyl-1,3,5-triazine in place of compound 5 (14% yield). Identification of compound 32 (Exact mass: 696.21) was made by the result of mass spectrometry (m/e=696).

Example 15

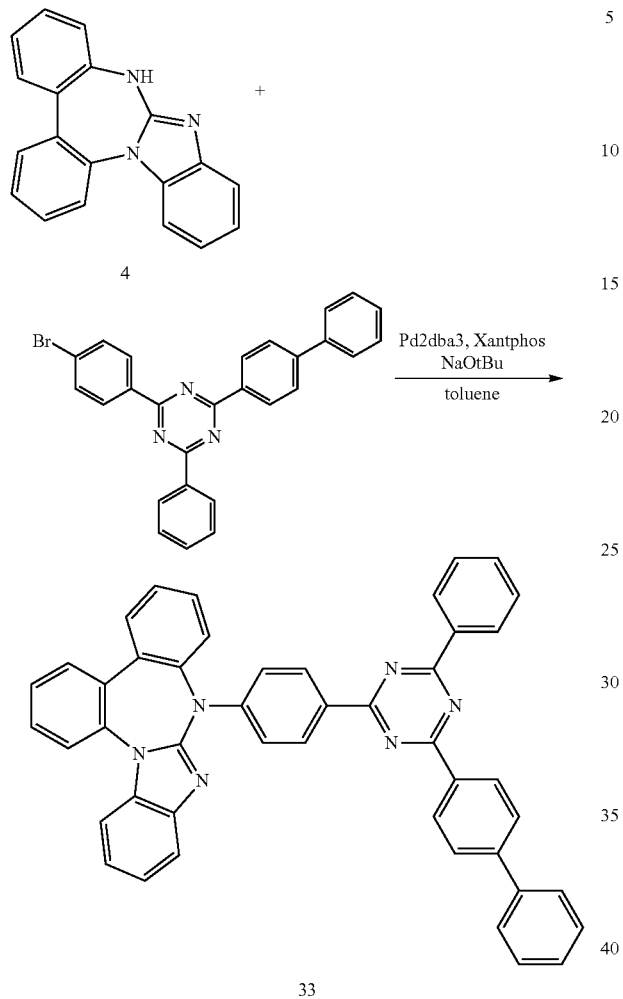

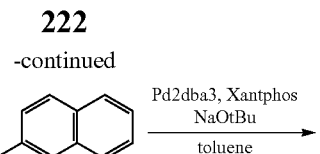

The compound 32 was synthesized in the same manner as in Example 1.4 (synthesis of compound 6) except for using 2-(4-bromophenyl)-4-phenyl-6-(4-phenylphenyl)-1,3,5-triazine in place of compound 5 (79% yield). Identification of compound 33 (Exact mass: 666.25) was made by the result of mass spectrometry (m/e=666).

Example 16

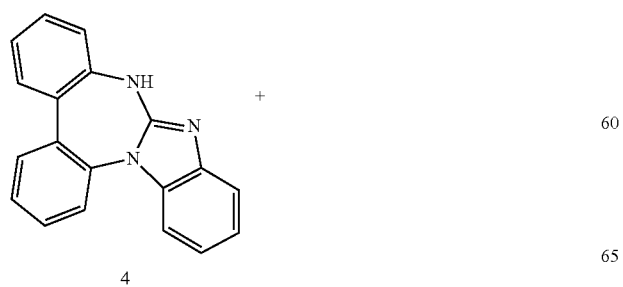

The compound 34 was synthesized in the same manner as in Example 1.4 (synthesis of compound 6) except for using 2-(4-bromophenyl)-4-(2-naphthyl)-6-phenyl-1,3,5-triazine in place of compound 5 (71% yield). Identification of compound 34 (Exact mass: 640.24) was made by the result of mass spectrometry (m/e=640).

Example 17

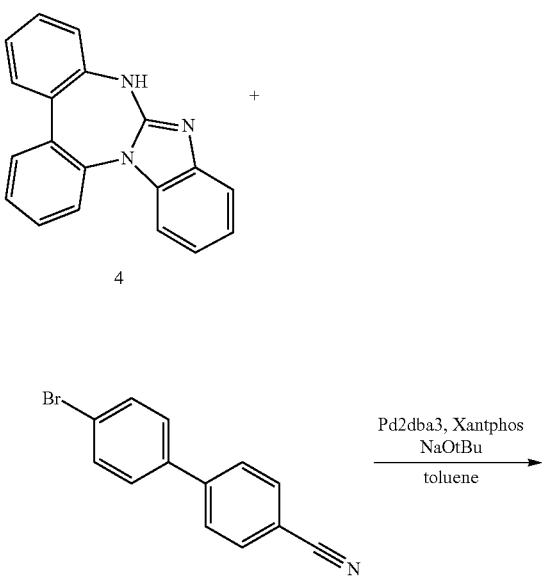

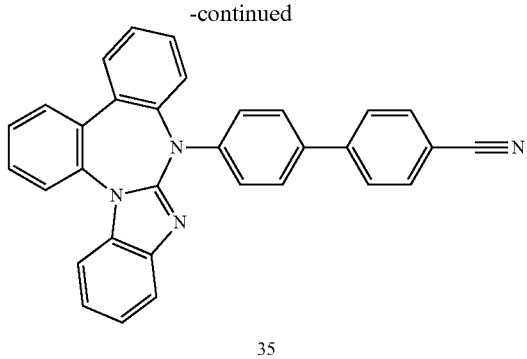

35

The compound 35 was synthesized in the same manner as in Example 1.4 (synthesis of compound 6) except for using 4-(4-bromophenyl)benzonitrile in place of compound 5 (32% yield). Identification of compound 35 (Exact mass: 460.17) was made by the result of mass spectrometry (m/e=460).

Example 18

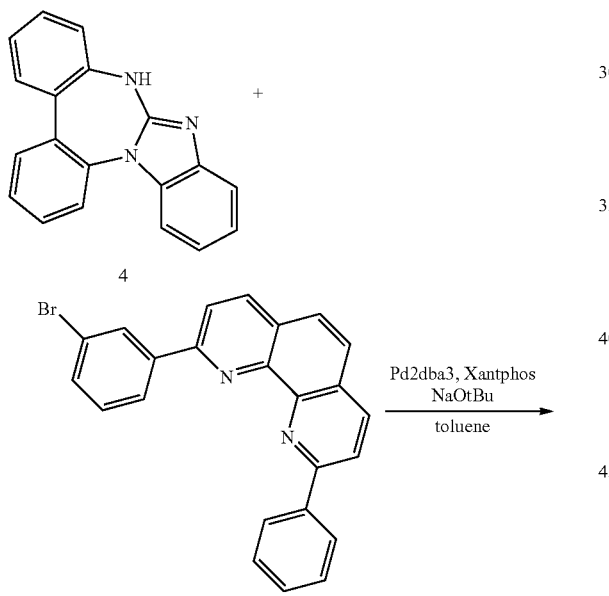

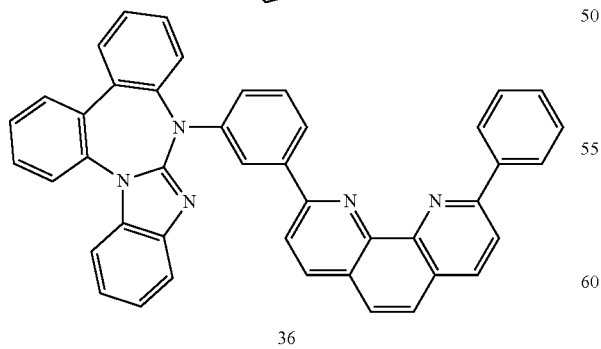

36

The compound 36 was synthesized in the same manner as in Example 1.4 (synthesis of compound 6) except for using 2-(3-bromophenyl)-9-phenyl-1,10-phenanthroline in place of compound 5 (30% yield). Identification of compound 36 (Exact mass: 613.23) was made by the result of mass spectrometry (m/e=613).

Example 19

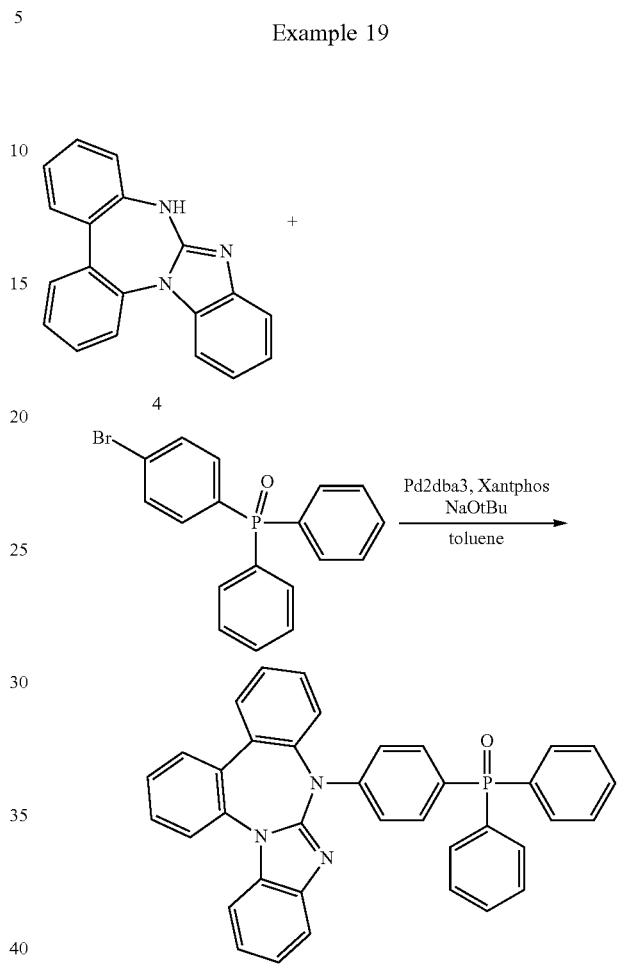

37

The compound 37 was synthesized in the same manner as in Example 1.4 (synthesis of compound 6) except for using 1-bromo-4-diphenylphosphoryl-benzene in place of compound 5 (31% yield). Identification of compound 37 (Exact mass: 559.18) was made by the result of mass spectrometry (m/e=559).

Example 20

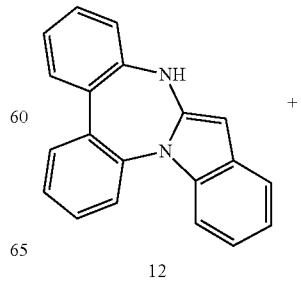

12

-continued

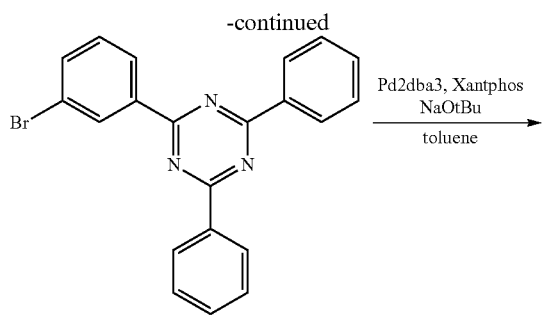

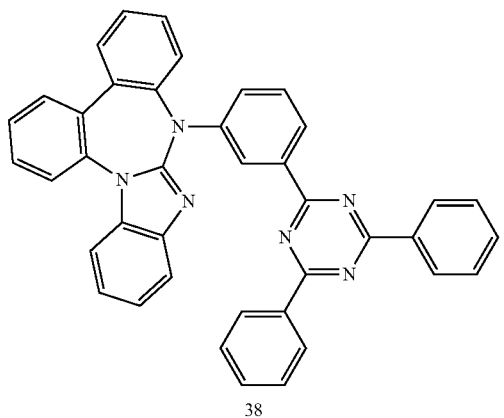

38

The compound 38 was synthesized in the same manner as in Example 1.4 (synthesis of compound 6) except for using compound 12 in place of compound 4 (82% yield). Identification of compound 38 (Exact mass: 589.23) was made by the result of mass spectrometry (m/e=589).

II Application Example

Application Example 1

Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound A was applied. Then 100 nm-thick of compound B and 60 nm-thick compound C were applied as hole transporting layer 1 and hole transporting layer 2, respectively. Subsequently, a mixture of 5% by weight of an emitter compound (Ir(ppy)$_3$), 47.5% by weight of a host (Compound 6) and 47.5% by weight of compound E were applied to form a 40 nm-thick phosphorescent-emitting layer. On the emitting layer, 30 nm-thick compound D was applied as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen.

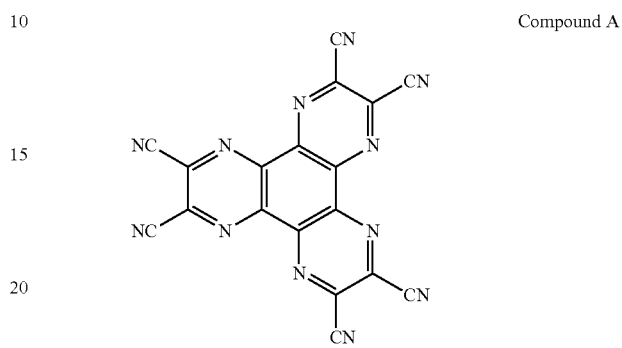

Compound A

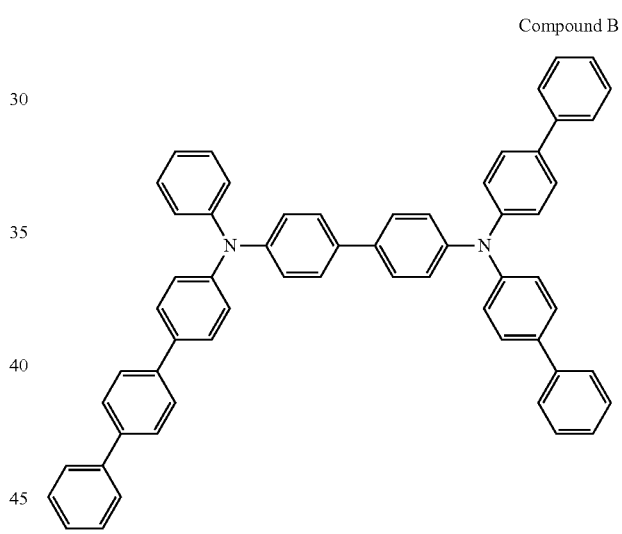

Compound B

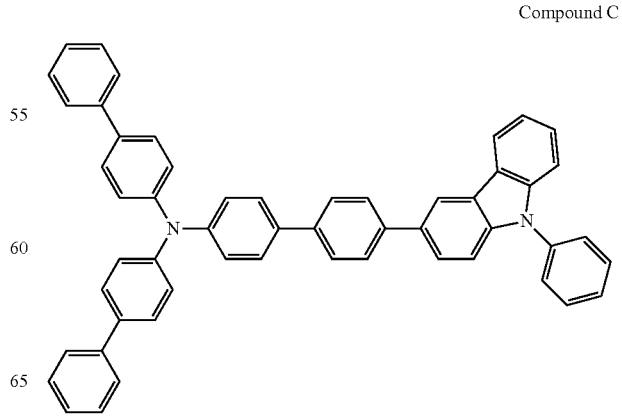

Compound C

Compound D

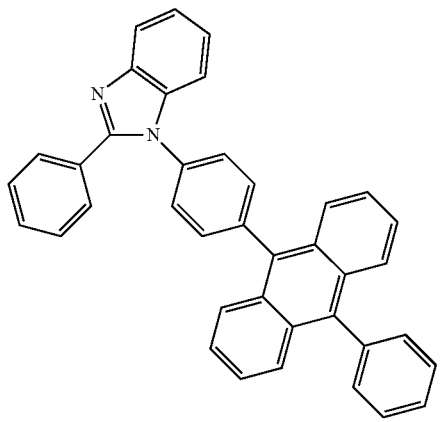

Compound E

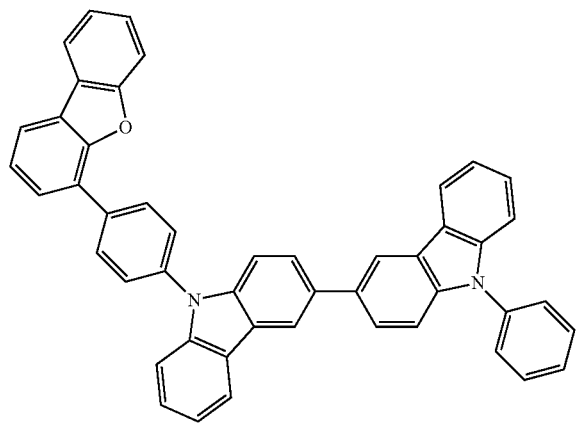

Ir(ppy)₃

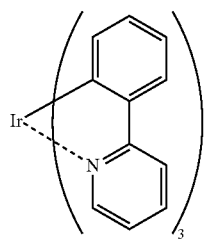

Compound 6

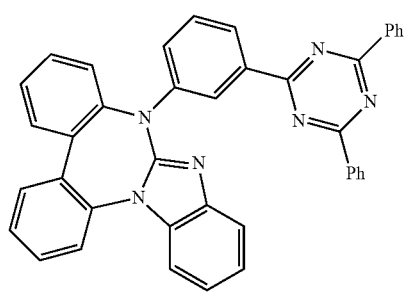

OLED Characterization

To characterize the OLED, electroluminescence spectra were recorded at various currents and voltages. In addition, the current-voltage characteristic was measured in combination with the luminance to determine luminous efficiency and external quantum efficiency (EQE). Driving voltage U and EQE were given at a current density of 10 mA/cm² and found to be 5.8 V and 16.3% respectively.

Application Example 2

A glass substrate with 130 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As the first layer, 5 nm-thick of electron accepting compound A was vapor-deposited. Then 80 nm-thick of aromatic amine compound B was applied as a first hole transporting layer. Successively, 10 nm-thick of aromatic amine compound H was applied as a second hole transporting layer. Then, a mixture of 4% by weight of an emitter compound I, 96% by weight of a host compound J were applied to form a 25 nm-thick fluorescent-emitting layer. On the emitting layer, a mixture of 50% by weight of Compound 6, 50% by weight of compound K were applied to form a 25 nm-thick electron transport layer. Finally, 1 nm-thick compound K was deposited as an electron injection layer and 80 nm-thick Al was then deposited as a cathode to complete the device. The device was sealed with a glass lid and a getter in an inert nitrogen atmosphere with less than 1 ppm of water and oxygen.

Compound H

Compound I

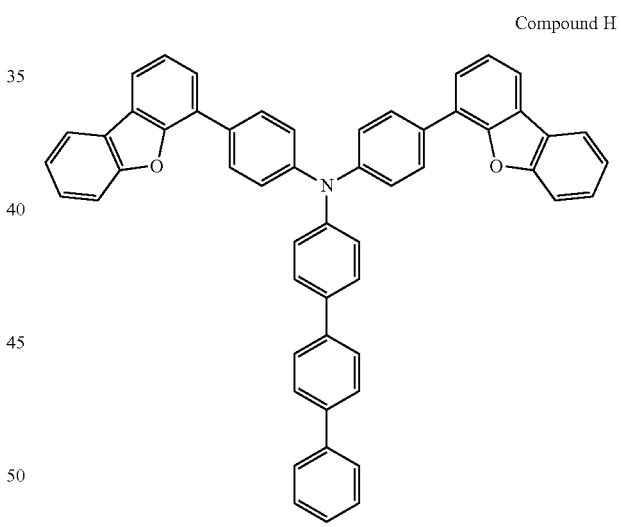

-continued

Compound J

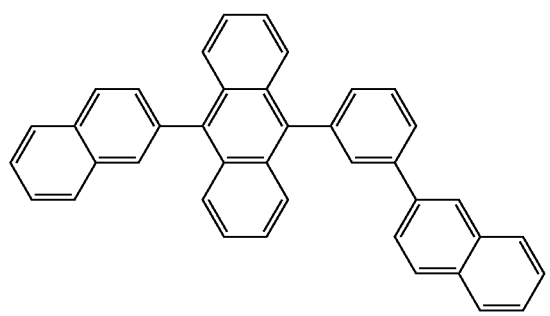

Compound K

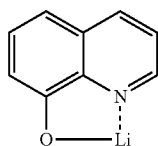

OLED Characterization

To characterize the OLED, electroluminescence spectra were recorded at various currents and voltages. In addition, the current-voltage characteristic was measured in combination with the luminance to determine luminous efficiency and external quantum efficiency (EQE). The EQE was given at a current density of 10 mA/cm² and found to be 9.5%.

Application Example 3

A glass substrate with 130 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As the first layer, 5 nm-thick of electron accepting compound A was vapor-deposited. Then 80 nm-thick of aromatic amine compound B was applied as a first hole transporting layer. Successively, 10 nm-thick of aromatic amine compound H was applied as a second hole transporting layer. Then, a mixture of 4% by weight of an emitter compound L, 96% by weight of a host compound M were applied to form a 25 nm-thick fluorescent-emitting layer. On the emitting layer, 5 nm-thick Compound 6 was applied as a first electron transport layer (a hole blocking layer). Then, a mixture of 50% by weight of compound N, 50% by weight of compound K were applied to form a 25 nm-thick electron transport layer. Finally, 1 nm-thick compound K was deposited as an electron injection layer and 80 nm-thick Al was then deposited as a cathode to complete the device. The device was sealed with a glass lid and a getter in an inert nitrogen atmosphere with less than 1 ppm of water and oxygen.

Compound L

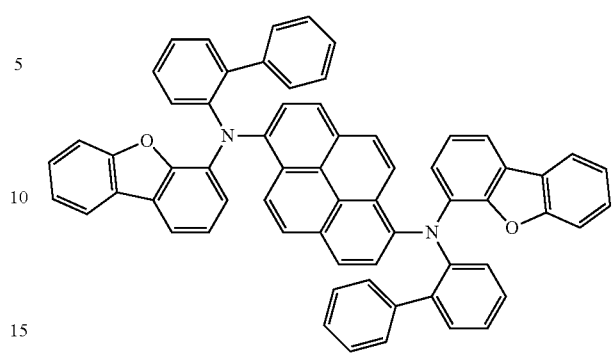

Compound M

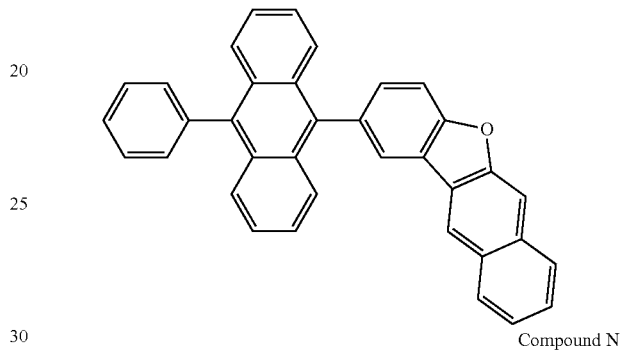

Compound N

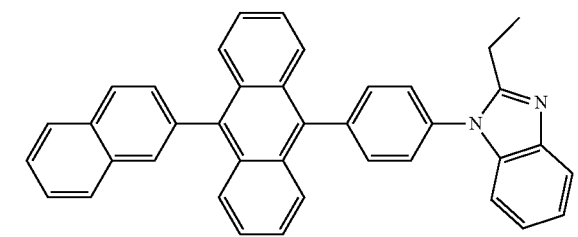

OLED Characterization

To characterize the OLED, electroluminescence spectra were recorded at various currents and voltages. In addition, the current-voltage characteristic was measured in combination with the luminance to determine luminous efficiency and external quantum efficiency (EQE). The EQE was given at a current density of 10 mA/cm² and found to be 9.6%.

Application Examples 4-16 and Comparative Example 1

Devices of application examples 4-16 and comparative example 1 were prepared in the same manner as in application example 3 except for using compound listed in the following Table 1 in place of compound 6.

OLED Characterization

To characterize the OLED, electroluminescence spectra were recorded at various currents and voltages. In addition, the current-voltage characteristic was measured in combination with the luminance to determine luminous efficiency and external quantum efficiency (EQE). The EQE was given at a current density of 10 mA/cm². The results are shown in Table 1.

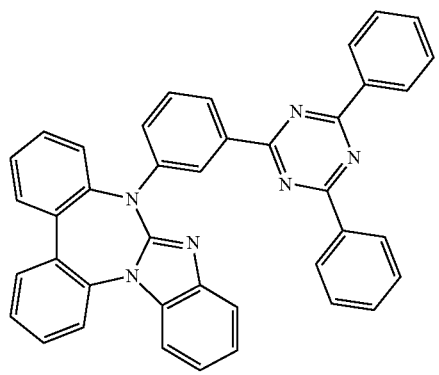
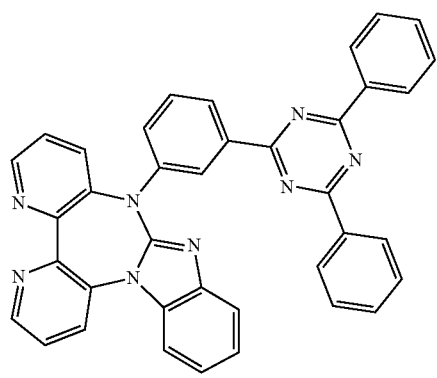
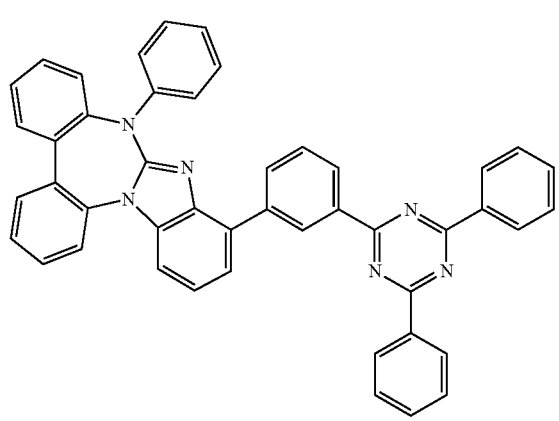
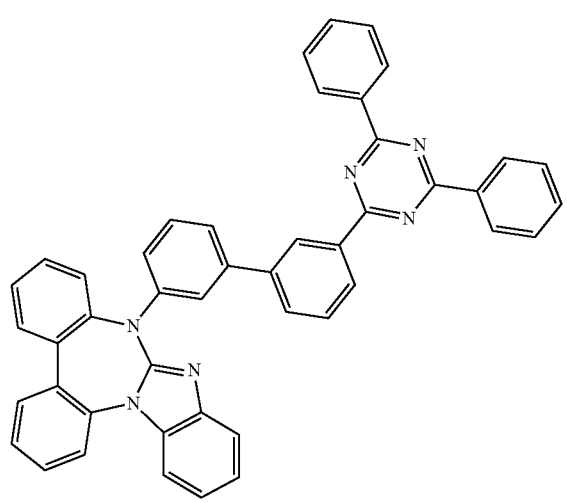
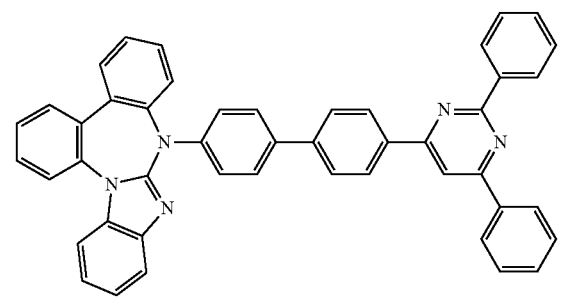
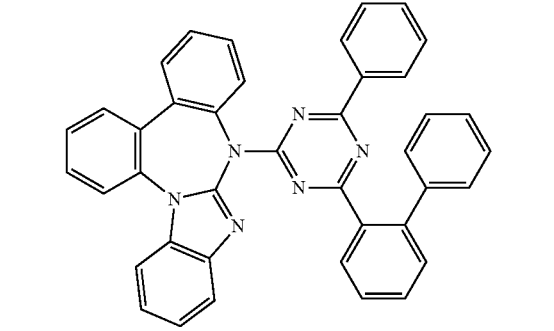
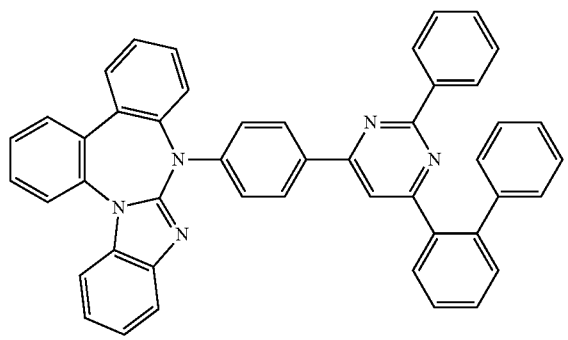

30
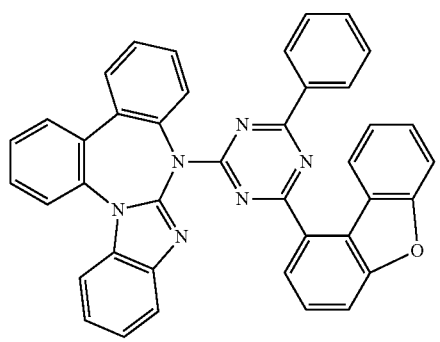
31
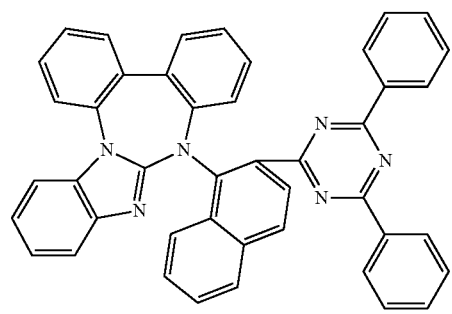
32
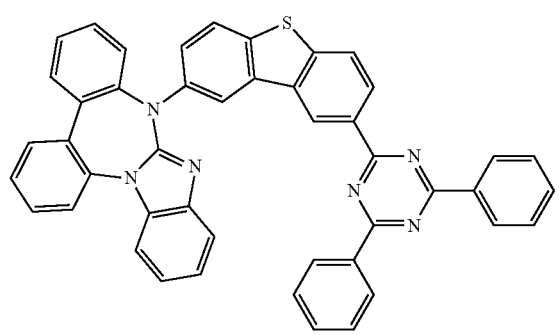
33
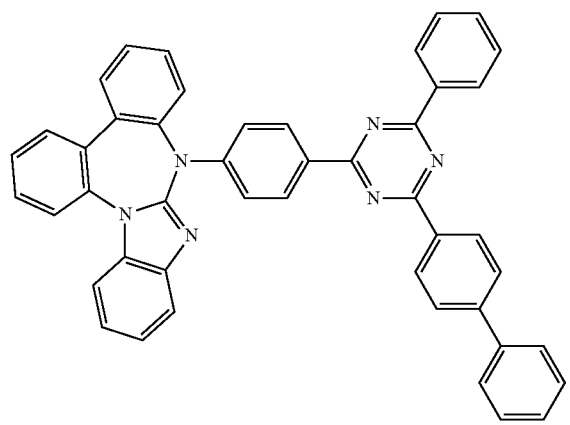
34
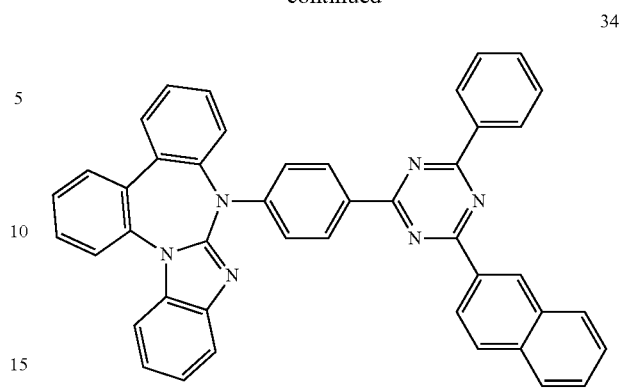
35
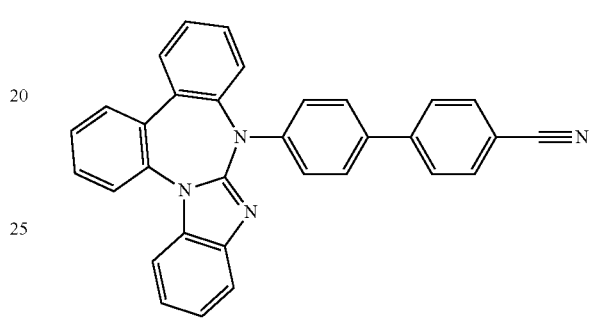
38
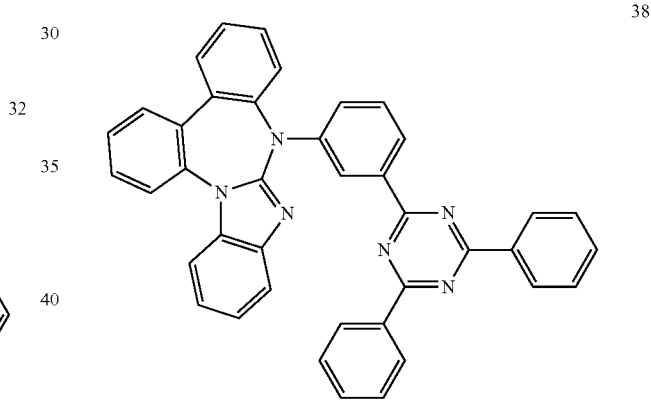
Compound O
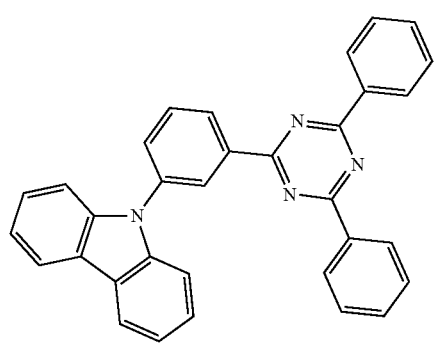
TABLE 1
|  | Compound | EQE(%) |
| --- | --- | --- |
| Application Example 3 | 6 | 9.6 |
| Application Example 4 | 23 | 9.1 |
| Application Example 5 | 25 | 9.5 |

TABLE 1-continued

| | Compound | EQE(%) |
|---|---|---|
| Application Example 6 | 26 | 9.8 |
| Application Example 7 | 27 | 9.8 |
| Application Example 8 | 28 | 9.7 |
| Application Example 9 | 29 | 9.7 |
| Application Example 10 | 30 | 9.1 |
| Application Example 11 | 31 | 9.5 |
| Application Example 12 | 32 | 9.4 |
| Application Example 13 | 33 | 9.0 |
| Application Example 14 | 34 | 9.1 |
| Application Example 15 | 35 | 9.1 |
| Application Example 16 | 38 | 9.5 |
| Comparative Example 1 | O | 8.4 |

Application Examples 17-18 and Comparative Example 2

A glass substrate with 130 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As the first layer, 5 nm-thick of electron accepting compound A was vapor-deposited. Then 80 nm-thick of aromatic amine compound B was applied as a first hole transporting layer. Successively, 10 nm-thick of aromatic amine compound H was applied as a second hole transporting layer. Then, a mixture of 4% by weight of an emitter compound L, 96% by weight of a host compound M were applied to form a 25 nm-thick fluorescent-emitting layer. On the emitting layer, a mixture of 50% by weight of the following compound 36, 37, or P, and 50% by weight of compound K were applied to form a 30 nm-thick electron transport layer. Finally, 1 nm-thick compound K was deposited as an electron injection layer and 80 nm-thick Al was then deposited as a cathode to complete the device. The device was sealed with a glass lid and a getter in an inert nitrogen atmosphere with less than 1 ppm of water and oxygen.

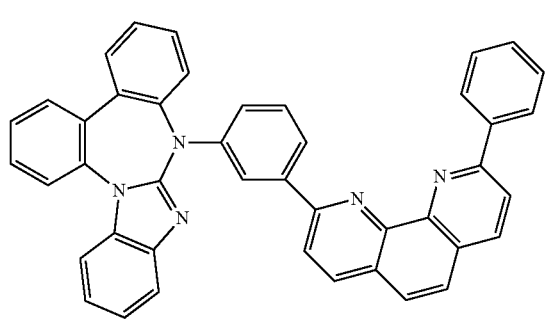

36

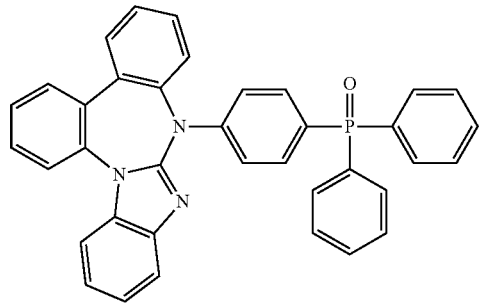

37

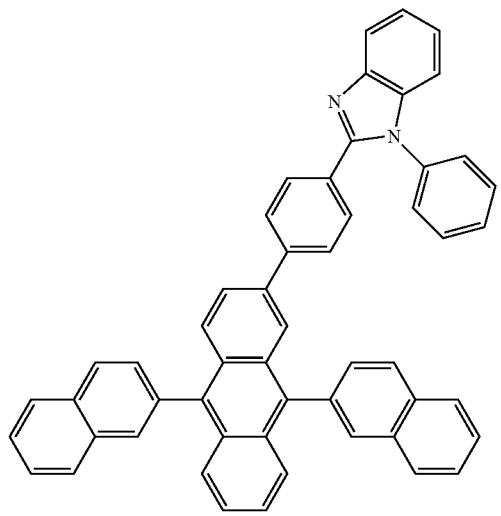

Compound P

OLED Characterization

To characterize the OLED, the time taken until the luminance was reduced to 95% of the initial luminance (95% luminance lifetime) was measured by driving the device at a current density of mA/cm². The results are shown in Table 2.

TABLE 2

| | Compound | 95% luminance lifetime (hr) |
|---|---|---|
| Application Example 17 | 36 | 210 |
| Application Example 18 | 37 | 310 |
| Application Example 2 | P | 155 |

REFERENCE SIGNS LIST

1: Organic EL device
2: Substrate
3: Anode
4: Cathode
5: Light emitting laser
6: Hole injecting/transporting layer
7: Electron transporting layer
8: Electron injecting layer
10: Emitting unit
11: Electron injecting and transporting unit

The invention claimed is:
1. A compound of formula (Ia):

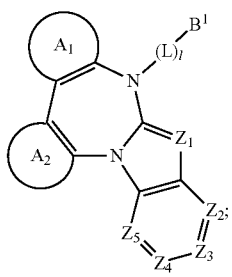

(Ia)

wherein
$A_1$ and $A_2$ each independently represent an aromatic hydrocarbon group having 6 to 30 ring carbon atoms which is optionally substituted or a heterocyclic group having 5 to 30 ring atoms which is optionally substituted;
$B^1$ is H, CN, an aromatic hydrocarbon group having 6 to 30 ring carbon atoms which is optionally substituted; a heterocyclic group having 5 to 30 ring atoms which is optionally substituted; or a cycloalkyl group having 3 to 30 ring carbon atoms which is optionally substituted;
L is a single bond, an alkylene group having 1 to 30 carbon atoms which is optionally substituted, a cycloalkylene group having 3 to 30 carbon atoms which is optionally substituted, a substituted silylene group having 2 to 30 carbon atoms, an aromatic hydrocarbon group having 6 to 30 ring carbon atoms which is optionally substituted, or a heterocyclic group having 5 to 30 ring atoms which is optionally substituted; and
l is 1, 2 or 3, with the proviso that when l is 2 or 3, L is the same or different in each occurrence,
$Z_1$ is N or $CR^1$,
$Z_2$ is N or $CR^2$;
$Z_3$ is N or $CR^3$;
$Z_4$ s N or $CR^4$;
$Z_5$ is N or $CR^5$; and
R1 is hydrogen, an alkyl group having 1 to 30 carbon atoms which is optionally substituted; a cycloalkyl group having 3 to 30 ring carbon atoms which is optionally substituted; an alkenyl group having 2 to 30 carbon atoms which is optionally substituted; an aromatic hydrocarbon group having 6 to 30 ring carbon atoms which is optionally substituted, an aralkyl group having 7 to 31 ring carbon atoms which is optionally substituted; or a heterocyclic group having 5 to 30 ring atoms which is optionally substituted,
$R^2$, $R^3$, $R^4$, and $R^5$ each independently represent hydrogen, CN, a halogen atom, an alkyl group having 1 to 30 carbon atoms which is optionally substituted; a cycloalkyl group having 3 to 30 ring carbon atoms which is optionally substituted; an alkenyl group having 2 to 30 carbon atoms which is optionally substituted; an aromatic hydrocarbon group having 6 to 30 ring carbon atoms which is optionally substituted; an aralkyl group having 7 to 31 ring carbon atoms which is optionally substituted; or a heterocyclic group having 5 to 30 ring atoms which is optionally substituted,
with the proviso that, two or more substituents selected from $R^2$, $R^3$, $R^4$, and $R^5$ may be bonded to each other to form a ring structure, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms,
wherein the optional substituent may further be optionally substituted with one or more groups selected from the group consisting of an aromatic hydrocarbon group having 6 to 30 ring carbon atoms and a heterocyclic group having 5 to 30 ring atoms.
2. The compound according to claim 1, wherein: the compound of formula (Ia) is represented by formula (Ia1) or (Ia2):

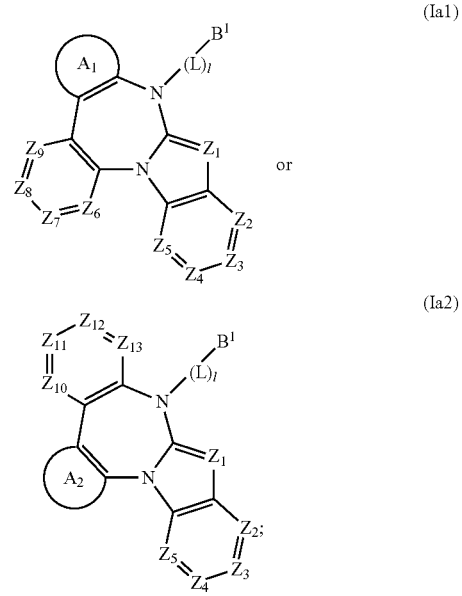

wherein
$A_1$, $A_2$, L, $B^1$ and l are defined in claim 1;
$Z_2$ is N or $CR^2$;
$Z_3$ is N or $CR^3$;
$Z_4$ is N or $CR^4$;
$Z_5$ is N or $CR^5$,
$Z_6$ is N or $CR^6$;
$Z_7$ is N or $CR^7$;
$Z_8$ is N or $CR^8$;
$Z_9$ is N or $CR^9$;
$Z_{10}$ is N or $CR^{10}$;
$Z_{11}$ is N or $CR^{11}$;
$Z_{12}$ is N or $CR^{12}$;
$Z_{13}$ is N or $CR^{13}$; and
$R^2$, $R^3$, $R^4$, $R^5$, $R^6$, $R^7$, $R^8$, $R^9$, $R^{10}$, $R^{11}$, $R^{12}$ and $R^{13}$ each independently represent hydrogen, CN, a halogen atom alkyl group having 1 to 30 carbon atoms which is optionally substituted; a cycloalkyl group having 3 to 30 ring carbon atoms which is optionally substituted; an alkenyl group having 2 to 30 carbon atoms which is optionally substituted; an aromatic hydrocarbon group having 6 to 30 ring carbon atoms which is optionally substituted; an aralkyl group having 7 to 31 ring carbon atoms which is optionally substituted; or a heterocyclic group having 5 to 30 ring atoms which is optionally substituted;

with the proviso that, two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^3$ may be bonded to each other to form a ring structure, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

3. The compound according to claim 1, wherein:
the compound of formula (Ia) is represented by formula (Iaa):

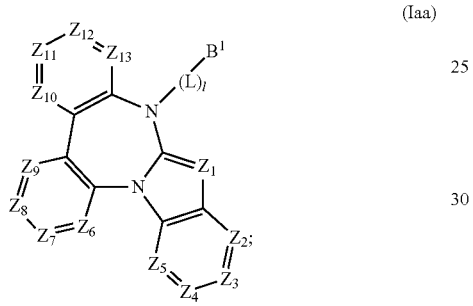

(Iaa)

wherein
L, $B^1$ and l are defined in claim 2;
$Z_2$ is N or $CR^2$;
$Z_3$ is N or $CR^3$;
$Z_4$ is N or $CR^4$;
$Z_5$ is N or $CR^5$;
$Z_6$ is N or $CR^6$;
$Z_7$ is N or $CR^7$;
$Z_8$ is N or $CR^8$;
$Z_9$ is N or $CR^9$;
$Z_{10}$ is N or $CR^{10}$;
$Z_{11}$ is N or $CR^{11}$;
$Z_{12}$ is N or $CR^{12}$;
$Z_{13}$ is N or $CR^{13}$; and
$R^2$, $R^3$, $R^4$, $R^5$, $R^6$, $R^7$, $R^8$, $R^9$, $R^{10}$, $R^{11}$, $R^{12}$ and $R^{13}$ each independently represent hydrogen, CN, a halogen atom, an alkyl group having 1 to 30 carbon atoms which is optionally substituted; a cycloalkyl group having 3 to 30 ring carbon atoms which is optionally substituted; an alkenyl group having 2 to 30 carbon atoms which is optionally substituted; an aromatic hydrocarbon group having 6 to 30 ring carbon atoms which is optionally substituted; an aralkyl group having 7 to 31 ring carbon atoms which is optionally substituted; or a heterocyclic group having 5 to 30 ring which is optionally substituted;

with the proviso that, two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ may be bonded to each other to form a ring structure, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

4. The compound according to claim 1, wherein:
the compound of formula (Ia) is represented by formula (Iaaa):

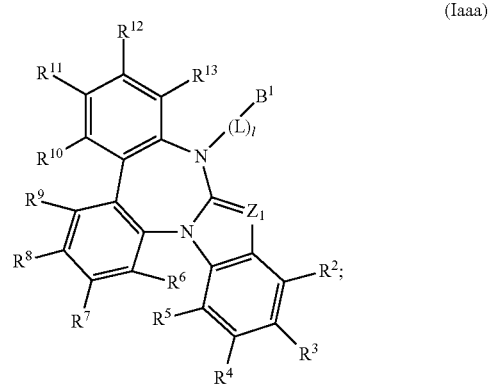

(Iaaa)

wherein
L, $B^1$ and l are defined in claim 2; and
$R^2$, $R^3$, $R^4$, $R^5$, $R^6$, $R^7$, $R^8$, $R^9$, $R^{10}$, $R^{11}$, $R^{12}$ and $R^{13}$ each independently represent hydrogen, CN, a halogen atom, an alkyl group having 1 to 30 carbon atoms which is optionally substituted; a cycloalkyl group having 3 to 30 ring carbon atoms which is optionally substituted; an alkenyl group having 2 to 30 carbon atoms which is optionally substituted; an aromatic hydrocarbon group having 6 to 30 ring carbon atoms which is optionally substituted; an aralkyl group having 7 to 31 ring carbon atoms which is optionally substituted; or a heterocyclic group having 5 to 30 ring which is optionally substituted;

with the proviso that, two or more substituents selected from $R^2$, $R^3$, $R^4$, and $R^5$, and/or two or more substituents selected from $R^6$, $R^7$, $R^8$ and $R^9$, and/or two or more substituents selected from $R^{10}$, $R^{11}$, $R^{12}$ and $R^{13}$ may be bonded to each other to form a ring structure, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

5. The compound according to claim 1, wherein:
L is a single bond, an aromatic hydrocarbon group having 6 to 30 ring carbon atoms which is optionally substituted, or a heterocyclic group having 5 to 30 ring atoms which is optionally substituted;

l is 1 or 2, with the proviso that when l is 2, L is the same or different in each occurrence; and $B^1$ is H; CN; an aromatic hydrocarbon group having 6 to 30 ring carbon atoms which is optionally substituted; or a heterocyclic group having 5 to 30 ring atoms which is optionally substituted, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

6. The compound according to claim 1, wherein:

$B^1$ represents general formula (IX):

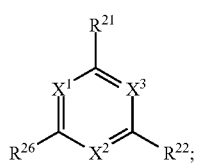

(IX)

wherein $X^1$, $X^2$ and $X^3$ each independently represent $CR^{23}$ or N;

$R^{21}$, $R^{22}$, $R^{23}$ and $R^{26}$ each independently represent hydrogen, a halogen atom, a alkyl group having 1 to 30 carbon atoms which is optionally substituted, an alkenyl group having 2 to 31 carbon atoms, a substituted or unsubstituted alkynyl group having 2 to 30 carbon atoms which is optionally substituted, alkoxy group having 1 to 30 carbon atoms which is optionally substituted, an aromatic hydrocarbon group having 6 to 30 ring carbon atoms which is optionally substituted, a heterocyclic group having 5 to 30 ring atoms which is optionally substituted, an aryloxy group having 6 to 30 ring carbon atoms which is optionally substituted, an alkylthio group having 1 to 30 carbon atoms which is optionally substituted, an arylthio group having 6 to 30 ring carbon atoms which is optionally substituted, a substituted silyl group having 3 to 60 carbon atoms, or a cyano group;

with the proviso that, among $R^{21}$, $R^{22}$, $R^{26}$ and $R^{23}$, if $X^1$, $X^2$ and/or $X^3$ are $CR^{23}$, any two of $R^{21}$, $R^{22}$, $R^{23}$ and $R^{26}$ may be bonded each other to form a ring structure; and one of $R^{21}$, $R^{22}$, $R^{26}$ and, if $X^1$, $X^2$ and/or $X^3$ are $CR^{23}$, $R^{23}$, represents a bonding site to $-(L)_l-$, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

7. The compound according to claim 1, wherein L is selected from the group consisting of a phenylene group which is optionally substituted, a biphenylene group which is optionally substituted, and a terphenylene group which is optionally substituted, and wherein when a group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

8. The compound according to claim 1, wherein:

L represents an aryl group having 6 to 30 carbon atoms which is optionally substituted; and $B^1$ represents CN, and wherein when the aryl group is optionally substituted the optional substituent is selected from the group consisting of a halogen atom, an alkyl group having 1 to 30 carbon atoms, an aromatic hydrocarbon group having 6 to 30 ring carbon atoms and a heterocyclic group having 5 to 30 ring atoms, wherein the optional substituent may further be optionally substituted with one or more groups selected from the group consisting of an aromatic hydrocarbon group having 6 to 30 ring carbon atoms and a heterocyclic group having 5 to 30 ring atoms.

9. A material for an organic electroluminescence device, the material comprising at least one compound according to claim 1.

10. An organic electroluminescence device, comprising an organic thin film layer between a cathode and an anode, wherein:

the organic thin film layer comprises one or more layers including a light emitting layer; and at least one layer of the organic thin film layer comprises at least one compound according to claim 1.

11. The organic electroluminescence device according to claim 10, wherein the light emitting layer comprises the at least one compound.

12. The organic electroluminescence device according to claim 10, wherein the light emitting layer comprises a phosphorescent material, which is an ortho-metallated complex comprising a metal atom selected from iridium (Ir), osmium (Os) and platinum (Pt).

13. The organic electroluminescence device according to claim 10, wherein an electron transporting layer is provided between the cathode and the light emitting layer, and the electron transporting layer comprises the at least one compound.

14. The organic electroluminescence device according to claim 10, wherein a hole blocking layer is provided between the electron transporting layer and the light emitting layer, and the hole blocking layer comprises the at least one compound.

15. An electronic equipment, comprising the organic electroluminescence device according to claim 10.

* * * * *